(12) United States Patent
Kim et al.

(10) Patent No.: US 8,360,069 B2
(45) Date of Patent: Jan. 29, 2013

(54) DEVICES AND METHODS FOR TREATMENT OF OBESITY

(75) Inventors: Steven Kim, Los Altos, CA (US); Joshua Makower, Los Altos, CA (US)

(73) Assignee: Vibrynt, Inc., Redwood City, CA (US)

( * ) Notice: Subject to any disclaimer, the term of this patent is extended or adjusted under 35 U.S.C. 154(b) by 962 days.

(21) Appl. No.: 12/250,509

(22) Filed: Oct. 13, 2008

(65) Prior Publication Data
US 2009/0036910 A1 Feb. 5, 2009

Related U.S. Application Data

(62) Division of application No. 11/407,701, filed on Apr. 19, 2006, now Pat. No. 8,070,768.

(51) Int. Cl.
*A61B 19/00* (2006.01)
*A61F 2/00* (2006.01)
*A61F 13/00* (2006.01)
*A61M 29/00* (2006.01)

(52) U.S. Cl. .......... 128/898; 600/37; 606/191; 606/192; 606/198

(58) Field of Classification Search .......... 606/191–194, 606/198; 128/898; 600/37
See application file for complete search history.

(56) References Cited

U.S. PATENT DOCUMENTS

| | | | |
|---|---|---|---|
| 233,475 A | 10/1880 | Cook et al. | |
| 659,422 A | 10/1900 | Shidler | |
| 780,392 A | 1/1905 | Wanamaker et al. | |
| 789,467 A | 1/1905 | West | |
| 1,461,524 A | 7/1923 | Goddard | |
| 2,579,192 A | 12/1951 | Kohl et al. | |
| 2,646,298 A | 7/1953 | Leary | |
| 2,697,624 A | 12/1954 | Thomas et al. | |
| 2,734,299 A | 2/1956 | Masson | |
| 2,825,592 A | 3/1958 | Semple | |

(Continued)

FOREIGN PATENT DOCUMENTS

EP 1 016 377 A2 7/2000

(Continued)

OTHER PUBLICATIONS

McMillan, et al., Arthroscopic Knot-tying techniques, pp. 81-95, 2003.

(Continued)

*Primary Examiner* — Gary Jackson
*Assistant Examiner* — Michael Mendoza
(74) *Attorney, Agent, or Firm* — Law office of Alan W. Cannon

(57) ABSTRACT

Implantable devices, instruments, kits and methods for treatment of obesity. One or more devices can be implanted adjacent to or in contact with the stomach to occupy a space to prevent the stomach from expanding into that space as food is taken into the stomach. Alternatively, one or more devices may be implanted and expanded to displace at least a portion of the wall of the stomach to decrease the internal volume of the stomach that is available to receive food. Devices may be anchored to one or more internal structures at one or more locations without piercing through the wall of the stomach. Devices can be implanted using minimally invasive methods, such as percutaneous or laparoscopic methods. Delivery instruments are also provided. An intra-gastric sizing device is provided to facilitate implantation of an extra-gastric device in some method embodiments.

15 Claims, 77 Drawing Sheets

U.S. PATENT DOCUMENTS

| | | | |
|---|---|---|---|
| 3,326,586 A | 6/1967 | Frost et al. | |
| 3,470,834 A | 10/1969 | Bone | |
| 3,521,918 A | 7/1970 | Hammond | |
| 3,571,864 A | 3/1971 | Oger et al. | |
| 3,664,435 A | 5/1972 | Klessig | |
| 3,713,680 A | 1/1973 | Pagano | |
| 3,756,638 A | 9/1973 | Stockberger | |
| 3,873,140 A | 3/1975 | Bloch | |
| 3,931,667 A | 1/1976 | Merser et al. | |
| 3,976,079 A | 8/1976 | Samuels et al. | |
| 4,006,747 A | 2/1977 | Kronenthal et al. | |
| 4,060,089 A | 11/1977 | Noiles | |
| 4,133,315 A | 1/1979 | Berman et al. | |
| 4,210,148 A | 7/1980 | Stivala | |
| 4,246,893 A | 1/1981 | Berson | |
| 4,291,698 A | 9/1981 | Fuchs et al. | |
| 4,328,805 A | 5/1982 | Akopov et al. | |
| 4,416,267 A | 11/1983 | Garren et al. | |
| 4,458,681 A | 7/1984 | Hophins | |
| 4,472,226 A | 9/1984 | Redinger et al. | |
| 4,485,805 A | 12/1984 | Foster, Jr. et al. | |
| 4,493,323 A | 1/1985 | Albright et al. | |
| 4,558,699 A | 12/1985 | Bashour | |
| 4,592,339 A | 6/1986 | Kuzmak et al. | |
| 4,592,342 A | 6/1986 | Salmasian | |
| 4,621,640 A | 11/1986 | Mulhollan et al. | |
| 4,669,473 A | 6/1987 | Richards et al. | |
| 4,694,827 A | 9/1987 | Weiner et al. | |
| 4,696,288 A | 9/1987 | Kuzmak et al. | |
| 4,705,040 A | 11/1987 | Mueller et al. | |
| 4,714,281 A | 12/1987 | Peck | |
| 4,723,547 A | 2/1988 | Kullas et al. | |
| 4,738,255 A | 4/1988 | Goble et al. | |
| 4,739,758 A | 4/1988 | Lai et al. | |
| 4,744,364 A | 5/1988 | Kensey | |
| 4,750,492 A | 6/1988 | Jacobs | |
| 4,803,985 A | 2/1989 | Hill | |
| 4,823,794 A | 4/1989 | Pierce | |
| 4,899,747 A | 2/1990 | Garren et al. | |
| 4,955,913 A | 9/1990 | Robinson | |
| 5,002,550 A | 3/1991 | Li | |
| 5,033,481 A | 7/1991 | Heyler, III | |
| 5,041,129 A | 8/1991 | Hayhurst et al. | |
| 5,084,061 A | 1/1992 | Gau et al. | |
| 5,100,421 A | 3/1992 | Christoudias | |
| 5,112,310 A | 5/1992 | Grobe | |
| 5,123,914 A | 6/1992 | Cope | |
| 5,129,912 A | 7/1992 | Noda et al. | |
| RE34,021 E | 8/1992 | Mueller et al. | |
| 5,151,086 A | 9/1992 | Duh et al. | |
| 5,188,104 A | 2/1993 | Wernicke et al. | |
| 5,217,470 A | 6/1993 | Weston | |
| 5,226,429 A * | 7/1993 | Kuzmak | 128/898 |
| 5,234,454 A | 8/1993 | Bangs | |
| 5,246,456 A | 9/1993 | Wilkinson | |
| 5,258,015 A | 11/1993 | Li et al. | |
| 5,259,399 A | 11/1993 | Brown | |
| 5,269,809 A | 12/1993 | Hayhurst et al. | |
| 5,292,344 A | 3/1994 | Douglas | |
| 5,334,200 A | 8/1994 | Johnson | |
| 5,354,271 A | 10/1994 | Voda | |
| 5,364,408 A | 11/1994 | Gordon | |
| 5,391,182 A | 2/1995 | Chin | |
| 5,405,352 A | 4/1995 | Weston | |
| 5,423,872 A | 6/1995 | Cigaina | |
| 5,428,123 A | 6/1995 | Ward et al. | |
| 5,433,723 A | 7/1995 | Lindenberg | |
| 5,445,608 A | 8/1995 | Chen et al. | |
| 5,470,337 A | 11/1995 | Moss | |
| 5,472,446 A | 12/1995 | Torre | |
| 5,480,406 A | 1/1996 | Nolan et al. | |
| 5,496,311 A | 3/1996 | Abele et al. | |
| 5,507,754 A | 4/1996 | Green et al. | |
| 5,545,171 A | 8/1996 | Sharkey et al. | |
| 5,545,178 A | 8/1996 | Kensey et al. | |
| 5,549,621 A | 8/1996 | Bessler et al. | |
| 5,554,162 A | 9/1996 | DeLange | |
| 5,573,540 A | 11/1996 | Yoon | |
| 5,591,177 A | 1/1997 | Lehrer | |
| 5,601,604 A | 2/1997 | Vincent | |
| 5,626,614 A | 5/1997 | Hart | |
| 5,634,936 A | 6/1997 | Linden et al. | |
| 5,647,836 A | 7/1997 | Blake, III et al. | |
| 5,690,691 A | 11/1997 | Chen et al. | |
| 5,716,368 A | 2/1998 | Torre et al. | |
| 5,725,557 A | 3/1998 | Gatturna et al. | |
| 5,846,254 A | 12/1998 | Schulze et al. | |
| 5,888,196 A | 3/1999 | Bonutti | |
| 5,931,788 A | 8/1999 | Keen et al. | |
| 5,938,669 A | 8/1999 | Klaiber et al. | |
| 5,951,590 A | 9/1999 | Goldfarb | |
| 5,961,440 A | 10/1999 | Schweich, Jr. et al. | |
| 5,971,447 A | 10/1999 | Steck, III | |
| 5,993,473 A | 11/1999 | Chan et al. | |
| 6,006,002 A | 12/1999 | Motoki et al. | |
| 6,013,053 A | 1/2000 | Bower et al. | |
| 6,067,991 A | 5/2000 | Forsell | |
| 6,080,160 A | 6/2000 | Chen et al. | |
| 6,097,984 A | 8/2000 | Douglas | |
| 6,102,922 A | 8/2000 | Jakobsson et al. | |
| 6,113,609 A | 9/2000 | Adams | |
| 6,143,006 A | 11/2000 | Chan | |
| 6,162,234 A | 12/2000 | Freedland et al. | |
| 6,174,280 B1 | 1/2001 | Oneda et al. | |
| 6,186,149 B1 | 2/2001 | Pacella et al. | |
| 6,270,530 B1 | 8/2001 | Eldridge et al. | |
| 6,420,452 B1 | 7/2002 | Gunatillake et al. | |
| 6,437,073 B1 | 8/2002 | Gunatillake et al. | |
| 6,447,533 B1 | 9/2002 | Adams | |
| 6,454,785 B2 | 9/2002 | De Hoyos Garza | |
| 6,475,136 B1 | 11/2002 | Forsell | |
| 6,488,691 B1 | 12/2002 | Carroll et al. | |
| 6,491,707 B2 | 12/2002 | Makower et al. | |
| 6,494,888 B1 | 12/2002 | Laufer et al. | |
| 6,500,148 B1 | 12/2002 | Pinchuk et al. | |
| 6,506,196 B1 | 1/2003 | Laufer | |
| 6,511,490 B2 | 1/2003 | Robert et al. | |
| 6,535,764 B2 | 3/2003 | Imran et al. | |
| 6,558,400 B2 | 5/2003 | Deem et al. | |
| 6,656,182 B1 | 12/2003 | Hayhurst | |
| 6,663,639 B1 | 12/2003 | Laufer et al. | |
| 6,669,713 B2 | 12/2003 | Adams | |
| 6,675,809 B2 | 1/2004 | Stack et al. | |
| 6,736,793 B2 | 5/2004 | Meyer et al. | |
| 6,746,460 B2 | 6/2004 | Gannoe et al. | |
| 6,755,869 B2 | 6/2004 | Geitz | |
| 6,773,441 B1 | 8/2004 | Laufer et al. | |
| 6,790,213 B2 | 9/2004 | Cherok et al. | |
| 6,821,285 B2 | 11/2004 | Laufer et al. | |
| 6,835,200 B2 | 12/2004 | Laufer et al. | |
| 6,869,395 B2 | 3/2005 | Page et al. | |
| 6,900,055 B1 | 5/2005 | Fuller et al. | |
| 6,908,487 B2 | 6/2005 | Cigaina | |
| 6,981,978 B2 | 1/2006 | Gannoe | |
| 6,994,715 B2 | 2/2006 | Gannoe et al. | |
| 7,033,373 B2 | 4/2006 | de la Torre et al. | |
| 7,037,344 B2 | 5/2006 | Kagan et al. | |
| 7,153,314 B2 | 12/2006 | Laufer et al. | |
| 7,167,750 B2 | 1/2007 | Knudson et al. | |
| 7,223,277 B2 | 5/2007 | DeLegge | |
| 7,255,675 B2 | 8/2007 | Gertner et al. | |
| 7,310,557 B2 | 12/2007 | Maschino et al. | |
| 7,334,822 B1 | 2/2008 | Hines, Jr. | |
| 7,338,433 B2 | 3/2008 | Coe | |
| 7,354,454 B2 | 4/2008 | Stack et al. | |
| 7,374,565 B2 | 5/2008 | Hassler et al. | |
| 7,402,166 B2 | 7/2008 | Feigl | |
| 7,416,554 B2 | 8/2008 | Lam et al. | |
| 7,534,248 B2 | 5/2009 | Mikkaichi et al. | |
| 7,618,426 B2 | 11/2009 | Ewers et al. | |
| 7,666,195 B2 | 2/2010 | Kelleher et al. | |
| 7,670,279 B2 | 3/2010 | Gertner | |
| 7,775,967 B2 | 8/2010 | Gertner | |
| 7,841,978 B2 | 11/2010 | Gertner | |
| 7,850,660 B2 | 12/2010 | Uth et al. | |
| 7,862,546 B2 | 1/2011 | Conlon et al. | |
| 7,988,617 B2 | 8/2011 | Gertner | |

| | | |
|---|---|---|
| 2001/0010005 A1 | 7/2001 | Kammerer et al. |
| 2001/0011543 A1 | 8/2001 | Forsell |
| 2001/0044639 A1 | 11/2001 | Levinson |
| 2002/0055757 A1 | 5/2002 | Torre et al. |
| 2002/0128684 A1 | 9/2002 | Foerster |
| 2002/0161382 A1 | 10/2002 | Neisz et al. |
| 2002/0161414 A1 | 10/2002 | Flesler et al. |
| 2002/0188354 A1 | 12/2002 | Peghini et al. |
| 2003/0021822 A1 | 1/2003 | Lloyd |
| 2003/0055463 A1 | 3/2003 | Gordon et al. |
| 2003/0055465 A1 | 3/2003 | Ben-Haim et al. |
| 2003/0093117 A1 | 5/2003 | Saadat |
| 2003/0208212 A1 | 11/2003 | Cigaina |
| 2004/0006351 A1 | 1/2004 | Gannoe et al. |
| 2004/0024386 A1 | 2/2004 | Deem et al. |
| 2004/0044353 A1 | 3/2004 | Gannoe |
| 2004/0044357 A1 | 3/2004 | Gannoe |
| 2004/0054352 A1 | 3/2004 | Adams et al. |
| 2004/0059289 A1 | 3/2004 | Garza Alvarez |
| 2004/0068224 A1 | 4/2004 | Couvillon et al. |
| 2004/0092892 A1 | 5/2004 | Kagan et al. |
| 2004/0097986 A1 | 5/2004 | Adams |
| 2004/0098060 A1 | 5/2004 | Ternes |
| 2004/0116949 A1 | 6/2004 | Ewers et al. |
| 2004/0122456 A1 | 6/2004 | Saadat et al. |
| 2004/0122473 A1 | 6/2004 | Ewers et al. |
| 2004/0148034 A1 | 7/2004 | Kagan et al. |
| 2004/0186503 A1 | 9/2004 | DeLegge |
| 2004/0193194 A1 | 9/2004 | Laufer et al. |
| 2004/0194790 A1 | 10/2004 | Laufer et al. |
| 2004/0243178 A1 | 12/2004 | Haut et al. |
| 2004/0243179 A1 | 12/2004 | Foerster |
| 2004/0243180 A1 | 12/2004 | Donnelly et al. |
| 2004/0260345 A1 | 12/2004 | Foerster |
| 2004/0267378 A1 | 12/2004 | Gazi et al. |
| 2005/0022827 A1 | 2/2005 | Woo et al. |
| 2005/0049718 A1 | 3/2005 | Dann et al. |
| 2005/0096638 A1 | 5/2005 | Starkebaum et al. |
| 2005/0159769 A1 | 7/2005 | Alverdy |
| 2005/0197687 A1 | 9/2005 | Molaei et al. |
| 2005/0203344 A1 | 9/2005 | Orban, III et al. |
| 2005/0216040 A1 | 9/2005 | Gertner et al. |
| 2005/0216042 A1 | 9/2005 | Gertner et al. |
| 2005/0222638 A1 | 10/2005 | Foley et al. |
| 2005/0228415 A1 | 10/2005 | Gertner |
| 2005/0261712 A1 | 11/2005 | Balbierz |
| 2005/0267405 A1 | 12/2005 | Shah |
| 2005/0267406 A1 | 12/2005 | Hassler, Jr. |
| 2005/0267533 A1 | 12/2005 | Gertner |
| 2005/0267595 A1 | 12/2005 | Chen et al. |
| 2005/0267596 A1 | 12/2005 | Chen et al. |
| 2005/0277960 A1 | 12/2005 | Hassler, Jr. et al. |
| 2005/0277974 A1 | 12/2005 | Hassler et al. |
| 2006/0009789 A1 | 1/2006 | Gambale et al. |
| 2006/0025789 A1 | 2/2006 | Laufer et al. |
| 2006/0025819 A1 | 2/2006 | Nobis et al. |
| 2006/0030884 A1 | 2/2006 | Yeung et al. |
| 2006/0058829 A1 | 3/2006 | Sampson |
| 2006/0089571 A1 | 4/2006 | Gertner |
| 2006/0089646 A1 | 4/2006 | Bonutti |
| 2006/0106288 A1 | 5/2006 | Roth et al. |
| 2006/0161186 A1 | 7/2006 | Hassler, Jr. et al. |
| 2006/0161256 A1 | 7/2006 | Ziegler et al. |
| 2006/0195139 A1 | 8/2006 | Gertner |
| 2006/0212053 A1 | 9/2006 | Gertner |
| 2006/0253131 A1 | 11/2006 | Wolniewicz |
| 2006/0264699 A1 | 11/2006 | Gertner |
| 2006/0265042 A1 | 11/2006 | Catanese, III et al. |
| 2006/0276871 A1 | 12/2006 | Lamson et al. |
| 2006/0282081 A1 | 12/2006 | Fanton et al. |
| 2007/0027358 A1 | 2/2007 | Gertner |
| 2007/0049970 A1 | 3/2007 | Belef et al. |
| 2007/0060940 A1 | 3/2007 | Brazzini et al. |
| 2007/0073318 A1 | 3/2007 | Carter et al. |
| 2007/0073323 A1 | 3/2007 | Carter et al. |
| 2007/0088373 A1 | 4/2007 | Baker |
| 2007/0112363 A1 | 5/2007 | Adams |
| 2007/0112385 A1 | 5/2007 | Conlon |
| 2007/0129738 A1 | 6/2007 | Kraemer et al. |
| 2007/0167982 A1 | 7/2007 | Gertner et al. |
| 2007/0173869 A1 | 7/2007 | Gannoe et al. |
| 2007/0173888 A1 | 7/2007 | Gertner et al. |
| 2007/0179335 A1 | 8/2007 | Gertner et al. |
| 2007/0203517 A1 | 8/2007 | Williams et al. |
| 2007/0233170 A1 | 10/2007 | Gertner et al. |
| 2007/0235083 A1 | 10/2007 | Dlugos |
| 2007/0239284 A1 | 10/2007 | Skerven et al. |
| 2007/0255308 A1 | 11/2007 | Williams et al. |
| 2007/0260259 A1 | 11/2007 | Fanton et al. |
| 2007/0276293 A1 | 11/2007 | Gertner |
| 2007/0276432 A1 | 11/2007 | Stack et al. |
| 2008/0015501 A1 | 1/2008 | Gertner |
| 2008/0033488 A1 | 2/2008 | Catanese, III et al. |
| 2008/0039894 A1 | 2/2008 | Catanese, III et al. |
| 2008/0051823 A1 | 2/2008 | Makower et al. |
| 2008/0051824 A1 | 2/2008 | Gertner |
| 2008/0051850 A1 | 2/2008 | Sparks et al. |
| 2008/0071306 A1 | 3/2008 | Gertner |
| 2008/0091237 A1 | 4/2008 | Schwartz et al. |
| 2008/0147002 A1 | 6/2008 | Gertner |
| 2008/0161717 A1 | 7/2008 | Gertner |
| 2008/0167647 A1 | 7/2008 | Gertner |
| 2008/0167648 A1 | 7/2008 | Gertner |
| 2008/0208240 A1 | 8/2008 | Paz |

FOREIGN PATENT DOCUMENTS

| | | |
|---|---|---|
| EP | 1 670 361 B1 | 6/2004 |
| EP | 1 602 392 A1 | 7/2005 |
| EP | 1 591 140 A1 | 11/2005 |
| EP | 1 520 563 A1 | 4/2006 |
| EP | 1 547 642 B1 | 8/2007 |
| EP | 1 607 071 B1 | 8/2007 |
| EP | 1 670 361 B1 | 4/2008 |
| WO | WO 87/00034 | 1/1987 |
| WO | WO 99/25418 | 5/1999 |
| WO | WO 9925418 | 5/1999 |
| WO | WO 00/09049 | 2/2000 |
| WO | WO 00/18330 A1 | 4/2000 |
| WO | WO 00/74573 A1 | 12/2000 |
| WO | WO 01/47435 A2 | 7/2001 |
| WO | WO 02/35980 A2 | 5/2002 |
| WO | WO 02071951 | 9/2002 |
| WO | WO 03/055420 A1 | 7/2003 |
| WO | WO 03095015 | 11/2003 |
| WO | WO 2004004542 | 1/2004 |
| WO | WO 2004014237 | 2/2004 |
| WO | WO 2004019765 | 3/2004 |
| WO | WO 2004021894 | 3/2004 |
| WO | WO 2004/037064 A2 | 5/2004 |
| WO | WO 2005007232 | 1/2005 |
| WO | WO 2005/009288 A2 | 2/2005 |
| WO | WO 2005/018417 A2 | 3/2005 |
| WO | WO 2005/018417 A3 | 3/2005 |
| WO | WO 2005018417 | 3/2005 |
| WO | WO 2005020802 | 3/2005 |
| WO | WO 2005/094447 A2 | 10/2005 |
| WO | WO 2006/020370 A2 | 2/2006 |
| WO | WO 2006/049725 A2 | 5/2006 |
| WO | WO 2006063593 A2 | 6/2006 |
| WO | WO 2006/108203 A2 | 10/2006 |
| WO | WO 2006127431 | 11/2006 |
| WO | WO 2006134106 A1 | 12/2006 |
| WO | WO 2007017880 A2 | 2/2007 |
| WO | WO 2007/067206 A2 | 6/2007 |
| WO | WO 2007064906 A2 | 6/2007 |
| WO | WO 2007/110866 A2 | 10/2007 |
| WO | WO 2008/006084 A2 | 1/2008 |

OTHER PUBLICATIONS

Buchwald—Overview of Barlatric Surgery. Journal of the American Collge of Surgeons. pp. 367-375, Mar. 2002.

Sharp, et al., The 4-S Modification of the Roeder Knot: How to Tie It. pp. 1004-1006, vol. 90, No. 6, Dec. 1997.

Akira., JP63277063, Japanese and English Abstract, Nov. 15, 1988, pp. 1-4.

About the Vertical Sleeve Gastrectomy. Mar. 24, 2006, pp. 1-1. http://obesityhelp.com/forums/VSG/about.html.

Abhyankar et al, Use of a tissue expander and a polyglactic acid (Vicryl) mesh to reduce radiation enteritis: case report and literature view, 21: pp. 755-757, Aug. 2005.
Brolin, Robert E., Gastric Bypass. vol. 81, No. 5, Oct. 2001, pp. 1077-1095. pp. 1129-1143.
Buchwald, Overview of Bariatric Surgery, vol. 194, No. 3, Mar. 2002, pp. 367-375.
Burnett, et al., The Use of a Pelvic Displacement Prosthesis to Exclude the Small Intestine from the Radiation Field Following Radical Hysterectomy, 79, pp. 438-443, 2000. http://www.idealibrary.com.
Cheng, Splenic Epidermoid Cyst, pp. 1-3, 1997.
DeMaria, Eric J., Laparoscopic Adjustable Silicone Gastric Banding. Vol. 81, No. 5, Oct. 2001, pp. 1129-1143.
Deitel, Mervyn., Overview of Operations for Morbid Obesity. vol. 22, No. 9, Sep. 1998, pp. 913-918.
Doherty, Cornelius., Technique of Vertical Banded Gastroplasty. vol. 81, No. 5, Oct. 2001, pp. 1097-1111.
Fried et al., Physical Principles of Available Adjustable Gastric Bands: How they Work. Obesity Surgery, 14, 2004, pp. 1118-1121.
Foglia et al, Management of giant omphalocele with rapid creation of abdominal domain, 41, pp. 704-709, 2006.
Gertner MD, Stomach Restriction with an Extragastric Balloon, pp. 1, Abstract for 2007.
Geliebter et al; Extra-abdominal pressure alters food intake, intragastric pressure, and gastric emptying rate. 1986, pp. R549-R552.
Hainaux et al., Laparoscopic adjustable silicone gastric banding: radiological appearances of a new surgical treatment for morbid obesity. 1999, Abdom Imaging 24: 533-537.
Hoffman et al., Morbidity after Intraperitoneal Insertion of Saline-Filled Tissue Expanders for Small Bowel Exclusion from Radiotherapy Treatment Fields: A Prospective Four Year Experience with 34 Patients, pp. 473-483, No. 7, vol. 60, Jul. 1994.
Konturek et al., Neuro-Hormonal Control of Food Intake; Basic Mechanisms and Clinical Implications, 2005, 56, Supp 6, 5-25. www.jpp.krakow.pl.
Lam et al., Huge Splenic Epidemoid Cyst: A Case Report, 1997; 60:113-6.
Laparoscopic Duodenal Switch, Mar. 24, 2006, http://wo-pub2.med.cornell.edu/chi.bin/WebObjects/PublicA.woa/5/w . . . p. 1-1.
Lee et al., Laparoscopic Vertical Sleeve Gastrectomy: A Novel Bariatric Procedure—superior to Estabilished Operations? pp. 1-27. 90th Annual Clinical Congress. New Orleans, LA, Oct. 10, 2004.
Med-484P, Product Profile , Mar. 30, 2007, pp. 1-2.
Malassagne, et al., Intra-abdonimal Sengstaken-Blakemore tube Placement for acute venous outflow obstruction in reduced-size Liver, Nov. 1996, 83, pp. 1086.
Marceau, et al., Malabsorptive Obesity Surgery. vol. 81, Oct. 2001, No. 5, pp. 1113-1127.
Mera, et al., Use of the Breast Implant for Liver Graft Malposition. vol. 5, No. 6, Nov. 1999, pp. 534-535.
Obesity Surgery Including Laparoscopy and Allied Care. vol. 16, No. 1, Jan. 2006, pp. 1-2. www.obesitysurgey.com.
Pomerri et al., Adjustable Silicone Gastric Banding of Obesity. , 1992, Gastrointest Radiol 17:207-210.
Schauer, et al., New applications for endoscopy: the emerging field of endoluminal and transgastric bariatric surgery, DOI:10.1007/s00464-006-9008-8, 2006.
The Sleeve Gastrectomy (or 2-Stage Procedure). 2006, pp. 1-2. http://surgicallyslim.com/sleeve.htm.
Tucker, Diana, Medical Device Daily. vol. 10, No. 102, May 26, 2006, pp. 1-10.
Walker, et al. Bladder Augmentation in Dogs Using the Tissue Capsule Formed Around a Perivesical tissue Expander, vol. 168, pp. 1534-1536, 2002.
Zwart et al., Gastric Motility: Comparison of Assessement with Real-Time MR Imaging or Barostat Experience1., 224: pp. 592-597, Aug. 2002.
Buchwald et al., "Bariatric Surgery: A Systematic Review and Meta-analysis", JAMA 2004, vol. 292, No. 14, pp. 1724-1737.
Buchwald et al., "Evolution of Operative Procedures for the Management of Morbid Obesity 1950-2000", Obesity Surgery 2002, 12:705-717.
Camerini et al., "Thirteen Years of Follow-up in Patients with Adjustable Silicone Gastric Banding for Obesity: Weight Loss and Constant Rate of Late Specific Complications" Obesity Surgery 2004, 14:1343-1348.
Cope et al., "Percutaneous Transgastric Technique for Creating Gastroenteric Anastomoses in Swine", Journal of Vascular and Interventional Radiology, 2004, 15:177-181.
Cummings et al., "Genetics and Pathphysiology of Human Obesity", An Annual Review of Medicine, 2003, 54:453-471/.
Johnston et al., "The Magnestrasse and Mill Operation for Morbid Obesity", Obesity Surgery 2003. 13:10-16.
Morino et al., "Laproscopic Adjustable Silicone Gastric Banding Versus Vertical Banded Gastroplasty in Morbidly Obese Patients" Analysis Obesity Surgery vol. 238, No. 6, 2003, pp. 835-842.
Roman et al., "Intragastric Balloon of Non-Morbid Obesity: A Retrospective Evaluation of Tolerance and Efficacy", Obesity Surgery, 2004, 14:539-544.
Sallet et al , Brazillian Multicenter Study of the Intrhastric Balloon; Obesity Surgery, 2004, 14, pp. 991-998.
Sjostrom et al., Lifestyle, Diabeters, and Cardiovascular Risk Factors 10 years after Bariatric Surgery, New England Journal of Medicine, 2004, 351, (6) 2683-2693.
Smith et al., "Modification of the Gastric Partitioning Operation for Morbid Obesity", Am. J. Surgery 142, Dec. 1981 pp. 725-730.
Smith et al., "Results and Comphoations of Gastric Partition: Four Years Follow-Up of 300 Morbidly Obese Patients", The American Journal of Surgery, 1983, (146) pp. 815-819.
Trumble et al., "Method for measuring long-term function of muscle-powered implants via radiotelemetry" J. Appl. Physiol. 2001,90: pp. 1977-1985.

* cited by examiner

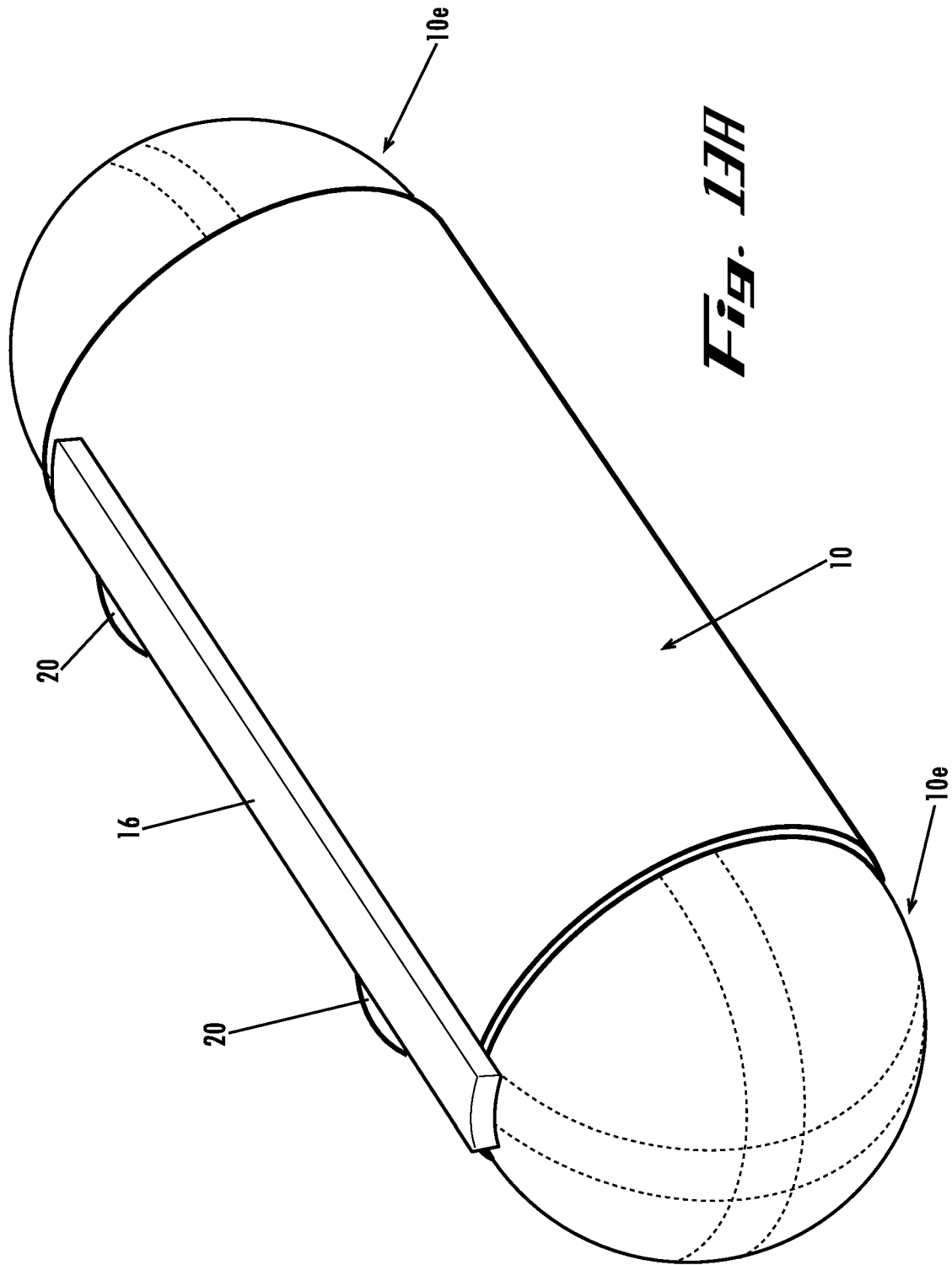

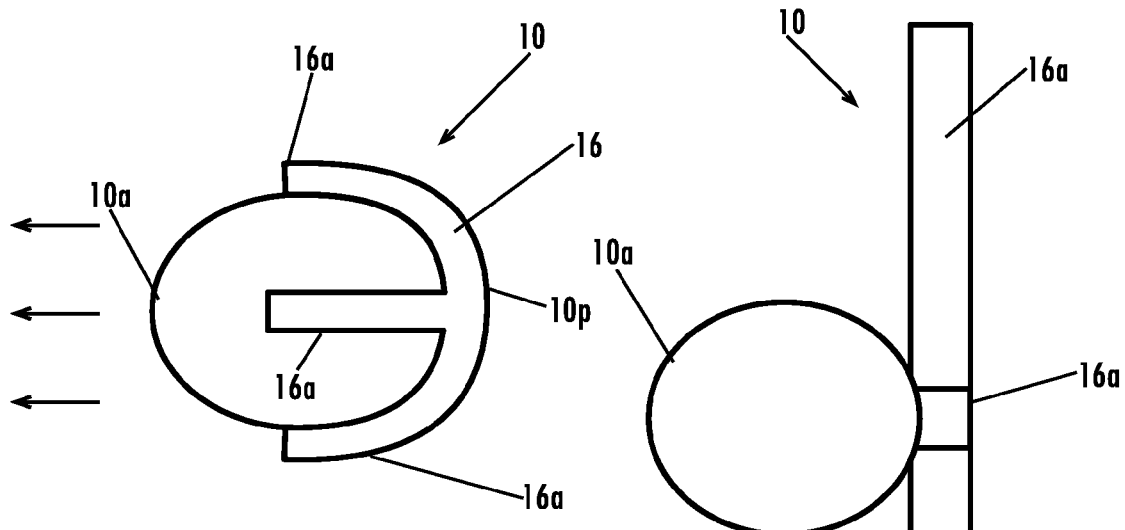
Fig. 15A
Fig. 15B
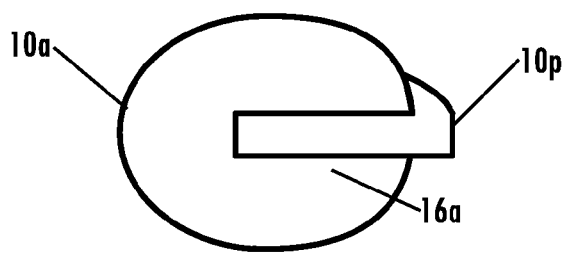
Fig. 16A
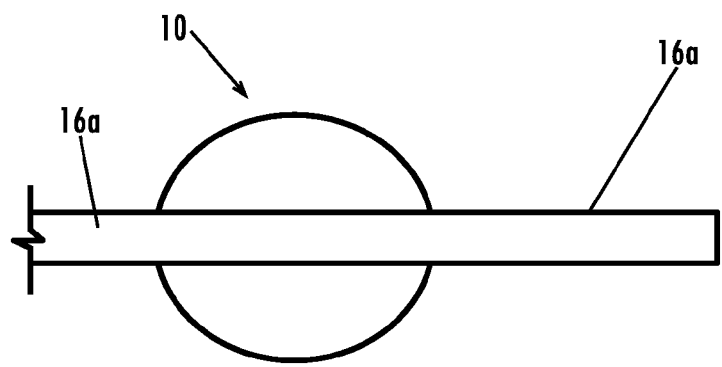
Fig. 16B

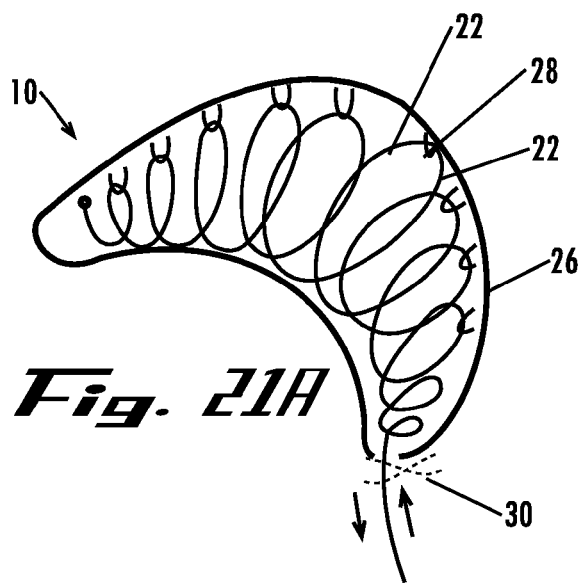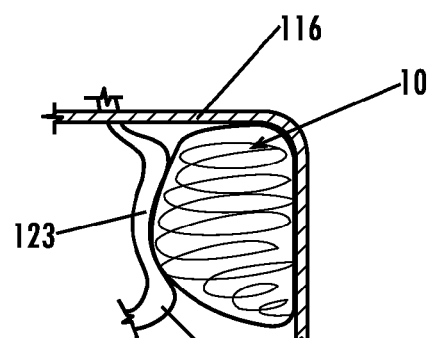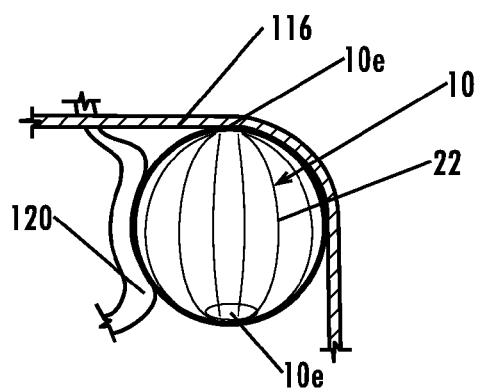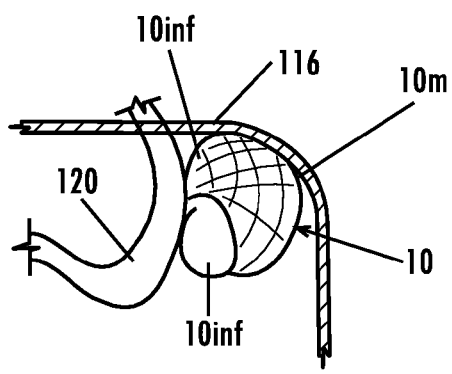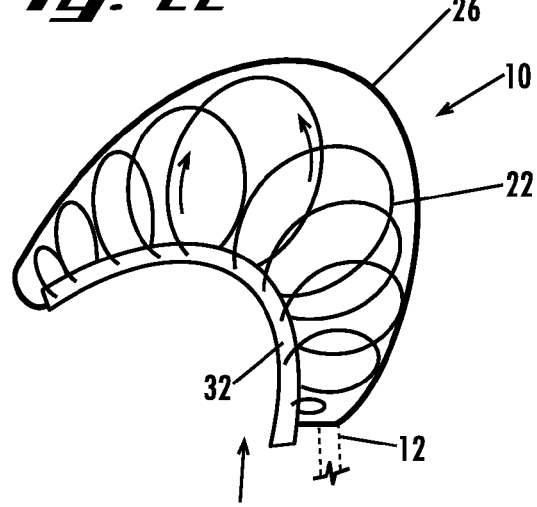

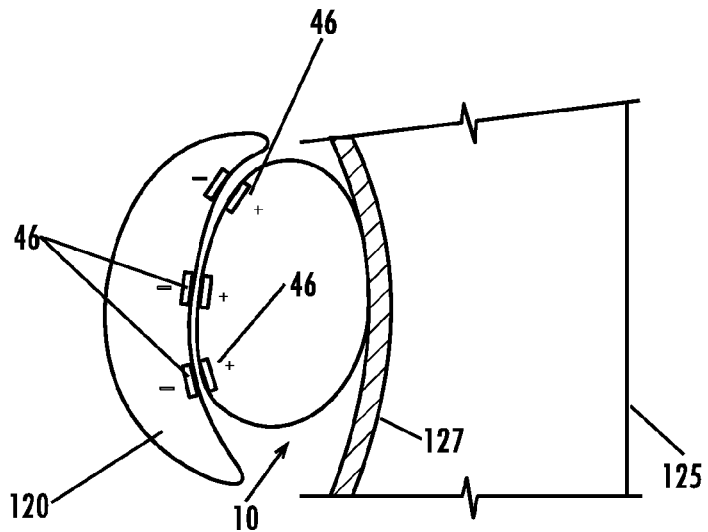
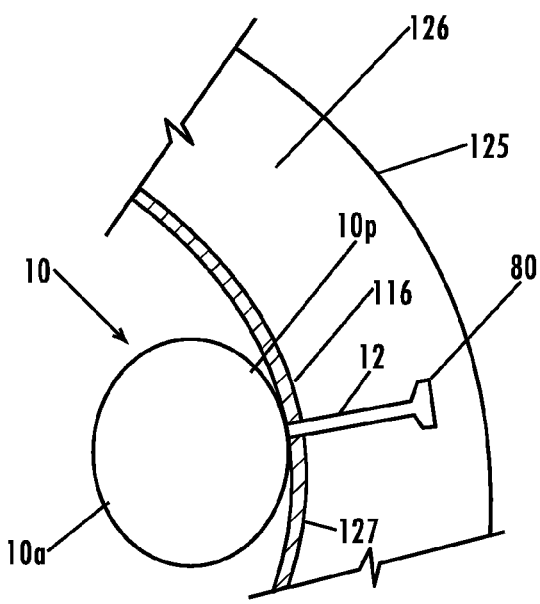
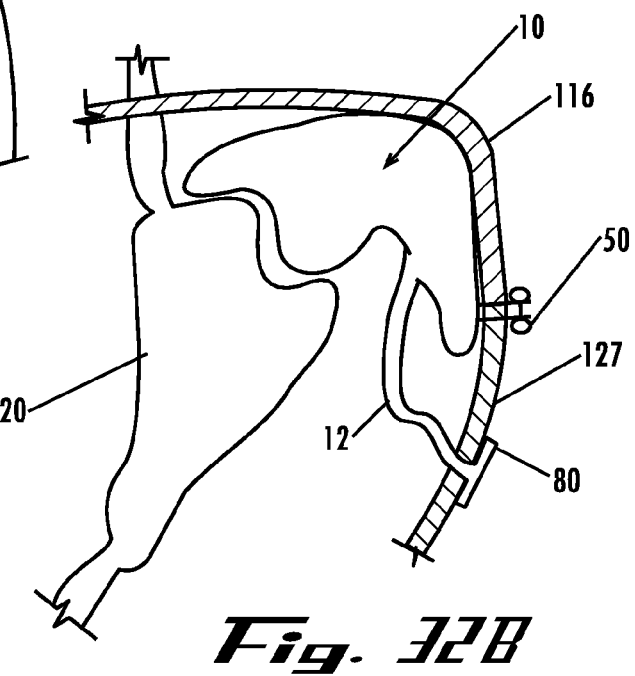

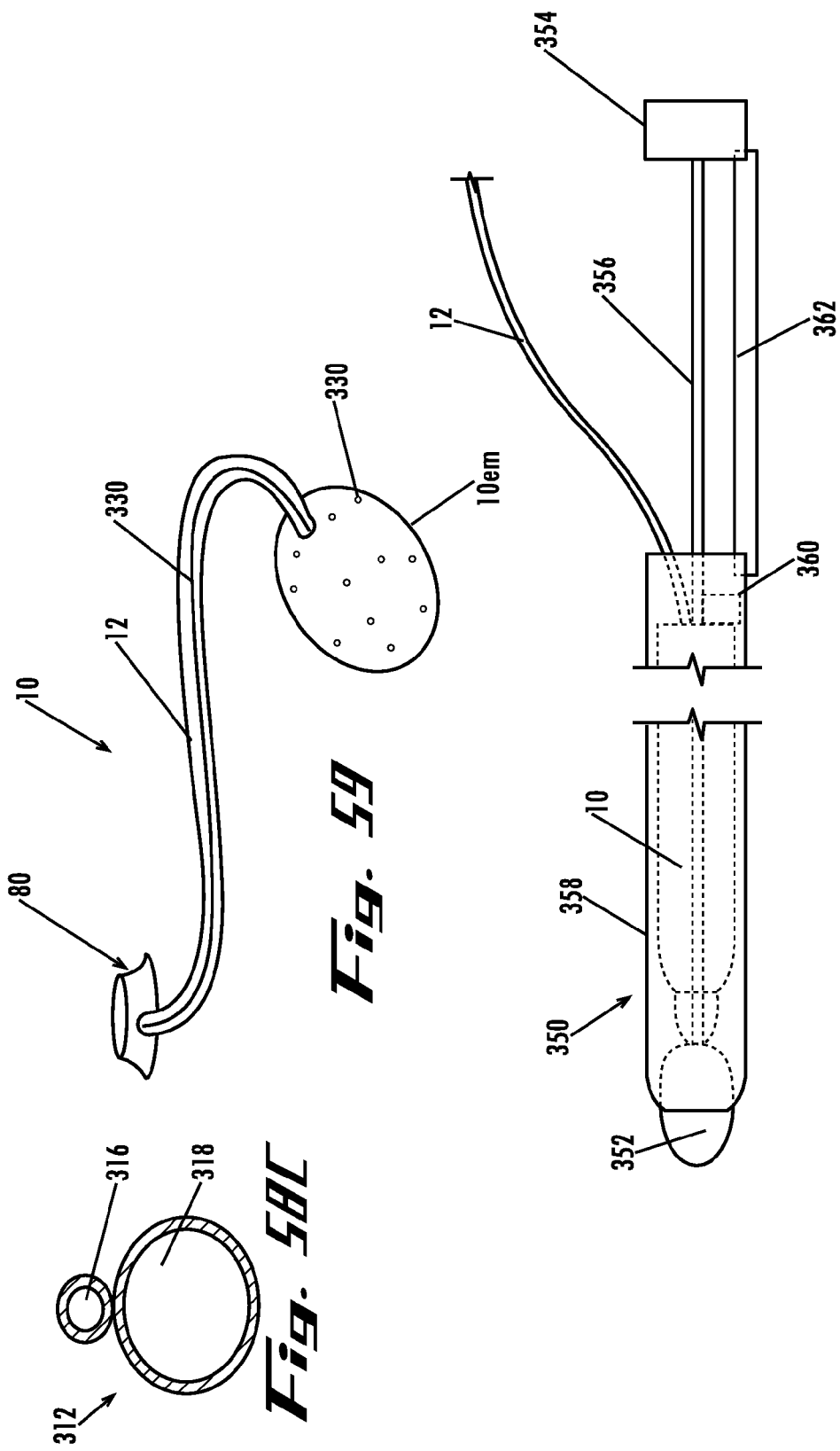

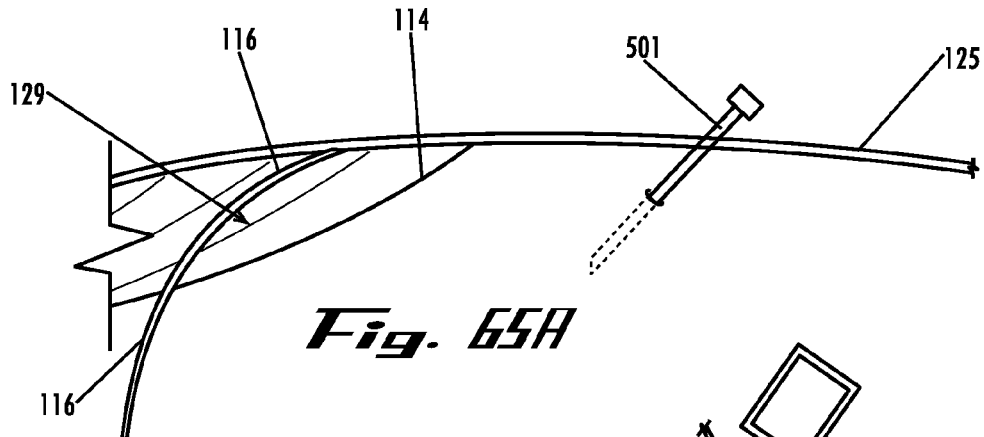
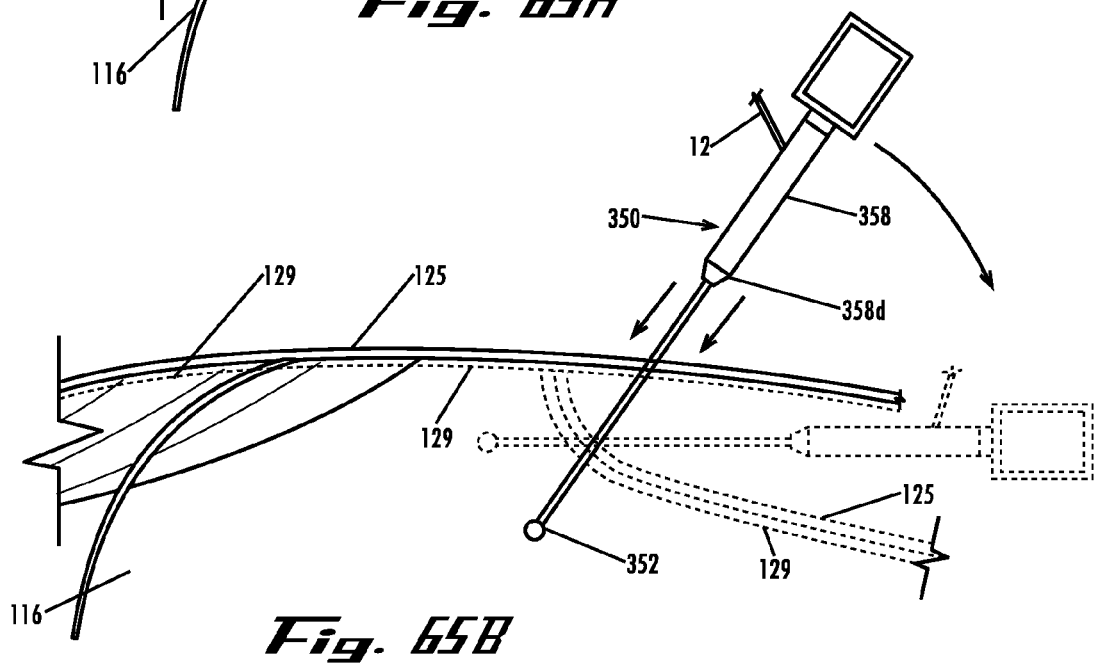
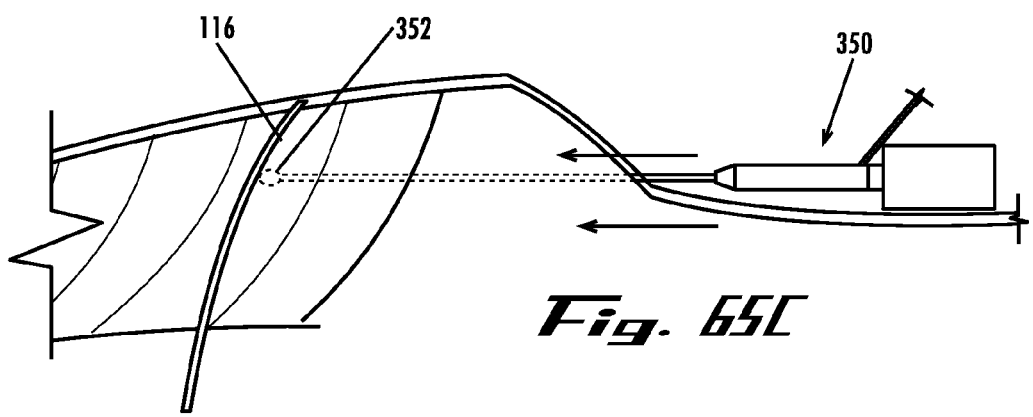

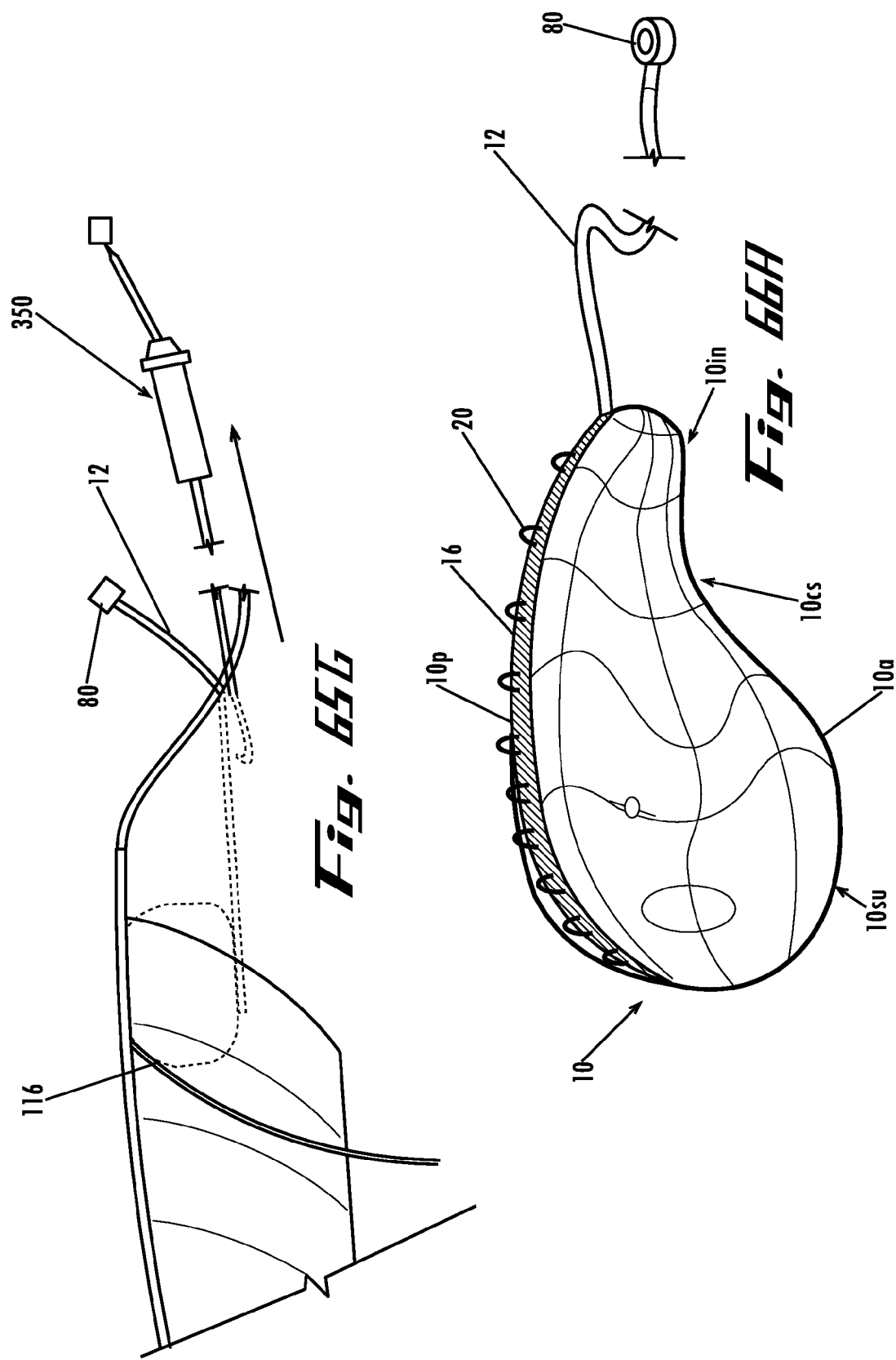

DEVICES AND METHODS FOR TREATMENT OF OBESITY

FIELD OF THE INVENTION

The present invention relates to treatment of obesity, more particularly to implantable devices and methods of implanting the devices in the abdominal cavity to treat an obese patient.

BACKGROUND OF THE INVENTION

Obesity has become a major health concern, both nationally and internationally. The National Center for Health Statistics (NCHS) estimates that over 120 million Americans are overweight, including about 56% of the adult population. Of these, about 52 million are considered obese, as measured by a body mass index (BMI) of 30% or greater. In Europe, an estimated 77 million people are obese, as measured by the same standard. This problem is not limited to western nations, as many developing countries are reported to have obesity rates over 75% of the adult population.

Co-morbidities that are associated with obesity include, but are not limited to type II Diabetes, high blood pressure, sleep apnea, stroke and arthritis, the symptoms of which often tend to be lessened or alleviated upon loss of weight by a person so affected.

In the U.S., options for treatment of obesity are currently quite limited. Current treatment methodologies typically rely upon surgically introducing a "malabsorptive" environment in the gastro-intestinal tract, a restrictive environment, or a combination of these. One available treatment method is gastric bypass surgery and another is referred to as gastric banding (one of these techniques if referred to as the LAPBAND™ procedure). These procedures are limited to only those patients with a BMI over 40 (or over 35, with co-morbidities present).

Gastric bypass procedures incur a great deal of morbidity and create a malabsorptive state in the patient by bypassing a large portion of the intestines. Serious side effects, such as liver failure have been associated with this procedure, as well as chronic diarrhea. Another surgical procedure that has a high degree of morbidity associated with it is known as the "Gastric Bypass Roux-en-Y" procedure. This procedure reduces the capacity of the stomach by creating a smaller stomach pouch. The small space holds only about one ounce of fluid. A tiny stomach outlet is also surgically created to slow the speed at which food leaves the stomach. Staples are used to create a small (15 to 20 cc) stomach pouch, with the rest of the stomach being stapled completely shut and divided from the stomach pouch. The small intestine is divided just beyond the duodenum, brought up, and connected to the newly formed stomach pouch. In addition to the considerable morbidity associated with this procedure, other disadvantages include "dumping syndrome", where stomach contents are literally "dumped" rapidly into the small intestine which may lead to nausea, weakness, sweating, faintness, and diarrhea; hernias resulting from the surgery; gallstones; leakage of the connection between the pouch and the intestine; stretching of the pouch that was formed; nutritional deficiencies; and possible dehiscence of the staples.

The LAPBAND™ is a band that, when placed, encircles the fundus-cardia junction and is inflatable to constrict the same. It does not reduce the volume of the stomach, but rather restrict passage of food into the stomach, the theory being that the patient will feel satiety with a much less volume of food than previously. Although the LAPBAND™ procedure is less invasive than a gastric bypass procedure, it also typically achieves less weight loss. Further, it is not a simple procedure and requires a substantial amount of training by a surgeon to become proficient in performing the procedure. Also, a substantial amount of dissecting and suturing is required because the pathway by which the band is introduced is not an existing pathway, and must be established by dissection. Great care is required to avoid blood vessels and nerves that may be in the intended pathway to be created by the dissection. After placing the band around the fundus-cardia junction, the ends of the band must be connected together and then it must be cinched down into place. Additionally, complications such as erosion at the fundus-cardia junction, slippage of the band from it's intended location, nausea/vomiting, gastroesophageal reflux, dysphagia and lack of effectiveness in causing weight loss have been reported.

Intragastric balloons have also been placed, in an attempt to fill a portion of the volume in the stomach, with the theory being that it will then require less food than previously, to give the patient a sensation of fullness or satiety. This procedure involves delivery of a balloon (typically, transorally) to the interior of the stomach and inflation of the balloon to take up a portion of the volume inside the stomach. However, intragastric balloons may also lead to complications such as obstruction, vomiting and/or mucosal erosion of the inner lining of the stomach. The balloon can break down over extended exposure to the stomach's acids, and in some cases, after breaking down, the balloon translated through the intestines and caused a bowel obstruction.

Gastrointestinal sleeves have been implanted to line the stomach and/or a portion of the small intestines to reduce the absorptive capabilities of the small intestine and/or to reduce the volume in the stomach, bid reducing the available volume to the tubular structure of the graft running therethrough. Although weight loss nay be effective while these types of devices are properly functioning, there are complications with anchoring the device within the stomach/GI tract, as the stomach and GI tract function to break down things that enter into them and to move/transport them through. Accordingly, the integrity of the anchoring of the device, as well as the device itself may be compromised over time by the acids and actions of the stomach and GI tract.

A sleeve gastrectomy, is an operation in which the left side of the stomach is surgically removed. This results in a much reduced stomach which is substantially tubular and mats take on the shape of a banana. This procedure is associated with a high degree of morbidity, as a large portion of the stomach is surgically removed. Additionally, there are risks of complications such as dehiscence of the staple line where the staples are installed to close the surgical incisions where the portion of the stomach was removed. Further, the procedure is not reversible.

In the laparoscopic duodenal switch, the size of the stomach is reduced in similar manner to that performed in a sleeve gastrectomy. Additionally, approximately half of the small intestine is bypassed and the stomach is reconnected to the shortened small intestine. This procedure suffers from the same complications as the sleeve gastrectomy, and even greater morbidity is associated with this procedure due to the additional intestinal bypass that needs to be performed. Still further, complications associated with malabsorption may also present themselves.

An inflatable gastric device is disclosed in U.S. Pat. No. 4,246,893, in which a balloon is inserted anteriorly of the stomach and posteriorly of the left lobe of the liver. The balloon is then inflated to compress the stomach so that it fills with less food that would ordinarily be possible. Not only does this device compress the stomach, but it also compresses the liver, as seen in FIG. 5 of the patent, which may cause complications with the liver function. Additionally, the balloon is simply placed into this location, and there is no assurance that it will not migrate and lose its effectiveness in compressing the stomach to the degree intended. Still further, the balloon is of a simple spherical design, and, as such, extends pressure outwardly in all directions. 360 degrees in all planes. Accordingly, the liver is compressed just as much as the stomach is. Also, the compression forces against the stomach are not ideal, as the spherical balloon conformation does not match the conformation of the expanding stomach. The stomach is not spherical when expanded, or concave with a constant radius of curvature, but expands into a designated space that allows the fundus to expand preferentially more than other parts of the stomach.

Brazzini et al. in WO2005/18417 discloses at least two or more expandable devices used to treat obesity, in which the devices are inserted through the abdominal wall and anchored against the external surface of the stomach wall by an anchoring mechanism that extends through the stomach wall and fixes to the internal surface of the stomach wall.

U.S. Patent Publication No. 2005/0261712 to Balbierz et al. describes capturing a device against the outer surface of the stomach wall to form a restriction that appears to function similarly to the restriction imposed by the LAPBAND™. The anchoring of the devices disclosed relies upon placement of features against the internal all of the stomach to form an interlock with the device which is placed against the external wall of the stomach.

U.S. Patent Publication No. 2005/0267533 to Gertner discloses devices for treatment of obesity that use one or more anchoring mechanisms that are passed through the wall of the stomach to establish an anchor.

U.S. Pat. No. 6,981,978 to Gannoe discloses devices for reducing the internal cavity of the stomach to a much smaller volume, which mall be used to carry out a bypass procedure. Stapling is employed to isolate the smaller volume in the stomach, and thus the same potential disadvantages are present as with other stapling procedures described herein.

U.S. Pat. No. 6,186,149 to Pacella et al. describes an occluder device that can be used as a dietary control device (see FIG. 8C). The occluder device is placed against the wall of the stomach and inflated to press inwardly, on the stomach wall. A frame is wrapped around the stomach wall and is inflated to press against the stomach wall. However, there is no disclosure of how the frame might be adjusted to maintain a position relative to the stomach wall as the size of the stomach varies.

Gastric reduction techniques have been attempted, such as by inserting instruments trans-orally and reducing the volume of the stomach by stapling portions of it together. However, this technique is prone to failure due to the staples pulling through the tissues that they are meant to bind.

Techniques referred to as gastric pacing endeavor to use electrical stimulation to simulate the normal feedback mechanisms of a patient that signal the brain that the patient is full, or satiated. While these techniques are less invasive than some of the other existing treatments, statistics to date have shown that the amount of weight lost by using such techniques is less than satisfactory.

Currently marketed drugs for weight loss, such as XENICAL®, MERIDIA® and Phen fen have largely failed, due to unacceptable side effects and complications, and sometimes to an ineffective amount of weight loss. Other drugs that are on the horizon include ACCOMPLIA® and SYMLIN®, but these are, as yet, unproven.

The risk and invasiveness factors of currently available surgeries are often too great for a patient to accept to undergo surgical treatment for his/her obesity. Accordingly, there is a need for less invasive, et effective surgical treatment procedures for morbidly obese patients (patients having a BMI of 35 or greater). Also, since the current surgical procedures are currently indicated only, for those patients having a BMI of 40 or greater, or 35 or greater when co-morbidities are present, it would be desirable to provide a surgical procedure that would be available for slightly less obese patients. e.g., patients having a BMI of 30 to 35 who are not indicated for the currently available surgical procedures. It would further be desirable to provide a surgical procedure that would be indicated for obese patients having a BMI in the range of 30-35, as well as for more obese patients.

SUMMARY OF THE INVENTION

The present invention discloses implantable devices, instruments and methods for treatment of obesity. In one embodiment, an implantable device is provided that includes an expandable main body member configured to be positioned adjacent a portion of a stomach of a patient, within the abdominal cavity of the patient; an anchor configured to fix a portion of the main body member in a position relative to at least one internal body structure, without piercing through a wall of the stomach; an adjustment member having a port that is accessible by an instrument to effect expansion or contraction of the main body, the adjustment member configured to be anchored to an abdominal wall or subcutaneously external to the abdominal wall, and a conduit connecting the main body with the adjustment member, wherein the device is configured to be implanted without piercing through the stomach wall.

A method of treating obesity in a patient is provided, wherein the method includes: making a percutaneous opening to the abdominal cavity of the patient, passing an expandable device, while in a contracted configuration, through the opening; positioning the expandable device adjacent the stomach of the patient; expanding the expandable device; and anchoring the expandable device, relative to at least one structure in the abdominal cavity, without piercing through a wall of the stomach.

A method of treating obesity in a patient is provided wherein the method includes: making a minimally invasive opening to the abdominal cavity of the patient; passing an expandable device, while in a contracted configuration, through the opening, positioning the expandable device adjacent the stomach of the patient; anchoring the expandable device to at least one structure in the abdominal cavity, without piercing through a wall of the stomach; and expanding the expandable device.

A method of treating obesity in a patient is provided wherein the method includes: making a percutaneous opening to the abdominal cavity of the patient; passing an expandable device, while in a contracted configuration, through the opening; positioning the expandable device adjacent the stomach of the patient; expanding the expandable device to occupy a volume of space and substantially prevent the stomach from expanding into the volume of space; and anchoring the expandable device to at least one structure in the abdominal cavity, without piercing through a wall of the stomach.

A method of treating obesity in a patient is provided wherein the method includes: making a minimally invasive opening to the abdominal cavity of the patient; passing an expandable device, while in a contracted configuration, through the opening; positioning the expandable device adjacent the stomach of the patient; passing an intra-gastric expandable device within the interior cavity of the stomach; expanding the intra-gastric expandable device to a predetermined size or pressure; expanding the expandable device to displace a portion of the stomach wall; monitoring the expanding of the expandable device and displacement of the portion of the stomach wall; and ceasing expanding the expandable device when the distance between the portion of the stomach wall being displaced and the intra-gastric expandable device reaches a predetermined distance or when a predetermined pressure is monitored via the intra-gastric expandable device.

A kit for treatment of obesity is provided including: an implantable, expandable body, member configured to be positioned adjacent a portion of a stomach of a patient, within the abdominal cavity of the patient; and an intra-gastric expandable device configured to be passed trans-orally into the interior cavity of the stomach, the intra-gastric expandable device comprising an inflatable main body configured to be received in the cavity of the stomach, and a conduit of sufficient length to extend out of the mouth of the patient when the inflatable main body is fully received in the cavity of the stomach.

A delivery device is provided for delivering an expandable device for treatment of obesity, percutaneously into an abdominal cavity of a patient. The device includes an elongated outer cannula having sufficient length to receive the expandable device when the expandable device is in a contracted configuration; an introducer nosecone, at least a proximal portion of which is configured to be received within a distal opening of the elongated outer cannula; a rod passing through the elongated cannula and interconnecting the introducer nosecone distally with a drive handle proximally, the rod being dimensioned to receive the expandable device thereover when the expandable device is in a contracted configuration, and the rod extending proximally of a proximal end of the outer cannula, by a distance greater than or equal to a length of the expandable device in a contracted configuration; a stop on the rod configured to be positioned proximally of a proximal end of the expandable device in a contracted configuration when the expandable device is mounted on the rod, to prevent backsliding of the expandable device; and a locking mechanism to prevent sliding of the elongated cannula proximally with respect to the rod when the locking mechanism is in a locked configuration, and to permit sliding of the elongated cannula proximally with respect to the rod when the locking mechanism is in an unlocked configuration.

An implantable device for treatment of obesity is provided which is configured to assume a contracted configuration as well as an expanded configuration, wherein the contracted configuration reduces a cross-sectional area of the device to a cross-sectional area suitable for passing the device through a port into the abdominal cavity using a minimally invasive procedure, and when in the expanded configuration, the device occupies a volume to prevent the stomach of a patient from expanding into the volume. The device further includes an anchor configured to fix the device in a position relative to at least one internal body structure, without piercing through a wall of the stomach.

An adjustment member configured to be anchored to a patient externally of a body cavity is provided, wherein the adjustment member is configured to be in fluid communication with a conduit leading into the body cavity. The adjustment member further includes a port that is accessible by an instrument to deliver fluid therethrough; and a homing mechanism configured to home a delivery needle into the port.

An adjustment member and a deliver, device are provided, wherein the adjustment member is configured to be anchored to a patient externally of a body cavity. The adjustment member is configured to be in fluid communication with a conduit leading into the body cavity. The adjustment member further includes a port that is accessible by a delivery needle of the deliver device to deliver fluid therethrough. The deliver needle includes a side opening for delivering fluid therethrough when a distal end of the delivery needle engages the port.

An implantable device for treatment of obesity is provided that includes: an expandable main body member configured to be positioned adjacent a portion of a stomach of a patient, within the abdominal cavity of the patient; an anchor configured to fix a portion of the main body, member in a position relative to at least one internal body structure, without piercing through a wall of the stomach; an adjustment member having a port that is accessible by an instrument to effect expansion or contraction of the main body, wherein the adjustment member is located in the expandable main body member; and a removable conduit having an expandable tip wherein upon implantation of the expandable main body the removable conduit is attached to the adjustment member and after expansion of the expandable main body the expandable tip is retracted and the removable conduit is removed.

A method of treating obesity is provided that includes: placing a space occupying device within an abdominal cavity in proximity to a stomach; expanding the space occupying device to reduce the space available for the stomach to expand; and leaving the space occupying device in proximity to the stomach for sufficient time to remodel the stomach.

A method of treating obesity is provided that includes: placing a space occupying device within an abdominal cavity in contact with a stomach; and expanding the space occupying device to constrain the stomach to a curved tubular shape.

A method of creating a feeling of satiety is provided, to include: positioning an expandable device in proximity to a stomach without penetrating a wall of the stomach; and expanding the expandable device to reduce an achievable maximum volume of the stomach, wherein the stomach is free to move.

A method of treating obesity is provided, including: positioning an expandable device in proximity to a stomach; and expanding the expandable device to surround portions of the stomach so as to constrain a largest capable dimension of the stomach by fifty, percent or more.

These and other features of the invention will become apparent to those persons skilled in the art upon reading the details of the devices, methods, instruments and kits as more fully described below.

BRIEF DESCRIPTION OF THE DRAWINGS

FIG. 15A illustrates a device provided with a relatively rigid exoskeleton having four arms that wrap partially around the inflatable member.

FIG. 15B illustrates the arms of the exoskeleton of the device of FIG. 15A in a straightened out configuration.

FIG. 16A shows a variation of the device of FIGS. 15A-15B in which the exoskeleton has only a pair of opposite arms.

FIG. 16B illustrates the arms of the exoskeleton of the device of FIG. 16A in a straightened out configuration.

FIG. 21A illustrates a mechanically expandable device that includes expandable coils routed through loops that are fixed to a membrane.

FIG. 21B illustrates a device of the type described with regard to FIG. 21A, having been implanted between the diaphragm and stomach and expanded to deform the wall of the stomach.

FIG. 22 illustrates another variation of a mechanically expandable device.

FIG. 23 illustrates a compound expandable device having been positioned between the diaphragm and stomach and expanded against the stomach to deform the stomach wall inwardly.

FIG. 24 illustrates another variation of a mechanically expandable device.

FIG. 31B illustrates that a surface of a device can be anchored to the stomach wall using one or more pairs of magnets.

FIG. 32A illustrates an expandable member anchored against the internal surface of the abdominal musculature or peritoneum, by fixing the conduit, connected to the expandable member, at the external surface of the abdominal muscles.

FIG. 32B illustrates a device having been positioned and expanded between the diaphragm and the stomach. An anchoring member is fixed to surface of the expandable member and extends through the diaphragm, where it is fixed against the external surface of the diaphragm.

FIGS. 58A-58C show examples of cross-sectional illustrations of different configurations for providing lumens to pass through an expandable member of an intra-gastric device.

FIG. 59 illustrates various portions of a device that may be provided with radiopaque markers and/or constructed partially or in whole from materials that are radiopaque.

FIG. 60 shows an embodiment of an instrument (e.g., delivery device) for delivering an extra-gastric expandable device to a target surgical location within the abdominal cavity of a patient.

FIGS. 65A-65G illustrate steps of a method of percutaneously implanting an expandable extra-gastric device according to another embodiment of the present invention.

FIGS. 66A-66L illustrate a device and steps of a method of percutaneously implanting the device according to another embodiment of the present invention.

FIGS. 72A-72C illustrate steps of a method of percutaneously implanting an expandable extra-gastric device according to another embodiment of the present invention.

FIGS. 73A-73B illustrate an embodiment of placement of a device having a single expandable member.

DETAILED DESCRIPTION OF THE INVENTION

Figure 1:
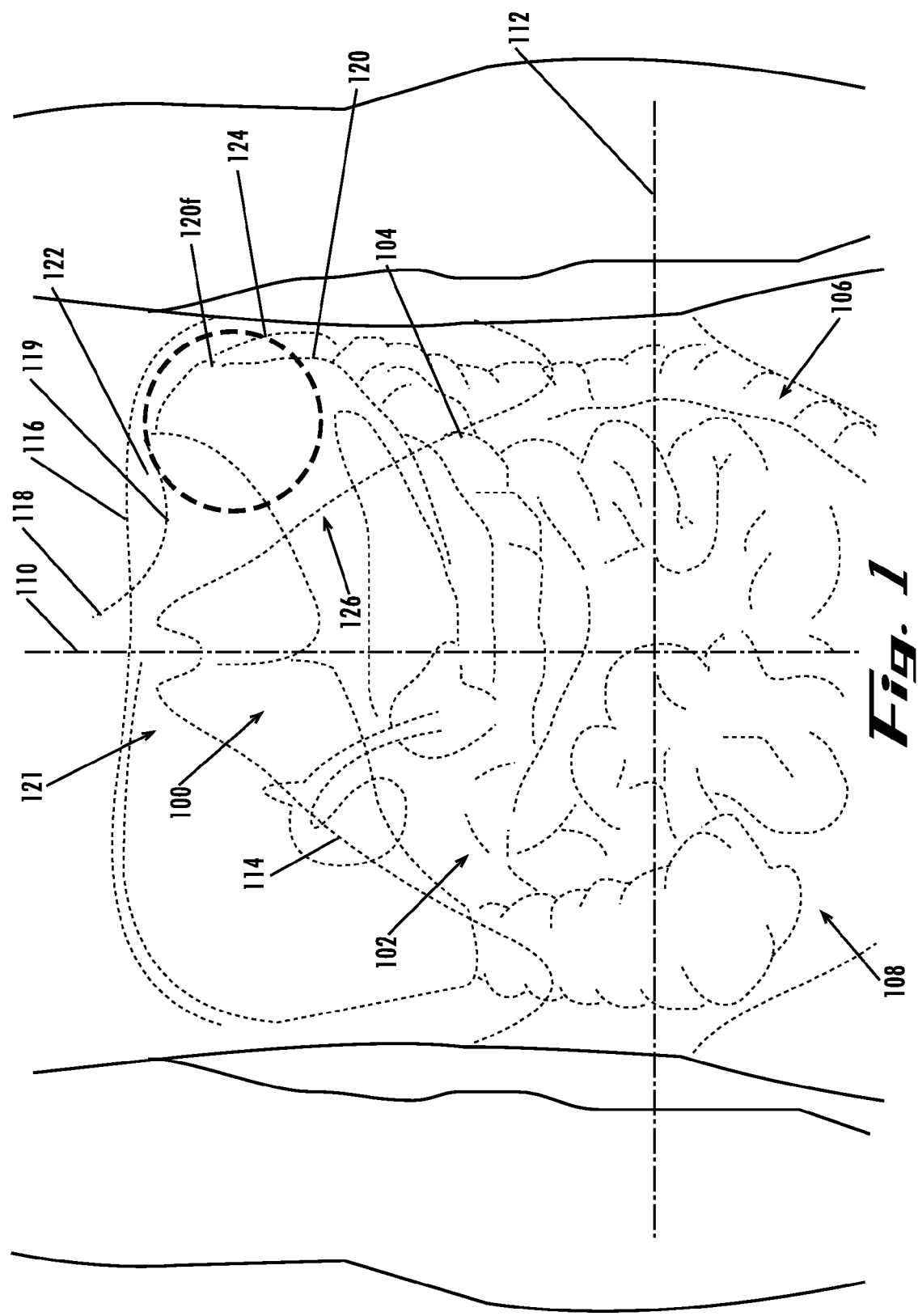
FIG. 1 illustrates the anatomy of the abdominal cavity and its contents, and surrounding features.

Before the present devices and methods are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. Thus, for example, reference to "an anchor" includes a plurality of such anchors and reference to "the incision" includes reference to one or more incisions and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DEFINITIONS

A "compliant" material refers to a material that is stretchable or expandable. This expansibility allows the material to increase in dimension substantially more than a noncompliant or semi-compliant material, prior to failure. For example, when formed as a balloon structure, a compliant material comprises an expansibility property of being able to increase its radius, beyond its formed radius, under pressure applied into the balloon, by 100 percent or more, without rupturing.

A "noncompliant" material refers to a material that, when formed as a balloon structure, can increase its radius beyond its formed radius, under pressure applied into the balloon, only up to about 10 percent or less prior to rupturing.

A "semi-compliant" material refers to a material that, when formed as a balloon structure, can increase its radius beyond its formed radius, under pressure applied into the balloons by an amount between about 10 percent and about 100 percent, prior to rupturing.

The "wall" of the stomach refers to all of the layers that make up the stomach wall, including the mucosa, submucosa, muscular layers and serosa. A "layer", "layer of the stomach wall" or "stomach wall layer" refers to a mucosal layer, submucosal layer, muscular layer or serosal layer.

A "proximal" end of an instrument is the end that is nearer the surgeon when the surgeon is using the instrument for its intended surgical application.

A "distal" end of an instrument is the end that is further from the surgeon when the surgeon is using the instrument for its intended surgical application.

An "internal body structure" when referred to as a structure to which a device is to be anchored, refers to a structure internal to the skin of a patient, and which can be within the abdominal cavity of the patient, or just outside of it, such as including the outer surface of a wall that partially defines the abdominal cavity. Structures to which a device can be anchored include, but are not limited to: one or more ribs, the intercostal muscles, the abdominal surface of the diaphragm, the stomach (but where the anchor does not pass through the wall of the stomach), the anterior abdominal wall, the posterior abdominal wall and the lateral abdominal wall, the esophagus, the angle of his in the stomach, the gastro-intestinal junction, the gastro-esophageal junction, the superior aspect of the omentum, peritoneum, liver, connective tissues, ligaments, and blood vessels.

A "body floss wire" is a wire that enters and exits the body in tow locations and passes inside the body between the two locations. This arrangement allows excellent control of the tension on the sire, as forces can be applied at both end portions of the wire that enter and exit the body. Additionally, this arrangement provides good control of devices being passed along the wire.

The preferred embodiments of the present invention prevent the possible issue of erosion caused by an expandable member, by not requiring anchoring to the stomach, and further, by not requiring a compression force to be applied when the stomach is not full of food. By allowing the stomach to move freely in the constrained spaced provided by the expandable member, the stomach's possible expansion size will be decreased, but there will be less opportunity for the formation of pressure necrosis since no one region will be subjected to concentrated forces. One additional physiological benefit of the expandable member may further be to substantially reduce the actual volume of the stomach itself, remodeling the organ as the muscle contracts into its new shape over the period of weeks or months (just as the heart remodels when constrained from over-expansion). Remodeling the stomach allows the expandable member to be implanted temporarily. The preferred embodiments also are positioned in a location to completely fill the space normally occupied by the fundus, thus moving the stomach medially and wedging the stomach between the expandable member and the medial and anterior aspects of the liver, and the spine posteriorly. This position also ensures that the expandable member is almost entirely maintained underneath the diaphragmatic umbrella beneath the ribs on the left side, thus concealing the expandable member, and preventing it from producing an unsatisfactory cosmetic result. Further, the preferred embodiments can have elements for anchoring on one or more locations along the abdominal cavity wall to prevent migration. Further, the preferred embodiments are provided with an outer surface that is very atraumatic. Preferred embodiments include at least one expandable member, preferably an inflatable member, made of a material or material composite that is impermeable to gas.

Abdominal Cavity Anatomy

Figure 1A:
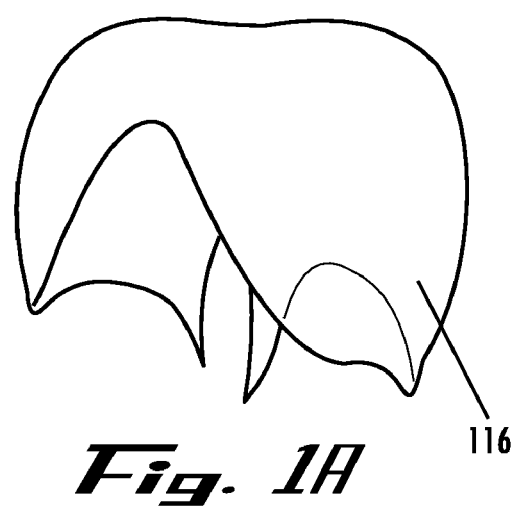
FIG. 1A is an illustration of a diaphragm in an isolated view, illustrating the conformation of the diaphragm as it exists in the body.
Figure 1B:
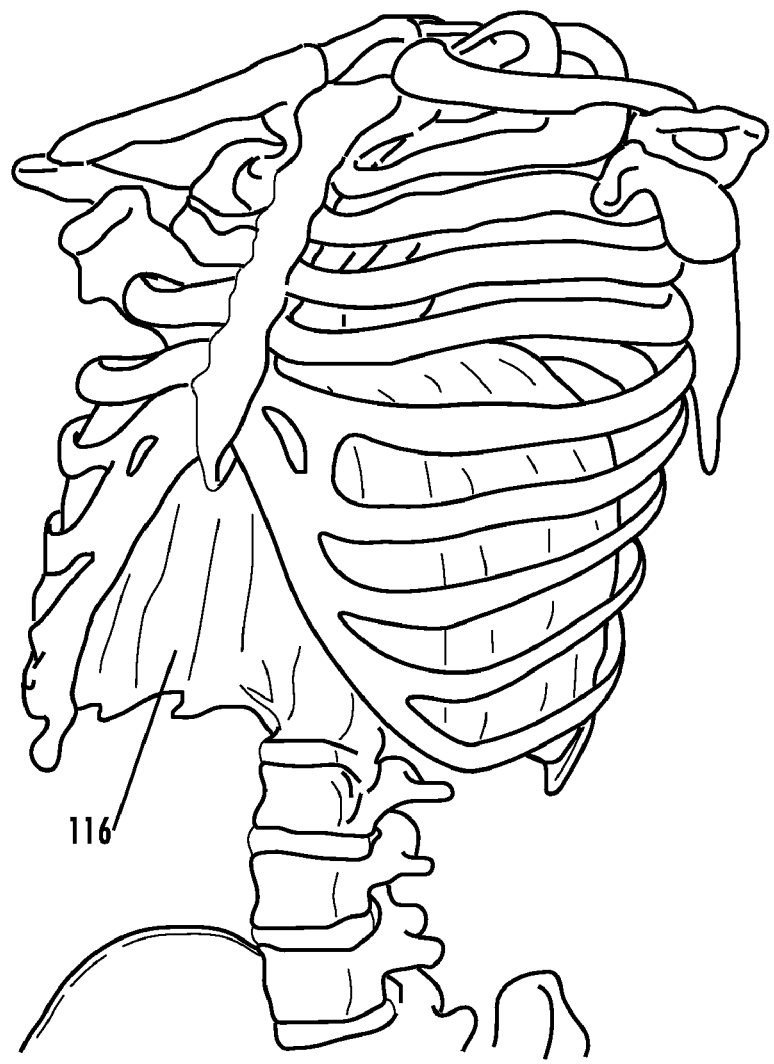
FIG. 1B illustrates the diaphragm in position relative to the rib cage.

FIG. 1 illustrates the anatomy of the abdominal cavity and its contents, and surrounding features. The abdominal cavity 100 is shown divided among four quadrants, the upper right quadrant 102, upper left quadrant 104, lower left quadrant 106 and lower right quadrant 108, as divided by the median axis 110 and transverse axis 112. The lower edge of the ribcage is illustrated by the dotted line 114 and the diaphragm is shown at 116. As seen in FIGS. 1A and 1B, the diaphragm 116 is shaped like a parachute and sits within the ribs. The esophagus 118 passes through the diaphragm 116 and joins with the stomach 120. The left lobe 122 of the liver 121 lies anteriorly of the esophagus 118 and the fundus-cardia junction 119. In one aspect of the invention, an expandable device is implanted in an extra-gastric location (i.e., outside of the stomach) generally indicated at 124, and then expanded to occupy a space that the fundus of the stomach would ordinarily expand into when the stomach is filled with food. The expanded device prevents this expansion by the fundus, thereby limiting the volume of the cavity in the stomach to a much smaller volume than if the fundus had been allowed to expand into the space. Alternatively, the device is expanded to apply pressure to the fundus of the stomach in a downward direction (e.g., in a direction toward the transverse axis 112 shown, with some transverse movement toward the median axis 110 shown), and optionally, additionally to the main body of the stomach, to reduce the volume inside the stomach to effect satiety in the patient with relatively less food ingested, relative to what the patient would require for satiety without the implant in place.

Figure 2A:
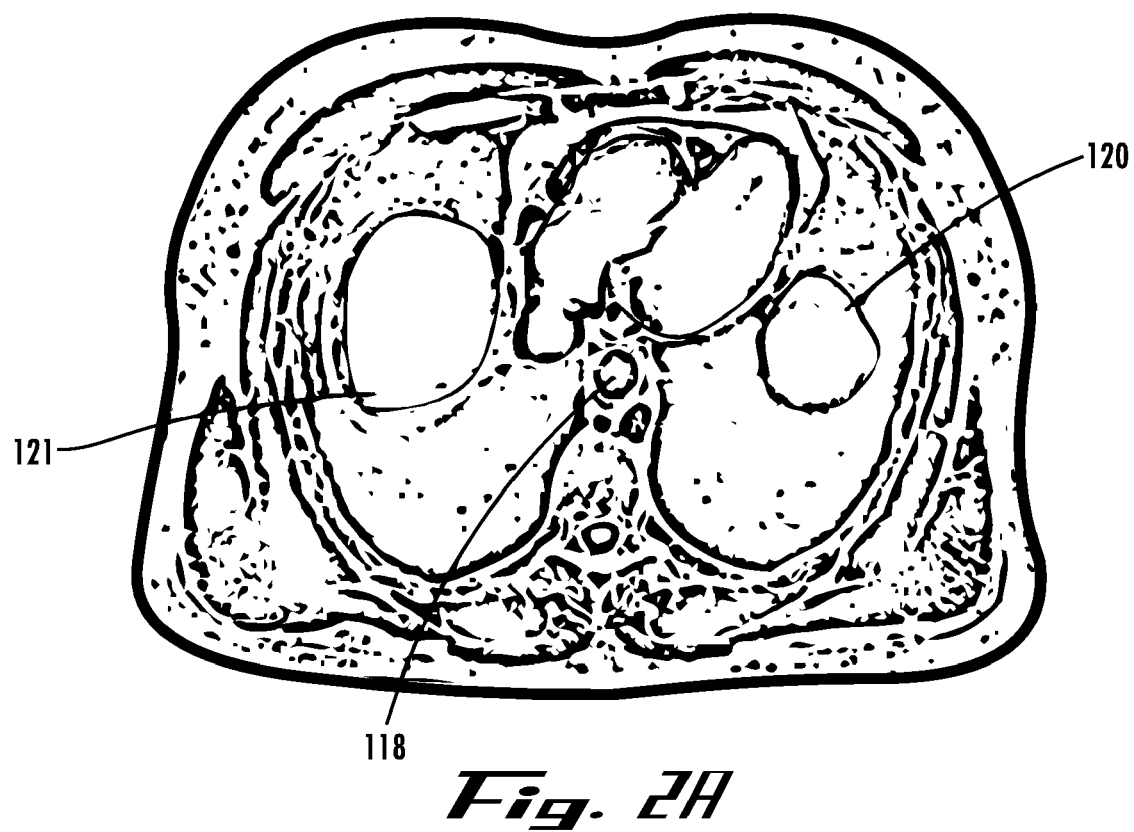
FIGS. 2A-2L are transverse cross-sectional illustrations of the abdominal cavity shown at sequential, incremental locations along the cavity.
Figure 2B:
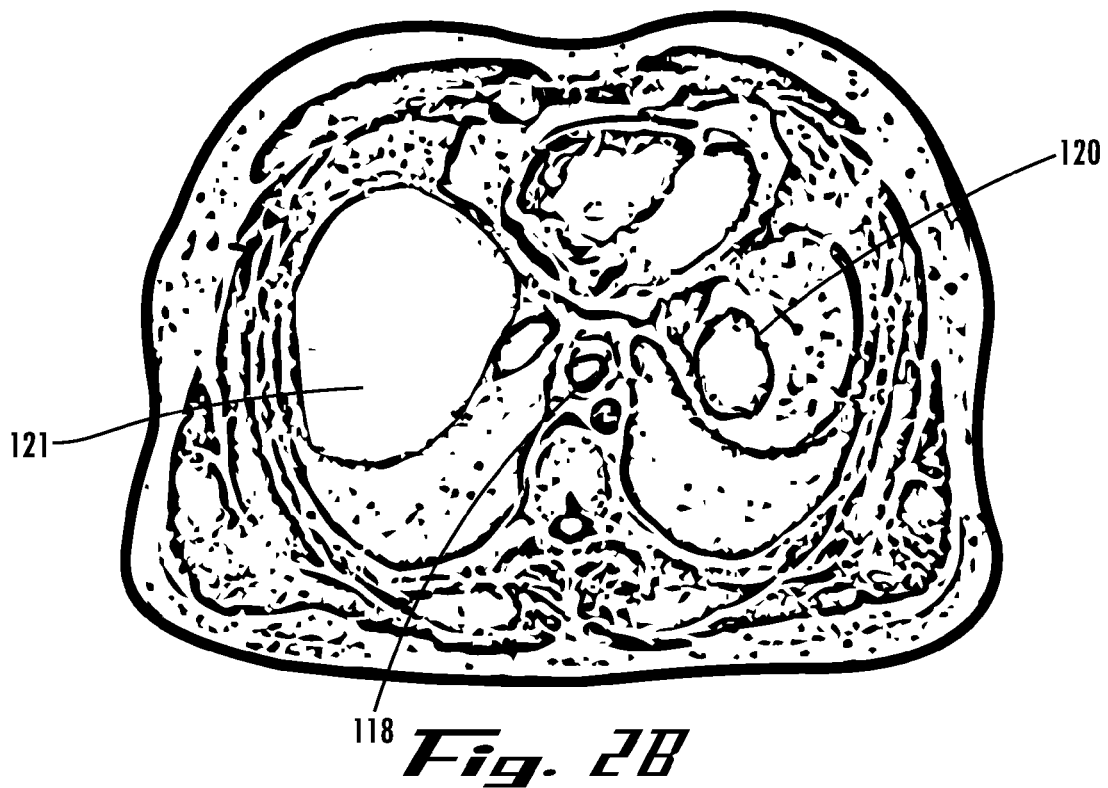
Figure 2C:
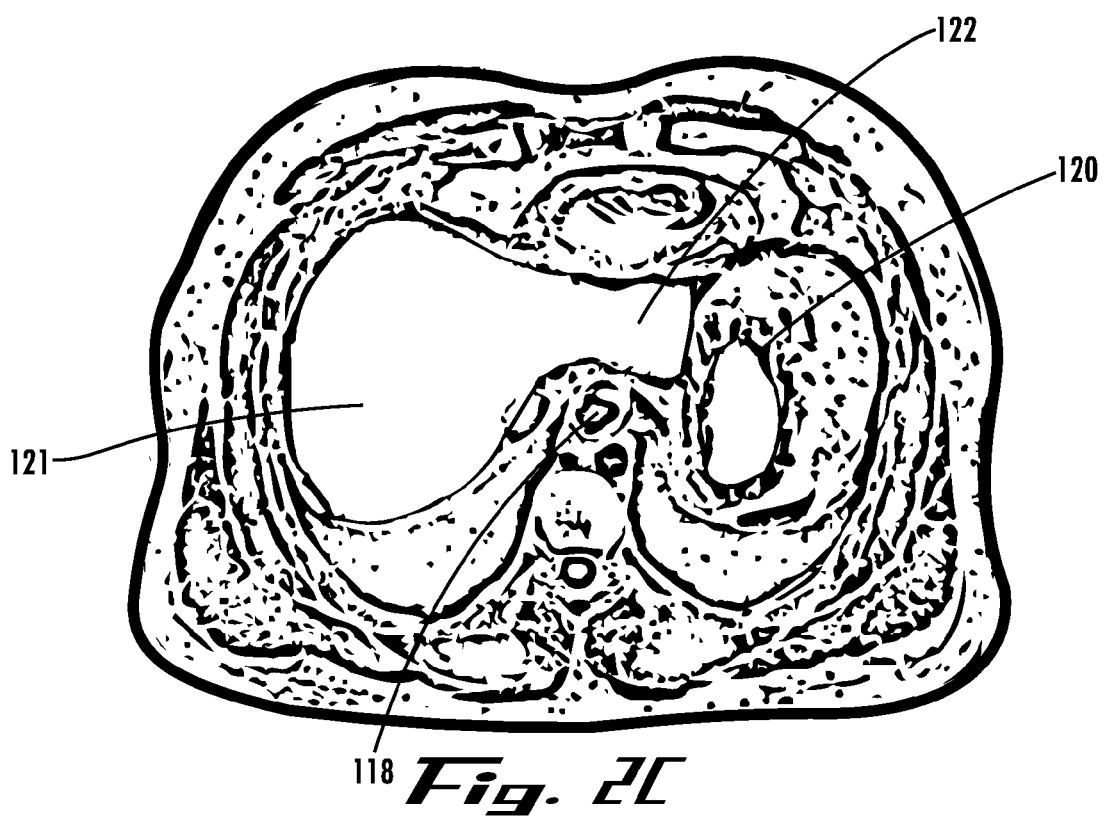
Figure 2D:
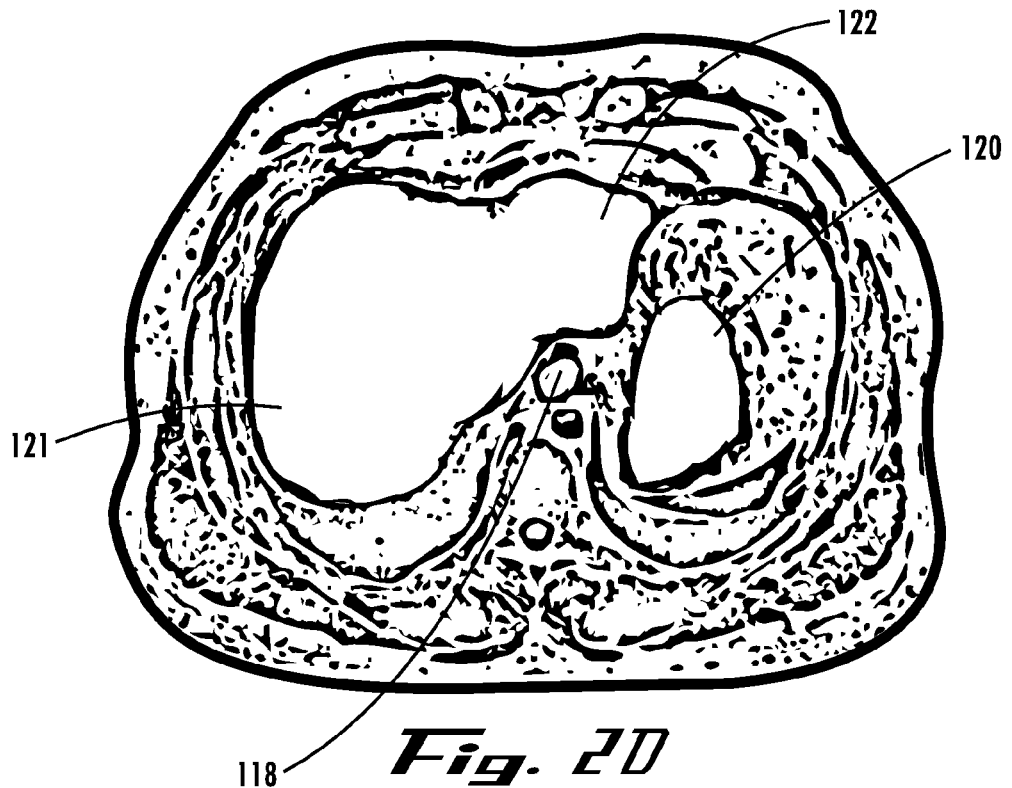
Figure 2E:
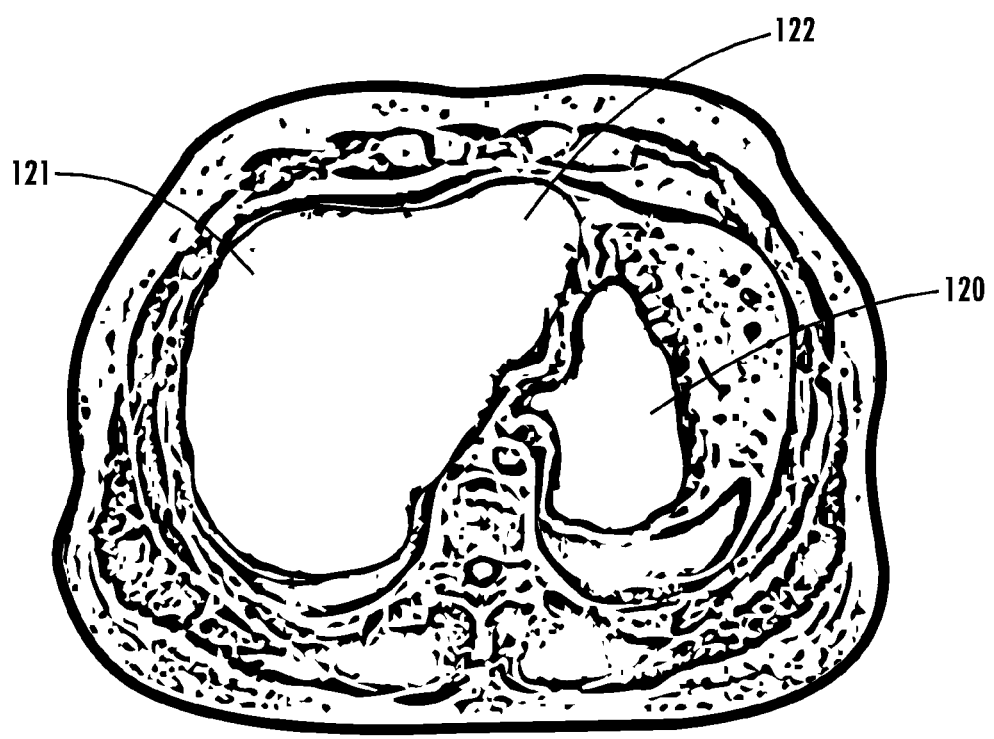
Figure 2F:
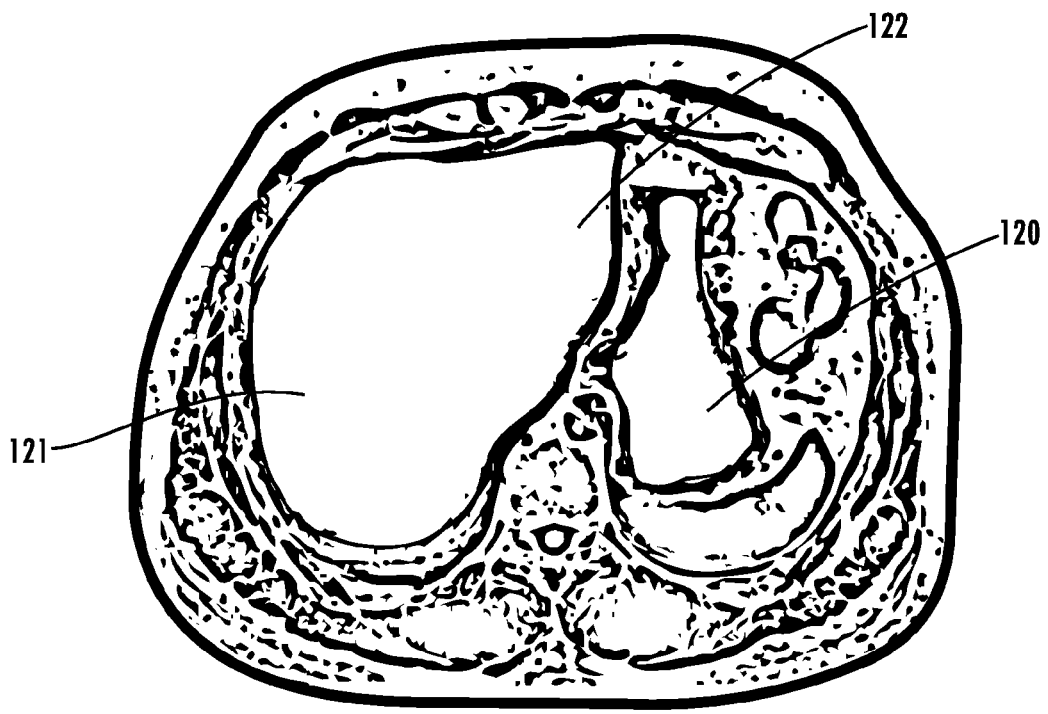
Figure 2G:
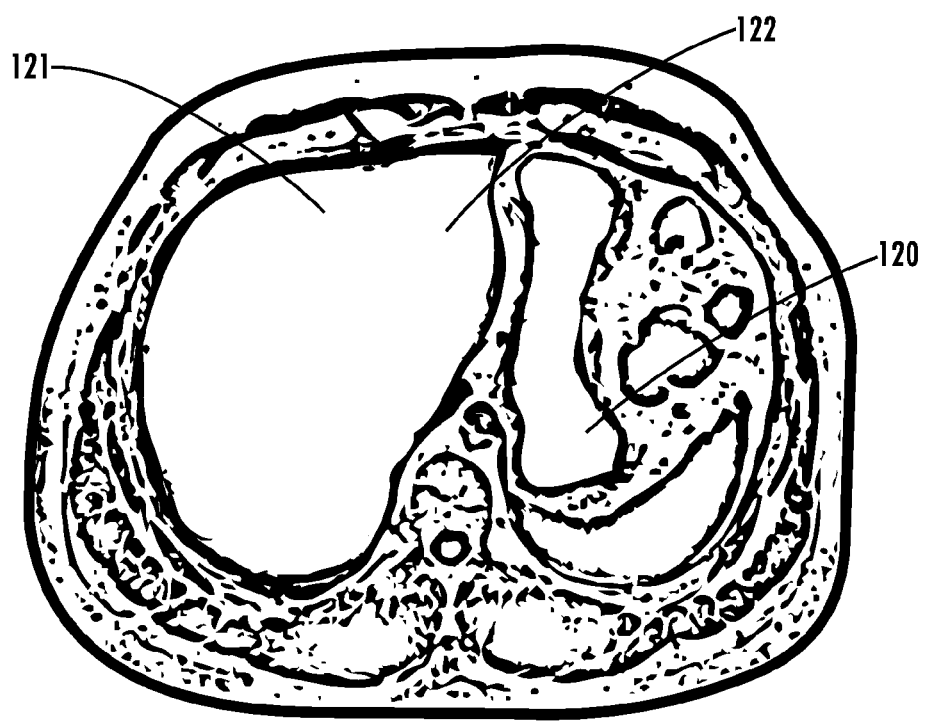
Figure 2H:
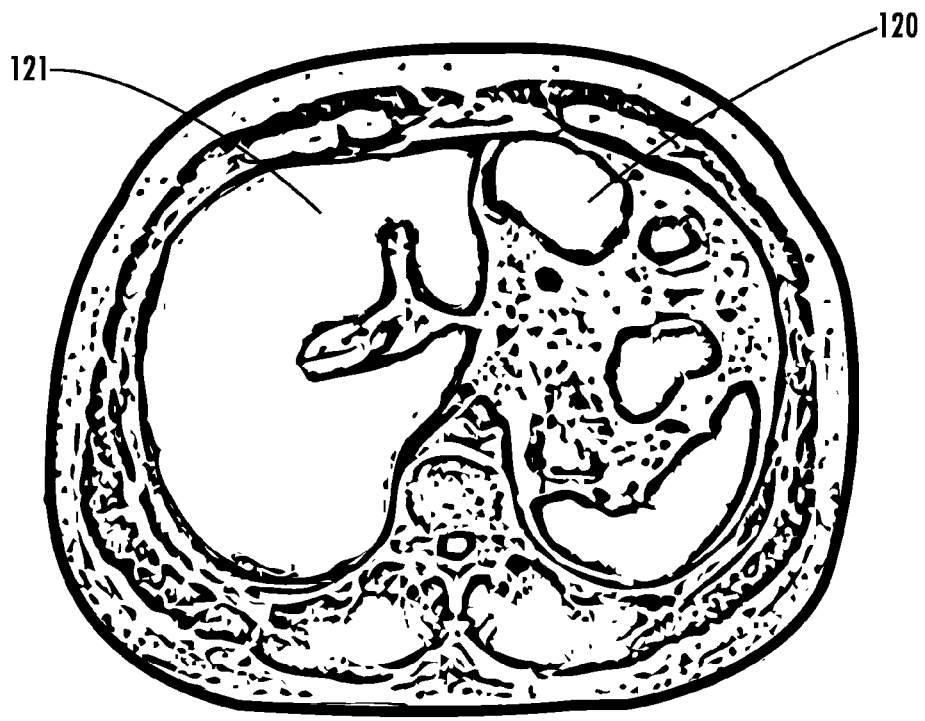
Figure 2I:
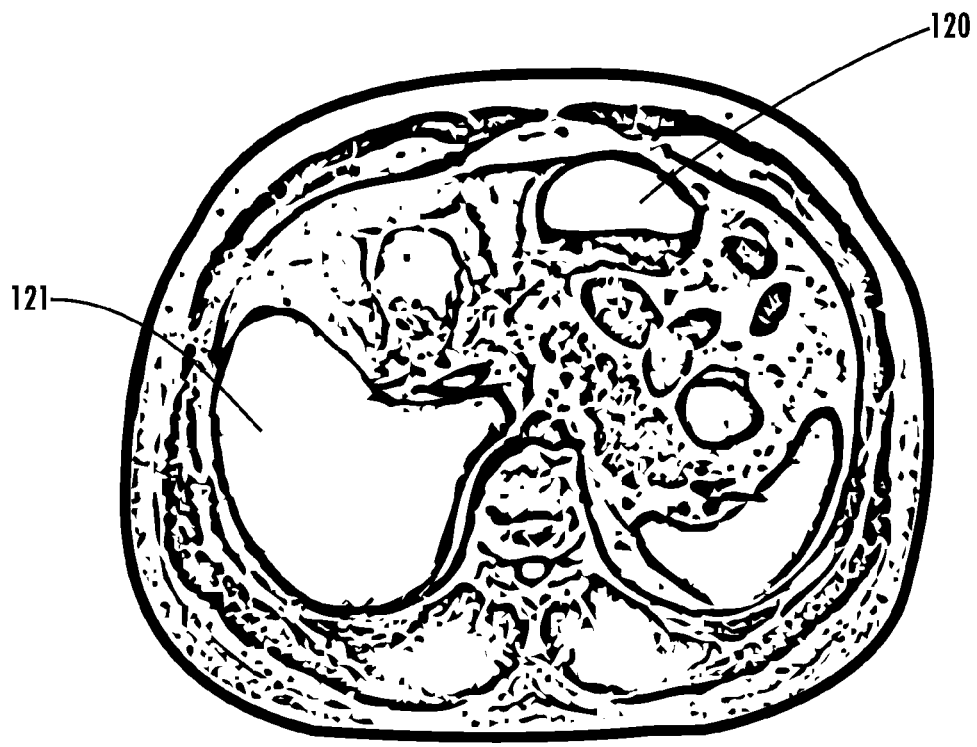
Figure 2J:
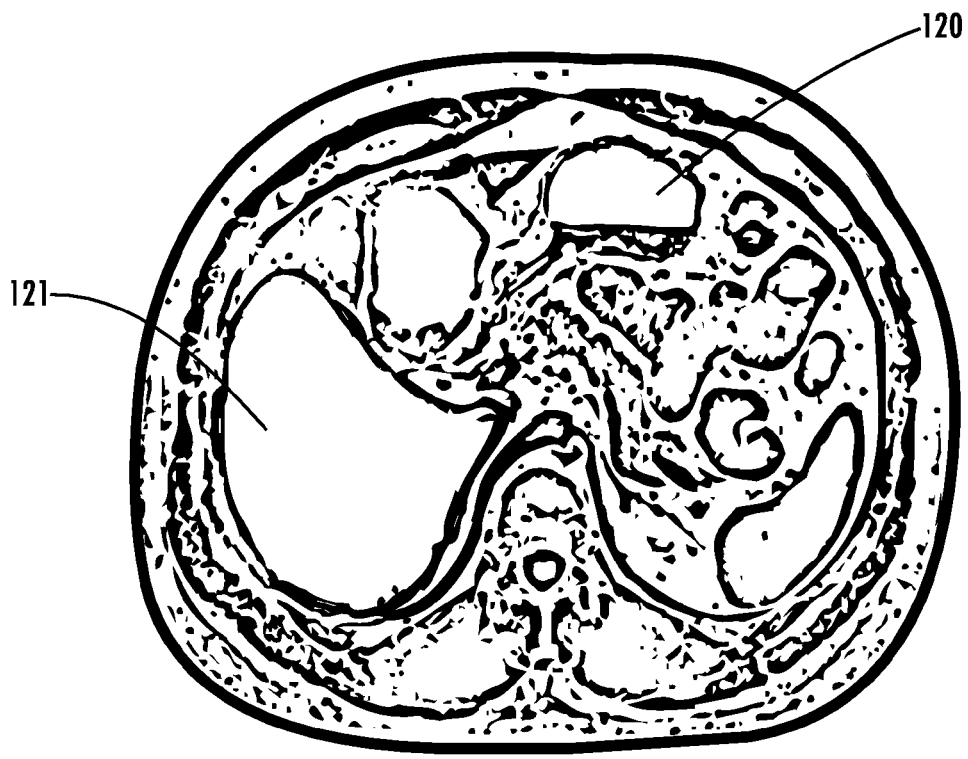
Figure 2K:
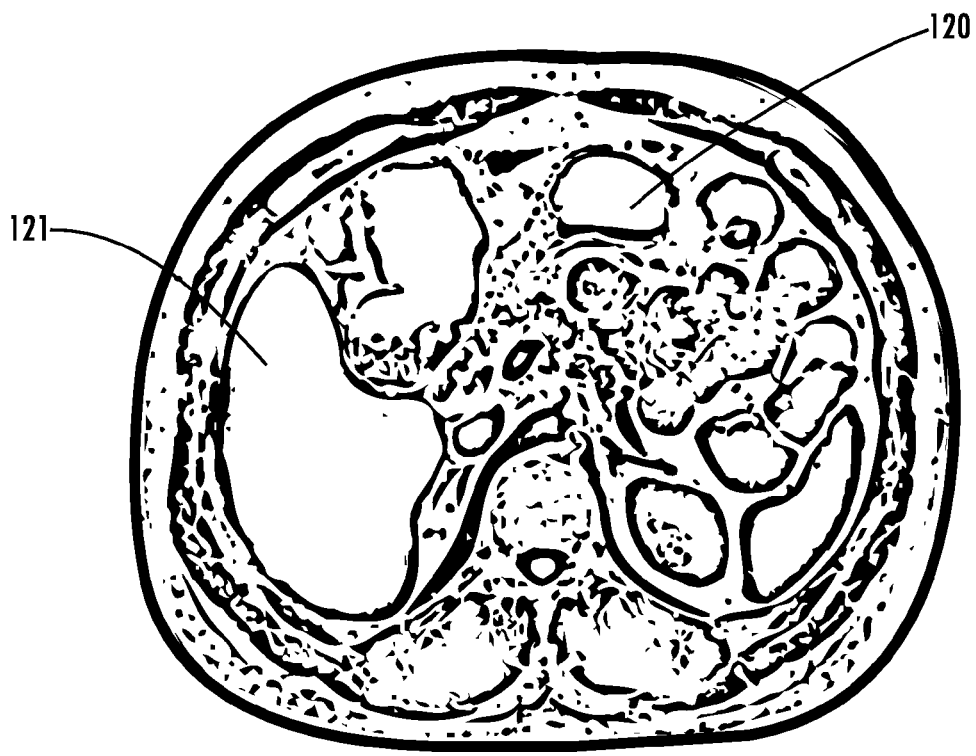
Figure 2L:
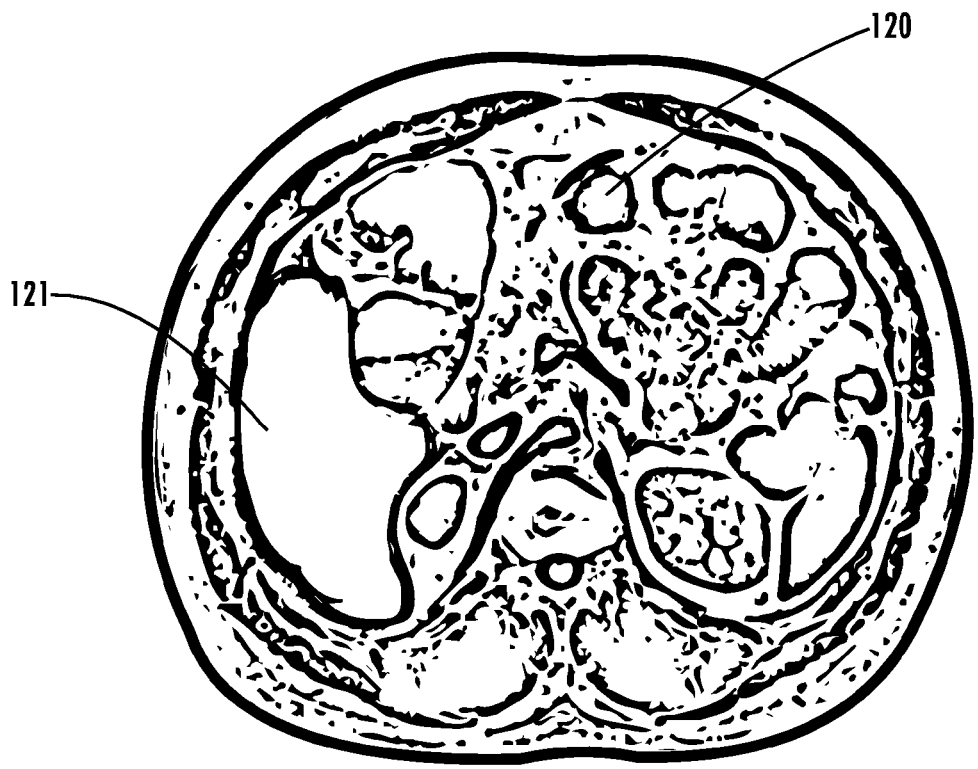

FIGS. 2A-2L are transverse cross-sectional illustrations of the abdominal cavity shown at sequential, incremental locations of the cavity. The illustrations are according to standard convention, where the view is taken from the root of the patient facing toward the head of the patient (in the direction of arrow 9 shown in FIG. 1). The view of FIG. 2A is just below the top of the diaphragm an is the most superior location shown, while FIG. 2L is a view of the most inferior location shown, with views 2A-2L incrementing by increments of about 1 to 5 cm in an inferior direction sequentially. The liver 121, esophagus 118 and stomach 120 are shown in their relative locations within the abdominal cavity in the views of FIG. 2A-2D. It can be observed that while the cross-sectional area of the esophagus 118 stays fairly constant throughout these views that the cross-sectional areas of the liver 121 and stomach 120 are sequentially increasing. In FIGS. 2E-2L, the esophagus 118 is no longer visible, but the variations in the relative cross-sectional areas of both the liver 121, and especially the stomach 120, can be readily seen by comparing the figs.

Devices

At least some embodiments of devices described herein can be implanted percutaneously, with a relatively quick and simple procedure that requires no general anesthesia and wherein only a single, small opening in a patient is required to deliver the device, which typically has a single expandable member that is self anchoring or can be easily anchored to maintain the simplicity and minimal invasiveness of the procedure.

In other embodiments, more complex configurations of expandable members are provided, where a device can contain one or more expandable members and implantation and anchoring can be performed laparoscopically. Any of the devices described wherein can, of course, be implanted using open surgical procedures. Devices that can be implanted percutaneously can alternatively be implanted using laparoscopic procedures.

Devices described herein can be implanted permanently, but are also configured for reversibility, to facilitate relatively simple removal procedures, should it be desired to remove a device. Alternatively, devices according to the present invention can be implanted temporarily, such as over a period of months, and then removed or disabled when further treatment is no longer required, or to allow an alternative treatment to be applied.

Expandable Member Configurations

One possible entry location for creating an opening through the patient's skin and into the abdominal cavil) for deliver) of the device is indicated by arrow 126 in FIG. 1, just below the bottom edge of the rib cane 114 and in a location generally aligned with the fundus of the stomach 120. The expandable device is inserted through the opening and traversed around the fundus to a location between the fundus 120f and the wall of the diaphragm. Depending upon the shape of expandable member 10em of device 11, expandable member, or portions thereof can be placed lateral, posterior and/or superior to the fundus of the stomach. Further, when in an expanded configuration, expandable member 10em can only abut or lie adjacent to the stomach wall, without imparting an) significant deformation forces thereto. However, when the patient eats and the stomach begins to fill, expandable member 10em in this case prevents the stomach from expanding into the volume occupied by expandable member 10em. In such a case, the stomach becomes "deformed" as it attempts to expand and can only expand in a limited fashion, if at all, around a portion of the perimeter of expandable member 10em. Thus, upon expanding the device, the device expands between the wall of the diaphragm 116 and the fundus 120f, exerting pressure on, or at least preventing expansion of the fundus. Because the expandable device is not attached to the stomach, the stomach is free to perform its normal function of mixing food in the stomach for digesting and pushing food out of the stomach. During all of this movement the stomach may slip behind, beside or on top of the expandable device, but the internal volume of the stomach will be held to its smaller volume as the expandable device is occupying the space into which the stomach would normally expand. Further details of methods for treatment of obesity, including procedures for implanting devices described herein are described below.

Figure 4:
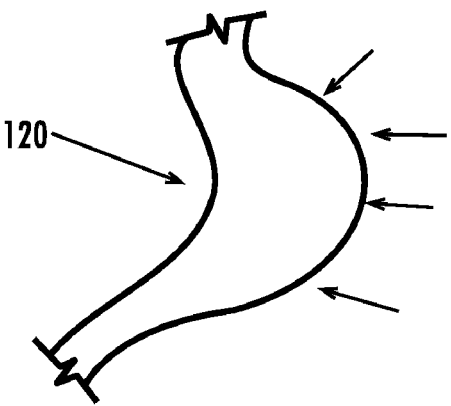
FIG. 4 illustrates (by arrows) potential locations on the stomach wall that can be compressed by one or more expandable devices as described herein.

As noted above, an expandable device can be implanted adjacent a surface of the stomach wall, either in contact therewith or at a predetermined distance therefrom, to prevent expansion of the stomach into a volume occupied by the expandable device. Alternatively, some embodiments of the devices described herein can be configured and placed to exert an external compression on one or more locations of the stomach to deform the stomach wall, thereby decreasing the internal volume of the cavity within the stomach that accepts food and liquid intake. FIG. 4 illustrates (by arrows) potential locations on the stomach 120 wall that can be compressed by one or more expandable devices as described herein.

Figure 3A:
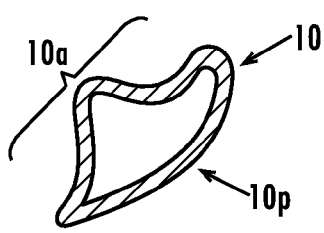
FIGS. 3A-3M show various embodiments of expandable devices which are inflatable to effect expansion thereof.
Figure 3B:
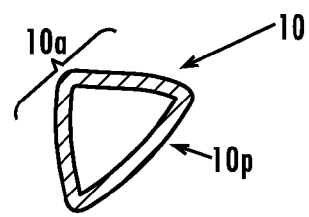
Figure 3C:
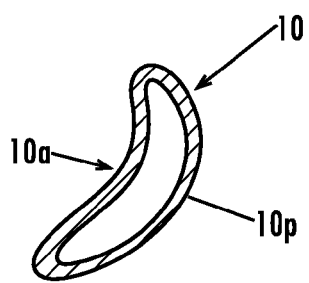
Figure 3D:
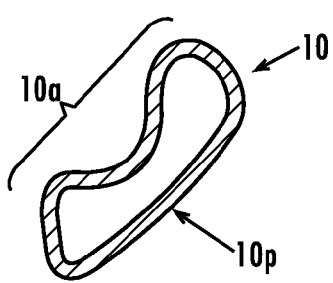
Figure 3E:
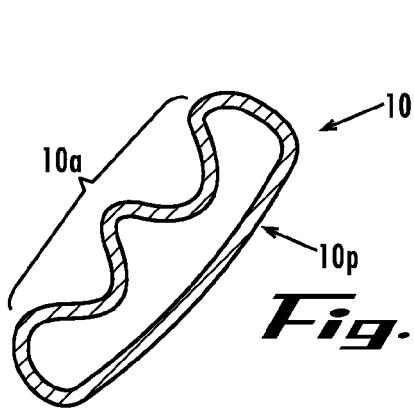
Figure 3F:
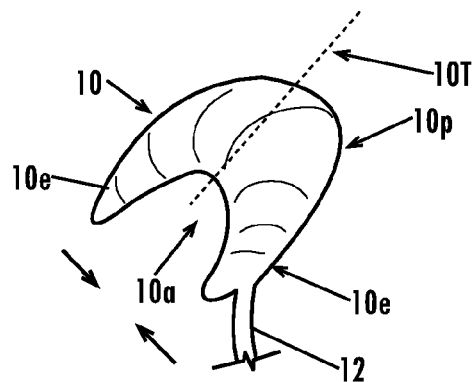

FIGS. 3A-3D show several different embodiments of expandable devices 10 which are inflatable to effect expansion thereof, and which are shown in cross-section in expanded configurations. Surfaces 10a are configured to abut the stomach wall, while other surfaces, typically surfaces 10p are configured to abut one or more other structures in the abdominal cavity. FIGS. 3F-3M are perspective illustrations of further variations of inflatable expandable devices 10 according to the present invention. In FIG. 3F, device 10 is substantially crescent-shaped, wherein end portions of the device, when device 10 is inflated, have first cross-sectional areas that are substantially less than the cross-sectional area of the central portion of device 10. The surface 10a, which is configured to be placed adjacent to a surface of the stomach wall, is substantially concave. End portions 10e tend to wrap around the wall of the stomach 120 as the central portion is placed adjacent to or against the stomach wall. Additionally, device 10 can be configured so that when inflated to expand device 10, ends 10e converge toward the central transverse axis 110T of device 10 (in the directions of the arrows shown) to form a closer fit against the stomach wall and/or apply additional resistive force to the expansion of the stomach wall. In any case, ends 10e help to prevent migration of device 10 relative to the stomach 120 in directions opposite to the directional arrows shown in FIG. 3F. FIG. 3F also shows a partial view of conduit 12 that is in fluid communication with device 10 and used to inflate device 10. Although conduit 12 is shown connecting at one end 10e of device 10, the present devices are not limited to this placement, as conduit 12 could be connected at other locations on the inflatable portions of devices 10.

Figure 3G:
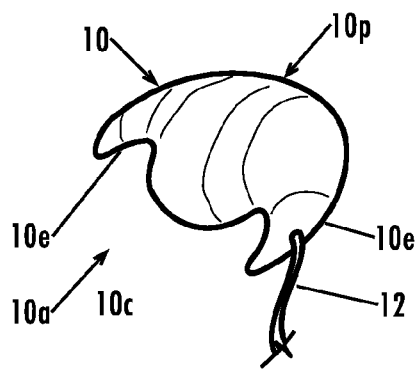

FIG. 3G shows a variation of the device of FIG. 3F, wherein the crescent shape has been modified to a modified-crescent shape, in which the surface configured to abut the stomach is convex at the central portion when device 10 is inflated, to provide increased deformation of the stomach wall, as compared to the amount of deformation applied by device 10 in FIG. 3F. End portions 10e function similarly to that described with regard to FIG. 3F. The "bulge" in the central portion 10c of device 10 can be created by molding such bulge into device 10 so that it is existent in device 11 even when in a contracted or deflated state. Alternatively, the portion of device 10 that forms the bulge can be formed with a thinner wall than the rest of device 110 or can otherwise be made to be more expandable (e.g., such as by making it more compliant than the remainder of the device).

Figure 3H:
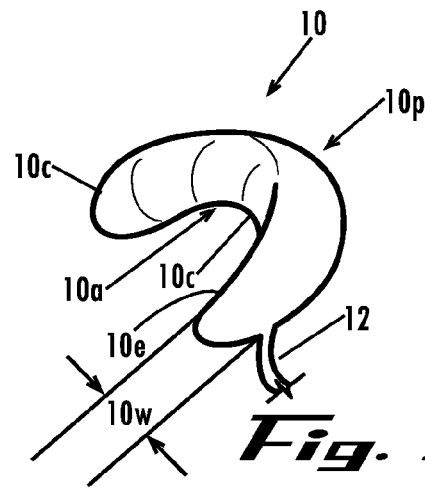
Figure 3I:
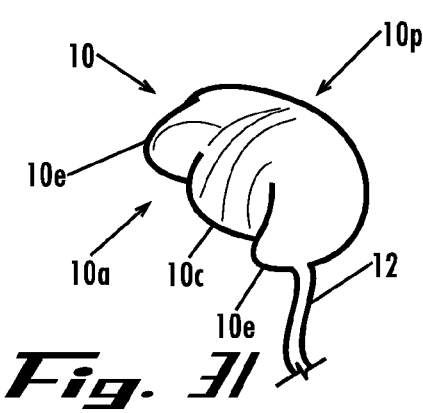

FIG. 3H shows a "cupped scoop" configuration, which, similar to the crescent configuration provides a concave surface 10a and a convex surface 10p. In this arrangement, ends 10e have cross-sectional areas, or at least widths 10w that are substantially as large as the cross-sectional area or width of central portion 10c. Additionally, the radius of curvature of surface 10a abut the longitudinal axis L of device 10 is much larger than that of the crescent design, which provides a broader contact surface for engaging the stomach wall. FIG. 3I shows a variation of the device of FIG. 3H, wherein the cupped scoop shape has been modified to a modified-cupped scoop shape, in which the surface configured to abut the stomach is convex at the central portion 10c when device 10 is inflated, to provide increased deformation of the stomach wall, as compared to the amount of deformation applied by device 10 in FIG. 3H. End portions 10e function similarly to that described with regard to FIG. 3F. The "bulge" in the central portion 10c of device 10 can be created by molding such bulge into device 10 so that it is existent in device 10 even when in a contracted or deflated state. Alternatively, the portion of device 10 that forms the bulge can be formed with a thinner wall than the rest of device 10, or can otherwise be made to be more expandable (e.g. such as by making it more compliant than the remainder of the device). In either of the embodiments of FIGS. 3G and 3I the central portion 10c, including portions of both surfaces 10a and 10p can, in combination, form a substantially spherical shape when inflated. Alternatively, the bulge in central portion 10c on surface 10a can have a curvature different from hemispherical, but still convex.

Figure 3J:
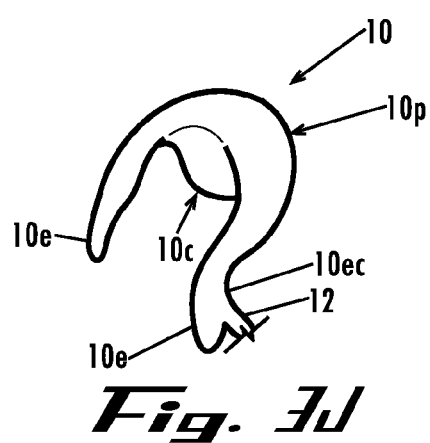

FIG. 3J shows a configuration of device 10 that is boomerang or sickle-shaped. Similar to the embodiments described above, end portions 10e can function to prevent migration of device 10 from its position adjacent a stomach wall and/or may provide additional displacement to prevent expansion of the stomach wall, further limiting the volume of the cavity inside the stomach 120. The bulge at the portion 10c between end portions 110e functions similarly to that described above with regard to FIGS. 3G and 3I and can be made in any of the same manners. Further alternatively, the bulge can be formed as a separately inflatable member, that is, a balloon that is inflatable and debatable independently of the main inflatable body of device 10. In such instances, conduit 12 can be provided with two lumens for separate control of inflation and deflation of the two balloons. The embodiments of FIGS. 3G and 3I can be similarly constructed. One or both ends 10e may contain an additional curve 10ec so that the distal end (or proximal end, depending on which end is curved) of end portion 10e is directed away from the stomach wall. This feature may help with positioning of device 10 adjacent the stomach 120, to further ensure that the ends of the device 10 do not catch on the stomach wall during placement, and/or to prevent the occurrence of pressure concentrations at the ends of the device against the stomach wall. Additionally, as will be described in further detail, the curve 10ec shown may prevent or substantially reduce pressure against the spleen 128 when device 10 is implanted between the stomach 120 and diaphragm 116 as described in an embodiment herein.

Figure 3K:
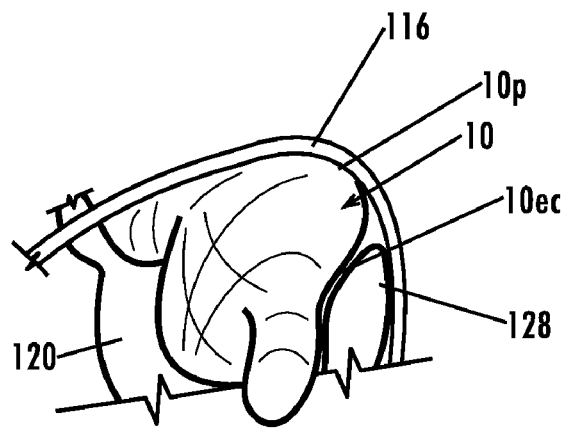

FIG. 3K illustrates a device 10 similar to that described with regard to FIG. 3G, but including a concave curvature 20ec on the proximal end portion of surface 10p that is configured to avoid contact with the spleen 128 or reduce pressure against the spleen 128 relative to a configuration where surface 10p has a continuous convex curvature. Thus, for example, when device 10 is positioned between the diaphragm 116 and stomach 120 and inflated as shown, surface 10ec does not contact or only contacts spleen 128 with minimal pressure, so that spleen 128 is not substantially compressed.

Figure 3L:
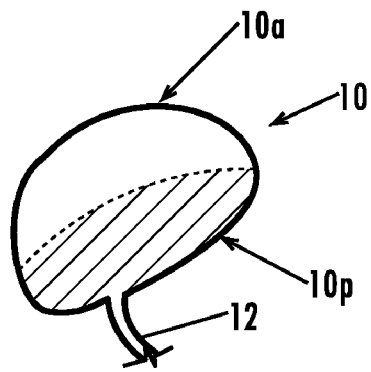

FIG. 3L shows an inflatable device 10 having a substantially flat surface 10p and a convex surface 10a. The substantially flat surface 10p can be particularly advantageous when device 10 is positioned so that surface 10p abuts the interior surface of the abdominal muscles, diaphragm, or some other structure that is adjacent the skin and subcutaneous layers of the patient. The flat surface top is configured so as not to expand, or to expand only minimally, as the majority of the expansion proceeds outwardly in the direction of surface 10a during inflation. This may prevent or substantially reduce a bulge from being visualized externally of the patient. Additional features can be provided to make surface 10p less expandable than surface 10a, as discussed below, to further prevent expansion of surface 10p under inflation pressure. Surface 10a, although shown as a continuous convex surface, can be modified to provide other surface conformations, including any of those shown and discussed above.

Figure 3M:
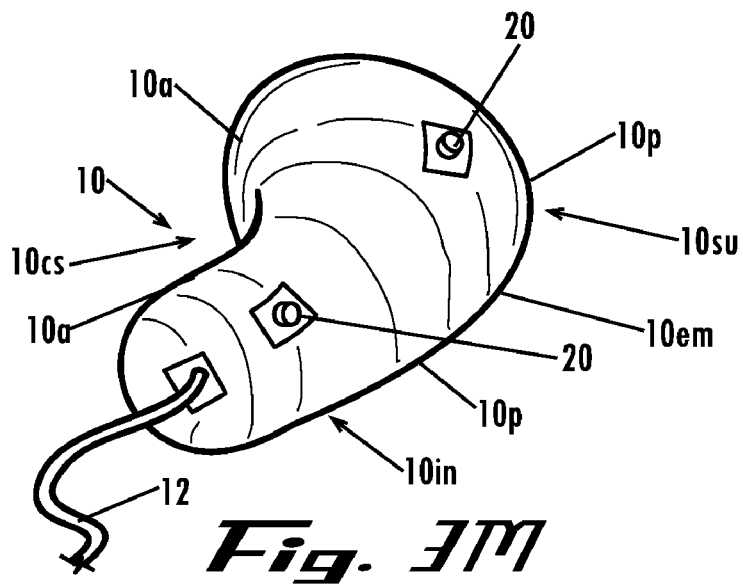

FIG. 3M illustrates another expandable member configuration in which expandable member 10em has a relatively large, bulbous superior portion 10su that tapers to an inferior tubular portion 10in. Tubular section 10in has a substantially smaller cross-sectional area than bulbous portion 10su. Bulbous portion 10su can have a substantially elliptical cross-sectional shape near the end of expandable member and tapers as it descends inferiorly toward tubular portion 10in, to form a concave groove or surface 10cs medially, that is configured to deform the stomach to have a smaller, sleeve-shaped inner cavity, as described further below, and to force the stomach 120 to be more centrally located in the abdominal cavity. The bulbous portion is configured to be positioned in the sub-diaphragmatic space, between the diaphragm 116 and the stomach 120 and, as it is inflated, moves the fundus medially towards the liver. When device is properly positioned, tubular portion 10in is inferior to bulbous portion 10su and, when inflated, applies pressure to the body of the stomach to effect conformational change by pushing it posteriorly against the spinal column. As inflated, device 10 rills in a sub-diaphragmatic space occupied by the omentum, a portion of the stomach, and a space into which the fundus is typically allowed to expand.

Figure 5A:
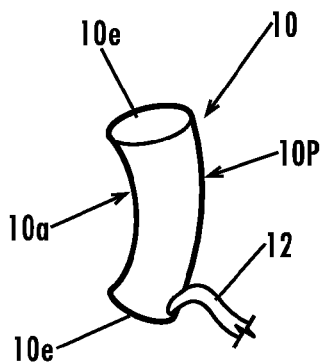
FIGS. 5A-5B illustrate an inflatable device that is substantially tubular and has closed ends, as well as one example of positioning the device to reduce the volume of the stomach cavity.
Figure 5B:
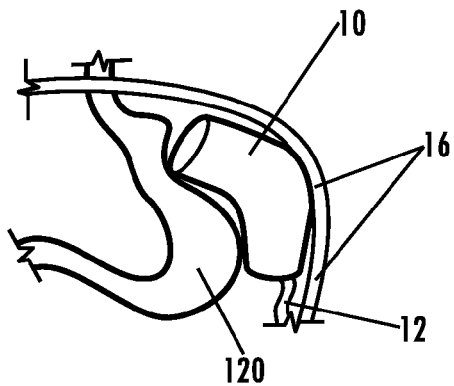

FIGS. 5A and 5B illustrate an inflatable device that is substantially tubular, and thus ends 10e have closed ends. The side walls can have a precurvature so that surface 10a is slightly concave and surface 10p is slightly convex, or can have one or more elbows designed therein. In either case, when device 10 is positioned between the diaphragm 116 and the stomach 120 of a patient, as illustrated in FIG. 5B, and inflated to displace the stomach wall, device 10 can also conform to the natural curvature of the diaphragm 116, either by the one or more elbows provided, or by deformation of the surface 10p under pressure.

Figure 6A:
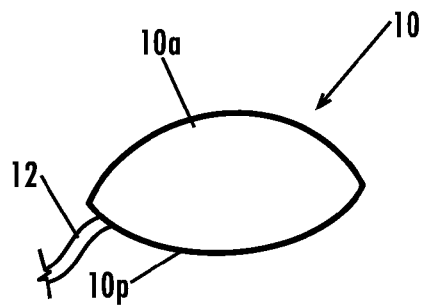
FIGS. 6A-6B illustrate a device which is football-shaped, as well as one example of positioning the device to reduce the volume of the stomach cavity.
Figure 6B:
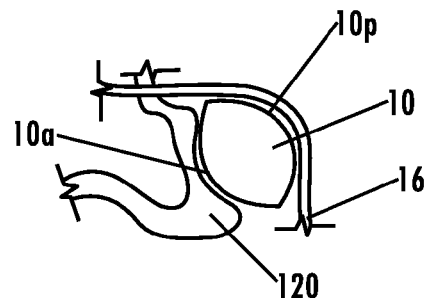

FIGS. 6A-6B illustrate another device 10 which is football-shaped, as well as one example of positioning device 10 to reduce the volume of the stomach cavity. In this regard, when positioned between the diaphragm 116 and stomach 120 as illustrated, the convex curvature of surface 10p when inflated conforms well to the curvature of the diaphragm 116, and the convex surface 10a can provide a larger amount of volume reduction in the cavity within the stomach, as a larger surface area of the stomach wall can be contacted and displaced by the inflated device, as compared with the tubular device shown in FIGS. 5A-5B.

Figure 7:
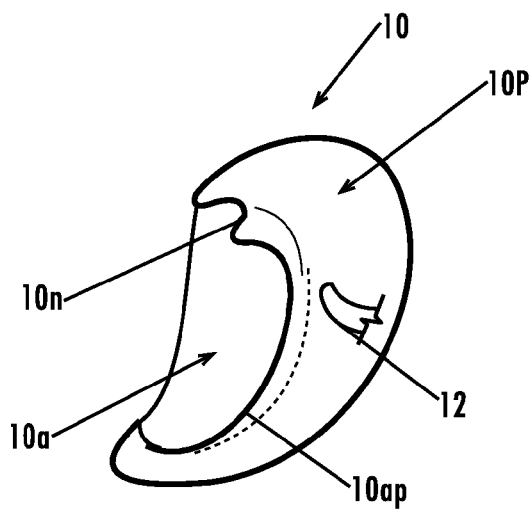
FIG. 7 illustrates a custom shaped device that is expandable via inflation.

FIG. 7 illustrates a device 10 that is expandable via inflation, having a custom shape. Surface 10p is convex and surface 10a is concave, and can be contoured to conform to the contour of the stomach wall. Surface 10a is dished (concave in axially orthogonal directions) and dimensioned to receive all or a portion of one side of the stomach in the dished space. The perimeter of the dish 10ap functions to assist in stabilization of device 10 when positioned against the stomach wall to receive a portion of the stomach, to prevent migration of device 10 with respect to the stomach 120. The convex surface, by its nature, functions to spread expansion forces generated during inflation of the device, over a surface or the internal body structure that it contacts. Concave surface 10a can be configured and dimensioned to receive the stomach and envelope superior and inferior end portions of the stomach. Alternatively, or in addition thereto, concave surface 10a can be configured and dimensioned to receive the stomach and envelop at least portions of anterior and posterior surfaces of the stomach. A notch or other recess 10n can also be formed in a superior end of perimeter 10ap, configured and dimensioned to receive the esophagus where it joins the stomach. This feature further resists migration of (i.e., anchors) device 10 once it has been properly positioned and inflated.

Figure 8:
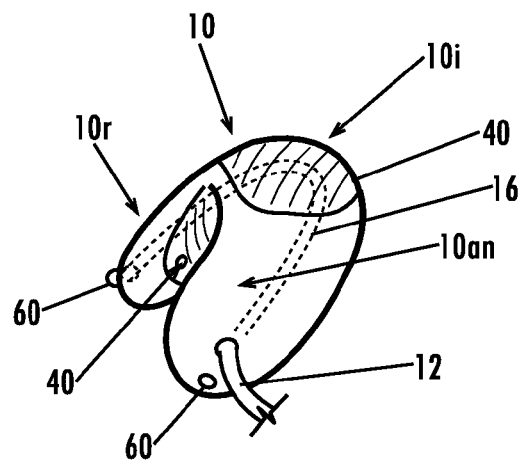
FIG. 8 illustrates a device that has a substantially U-shaped external surface when inflated.

FIG. 8 illustrates a device 10 that has a substantially U-shaped external surface when inflated that is defined by the portions of surface 10p contributed by retrogastric limb 10r, intermediate portion 10i and anterogastric limb 10an. All portions can be inflatable, or, alternatively, only one or some portions can be inflatable. For example, retrogastric 10r and anterogastric 10an limbs can be inflatable, while intermediate portion may not be, but mats be a resilient non-inflatable portion. Additionally, an inflatable bulge can be inflated to extend the surface 10a of such a non-inflatable intermediate portion. The inflatable bulge can be inflated together along with the limbs, or independently, in a manner discussed previously. Further alternatively, one or both limbs may not be inflatable, while one the intermediate portion and/or bulge are inflatable. Further, reinforcing structures can be provided with this device 10, as well as other devices described herein. When an inflatable bulge member is formed on the surface 10a of intermediate portion 10i, the bulge member, when inflated, extends within the internal U-shape of the device on internal surface 10a of device 10, to advance toward the stomach, while retrogastric 10r and anterogastric loan limbs engage peripherally around surfaces on the stomach. In one example of use, device 10 can be positioned over the fundus so that the contact surface 10a of intermediate portion 10in (with or without the bulge) is positioned adjacent the wall of the fundus, and wherein retrogastric 10r and anterogastric 10an limbs engage peripherally (retrogastrically and anterogastrically, respectively) around the fundus.

Figure 79:
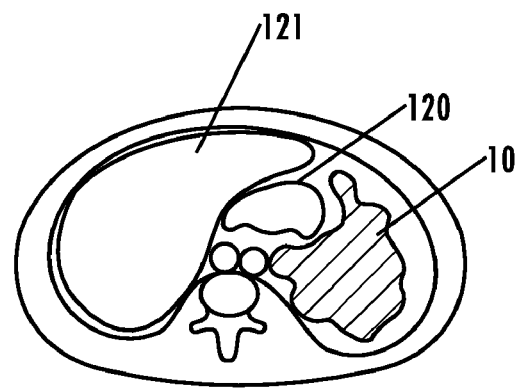
FIG. 79 diagrammatically illustrates the use of a space filling foam that can be use as the expandable member of a device described herein.
Figure 80A:
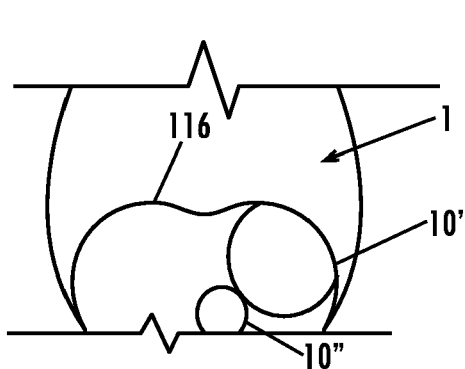
FIGS. 80A-80E diagrammatically illustrate the use of multiple expandable members that can be used together to occupy the space in the sub-diaphragmatic region.
Figure 80B:
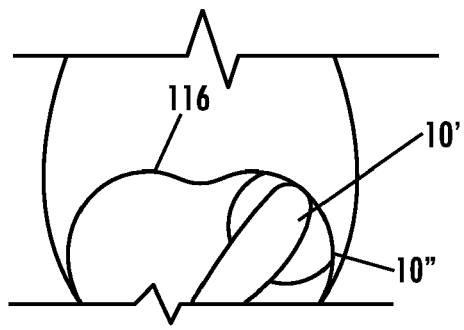
Figure 80C:
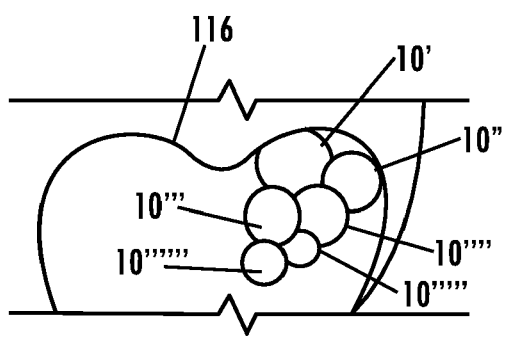
Figure 80D:
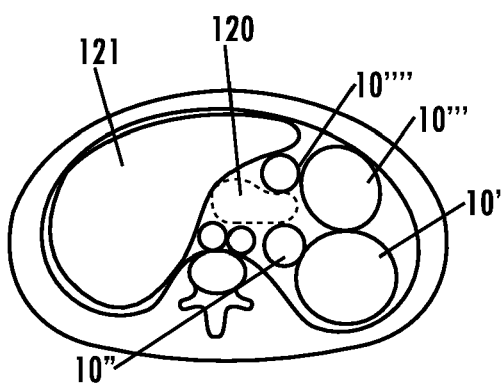
Figure 80E:
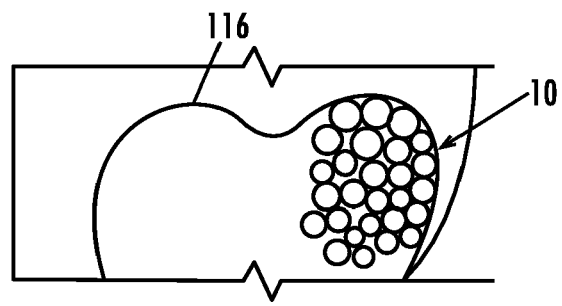

FIG. 79 diagrammatically illustrates the use of a space filling foam that can be use as the expandable member 10. The foam can be sprayed in place or injected in order to fill up substantially ally of the sub-diaphragmatic space into which the fundus normally expands.

FIGS. 80A-80E diagrammatically illustrate the use of multiple expandable members 10 that can be used together to occupy the space in the sub diaphragmatic region to achieve the effect of the embodiments described above. The multiple expandable members can have an) of the shapes previously described and can be shaped so as to interlock with one another to achieve the desired shape and/or prevent migration of the members. In some embodiments the multiple expandable members can be strung together. In other embodiments the multiple expandable members can stick to one another.

Expandable Member Construction

The inflatable members of the inflatable devices described herein can include compliant, noncompliant or semi-compliant materials, or any combination of these. Examples of compliant materials suitable for use in an inflatable member as described herein include, but are not limited to: silicone, latex rubber, and polyurethane. Examples of useable semi-compliant materials include, but are not limited to: nylon, polyethylene, polyester, polyamide and polyurethane, see for example, U.S. Pat. No. 6,500,148, which is hereby incorporated herein, in its entirety, by reference thereto. Polyurethane, nylon, polyethylene and polyester can be compliant or semi-compliant materials, depending upon the specific formulation and hardness or durometer of the material as produced. Examples of noncompliant materials that can be used in the construction of inflatable members described herein include, but are not limited to: polyethylene terephalate (PET) and urethane. Urethane can be a compliant, semi-compliant or non-compliant material depending upon its specific formulation and hardness or durometer. Compliant, semi-compliant and noncompliant categories are not solely material limited, but are better defined by their expansion characteristics, as noted above. Some materials are best suited for use in one of these categories (e.g., silicone and latex work well to make compliant structures), but other materials can be formulated and/or constructed to provide compliant, semi-compliant or noncompliant properties.

The expandable member 10em of device 10 can have a soft and atraumatic outer surface to prevent damage to nearby organs and structures. In at least one inflatable embodiment, expandable member 10em must be able to hold carbon dioxide ($CO_2$) gas without significant leakage. Silicone is one example of a compliant material that can provide the desirable soft and atraumatic outer surface of an expandable member, and is desirable due to its mechanical properties as well as its successful history, as a long term implant material. However, silicone is somewhat porous and thus may not be ideal to hold $CO_2$ gas, even at low pressures. Accordingly, the inner surface of an expandable member 10em having an outer silicone layer can have a lining or coating which has minimal gas permeability, as described in further detail below. Such a lining can be provided in the form of a dual layer or multilayer construction, where the layers are covalently bonded to each other by co-extrusion, co-molding, solvent bonding, dip coating, spray coating, etc. or to where the two or more layers are independent of each other, allowing relative movement.

The inflatable member of a device 10 can be constructed primarily of a compliant material such as silicone, for example, in which case, the expandability of the inflatable member is substantially isotropic, so that the inflatable member expands outwardly bye equal amounts in all directions. Alternatively, the wall thickness of the inflatable member can be varied so as to vary the expansion characteristics of the inflatable member, to tailor its expansion properties to a desired performance. As one example of this, the wall including surface 10p can be formed thicker than the wall including surface 10a. In this instance, upon inflation, surface 10a will expand outwardly by a greater distance than surface 10p. A device 10 having a substantially flat surface, such as the one shown in FIG. 3L, for example, can have a thicker wall that includes the flat surface 10p, relative to the wall that includes the surface 10a. Further complexities can be introduced into the expansion properties of an inflatable member by varying the thickness of the wall along the same surface. For example, in the football shaped device 10 shown in FIG. 6A, the central portion of the wall that includes surface 10a can be formed thinner than the end portions of the wall that includes surface 10a. As will be readily apparent, numerous variations in wall thicknesses at various locations can be designed to provide a custom expansion profile. Additionally, the provision of a thicker wall adds strength to the device 10. For example, by making the wall containing, surface lop relatively thicker, this provides added support for maintaining the device in contact with an internal structure in the abdominal cavity, and for maintaining some integrity to the shape of the inflatable member.

Figure 9A:
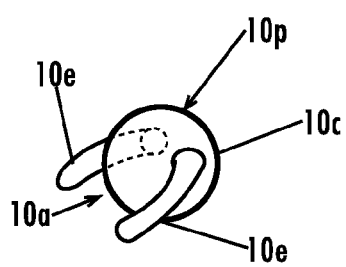
FIGS. 9A-9B illustrate embodiments of devices having end portions that are less compliant than a central portion.

Another technique for producing an inflatable member with a customized expansion profile includes forming the inflatable member from a combination of two or more of a compliant material, a semi-compliant material, and a non-compliant material. For example, the end portions 10e of device 10 can be made from a semi-complaint material or noncompliant material, while the central portion 10c can be made of a compliant material. In this way, end portions 10e expand less than central portion 10c when device 10 is inflated. Additionally, especially when a noncompliant material is used, end 10e provide greater lateral support in contacting the wall of the stomach, and are less deformable than if made of a compliant material. The portions of the inflatable member that are formed of different materials can be co-molded together, or bonded together using adhesives and/or solvents, or heat sealed to provide an integral inflatable member as illustrated in the devices of FIGS. 3A-8. Volume of a device is increased by stretching or deforming in response to a force or pressure, such as by inputting a fluid into the inner cavity defined by the device. In addition to the non-expanded shape and size of the expandable member of the device prior to inputting fluid, volume can also be influenced by the compliance of the material used to make the expandable member, as well as the wall thickness of the material used to make the expandable member. In the example of FIG. 9A, end portions 10e are formed of a material that is less compliant (e.g., noncompliant or semi-compliant) than the material that central portion 10c is formed of. For example, portions 10e can be formed of polytetrafluoroethylene (PTFE) or PET, and central portion 10c can be formed of silicone, or other compliant material. Alternatively, end portions 10e can be solid and thus noncompliant. End portions 10e can be joined to central portion 10c by solvent bonding, heat bonding, adhesives, etc. End portions 10e can be in fluid communication with central portion 10a, or they can be independently inflatable through a second lumen, as described above. In this arrangement, end portions 10e remain substantially in their present configuration, and thereby maintain an intended distance therebetween to fit the perimeters of the stomach wall as intended, while central portion 10a expands to deform the stomach wall inwardly.

Figure 9B:
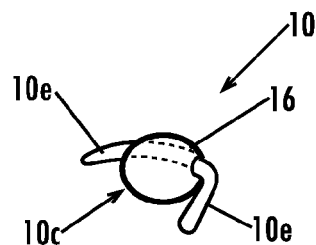

FIG. 9B shows an alternative arrangement to the device shown in FIG. 9A. In FIG. 9B, the end portions 10e are integral with and in fluid communication with one another, and wrap around the surface 10p of central portion 100c. This construction provides even greater structural rigidity in the end members, since they are interconnected or integral with a portion made from the same noncompliant (or semi-compliant) material. As in FIG. 9A, end portions 10e can be in fluid communication with central portion 10c so as to be inflated via the same input lumen. Alternatively, end portions 10e can be independently inflatable. The integral end portions member can be glued or otherwise fixed to central portion 10c. As another alternative, the end portions (and/or the piece integrally connecting them) are be inflatable, but can be foam filled, or solid polymer.

Inflatable members described herein can be inflated with gas or liquid or both. Examples of gases or liquids that can be used to inflate inflatable members/devices 10 include, but are not limited to: carbon dioxide, helium, isotonic dextrose solution, iostonic saline solution, air. It may be preferable to inflate with one or more gases, to minimize the weight of the implanted device 10, as a heavier, fluid-filled device may be more noticeable to the patient. Alternatively, devices 10 can be inflated with a porous gel that is porous or microporous to encapsulate air or other gas bubbles, thereby reducing the weight of the gel while still permitting it to apply volumetric pressure to expand am inflatable member. Such gels may be settable, such as ultra-violet (uv) curable or otherwise chemically curable, or, alternatively, can remain in the gel state, so that they can be readily removed or added to, to increase or decrease the amount of inflation/expansion of the expandable member. Gels can be made from a flowable viscoelastic substance made of a polymer mixture, such as silicone oil, boric acid, hyaluronic acid, polyacrylic acid or combinations thereof for example. The gel, as delivered into the expandable member 10*em* (e.g., such as by injection or the like) can be aerated or infused with carbon dioxide or an inert gas to create a deformable or non-deformable cellular structure that encapsulates the gas in cells, and thus has relatively low mass but still has significant resistance to compression or deformation.

When inflating an inflatable member with a pressurized gas, some materials, especially the compliant materials such as silicone and the like, may have an inherent porosity that may not adequately maintain a desired pressure within the membrane or wall of the inflatable member over an extended period of time. This seepage or slow leakage of gas from the inflatable member may require a patient to have the implant checked more frequently then required for other physiological concerns, to ensure that it is maintaining adequate pressure and thus is expanded to the extent desired to perform the desired amount of deformation of the stomach. One way of eliminating or substantially reducing such seepage is to coat an inner or outer surface of the inflatable member with a "gap-filling" substance, such as a gel or an oil, to fill in and seal the porosity of the material used to form the inflatable member.

Figure 10A:
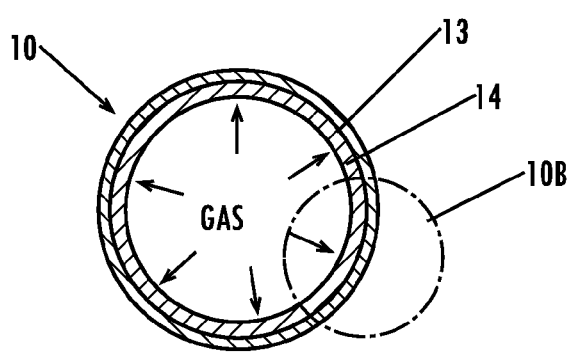
FIG. 10A illustrates an inflatable member 10 having an inner liner that is less porous that the outer membrane of the device.
Figure 10B:
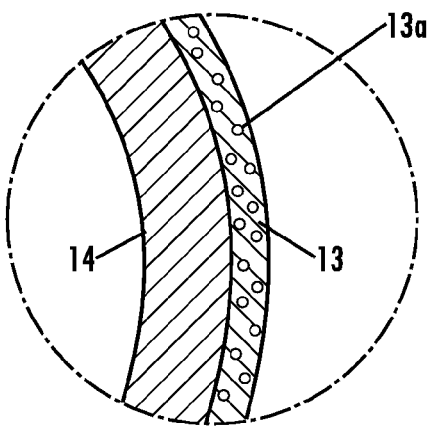
FIG. 10B is a magnified view of the encircled portion 10B of FIG. 10A.

Another way of eliminating or substantially reducing such seepage is to provide an inner liner inside the wall of the inflatable member. FIG. 10A illustrates an inflatable member 10 having an inner liner 14 that is less porous that the outer membrane 13 of device 10. As shown in FIG. 10B, liner 14 is made of a material that has less porosity than the outer layer of inflatable material 13 forming inflatable member 10, that is relatively more porous (see pores 13*a*). Layer 14 can be bonded to layer 13, or not. One way of bonding layer 13 to layer 14 is to overmold layer 13 on liner 14. In one example, layer 13 is formed from silicone and layer 14 is formed from polyurethane. In another example, layer 13 is formed from silicone and layer 14 is formed from polyester. Of course, other materials can be substituted for layers 13 and 14 to perform similar functions. Outer layer 13 should be inflatable, and relatively non-porous, with outer surface characteristics suitable for contacting the stomach and other structures in the abdominal cavity. In this regard, silicone and other relatively soft, elastic materials provide good atraumatic interfaces. The inner liner 14 should be less porous than the outer layer, and can be compliant, semi-compliant or non-compliant.

Figure 11:
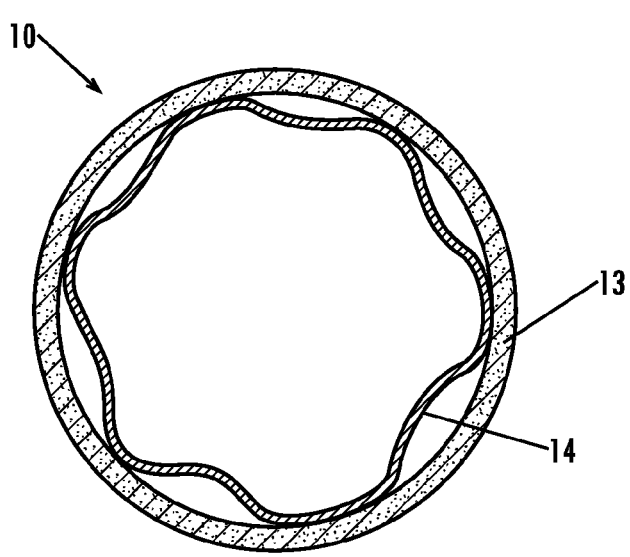
FIG. 11 illustrates a device wherein the inner liner is separate from the outer layer.

An example where inner liner 14 is separate from outer layer 13 is illustrated in FIG. 11. In the example shown, liner 14 is a relatively non-compliant or semi-compliant layer relative to compliant layer 13. The view of FIG. 11 shows device 10 in an inflated configuration. The walls of liner 14 are wavy, and may have folds and creases, as the fully expanded liner 14 can designed to be as large or larger than the outer layer 13. In this way, outer layer 13 can begin to stretch without fully inflating the inner layer 14. For example, in a partially expanded configuration, neither layer is stretched. As fluid is inputted into the expandable member, the outside layer 13 becomes stretched prior to fully inflating the inner layer 14, as shown in FIG. 11. This may be sufficient expansion of the device, depending upon the application. The device can be further expanded so that the walls of layer 14 no longer have folds or creases therein, as layer 13 expands still further under the greater pressure applied. If layer 14 is semi-compliant, it can even be stretched somewhat under increased pressure. As a polymeric layer expands and its wall becomes thinner, the seepage rate through the layer of a gas under pressure increases. Since the inner layer is not stretched (or stretched ver little), or is essentially non-permeable, it retains its maximum ability to prevent seepage therethrough, while, at the same time, the outer layer 13 becomes fully expanded and smooth for interfacing with the structures in the abdominal cavity.

For example, layer 14 can be made from poly urethane and layer 13 can be made from silicone, although substitutes for each layer can be made, as already noted. Further, even by forming layers 13 and 14 both from a compliant material such as silicone, some reduction in seepage rates is achieved.

Figure 12A:
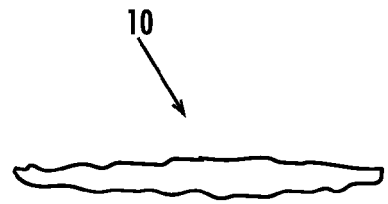
FIGS. 12A-12B illustrate another approach to reducing or minimizing the seepage rate through an inflatable member.
Figure 12B:
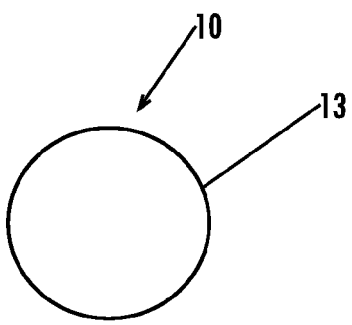

FIGS. 12A-12B illustrate another approach to reducing or minimizing the seepage rate through an inflatable member. FIG. 12A illustrates inflatable device 10 in a compact deflated configuration, wherein no or a minimal amount of inflation medium exists within the inflatable member. Upon inflation of device 10, the inflatable member is inflated only up to a maximum pressure before the wall 13 begins to elastically deform. Because the wall 13 does not elastically deform, the inflated device of FIG. 12B maintains the same porosity and seepage performance that it had in the deflated configuration, as opposed to elastically deforming the inflatable member, which may increase the seepage rate, as discussed above. The wall thickness and or material for constructing the inflatable member of device 10 in this situation can be chosen so that the maximum pressure before elastic deformation is sufficient to fill a space into which the stomach would normally expand if the device were not placed there, and to prevent the stomach from expanding into the space. In one embodiment, in order to occupy the space to prevent the stomach from expanding into the space, device 10 is inflated, but not to elastic deformation, and positioned adjacent the stomach to fill a volume of space that device 10 then prevents the stomach from expanding into. Alternatively, device 10 can be made from a compliant material and configured to fill the space when in an elastically deformed configuration.

Device 10 can further include one or more reinforcing elements 16,40 (e.g., see FIG. 8) that can be attached externally of the inflatable member or can be molded into the inflatable member. For example, reinforcing elements can be made from hard plastics, such as polycarbonate, glass-filled polymers, polyvinyl chloride, or thicker layers of elastomers, such as polyester, polyurethane, etc, or from PTFE, biocompatible malleable metals, or fiber reinforced polymers. A reinforcing element can be positioned in a mold in a predetermined configuration and then molded into the inflatable member by molding the inflatable member around the reinforcing element. Alternatively, reinforcing elements 16,40 can be bonded to the expandable member by heat, adhesives and/or solvents.

Figure 13B:
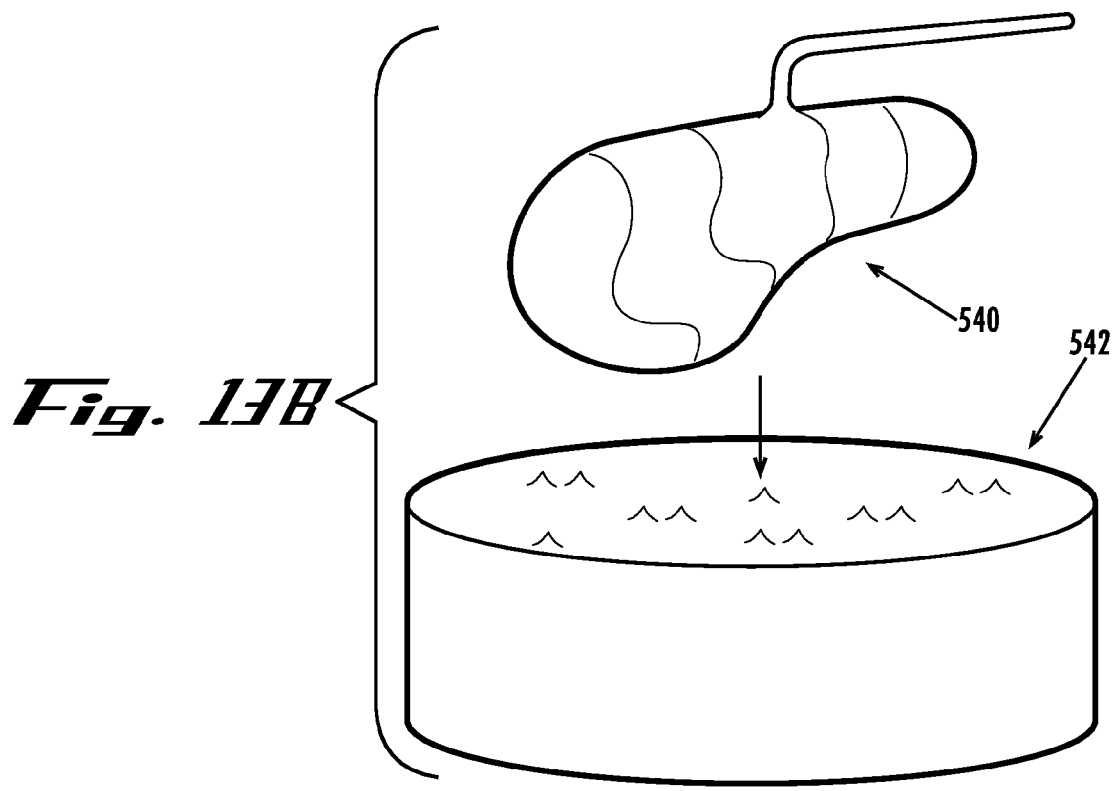
FIGS. 13B-13I illustrate one approach to fabricating a dual layer inflatable member for a device described herein.
Figure 13C:
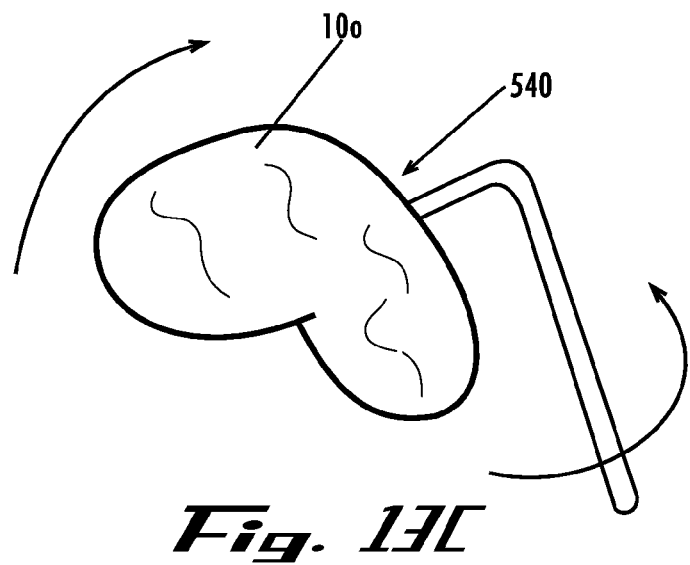
Figure 13D:
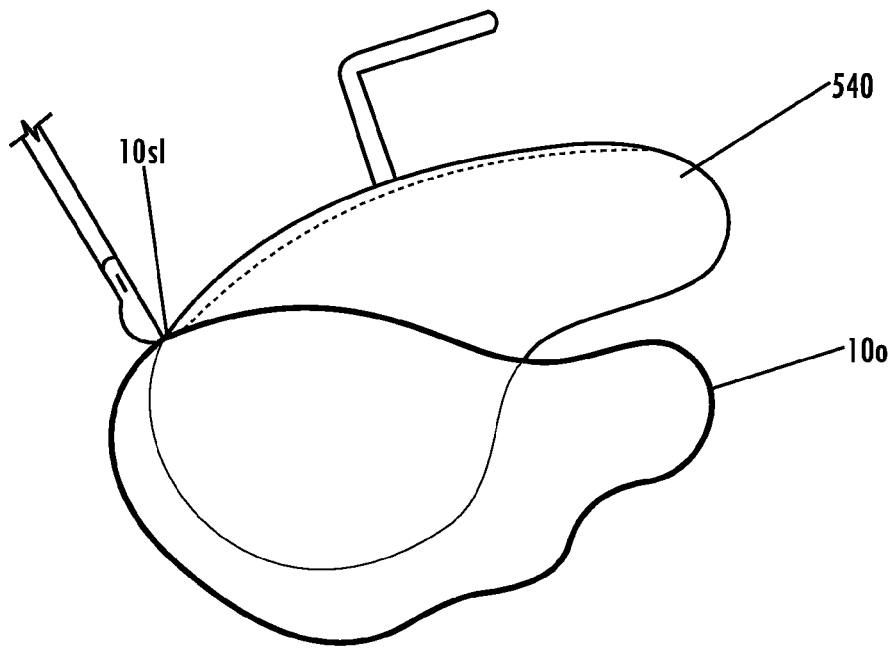
Figure 13J:
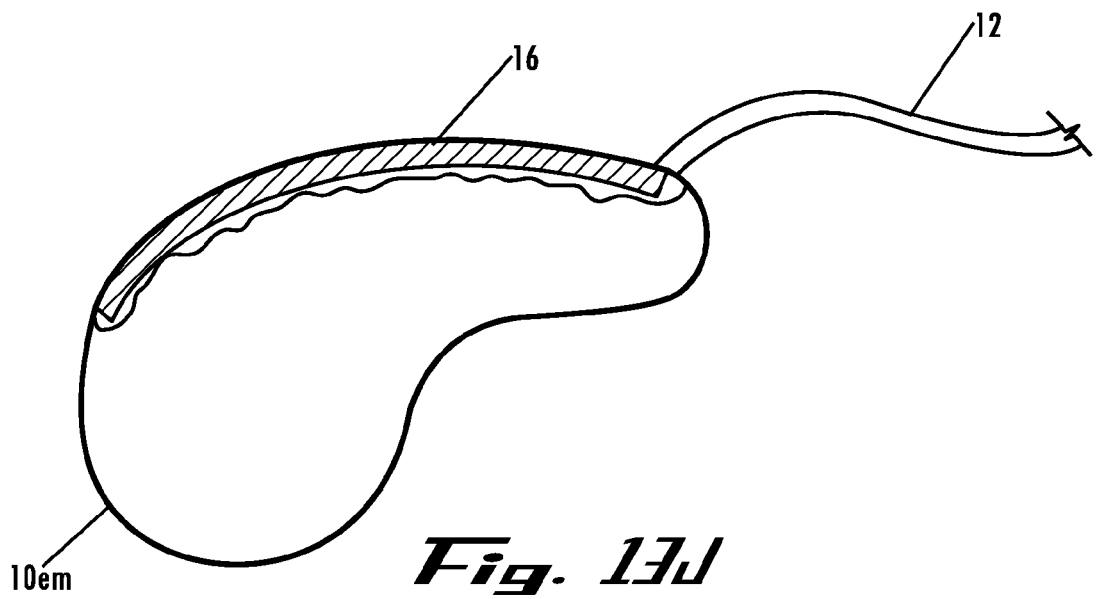
FIG. 13J illustrates a single layer inflatable member manufactured according to one method embodiment described herein, including steps described with regard to FIGS. 13B-13D.
Figure 13E:
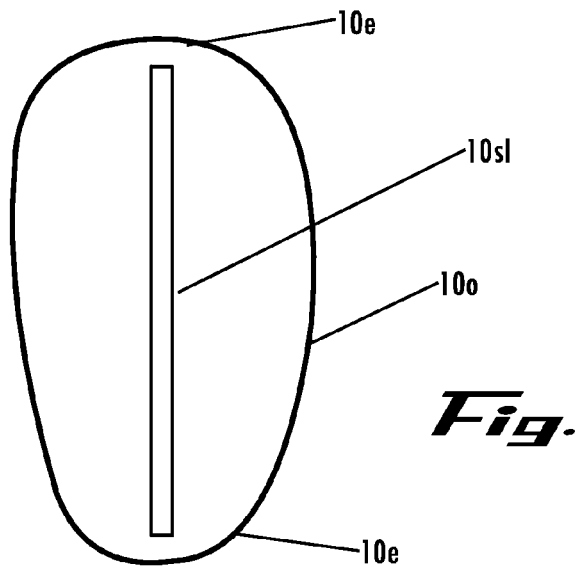
Figure 13F:
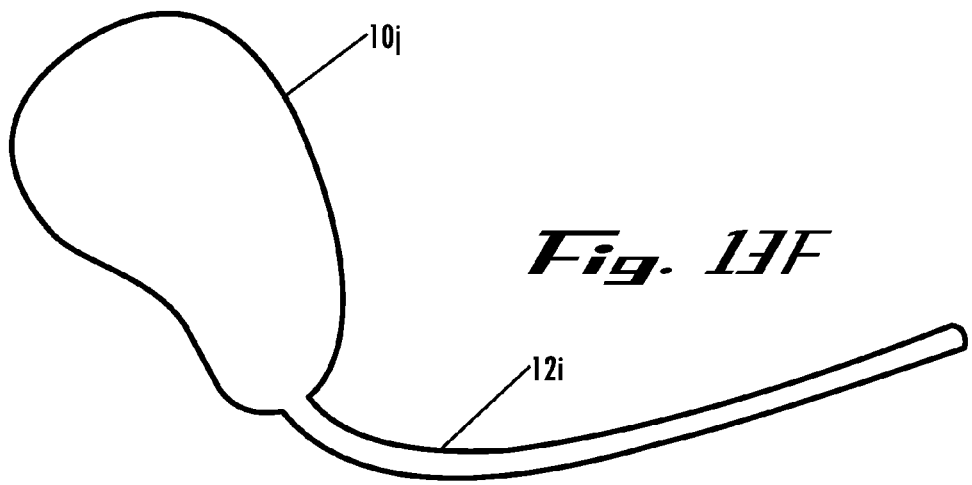
Figure 13G:
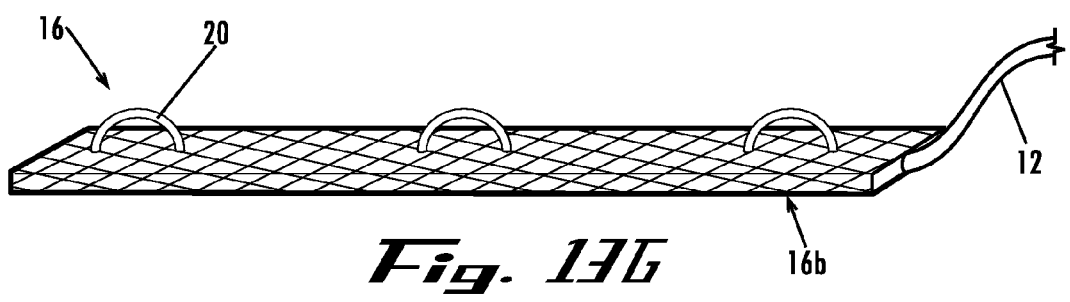
Figure 13H:
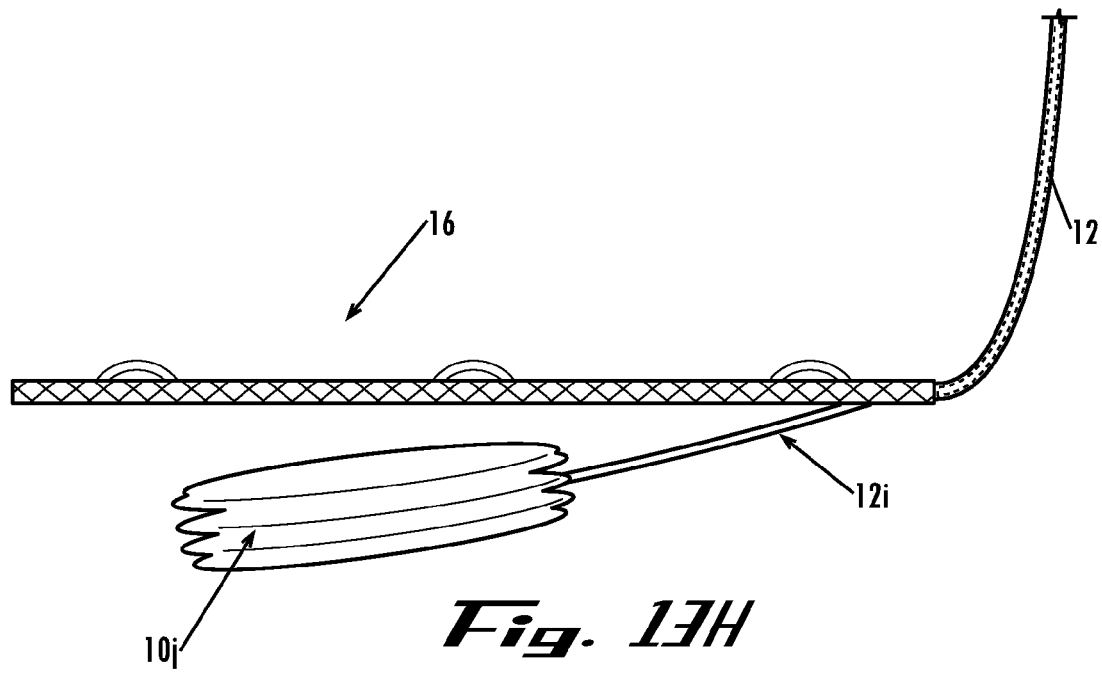
Figure 13I:
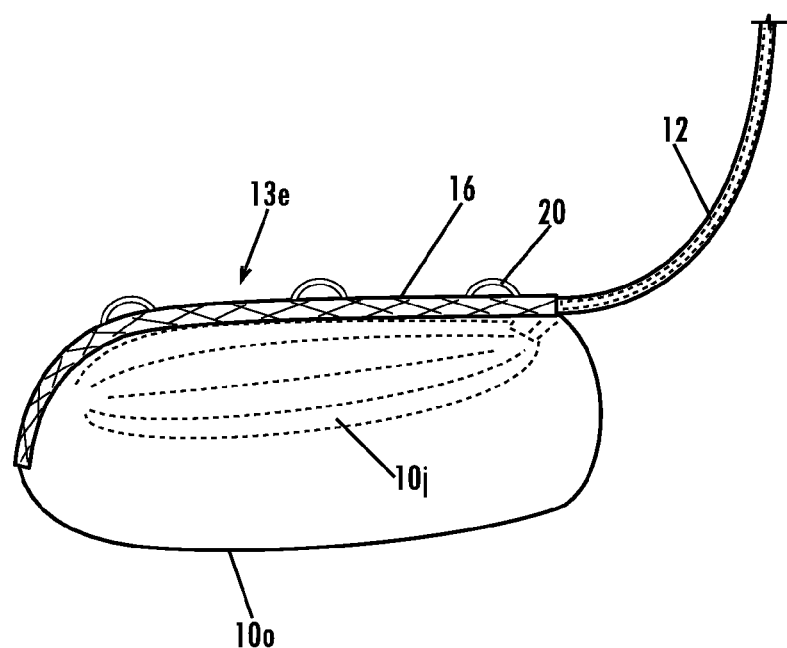
Figure 13A:
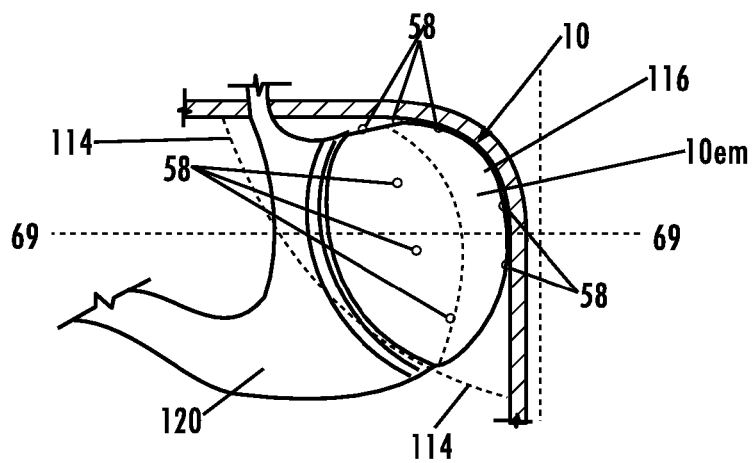
FIG. 13A is a perspective illustration of an inflatable device, the main body of which is substantially tubular or cylindrical with end portions that are substantially hemispherical.

FIG. 13A is a perspective illustration of an inflatable device 10, the main body of which is substantially tubular or cylindrical with end portions 10*e* that are substantially hemispherical. Device 10 includes a fiber-reinforced polymer portion 16 (e.g., Fiber-reinforced silicone strip) that reinforces the strength of the attachment of anchor features 20 that are adapted to anchor device 10 to at least one internal structure in the abdominal cavity, which is described in more detail below. Reinforced portion 16 can be extended over end portions (as shown in phantom), as well as additionally established in a cross pattern or other pattern to reinforce the end portions 10*e* and make them less expandable.

FIGS. 13B-13I illustrate one approach to fabricating a dual layer inflatable member for device 10. The outer layer 10*o* is preferably formed from a compliant, relatively soft polymer to provide an atraumatic interface with the stomach wall. For example, outer layer can be silicone, latex rubber, or other soft, compliant elastomer. FIGS. 13B-13D illustrate one method of manufacturing outer layer 102. A mold 540 that has an outer surface conformation that is what matches the desired conformation of outer layer 10o is dipped into a vat 542 of liquid polymer of the material that layer 102 is to be formed of. After a predetermined time, mold 540 is pulled out of vat 540 and agitated to equally distribute the polymer layer that has accumulated on the mold, while the polymer cures or solidifies see FIG. 13C. The steps in FIGS. 13B and 13C can be repeated until layer 10o has obtained the desired wall thickness. Other materials and/or structures (such as fiber reinforcement, anchoring structures, etc.) can be molded into the layer 10o by placing such materials or structures on the outer surface of the polymer accumulated on the mold, between dips, and then dipping and agitating for one or more repeated cycles.

After finishing the cycles of steps 13B and 13C, and after sufficient curing, the layer 10o is cut from mold 540, such as by cutting a slot or opening 10sl aligned with the shaft 541 that extends from mold 540 and peeling layer 100 from the mold 540, as illustrated in FIG. 13D. Opening 10sl is dimensioned to permit the passage of an inner layer therethrough, in a manner as described below. Outer layer 10, as removed from mold 540, is illustrated in FIG. 13E. In the example shown in FIG. 13E, opening 10sl is a slot that generally extends between ends 10e. The inner layer can be formed of a somewhat less compliant material, such as a semi-compliant or noncompliant material. In the example shoot in FIG. 13F, inner liner is formed from polyurethane. A conduit 12i configured to connect with conduit 12 is provided that extends from and is in fluid communication with inner liner 10j. Inner liner 10j may be less porous than outer member 10o, for reasons discussed above, and is inflatable to expand member 10j. However, inner liner 10j may or may not be elastically deformed when inflating device 10 to its expanded configuration, while outer layer 100 typically will be elastically deformed upon inflation of device to an expanded configuration. Alternatively, device 10 can be inflated to an expanded configuration where neither inner liner 10j nor outer layer 10o are elastically deformed or stretched.

FIG. 13G shows a reinforced element 16 used to integrate the two inflatable layers 10j and 10o. In the example shown, reinforcing member 16 comprises a fiber-reinforced silicone strip that includes tabs or loops 20 useful for delivering and/or anchoring device 10. However, other materials and shapes can be provided when constructing reinforcing element 16. Conduit 12 extends proximally from reinforcing element 16, with also a distal end (not shown) opening from a bottom surface 16b thereof that is configured to be in fluid communication with conduit 12i.

To assemble the inflatable member, conduit 12i is in fluid communication with to the distal end of conduit 12 and sealed, such as by a pressure fit and/or adhesives. Inner inflatable member is deflated to a compressed configuration, and may be further compacted by folding or scrunching the walls together, as illustrated in FIG. 13G. Next, inner inflatable member 10j and conduit 12i are inserted through opening 10sl and reinforcing member 16, which overlaps opening 10sl, is adhered over opening 10sl to seal the outer member 10o so that an enclosed, inflatable space that is substantially leak-proof to fluid and/or gas under pressure results. The resulting inflatable expandable member 10em is illustrated in FIG. 13I. Although the above steps have been described with regard to manufacturing a dual layer inflatable member, it is noted that a single layer inflatable member can be manufactured similarly. Also, an inner layer of a dual layer inflatable member can be manufactured using techniques as described with regard to FIGS. 13B-13D, for example. To manufacture a single layer inflatable member, the layer generated by steps shown in FIGS. 13B-13D is then sealed with a reinforcing strip 16, as illustrated in FIG. 13J. In any of these embodiments, reinforcing strip 16 can be prefabricated to incorporate fixation structures (e.g., anchors), conduit 12, internal valve structures for controlling pressure within expandable member 10em via conduit 12 and/or radiopaque markers.

Figure 14A:
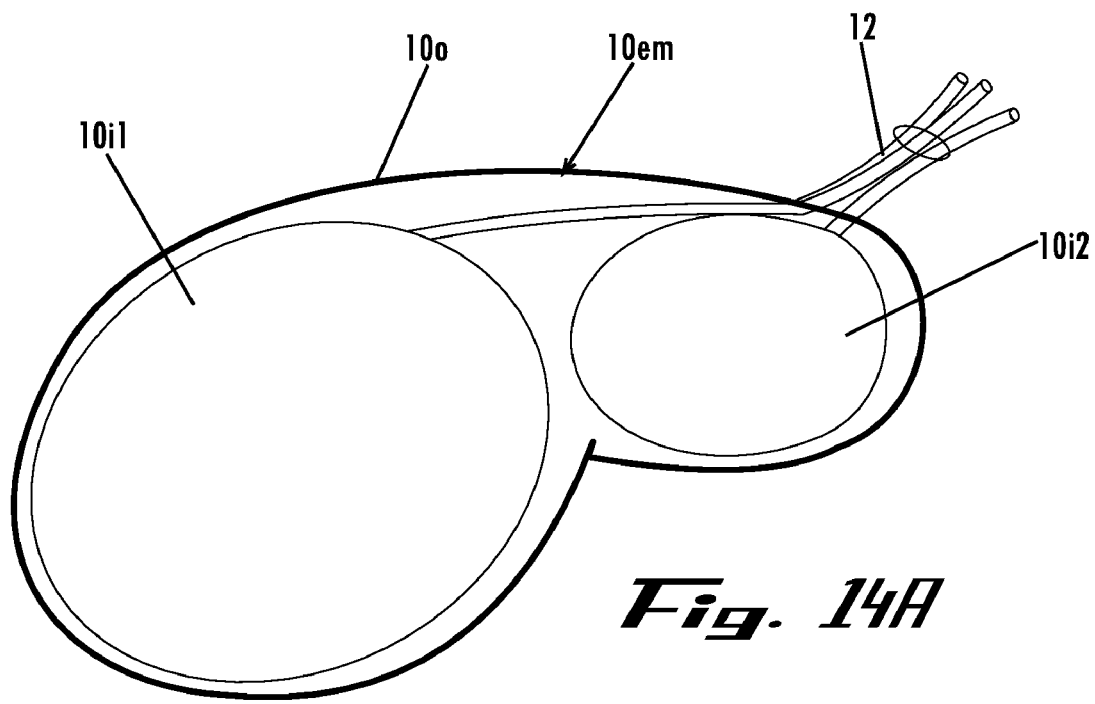
FIG. 14A illustrates an expandable member that is provided as a dual layer expandable member, wherein an outer layer surrounds both inner inflatable elements, each of which are independently inflatable.

Expandable member 10em can be configured to have more than one independent inflatable member or chamber. For example, FIG. 14A illustrates expandable member 10em that is provided as a dual layer expandable member, wherein outer layer 10o surrounds both inner inflatable elements 10i1 and 10i2, each of which are independently inflatable. In the embodiment shown, each of members 10o, 10i1 and 10i2 is independently inflatable via dedicated inflation tube 546, 547 and 548 that pass through conduit 12 and connect to the three respective inflatable members, respectively. This allows differential expansion of expandable member 10em. For example, if more displacement of the stomach 120 is desired in the area contacted by member 10i1 and outer member 10o than what is desired in the area contacted by member 10i2 and outer member 100, then member 10i can be inflated to a higher volume than member 10i2 to effect more movement by member 10i1. Also, it is noted that similar functionality, can be obtained in a single layer arrangements for example, like that shown, only without the outer layer 10o. In such an arrangement, members 10i1 and 10i2 would still be independently inflatable. Members 10i1 and 10i2 can be connected together, for example using fixation structures and techniques described herein, to prevent the members from migrating away from one another.

Figure 14B:
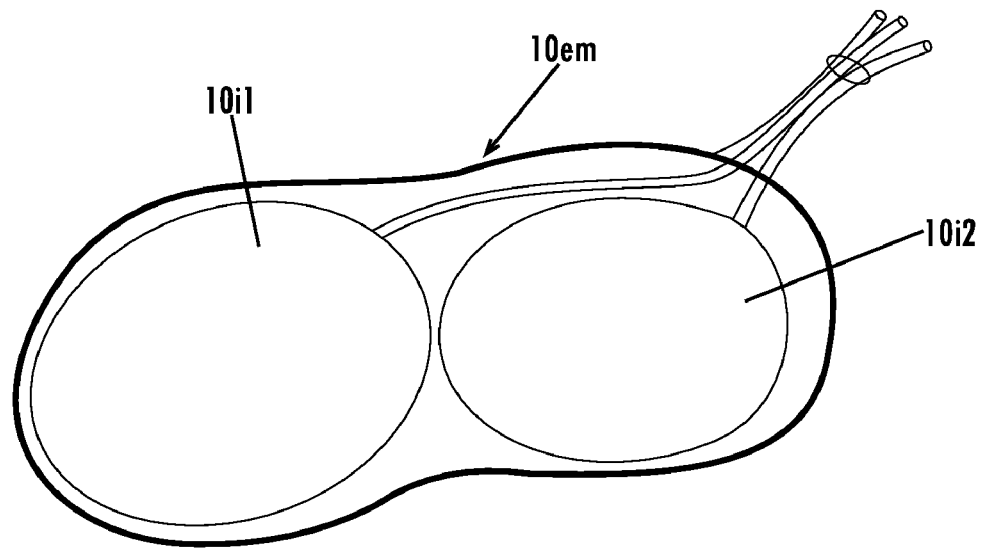
FIG. 14B illustrates an example where the expandable member of FIG. 14A has been resized.

FIG. 14B illustrates an example where the expandable member 10em of FIG. 14A has been resized (such as by reducing the volume in member 10i1 and/or increasing the volume in member 10i2) so that the members 10i1 and 10i2 are approximately the same size.

Reinforcing elements 16 can be configured to provide a more rigid frame or structure to maintain the inflatable member in a desired orientation or configuration when inflated and when applying forces to the stomach. The reinforcing elements can be arranged to provide a relatively rigid "exoskeleton" or "endoskeleton" of the inflatable member. Such frames can be constructed of any of the material described above for reinforcing elements 16, particular rigid plastics, stainless steel, nickel-titanium alloys, titanium, etc. FIG. 15A illustrates device 10 provided with a relatively rigid exoskeleton having four arms 16a that wrap partially around the inflatable member and are spaced equidistantly apart by 90 degrees and joined together at the surface 10p of device 10. As the inflatable member is expanded/inflated, the flexure of skeleton 16 causes a directed expansion, and thus assertion of force by the inflatable member in the direction toward the stomach 120 via surface 10a. Alternatively, arms 16a can be formed of an elastic material and are deformed as device is anchored against an internal structure, such as when device is anchored against the diaphragm and ribs (described in more detail below). In this case, the flexure is caused by anchoring against the internal structure. Should device 10 become detached from its anchoring and migrate, in this example, flexible arms straighten out (as illustrated in FIG. 15B) and this prevents further migration of the device 10. FIG. 16A shows a variation in which skeleton 16 has only a pair of opposite arms 116a. This structure can be made from any of the materials as described above with regard to FIG. 15A. FIG. 16B shows an example of a migration prevention feature provided when the arms 16a of the device of FIG. 16A are formed to be elastically biased to the straight configuration, and when arms 16a are not constrained, such as when device is dislodged from its anchored position.

Figure 17:
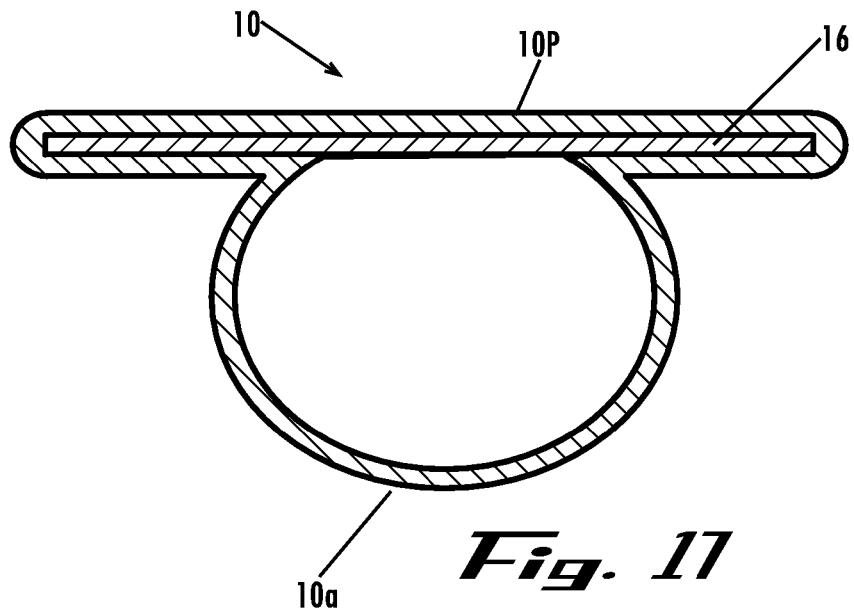
FIG. 17 is a cross sectional illustration of a device having a reinforcing element molded therein.

FIG. 17 is a cross sectional illustration of a device 10 having a reinforcing element 16 molded therein. Reinforcing element 16 in this example is a substantially planar "endoskeleton" and, when anchored to an internal structure broadens the base of attachment of the device, rendering the device more stable its position and also spreading the expansion forces over a larger area of the internal structure to which the device is fixed, over surface 10p, while concentrating expansion forces to the stomach via surface 10a. Reinforcing element 16 can be formed of any of the materials described above, typically metal or substantially rigid polymer.

Figure 18:
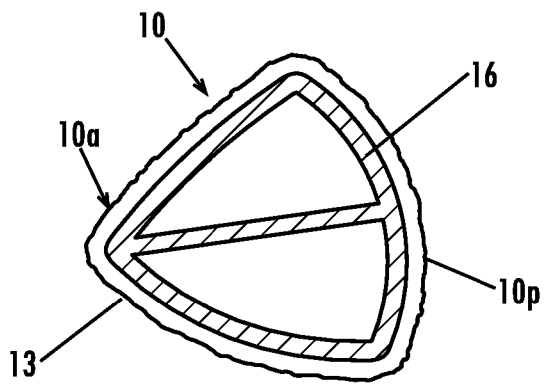
FIG. 18 illustrates an inflatable device having an endoskeleton.

FIG. 18 illustrates another embodiment of an inflatable device 10 with an endoskeleton 16. In this embodiment, endoskeleton 16 defines the entire framework for the shape of the inflatable member, thereby maintaining the designed surface shape of both surfaces 10a and 10p.

Figure 19A:
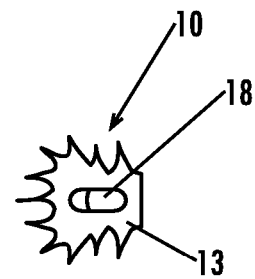
FIG. 19A illustrates a self-inflatable device in a deflated configuration.
Figure 19B:
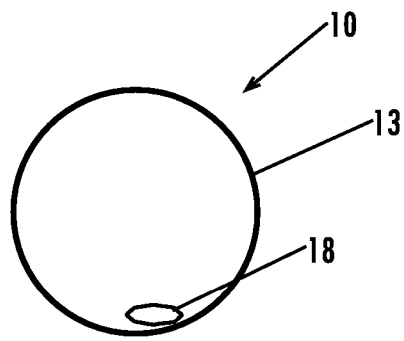
FIG. 19B illustrates the device of FIG. 19A after self-inflating.

Inflatable devices 10 can be inflated via a conduit 12 connecting device 10 with a source of inflation medium located outside of the patient, as described in more detail below. Alternatively, device 10 can be configured to be self inflate such as by initiating a chemical reaction within device 10 to produce pressurized gas and expand the device, once the device has been properly implanted in an intended location. FIG. 19A illustrates an inflatable device formed from a non-compliant material (a device having a compliant inflatable member or semi-compliant inflatable member can also be used, and a compliant inflatable member may not have folds in it in the deflated configuration) in a deflated configuration and containing capsule 118. Once device 10 has been properly implanted, anchored and positioned as desired, capsule 18 is squeezed, crushed, or otherwise deformed, using graspers, or other similar surgical instrument. This deformation increases the pressure within capsule 18, causing a membrane separating reactants in the capsule to rupture, at which time the chemical reactants react with one another to generate pressurized fluid. For example, the reactants can combine to generate a chemical reaction that creates gas as an end product. Combining an acid and a base will produce a gas to inflate device 10. One such combination to produce $CO_2$ is acetic acid and bicarbonate of soda. The amounts of chemicals contained in capsule 18 can be predetermined to generate an amount of gas sufficient to inflate device 10 to a predetermined pressure, as illustrated alter completion of the chemical reaction in FIG. 19B.

Figure 20A:
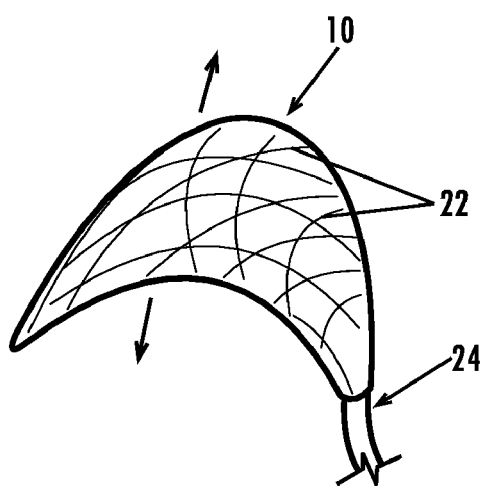
FIG. 20A shows a self expanding device comprising a self-expanding body formed of intersecting resilient structural elements.
Figure 20B:
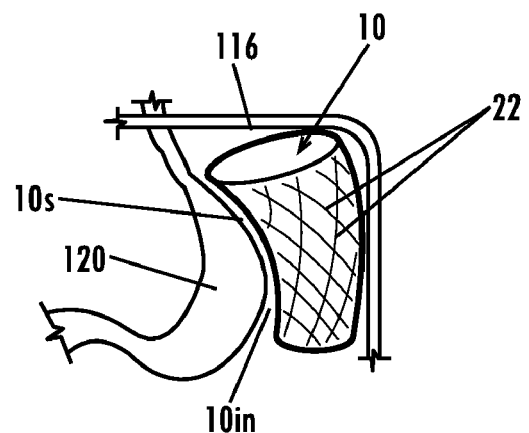
FIG. 20B illustrates another example of a self-expanding device comprising intersecting struts, wherein the device has been positioned between the diaphragm and stomach and expanded against the stomach.

As an alternative to inflatable members, expandable devices are provided that are expanded via a mechanically expandable mechanism. For example, FIG. 20A shows self expanding device 10 comprising a self-expanding body formed of intersecting resilient structural elements (in this case, struts) 22 that can be made of a resilient steel such as spring steel, nickel-titanium alloy, titanium or other biocompatible, resilient metal, or resilient biocompatible polymer, for example. Device 10 is collapsible to a compressed configuration so as to be deliverable through a sheath 24 to a target site where device is to be expanded and positioned for implantation. Device 10 is biased toward the expanded configuration, so that upon being ejected from sheath 24, device 10 self expands to the expanded configuration, in the directions of the arrows shown in FIG. 20A. Device 10 can be optionally covered with an elastic membrane 26 to prevent adhesions or ingrowth into the lattice of struts forming the expandable cage or basket. Implantation of device 10 is reversible, as device 10 can be collapsed by drawing it back into sheath 24 in a subsequent procedure to remove the device, as tension of the device and drawing it into the opening of the sheath will cause struts to move back into the contracted configuration. FIG. 20B illustrates another example of a self-expanding device 10 comprising intersecting struts 22, wherein the device has been positioned between the diaphragm 116 and stomach 120 and expanded against the stomach to deform the fundus inwardly. The device 10 of FIG. 20B is in the form of a basket and expands anisotropically, so as to expand more at the superior portion 10s of surface 10a than at the inferior portion 10i, to focus the deformation on the fundus portion of the stomach. It should be noted that any of the mechanically expanding embodiments discussed herein can be shaped to take on a variety of expanded conformations, including any of those discussed above with regard to the inflatable devices.

FIG. 21A illustrates a mechanically expandable device 10 that includes expandable coils 22 routed through loops 28 that are fixed to membrane 26. The non-expanded shape of membrane 26 may function to guide the overall expanded shape of device 10. Membrane 26 can be made from a compliant material, such as an elastomer, or from a semi-compliant or noncompliant material, or from some combination of these three classes of materials. Membrane 26 can include reinforcing structure at the locations where loops 28 are affixed thereto. After device 10 is positioned where it is desired to implant the device, a wire (which can be partially inserted prior to delivering the device into the abdominal cavity, including threading the wire though some or all of loops 22), is advanced into membrane 26 to expand the diameter of coils 22, thereby expanding the device into its expanded conformation. The wire forming the loops can be entirely received within membrane 26 in order to complete the implantation. Alternatively a small portion of the wire can be left extending from membrane 26 and a locking mechanism 30 (shown in phantom), such as a clamp, or other alternative locking mechanism, can be provided to maintain the desired orientation and size of the coils 22 within membrane 26. With this option, locking mechanism 30 can be temporarily unlocked to adjust the amount of expansion of device 10 (such as by varying the relative diameters of loops 22) by advancing more of the wire into the membrane 26 to expand the device 10, or alternatively, by withdrawing more of the wire out of membrane 26 to decrease the size of device 10. This feature may be utilized initially during implantation of the device, or later on, in a follow up procedure to adjust the size of the device. Further alternatively, the wire can be extended out through the patient, where locking mechanism 30 can be provided on an access device implanted subcutaneously in the patient (as described below) or even fixed externally to the epidermis of the patient.

Implantation of device 10 is reversible, as the wire can be drawn back out through loops 28, thereby, removing the wire, or at least reducing the diameter of coils 22 to a small enough dimension to remove the device 10 though a sheath, cannula or other guide structure via a port or other small opening. FIG. 21B illustrates a device 10 of the type described with regard to FIG. 21A, having been implanted between the diaphragm 116 and stomach 120 and expanded to deform the wall of the stomach 120 over substantially the full length of the stomach 120, reducing the internal cavity 123 within the stomach 120 to a small tubular like structure, roughly, banana-shaped to produce the same affect as a sleeve gastrectomy, but without any cutting into the stomach being required. Although shown as only one device 10 having been implanted, it should be noted here that a plurality of devices 10 may be implanted to accomplish a similar compression of the stomach. A single device 10 of complex shape can be provided to accomplish varying amounts or distances of displacement of the stomach at different locations as noted. A single device (whether complex or simple shape) may be best for procedures involving only a single entry location or opening, such as percutaneous procedures. It may be further advantageous to provide such single devices with shapes that need little anchoring and are easily positioned, as this further simplifies the procedure.

FIG. 22 illustrates another variation of a mechanically expandable device comprising substantially parallel struts 22 that are fixed at proximal and distal ends 10e of device 10. Struts 22 can be formed from any of the materials described above for members 22 of the devices of FIGS. 20A-21B, and are resiliently biased to the expanded configuration shown in FIG. 22 (in this case, a substantially, spherical configuration) but are collapsible under force to reduce the size of the device for passing it through a port or other small opening in the patient. Device 10 can be optionally covered with a membrane to prevent adhesions or ingrowth into the device between struts 22. FIG. 22 illustrates self-expanding device 10 having been positioned between the diaphragm 116 and stomach 120 and expanded against the stomach to deform the stomach wall inwardly.

FIG. 23 illustrates a compound expandable device 10 having been positioned between the diaphragm 116 and stomach 120 and expanded against the stomach to deform the stomach wall inwardly. In this example, device 10 includes a mechanically expandable portion 10m (shown as intersecting struts 22, although other mechanically expandable configurations, such as those described, can be substituted) with one or more inflatable portions 10inf connected thereto. In the example shown inflatable members 10inf are attached to form surface 10a, and can be independently inflatable, or fluidly connected so as to be inflated through the same inflation lumen. Upon inserting device 10, the mechanically expanding portion 10m is first allowed to self expand, after which, the inflatable portion(s) can be adjustably inflated to produce additional deformation of the stomach, as well as to provide a softer interface between the stomach wall and device 10.

FIG. 24 illustrates another variation of a mechanically expandable device 10. Device 10 includes expandable rings 22 that are mounted substantially parallel to one another through guide tube 32. Rings 22 can be made from any of the materials described above with regard to FIG. 19A, and are resiliently biased to the expanded configuration shown in FIG. 23. However, rings 22 can be deformed to a much smaller cross-sectional configuration, b, "flattening" them against the guide tube 32, as well as by squeezing them to ovaloid shapes in directions perpendicular to guide tube 32. In this regard, device 10 (with or without a membrane 26 enclosure) can be maintained in compressed configuration by a sheath (not shown) for deliver, through a port or other small opening in the patient and advancement to a target location where device 10 is to be positioned. Upon removing the sheath, device 10 then self-expands to the configuration shown in FIG. 24. Alternatively, when device 10 is enclosed by membrane 26 as shown, membrane 26 can optionally be in fluid communication with an external source of vacuum via tube 12 (or, further optionally, through tube 32). In this case, device 10 can be compressed to a small cross-section, compressed configuration by drawing a vacuum on membrane 26. Additionally, rings 22 can be optionally folded by mechanical means (including by hand) against tube 32 and/or compressed into the ovaloid shapes to assist the compression of the device by applying vacuum to membrane 26. Any way, once in the compressed configuration, the maintenance of vacuum within membrane 26 is sufficient to maintain rings 22 in the compressed configuration. By removing the vacuum on membrane 26, rings 22 can self-expand as being biased to the expanded configuration. Additionally, membrane 26 can be pressurized via the same channel used to draw vacuum on the membrane to compress device 10. Pressurization may be temporary, to assist the expansion of device 10, or may be maintained (such as by a pressure valve in an access mechanism discussed below) to assist in providing pressure against the stomach wall and/or to provide a softer interface between device 10 and the stomach tall.

When in the compressed configuration, device 10 can then be inserted through a port or other small opening by sliding tube 32 over a guidewire having been installed to lead to the target surgical area, for example. Once properly positioned and expanded, the guidewire can be withdrawn, leaving device in its intended position. Implantation of device 10 is reversible, as device 10 can be collapsed by drawing vacuum on the membrane 26. Alternatively, rings 22 can be individually removed from within device 10 to reverse the implantation procedure.

Figure 25:
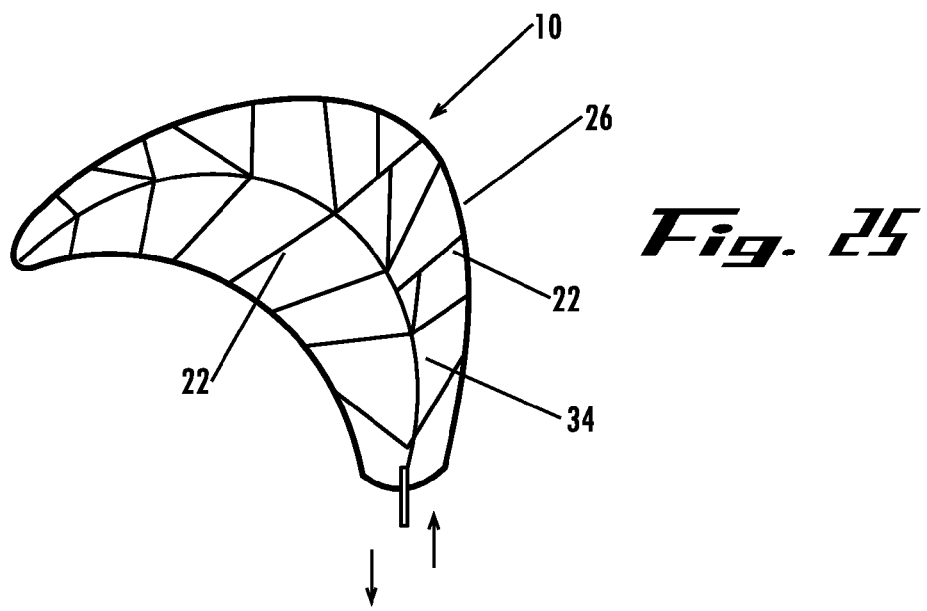
FIG. 25 illustrates another example of a mechanically expandable device.

FIG. 25 illustrates another example of a mechanically expandable device 10 which can be self-expanding, such as by biasing the struts 22 that extend from central spine 34 to the expanded configuration shown. Struts 22, in the expanded configuration, extend from spine 34 similar to the veins in a leaf. Struts 22 and spine 34 can be made from any of the same materials described above for making struts 22 in FIG. 20A. A membrane 26 can be provided to enclose struts 2 and spine 34. Spine 34 can be provided to extend proximally of membrane 26, such that when spine 34 is retracted in the proximal direction with respect to membrane 26 (in the direction of the down arrow shown in FIG. 25), struts 22 are biased inwardly toward spine 34, to a compressed configuration, useful for delivering the device from a location external of a patient to a surgical target site. Upon releasing tension on spine 34 (or advancing spine 34 relative to membrane 26 in the direction shown by the up arrow in FIG. 25), struts expand to the expanded configuration shown in FIG. 25. Implantation of device 10 is reversible, as device 10 can be collapsed by drawing spine 34 proximally, in a manner as described above.

Surface Features

The external surfaces of devices are designed to provide atraumatic, non-irritating interfaces with the internal structures in the abdominal cavity that are to be contacted. Surfaces 10a designed to interface with the stomach wall can be smooth and designed to reduce friction therewith. Similarly, surfaces 10p designed to abut another internal structure, such as the diaphragm, abdominal muscles, or other structure can be designed to be smooth and to reduce friction between the device surface and the internal structure. These smooth features, as with other surface features described herein, can be designed into the existing surfaces of the device, or can be provided by attaching an additional layer to a portion of the surface of the device where the feature is desired. For example, smooth, non-frictional surfaces can be provided by the surface of the balloon material of an inflatable device, or by polishing metallic struts of a mechanically expanding device and/or radiusing edges thereof. Alternatively, all or a portion of a surface can be coated with a low friction material, e.g., PTFE, hydrogels, covalently-bonded lubricant or jelly, etc., or can be modified so that the surface has a microporous, sponge-like quality able to microabsorb body fluids and thereby create a low friction surface. A porous polymeric layer can be coated over all or a portion of a device surface and impregnated with a lubricious material, such as hydrogels, for example.

Figure 26:
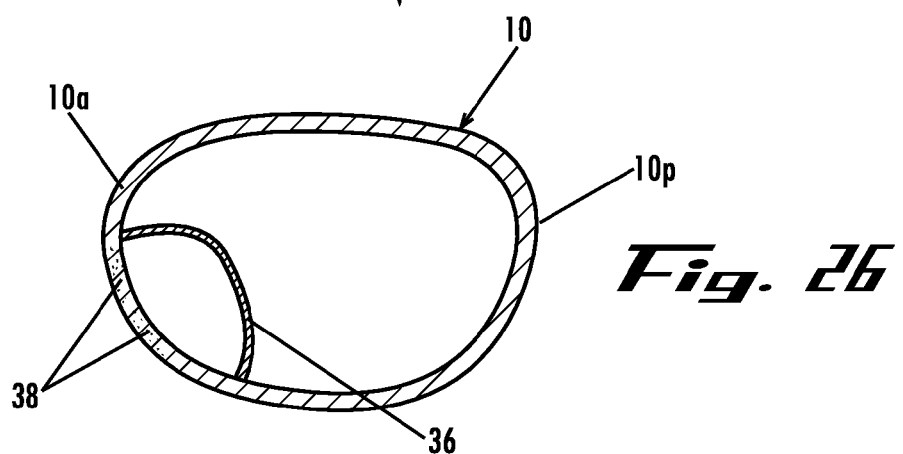
FIG. 26 illustrates a device provided with a reservoir.

In addition to providing a low friction surface, reduction of irritations and/or prevention of adhesions with hydrogels, linked surface polymers, or phosphorylcholine, other treatments can be provided by a treatment- or drug-eluting coating 40 over all or a portion of a device surface. Such a coating 40 can be impregnated with a substance to be diffused out of the coating over time, or can be provided with other known time-release mechanisms. Examples of substances that can be provided in such a coating include, but are not limited to: anti-obesity drugs, other drugs for treating co-morbidity that can be associated with the patient's obesity, antiproliferative drugs such as rapamycin, TAXOL®, MYCITAXOL®, or the like; heparin; anti-inflammation, drugs such as ibuprofen, acetaminophen or aspirin; steroidal anti-inflammatories such as fluticasone, mometasone, triamcinalone, prednisone, methylprednisone or the like; other non-steroidal anti-inflammatory drugs, and/or pain medications, such as lidocaine, bupivacaine, etc. Additionally, or alternatively, device 10 can be provided with a reservoir 36 (as illustrated in FIG. 26) to hold one or more of the treatment substances just described. Treatment substances can be delivered to the surface of device 10 through one or more pores or channels 38 via diffusion, or by an active drug delivery pump of a type currently known in the art, which can be configured for continuous or intermittent timed release of the substance.

Figure 27:
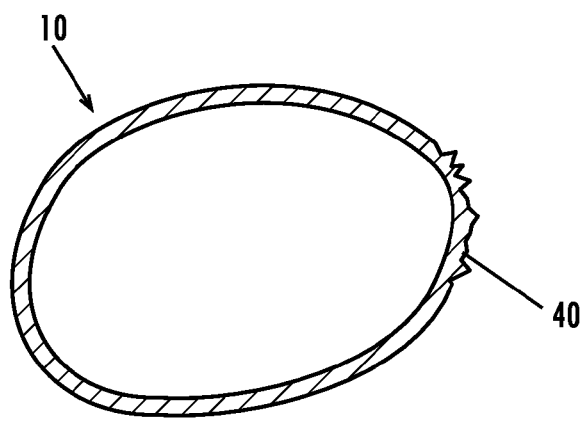
FIG. 27 illustrates a device having a roughened surface portion.
Figure 28:
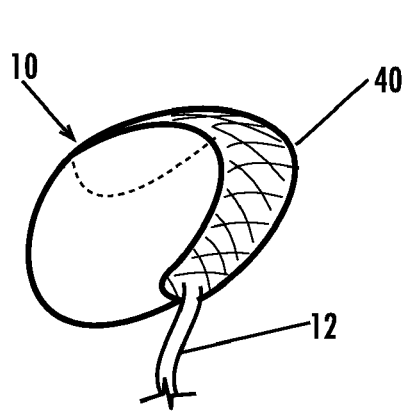
FIG. 28 shows an example of a device having a backing or patch to provide additional structural integrity to a portion of the device.

Referring to FIG. 27, one or more surface portions can be roughened, or made to have increased porosity, relative to the remainder of the surface, to increase friction when contacted with an internal structure to help prevent migration of device 10 and/or to promote a healing response and subsequent ingrowth of tissue into the roughened or porous surface to function as an anchor of the device, as also described below with regard to anchoring. Such roughened or increased porosity surface can be formed into the surface of inflatable device 10, as shown in FIG. 27, or can be formed by attaching an additional layer of material to the surface, such as a fiber-reinforced silicone patch, a patch of fiber-lined polyester, a patch of a material that is more porous than the porosity of the surface of the device, or other layer configured to provide the desired characteristics. In addition to providing a roughened, more porous, and/or drug eluting function, a backing or patch 40 can also provide additional structural integrity to a portion of device 10 to reduce the amount of expansion of that portion of the device relative to the remainder of the expandable body. FIG. 28 shows an example of this. Further, backings, patches or reinforcing layers 16,40 can be used to reinforce attachment of other structures to the expandable device, such as anchors for example, e.g., see FIG. 13A. One or more locations on the surface of a device 10 can also be configured to be radiopaque, as described in more detail below.

Anchoring

Figure 29:
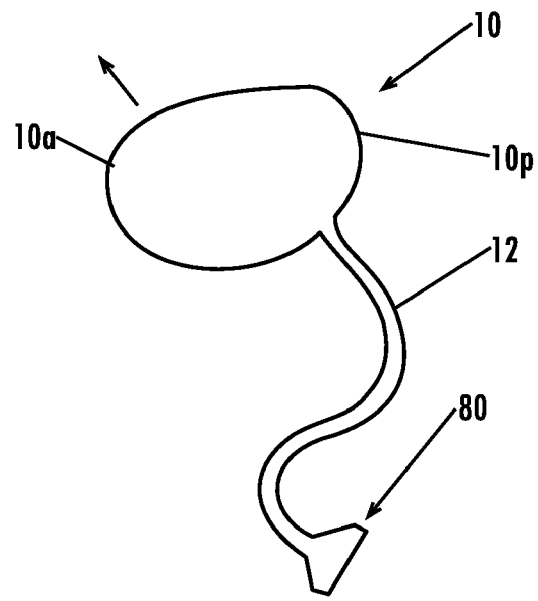
FIG. 29 illustrates a device and show an expandable member conduit and adjustment member of the device.

Although it mats be desirable to allow the stomach and other organs in the abdominal cavity to move relative to device 10, it is also desirable to anchor device 10 relative to at least one internal body structure to prevent migration of the positioning of device 10. FIG. 28 illustrates a device with the expandable member including surfaces 10a and 10p, and an adjustment member 80 (described in further detail below) including an inflation port, wherein adjustment member 80 is in fluid communication with the expandable member by conduit 12. Conduit 12 is typically flexible and can be made from any or the polymeric materials described above for making the inflatable, expandable member 10em. Typically silicone or reinforced silicone can be used. In any case, conduit 12 is constructed to be flexible and kink-resistant, and for connection to an inflatable, expandable member, to have low or no permeability to pressurized fluids to be used to inflate expandable member 10em. Further, conduit 12 is formed to have sufficient length to interconnect the expandable member with adjustment member 80 when the expandable member is positioned in a target surgical area within the abdominal cavity, adjacent the stomach and in an expanded configuration, and when adjustment member is positioned outside of the abdominal cavity, typically fixed to the abdominal muscles, externally of the abdominal cavity, or in some other subdermal location outside of the abdominal cavity. In these situations, anchoring of adjustment member to the abdominal wall or other location external of the abdominal cavity can prevent migration of the expandable member in a direction indicated by the arrow in FIG. 29, although this is typically not the case, since conduit 12 is not typically designed as a tether and is intended to be left slack when the expandable member is properly positioned and adjustment member is anchored. In any event, conduit 12 will not prevent migration of the expandable member in any other direction, including downwardly, which can be a direction that the expandable member can be urged to migrate by forces such as peristaltic activity of the stomach; gravity; etc. Accordingly, adjustment member 80 and conduit 12, in the arrangement described, without further fixation, do not provide an anchor. However, other arrangements are described herein where adjustment member and conduit can be arranged to anchor the expandable member 10em.

In order to prevent or minimize the potential of migration, it is desirable to anchor the expandable member in at least one location to an internal structure in the abdominal cavity. Anchoring techniques described below can be carried out by themselves, or in combination with one or more other anchoring techniques described. As noted above, one way of providing an anchor is to provide a roughened surface or surface of increased porosity to increase friction between the expandable member and the internal structure it is contacting and/or to promote tissue ingrowth. Additionally or alternatively, adhesives can be applied to one or more surfaces of the expandable member of device 10 to be fixed to one or more internal structures. Additionally or alternatively, adhesives can be applied to the surface(s) of the internal structure(s) where contact by the device is to be made for anchoring device 10 thereto. Adhesives can be applied to such structures via a conduit inserted into the abdominal cavity from a location external of the patient, wherein adhesives can be flowed or sprayed onto such structures.

Figure 30:
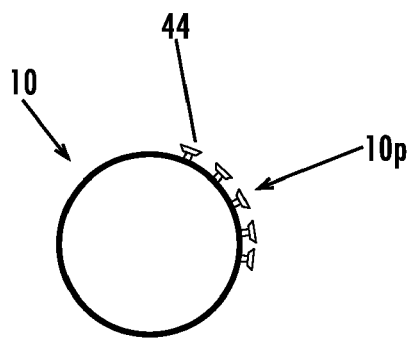
FIG. 30 illustrates an expandable member having suction members on the surface thereof.

Another anchoring mechanism can be provided by placement of one or more suction members 44 on the surface of the expandable member of device 10 (an example of which is shown in FIG. 30). Alternatively, one or more suction members 44 can be fixed to the internal structure (such as by suturing, hooks, adhesive, etc.) to which the expandable member is to be anchored. In the example shown in FIG. 30, suction members 44 are suction cups, although other configurations of suction producing features can be substituted as suction members (e.g., members having elongated suction chambers, etc.).

Figure 31A:
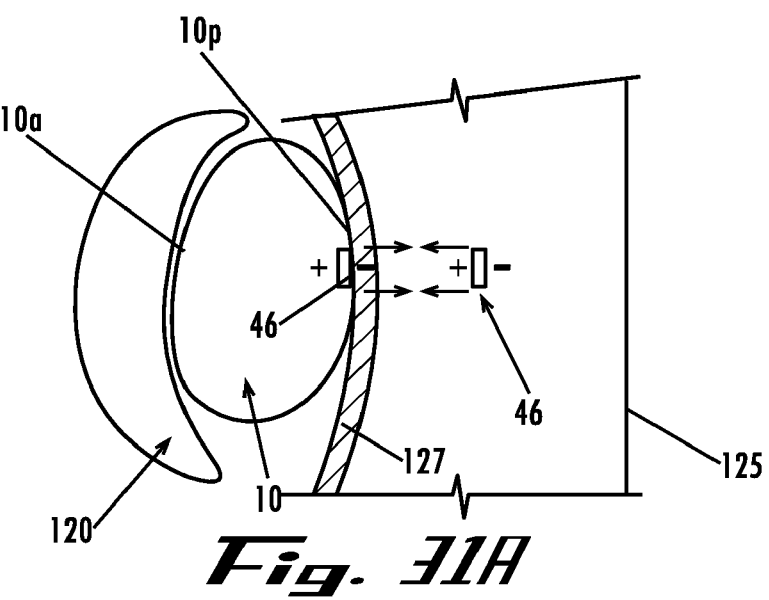
FIG. 31A illustrates that anchoring can be performed using one or more pairs of magnets oriented to attract to one another.

FIG. 31A illustrates that anchoring can be performed using one or more pairs of magnets 46 oriented to attract to one another. In the example shown in FIG. 31A device 10 is anchored to an internal surface of the abdominal wall or abdominal muscle by fixing a first magnet to surface 10p of the expandable member of device 10, while fixing another magnet 46 subcutaneously in a position to align with the other magnet 10 at a location where surface 10p is desired to be anchored, and with opposite poles of the magnets 46 facing each other. It will be readily understood that more than one pair of magnets can be arranged to establish the anchoring. The magnets can be fixed by adhesives, suturing, or other alternative fixing means. When the expandable member includes a polymeric surface, magnet(s) 46 can be molded into the polymeric wall of the expandable member, or fixed to the internal surface of the polymeric wall. Further alternatively, the magnet(s) 46 opposing the magnet(s) 46 on the expandable member can be fixed to the opposite wall of the structure (i.e., outside of the abdominal cavity) to which device 10 is to be anchored (e.g., the external wall of the abdominal muscle in this example), embedded within the internal structure to be anchored to, or fixed to the skin, on the internal side of the skin layer.

Further alternatively or additionally surface 10*a* of device 10 can be anchored to the stomach wall using one or more pairs of magnets 46, as illustrated in FIG. 31B. Magnet(s) can be attached to the stomach wall either on an internal surface of the wall, external surface of the wall, or embedded between layers of the wall. Magnet(s) 46 can be fixed to the wall of device including surface 10*a* in any of the manners described above with regard to attaching magnet(s) to the wall of device 10 that includes surface 10*p*.

The conduit 12 interconnecting the expandable member and adjustment member 80 of device 10 can be configured to anchor the expandable member to an internal structure. In the example illustrated in FIG. 32A, the expandable member of device 10 is anchored against the internal surface of the abdominal musculature 127 or peritoneum, by fixing conduit 12 at the external surface of the abdominal muscles, where it passes through, conduit 12 can be provided with a collar or suture ring to suture the conduit at this location, or provided with other fixation features as described below. Conduit 12 can be reinforced, especially in the location between the proximal fixation to the location external of the abdominal cavity and the expandable member, to withstand being maintained under tensile forces to anchor the expandable member. Reinforcements can include fiber reinforcement, steel or polymer meshes or coils, etc. In FIG. 32A, adjustment member is fixed subcutaneously, in the subcutaneous fat 126, or alternatively to a subdermal layer of the skin. Alternatively, adjustment member 80 can be placed just proximally of the fixation of conduit 12 to the abdominal wall and may not require further fixation in this instance.

Further alternatively, the expandable member of device 10 can be anchored to one or more internal structures by one or more conduits, rods, tethers, or other elongated structure designed to support a sustained tensile force to maintain one or more surfaces of the expandable member anchored against one or more internal structures. FIG. 32B illustrates a device having been positioned and expanded between the diaphragm 116 and the stomach 120. Anchoring member (in this example, a conduit) 50 is fixed to surface 10*p* of the expandable member and extends through the diaphragm 116, where it is fixed against the external surface of the diaphragm 116 by suturing or other fixation techniques described herein. Additionally, in this example, conduit 12 passes through another location of the abdominal musculature and is not configured to anchor the expandable member, but fluidly connects the expandable member with adjustment member 80 which is fixed to an external surface of the abdominal musculature or otherwise subcutaneously.

Figure 33:
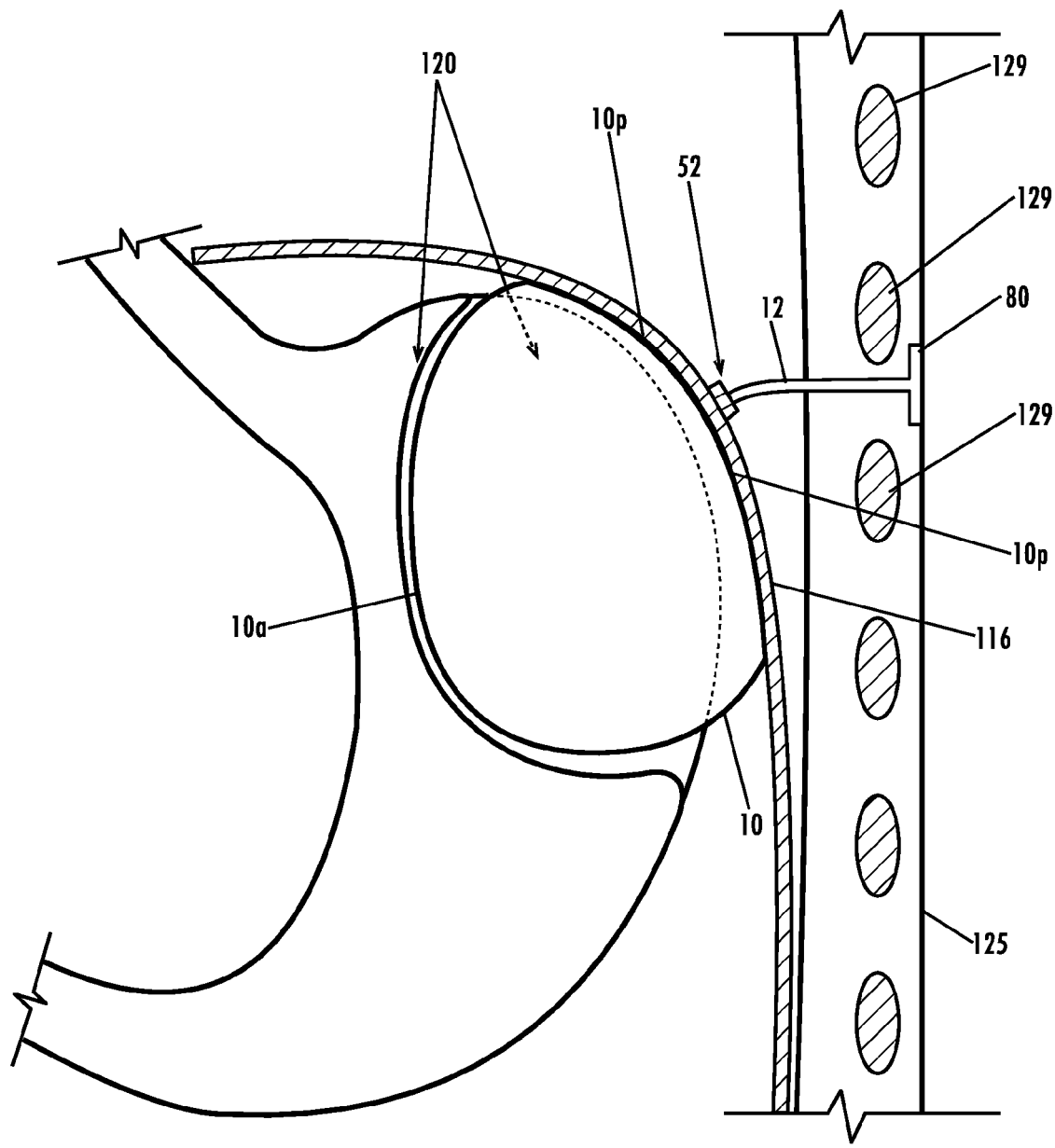
FIG. 33 shows another example of utilizing the conduit that extends from the expandable member to anchor the expandable member of the device to a structure inside the abdominal cavity.

FIG. 33 shows another example of utilizing conduit 12 to anchor the expandable member of device 10 to a structure inside the abdominal cavity. In this example, device 10 is positioned between the diaphragm 116 and stomach 120 and expanded to press inwardly on the stomach 120, including, the fundus portion of the stomach. The solid line shows the stomach wall as depressed by the expanded device 10, and the dotted line shows the natural position of the stomach wall 120, prior to placement and expansion of device 10. Although the deformed stomach wall 120 and the surface 10*a* are shown with a slight space therebetween in this and other figs. in this disclosure, this is done for clarification to more easily identify the interfacing walls of the stomach and device. Actually, surface 40*a* is, of course, pressed against the outer surface of the stomach wall 120. Conduit 12 is passed through the diaphragm 116, and by drawing on conduit 12, surface lop can be abutted against the inner wall of the diaphragm 116, as shown. Conduit 12 can be provided with threading around an external surface thereof, at least in the region where anchoring is to be performed, and a plastic or metallic stop member 52 (e.g., "nut") having mating threads can be threadably adjusted over the threaded portion of conduit 12 to anchor the expandable member against the diaphragm 116. Stop member 116 can be adjusted by tightening or loosening via the threads, to increase or decrease the force with which the expandable member contacts the inner wall of the diaphragm 116. Other anchoring arrangements can be substituted for the nut and threading anchoring mechanism, as described herein. The portion of conduit 12 that is proximal to slop member 52 need not be held under tension, thereby reducing the possibility of anchoring problems with adjustment member 80. Adjustment member 80 can be anchored subcutaneously in any of the manners described herein, as conduit 12 can be passed between ribs 129 to connect adjustment member 80 with the expandable member of device 10. When the expandable device is an inflatable device, such as is shown in FIG. 33, adjustment member contains a valve to allow pressurized fluid to be inputted or outputted therefrom to increase or reduce pressure in the expandable member, respectively. For mechanically expandable members, adjustment member can include a wire or other control mechanism for adjusting the amount of expansion of the expandable member in any of the manners described herein.

Figure 34A:
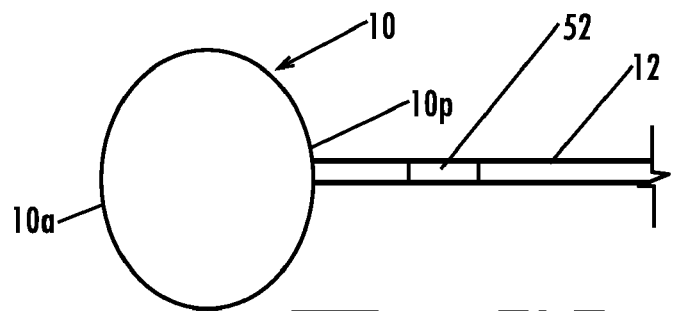
FIGS. 34A-34B illustrate another anchoring arrangement for anchoring an expandable member of a device to an internal structure in the abdominal cavity.
Figure 34B:
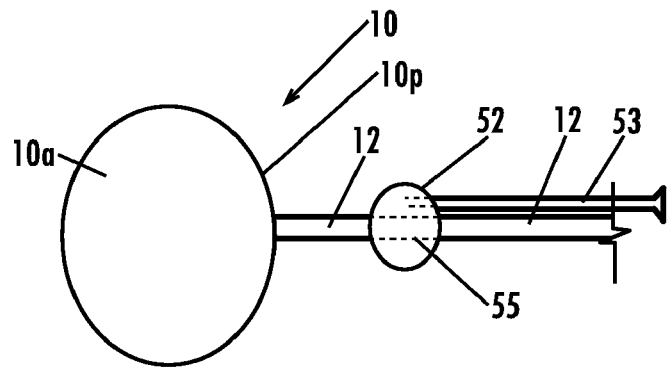

FIGS. 34A-34B illustrate another anchoring arrangement for anchoring an expandable member of device 10 to an internal structure in the abdominal cavity. In this arrangement, an expandable stop member 52 is provided, to anchor a surface of the expandable member against an internal structure, such as the internal wall of the diaphragm, in a similar manner to that described with regard to FIG. 33, or to the internal wall of the abdominal wall, or peritoneum, or other internal structure. Rather than a threaded nut stop member 52 in this instance, is inflated, after being passed through a wall of the structure that device 10 is to be anchored to. Upon inflating stop member 52, it expands to have a cross-sectional dimension that is incapable of passing back through the opening in the wall of the structure, thereby anchoring a surface of the expandable member against an internal wall of the structure. A lumen 53 can be provided to inflate stop member 52, and lumen 53 can run internally of conduit 12. Additionally, a conduit that connects adjustment member (not shown) to the expandable member of device 10 passes through expandable stop member 52, as shown in phantom lines.

Figure 35:
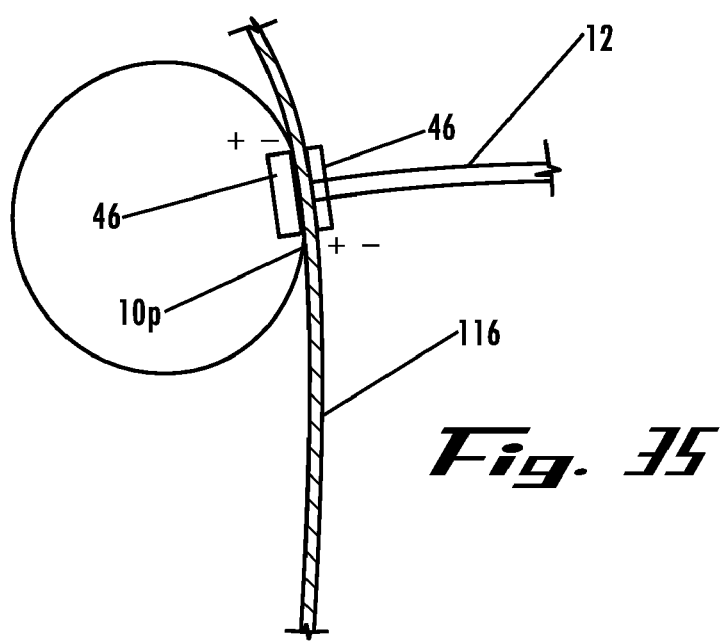
FIG. 35 shows another variant of an anchoring arrangement in which magnets are arranged to anchor a surface of the expandable member to the internal surface of the diaphragm.

FIG. 35 shows another variant of an anchoring arrangement in which magnets 46 are arranged to anchor surface 10*p* of the expandable member to the internal surface of the diaphragm 116. The magnet 46 fixed to the expandable device can be fixed by any of the techniques described above. The magnet 46 that is drawn, by magnetic attraction, to the outer surface of the diaphragm can be slidable over conduit 12. This magnet can optionally be additionally fixed by suturing or adhering it to the external wall of the diaphragm, for example.

Figure 36:
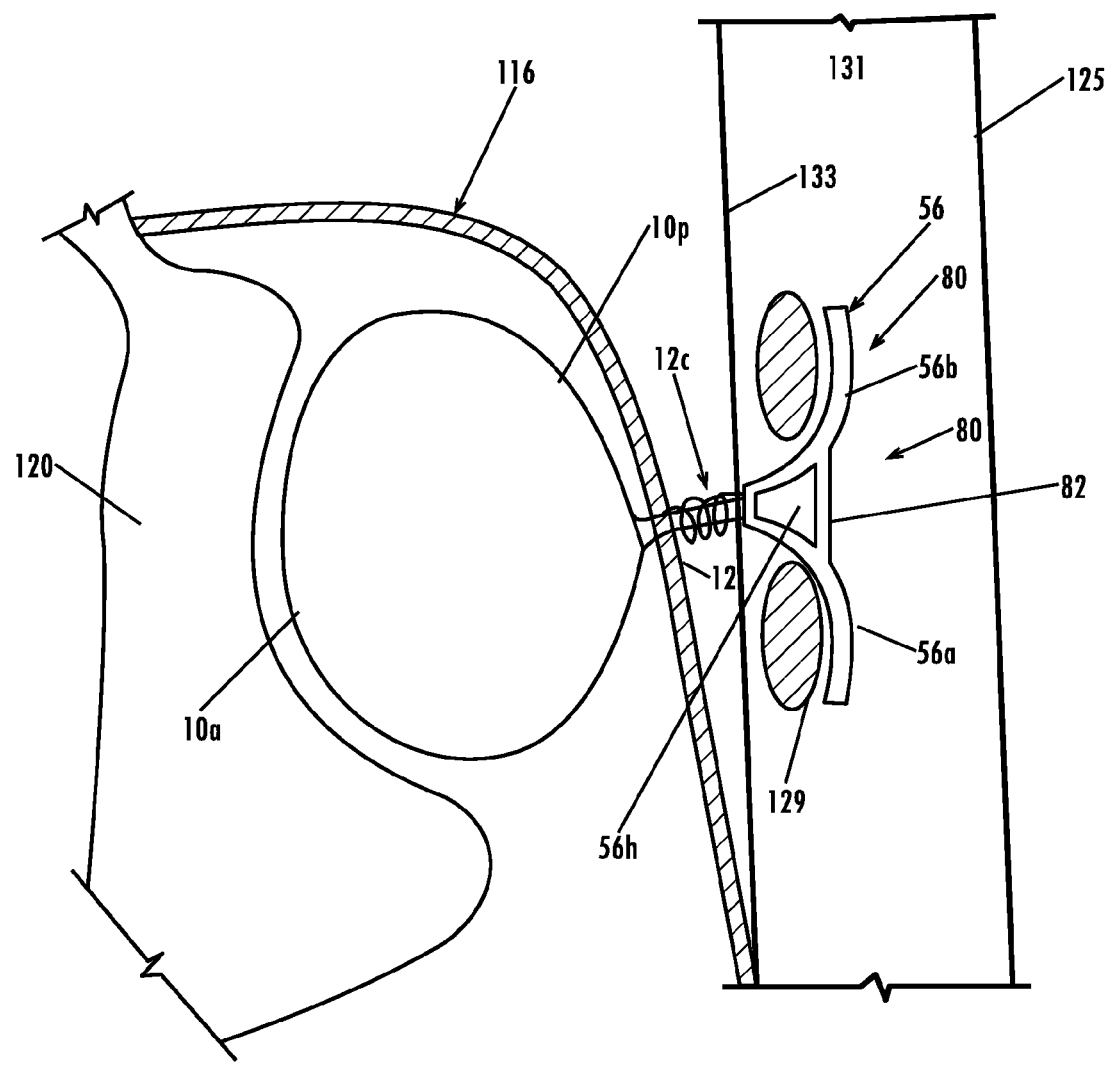
FIG. 36 illustrates a low profile adjustment member that also functions as a stop member used to anchor a surface of the expandable member of the device against an internal structure in the abdominal cavity.

FIG. 36 illustrates a low profile adjustment member 80 that also functions as stop member 56 used to anchor a surface of the expandable member of device 10 against an internal structure in the abdominal cavity. Stop member and adjustment member 56,80 includes wings 56*a* and 56*b* configured to follow the contour of adjacent ribs between which conduit 12 or a tether, connected to the expandable member, is passed. For example, wings 56a,56b can be curved to generally follow the contour of the ribs 129. In the example shown in FIG. 36, device 10 is positioned between the diaphragm 116 and stomach 120 and expanded to press inwardly on the stomach wall via surface 10a and to abut the internal surface of the diaphragm 116 via surface 10p. In this example, conduit 12 is provided and is passed though an opening in the diaphragm, through the pleural space 131 and the chest wall 133, wherein it is connected to stop member 56. Conduit 12 can be coiled 12c to prevent or reduce the risk of shearing, in the location shown. Stop member 56 includes a rigid tapered housing 56h (which can be metal or rigid polymer and can be conical in shape) configured to be inserted between adjacent ribs 129, as wings 56a,56b abut against the external surfaces of the adjacent ribs 129 (or tissue overlying the ribs). In the embodiment shown, the expandable member is an inflatable member and conduit 12 fluidly connects the expandable member with adjustment member 80 that is integrated with stop member 56. An elastomeric seal 82 can be provided for repeated entry into adjustment member and the valve (not shown) contained therein, to inflate or remove pressurized fluid from the expandable member. Although it is possible to use elastomeric seal 82 (e.g., which can be made of elastomeric and/or gel material that reseals itself after a needle puncture) only for flow control through conduit 12 and thus into and out of expandable member 10em, typically an additional mechanically operated valve is included in the flow path for such control, with elastomeric seal 82 acting as a backup safety valve and also preventing other substances from entering adjustment member 80. The additional valve can be actuated by, docking an input mechanism (such as a needle, or the like) with adjustment member 80. Alternatively, a two-way, pressure activated valve can be installed that allows flow therethrough (either input or output) only when a predetermined pressure gradient across the valve has been met or exceeded. The predetermined pressure gradient value can be different in the input direction than in the output direction. For mechanically expandable members, adjustment member can include a wire or other control mechanism for adjusting the amount of expansion of the expandable member. In any case, stop member can be fixed to conduit 12, (or a tether, or other slender elongated structure designed to maintain tension between stop member 56 and the expandable member of device 10). Conduit 12 can be additionally anchored at the location of the diaphragm using a nut, magnetic or other fixation mechanism described herein.

Figure 37A:
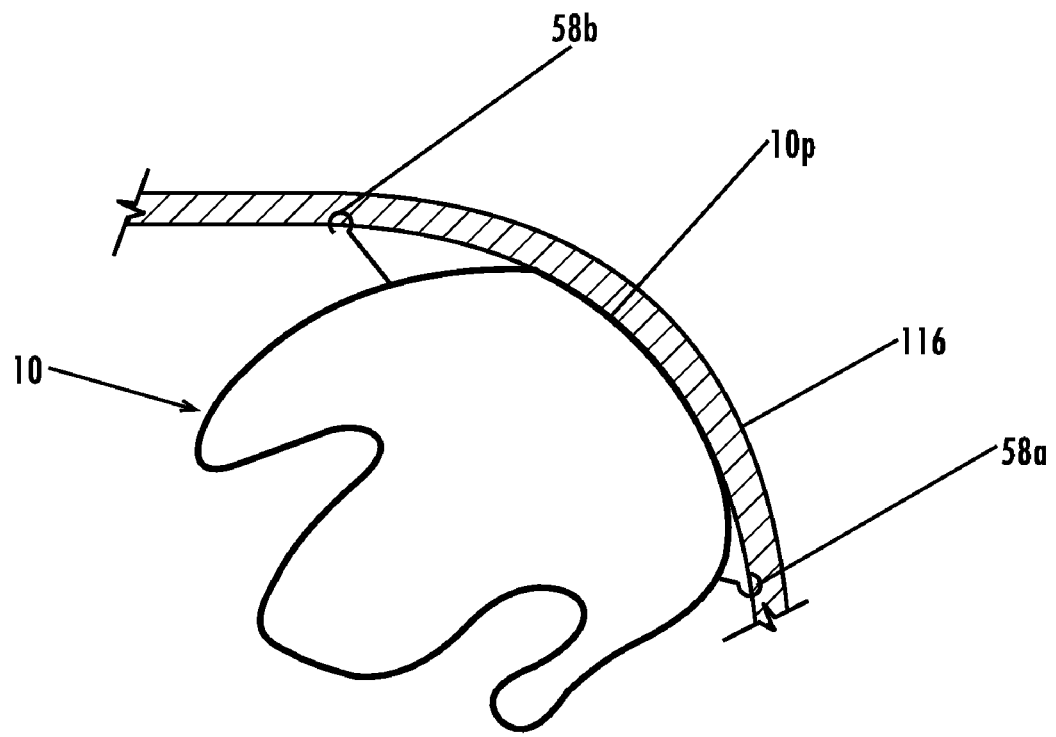
FIG. 37A shows an example in which the expandable member of a device is tethered to two locations on the internal surface of the wall of the diaphragm.
Figure 37B:
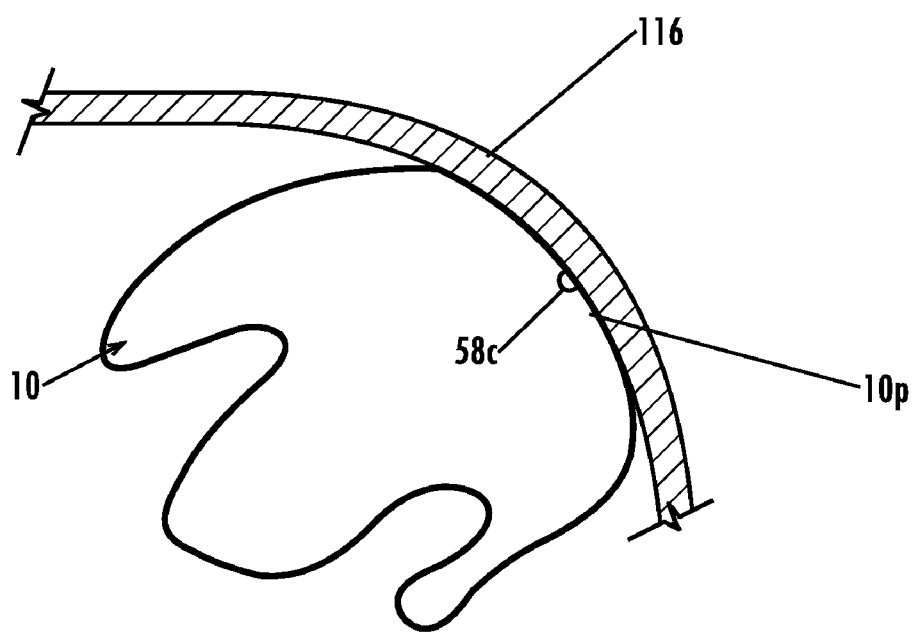
FIG. 37B illustrates that a surface of the expandable member can be fixed directly to the internal structure.
Figure 37C:
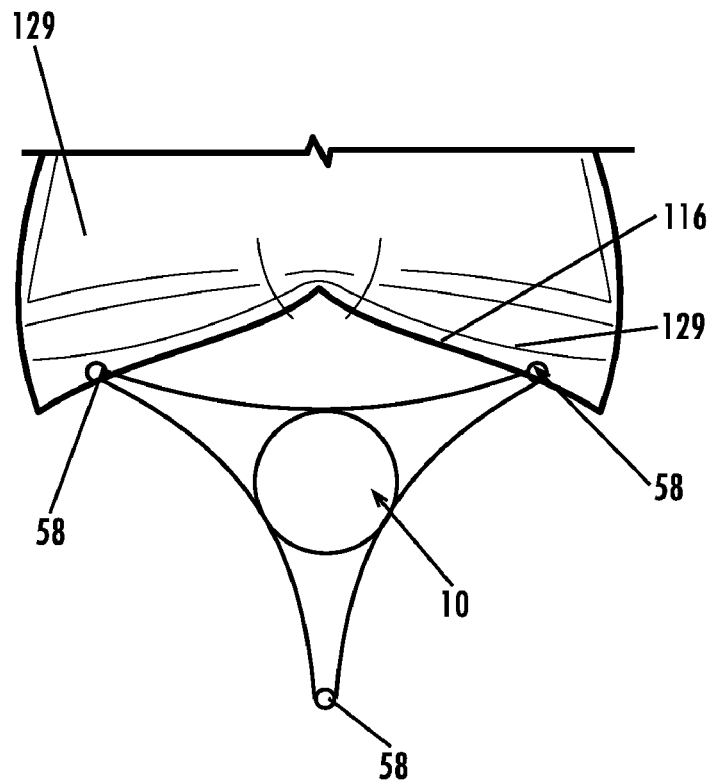
FIG. 37C illustrates an example where the expandable device is tethered to three anchor points, two on the internal wall of the diaphragm and/or ribs, and a third located inferiorly in the abdominal cavity, such as on the peritoneum or inner wall of the abdominal muscles.

The expandable member of device 10 can be fixed or tethered to an internal structure in the abdominal cavity without piercing through the structure or through a wall of the structure. FIG. 37A shows an example in which the expandable member of device 10 is tethered to two locations 58a, 58b on the internal surface of the wall of the diaphragm, such as by using sutures, wires or other tensioning members designed to be maintained under slight tension. There can even be a slight amount of slack in the tensioning members, as long as they substantially retain the device in its intended location where it is placed. Tensioning members maintain surface lop of the expandable member against the inner surface of the diaphragm. Alternatively, as shown in FIG. 37B, surface 10p can be fixed directly 58c to the internal structure, such as by suturing or other anchoring expedient as described herein. FIG. 37C illustrates an example where expandable device 10 is tethered to three anchor points, two on the internal wall of the diaphragm and/or ribs, and a third located inferiorly in the abdominal cavity, such as on the peritoneum or inner wall of the abdominal muscles. Tethers 59 are fixed to the expandable member, or are threaded therethrough in a manner as described below, and are fixed to the anchor points by tying, clipping or other fixation expedient. FIG. 8 illustrates features 60 that can be provided for routing one or more tethers therethrough. Features 60 in FIG. 8 are openings provided through the polymeric walls of the inflatable member 10, which are dimensioned to allow a tether to pass therethrough. These features can also be useful for delivering device 10 to the target surgical site via a tether or guidewire, as will be discussed in more detail below. Such openings can also be formed in the structural elements of mechanically expanding devices to accomplish the same functions. Alternatively, loops 20 can extend from the external surface of the expandable member to allow one or more tethers to be passed therethrough.

Figure 38:
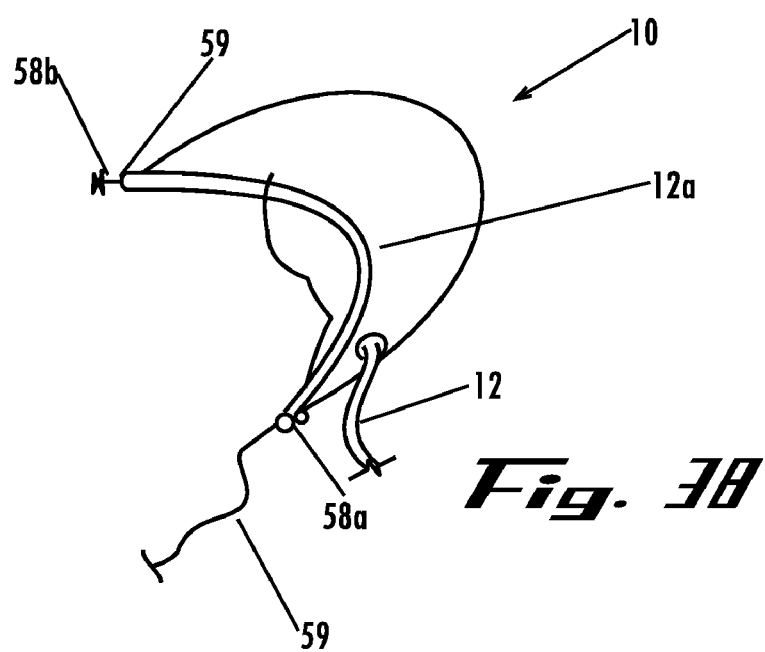
FIG. 38 illustrates an inflatable device in which a conduit extends through the inflatable device to allow a suture or tether to be passed therethrough.

FIG. 38 illustrates an inflatable device 10 in which a conduit 12a extends through the inflatable device to allow a suture or tether to be passed therethrough. A similar arrangement can be provided through a mechanically expanding device. Conduit 12a is sealed with the walls of the inflatable member at both ends where it enters and exits the inflatable member, to allow the inflatable member to seal and be inflated without losing pressure at these junctures. Note that a separate conduit 12 is provided for inflation of the inflatable member. The conduit 12 that passes through the expandable member can be used, with a tether, suture or guide wire passed therethrough, to deliver device 10 to a target surgical site and/or to anchor device 10 to two anchor points 58a,58b on one or more internal structures. The suture, tether or other tensioning member 59 can be cut off at the anchoring location 58a to complete the tethering procedure.

Figures 39A, 39B, 39C:
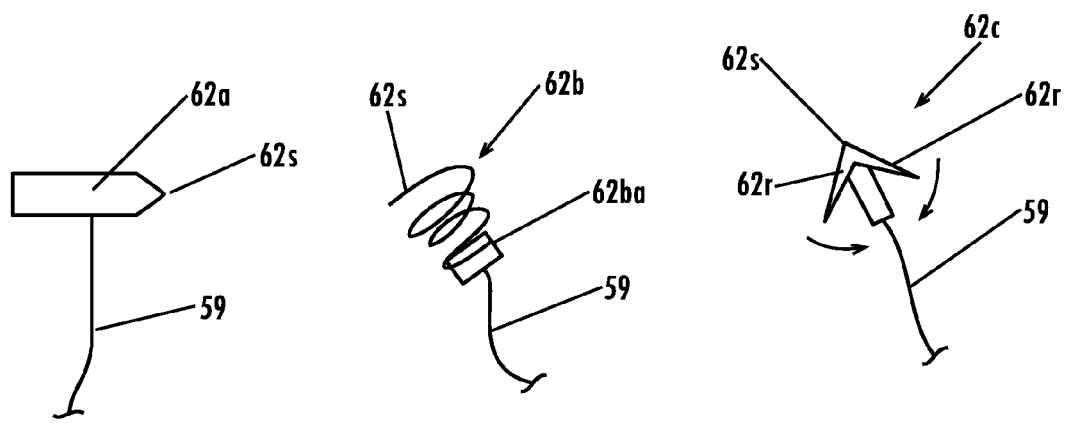
FIGS. 39A-39D show various embodiments of fixation structures that can be used to establish the anchoring of a suture, tether, wire, or other tensioning member when tethering or suturing a device to an internal structure.

A variety of different fixation structures 62 can be used to establish the anchoring of a suture, tether, wire, or other tensioning member when tethering or suturing device 10 to an internal structure, including, but not limited to the fixation structures illustrated in FIGS. 39A-39D. FIG. 39A shows a T-bar configuration 62a that can be affixed to a distal end of a suture, tether, or the like 59. T-bar 62a can be rotated relative to the tether or suture 59 to align its longitudinal axis with the longitudinal axis of the tether or suture 59 and so that the sharpened end 62a points distally away from the distal end of tether or suture 59. Upon inserting T-bar 62a through tissue of an internal structure, tether or suture 59 can then be withdrawn slightly proximally, whereupon T-bar 62a rotates to the substantially perpendicular configuration shows, thereby anchoring tether or suture 59 in the tissue of the structure.

FIG. 39B shows a coiled, or cork-screw type of fixation structure 62b that can be fixed to the end of tether or suture 59. If the tether, wire or other tensioning member 59 is torsionally rigid, then the tensioning member 59 can be turned from a proximal location to drive the coiled fixation structure 62b into the tissue of the structure to be anchored to. Otherwise, a tool can be used to engage the base 62ba of fixation structure to turn it into the tissue.

FIG. 39C illustrates a barbed fixation structure 62c provided with a sharpened or pointed distal end 62s. Barbs 62r are resiliently flexible, such that when the distal tip is driven into the tissue of the structure to be anchored to, barbs 62r deflect toward the main shaft of the structure 62c in the directions of the arrows shown. Upon passing through the surface layer of the tissue and into softer tissue, or upon passing through a wall of the structure, the tensioning member can be retracted slight proximally, whereupon barbs 62r extend outwardly in opposite directions, to resume the configuration shown in FIG. 39C, thereby opposing the retraction force and anchoring the tensioning member in the tissue.

Figure 39D:
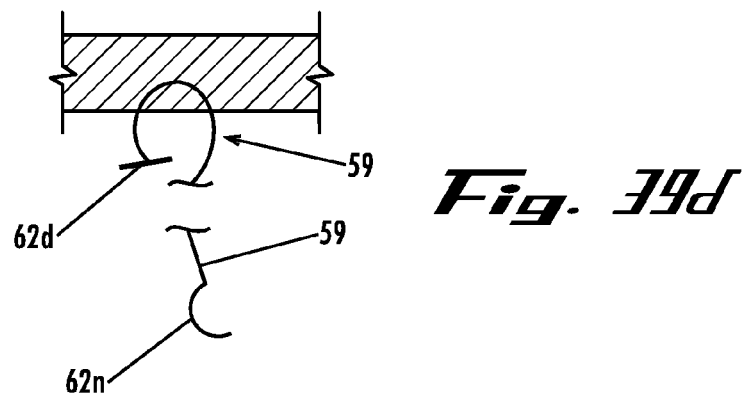

FIG. 39D illustrates a fixation structure 62d such as a pledget, block or other enlarged structure that functions to anchor the tensioning member. The other end of the tensioning member 59 can have a needle, or other sharpened, rigid structure 62n affixed thereto. To establish the anchor, needle 62n is passed through a portion of the tissue (or a wall) of the structure to be anchored to and directed back out of the tissue, on the same side of the tissue entered, as illustrated. Tensioning member 59 is then drawn through the pathway in the tissue established by needle 62n by drawing needle 62n proximally until enlarged member 62d abuts the surface of the tissue, preventing tensioning member 59 from being drawn further in that direction. The tensioning member can then be tied off to complete the anchor.

Figure 40:
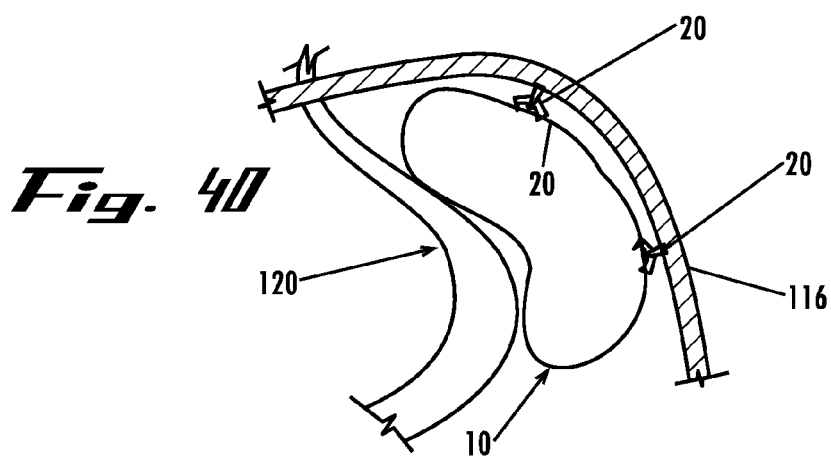
FIG. 40 illustrates a device anchored to an internal structure, wherein the internal structure has loops fixed thereto.
Figure 41:
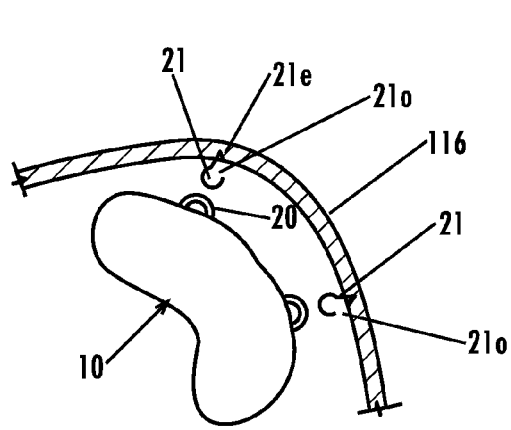
FIG. 41 illustrates a pair of hooks having been fixed on the internal wall of the diaphragm in locations spaced to engage loops on the device.

Alternative to or in addition to providing loops 20 on device 10 to be anchored to one or more internal structures, loops 20 can be fixed to one or more internal structures to be anchored to, as illustrated in FIG. 40. Loops 20 can be fixed to the internal structure by sutures and/or using fixation structures 62 as described above. FIG. 40 shows loops 20 fixed to device 10 which are sutured to loops 20 fixed to the internal surface of the diaphragm 116. Alternatively, one or more hooks 21 can be fixed to the internal structure to which device 10 is to be anchored. FIG. 41 illustrates a pair of hooks 21 having been fixed on the internal wall of the diaphragm 116 in locations spaced to engage loops 20 on device 10. One end 21e of hook 21 can be passed into the diaphragm wall to fix hook thereto, without passing entirely through the diaphragm wall, or alternatively end 21e can be passed entirely through the wall and then looped back into the tissue of the diaphragm 116. The other end of hook 21 forms a loop like configuration, with a slight opening 21o to receive loop 20 therethrough. Upon receiving loop 20, opening 21o can be pinched off to close the loop using graspers, or other tool to prevent loop 20 from escaping back out of the hook 21. Further alternatively, hooks 21 can be provided to extend from device 10, to engage loops fixed to an internal structure, or to be directly driven into the internal structure, in which case, the hooks can be barbed. Hooks 21 can be concealed from exposure until device 10 is delivered to a target surgical site and ready to be anchored, at which time, hooks can be revealed, such as by drawing them out from the device using graspers or other similar tool.

Figure 42:
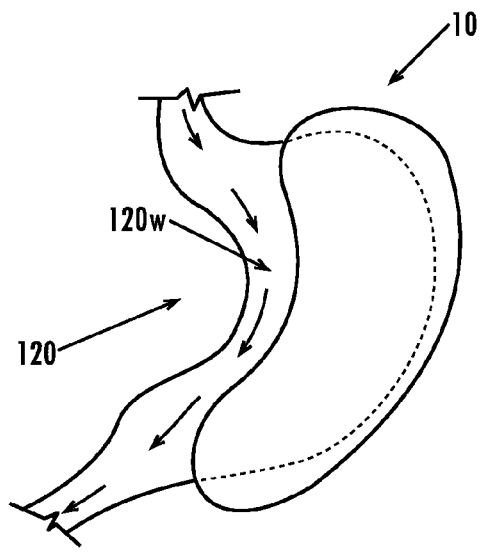
FIG. 42 shows an embodiment in which the device is shaped to match the curvature or follow the contours of the stomach.

As indicated above, device 10 can be adhered to the stomach 120 without penetrating the inner surface of the stomach. FIG. 42 shows one embodiment in which device 10 is shaped to match the curvature or follow the contours of the stomach 120. In this example, the expandable member of device 10 expands by inflation. Device 10 is positioned against the anterior surface of the stomach 120 as shown and inflated to compress the stomach walls together under the area covered by device 10 to create a narrow pathway 102w for food to travel through. The effects of this procedure are thus similar to that provided by a sleeve gastrectomy, but without having to surgically remove a portion of the stomach 120, or cut into the stomach 120 or staple the stomach 120. Device 10 can be adhered to the stomach 120 and/or the peritoneum or diaphragm or chest wall or ribs, using a cyanoacrylate-based adhesive or other biocompatible, surgically-approved adhesive. The surface of the device 10 to be adhered to the stomach or other structure can be adhered, for example, by injecting adhesive through a lumen of a multi-lumen port, such as through a lumen in conduit 12 when conduit 12 is provided with multiple lumens, to deliver the adhesive to the surface to be adhered, thereby adhering it to the intended structure. Additionally, or alternatively, device 10 can be anchored using any of the other mechanical fixation members described herein and/or inflatable member shapes configured to perform an anchoring function.

Figure 43:
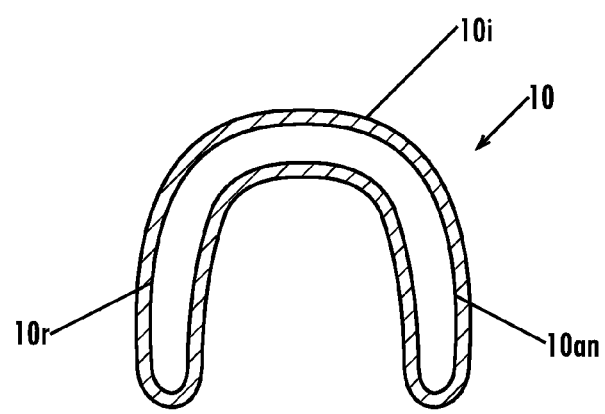
FIG. 43 illustrates a cross-sectional view of the device of FIG. 42.

Alternatively, device 10 can be shaped to have an anterogastric limb 10an and a retrogastric limb 10r, each of which are inflatable and shaped to match the curvature or follow the contours of the stomach 120. FIG. 43 illustrates a cross-sectional view of such a device 10. Limbs 10an and 10r are interconnected by an intermediate section 10i, all of which can be in fluid communication to provide a single inflatable member, having the appearance of a curved hot dog bun or taco shell. Alternatively, the intermediate section can be a structural member that is not inflatable, but is resiliently biased, which can include spring steel or other resiliently biased structural element(s), to maintain limbs 10an and 10r in a predetermined, juxtaposed configuration. In either case, anterogastric limb 10an, when device 10 is positioned on the stomach, would appear the same as in FIG. 42, and retrogastric limb 10r would cover a portion of the posterior surface of the stomach 120 in substantially a mirror image of that shown in FIG. 42. Upon expansion, limbs 10an and 10r expand to compress the anterior and posterior wall portions of the stomach together, with the resulting effects as described in FIG. 42. The device 10 of FIG. 43 can be adhered to the stomach 120, as described with regard to the embodiment of FIG. 42, but alternatively, the clamping action of limbs 10an and 10r can function to anchor device 10 with respect to the stomach 120 without the use of adhesives. Further optionally, intermediate section 10i (and/or one or both limbs) can be anchored to an internal structure other than the stomach using any of the techniques and/or fixation structures described herein.

Further optionally, one or more resiliently biased members can be incorporated into or around the limbs and intermediate section of device 11. For the arrangement where all sections are inflatable, such resiliently biased members can be molded into the walls of the inflatable member. Resiliently biased members can be biased toward a configuration wherein the limbs 10an, 10r apply compressive force to the walls of the stomach.

Figure 44A:
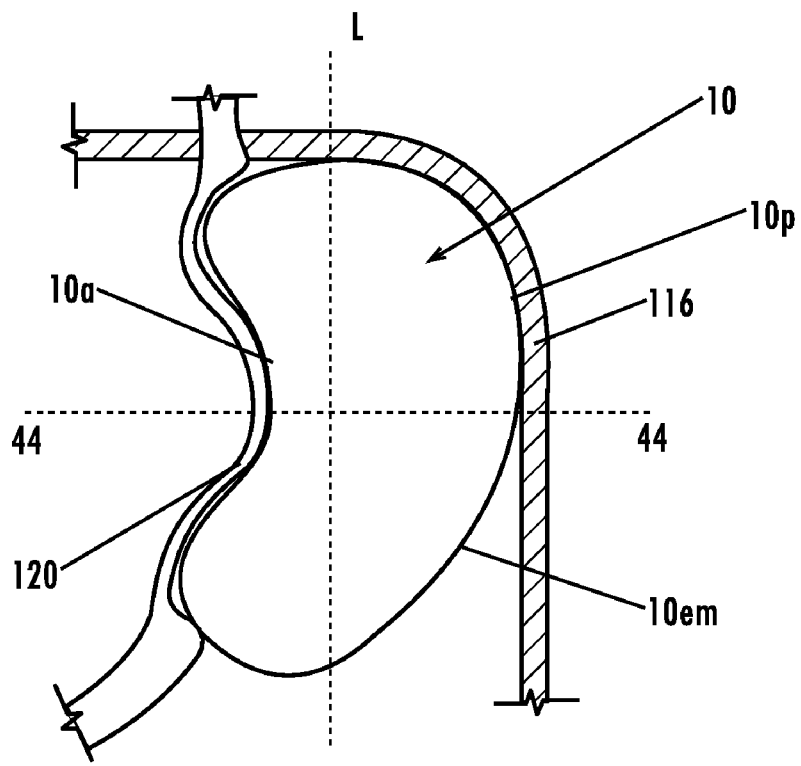
FIGS. 44A-44B illustrate another expandable member shape, and its use for deforming the stomach to provide effects similar to that provided by a sleeve gastrectomy.
Figure 44B:
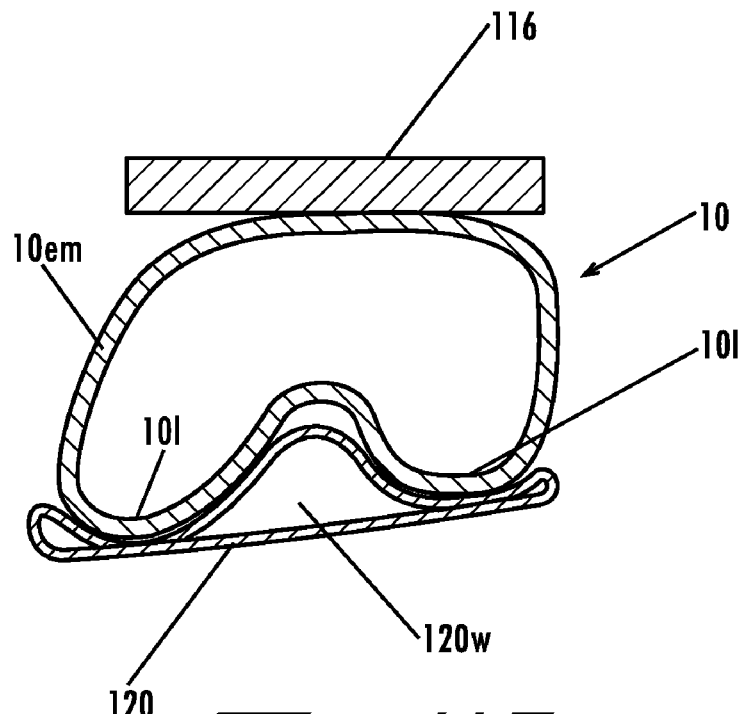

FIGS. 44A-44B illustrate another expandable member 10em shape, and its use for deforming the stomach to provide effects similar to that provided by a sleeve gastrectomy, but without having to surgically remove a portion of the stomach 120, or cut into the stomach 120 or staple the stomach 120. In this procedure, device 10 can be positioned between the diaphragm 116 and stomach 120 and expanded to compress posterior and anterior portions of the lateral walls of the stomach together. This compression can cause the walls to contact, or nearly contact one another. The surface 10a of expandable member 10em of device 10 is undulating in a direction transverse to a longitudinal axis L of the expandable member 10em, as can be seen in the cross-section view of FIG. 44B taken along line 44-44 in FIG. 44A. First and second lobes 101 protrude at anterior and posterior portions of surface 10a along substantially the full length of surface 10a, while a recess or valley 10v is formed therebetween that runs substantially over the full length of surface 10a. Surface 10p can be shaped to follow the curvature of the diaphragm in a location where it expands against the diaphragm. As shown, expandable member 10em is an inflatable expandable member, although a mechanically expandable member, or combination of mechanically expandable portion(s) and inflatable portions(s) can be substituted.

When device 10 is properly positioned as described, and expandable member 10em is expanded, as shown in FIG. 44A, the anterior and posterior portions of the cavity inside the stomach 120 are closed off as described, leaving a narrow channel 120w passing therebetween. Device 10 can be anchored to the diaphragm and/or the ribcage and/or relative to the stomach using one or more of the anchoring methods and features described herein.

Another fixation or anchoring technique, where adhesives are used for anchoring, includes the use of a receptacle that is adhered to the stomach 120 and/or other internal structure and is configured to receive the expandable member of device 10. This allows easy reversibility of a procedure by allowing the expandable member to be simply removed from the receptacle without having to attempt to dissolve, cut or otherwise reverse the anchoring produced by the adhesives. Additionally, this arrangement allows another expandable member to be inserted into the receptacle after removing a damaged or faulty device.

Figure 45:
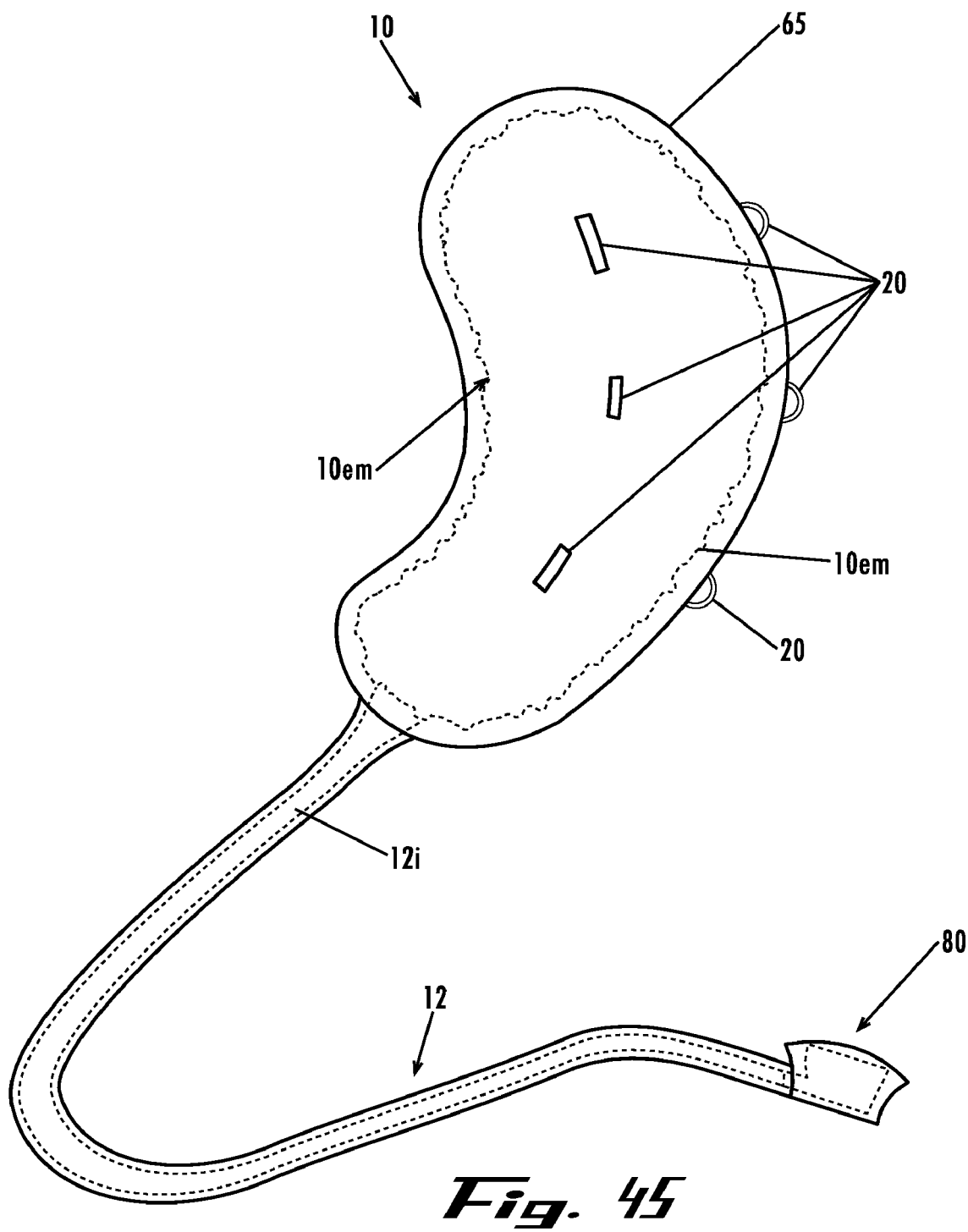
FIG. 45 shows a device wherein a receptacle is shaped and configured to receive an expandable member having a shape of the embodiment described in FIG. 42.
Figure 46:
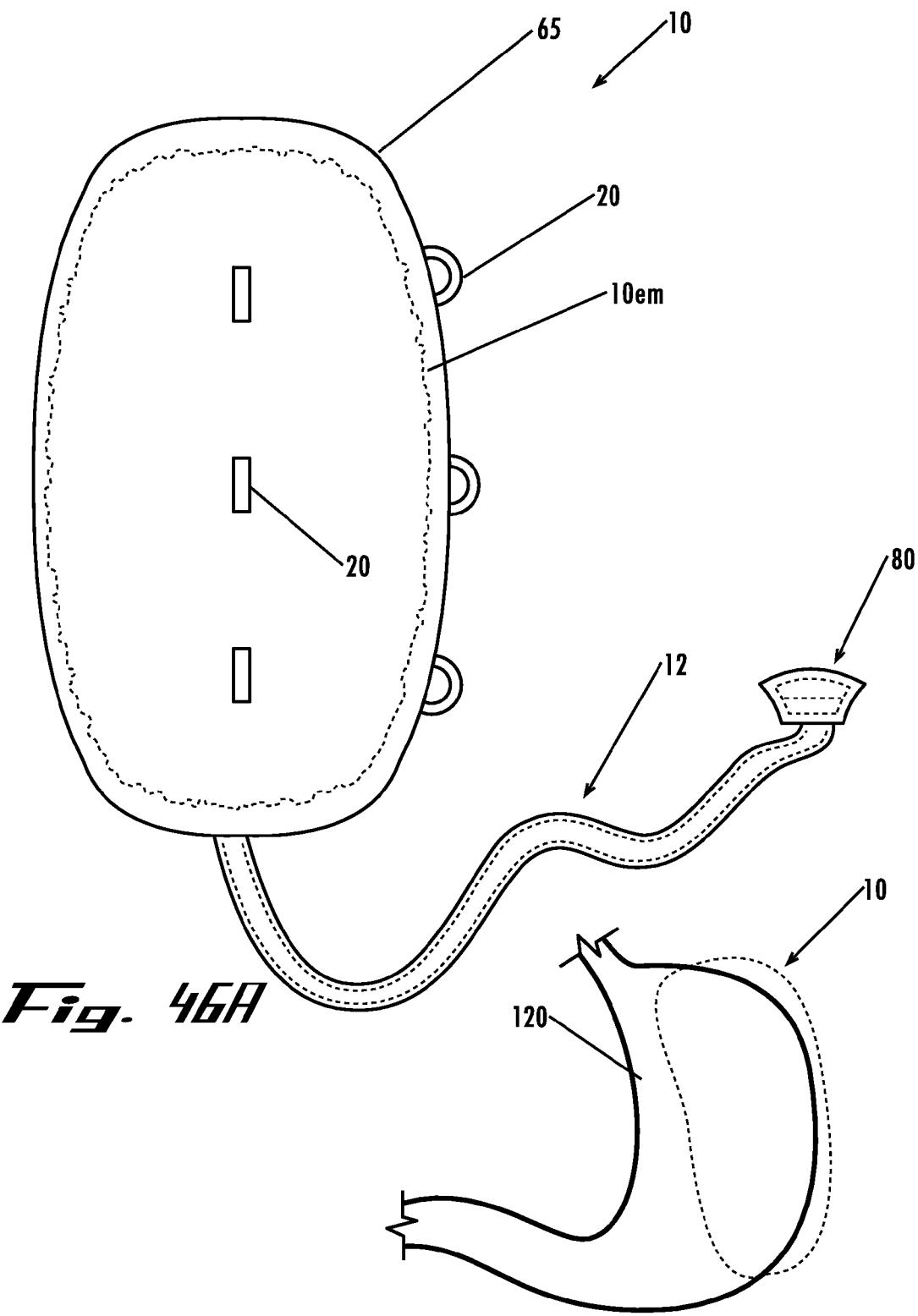
FIG. 46A illustrates another example of a device having a receptacle that receives an expandable member therein.
FIG. 46B illustrates the placement of the device of FIG. 46A anteriorly on the stomach to perform a procedure similar to that described with regard to FIG. 42.

FIG. 45 shows a device wherein receptacle 65 is shaped and configured to receive inflatable member 10em having a shape of the embodiment described in FIG. 42. Receptacle 65 can be formed from flexible, thin walled, polymer, such as silicone, latex rubber, polyurethane, etc. As noted, receptacle 65 can be adhered to the stomach and/or one or more other internal body structures using adhesive. Alternatively, or in addition thereto, receptacle 65 can be provided with loops, tabs, or other anchoring structures 20 that can be sutured or tethered to one or more internal body structures. Anchoring structure 20 can be provided, for example on an anterior surface of receptacle 65, as shown, and or on a lateral surface, as shown. After receiving the expandable member 10em, receptacle 65 can be closed by suturing, VELCRO® or other reversible closing expedients. Alternatively, by tethering or suturing receptacle 65 to one or more internals structures, the tether under tension can operate to maintain the receptacle 65 closed around the expandable member 10em. In the embodiment shown, conduit include an inner non-fluid permeable, flexible polymer, such as polyurethane or the like, tubing 12i surrounded by a silicone outer tubing 12o. The shape of receptacle 65 can be varied to many different shapes, like those discussed for the shapes of the expandable member 10em, for example. FIG. 46A illustrates another example of a device having a receptacle 65 that receives expandable member 10em therein, and FIG. 46B illustrates the placement of device 10 of FIG. 46A (in phantom lines) anteriorly on the stomach to perform a procedure similar to that described above with regard to FIG. 42.

It should be further noted that the geometry or shape of the expandable member itself can function as an anchor by engaging or wedging of portion thereof against an internal structure in the abdominal cavity. For example, device 10 can be anchored by wedging expandable member 10em in a location where it is prevented from easily migrating, due to the size, shapes and locations of the surrounding abdominal organs, In one example, expandable member 10em is expanded to a size large enough to nearly fill the subdiaphramatic space, so that it becomes wedged between the diaphragm, the stomach, the spleen, the posterior and/or lateral and/or anterior abdominal walls and the aorta, and the pancreato-splenic ligament.

Figure 19C:
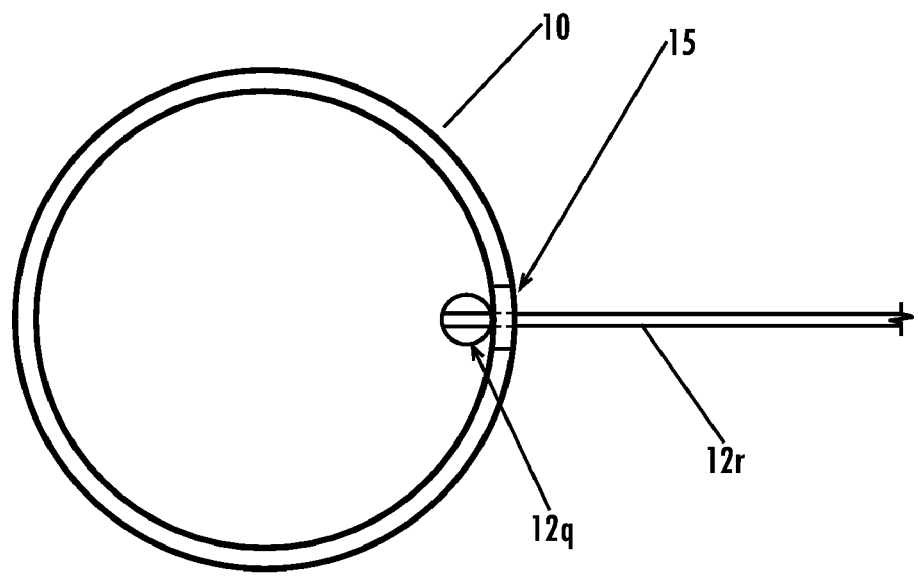
FIG. 19C illustrates a device having an inflatable member that has a valve in the wall thereof.

An adjustment member 80 can be connected to the expandable member via a conduit 12, as already described. Although in adjustment member is not necessarily required for a mechanically expandable device, one can optionally be provided to allow reversal of the procedure by collapsing the expanded member frame using a draw wire or cable attached to the expandable frame, in any of the manners described above. An adjustment member is not necessarily required for an inflatable device, either, e.g., such as in the case of the self-inflating device described above with regard to FIGS. 19A-19B, or as shown in FIG. 19C. The expandable member 10em shown in FIG. 19C has a valve 15 in the wall thereof. The valve 15 is a self-sealing valve such as an elastomeric or gel membrane. Initially, a removable inflation tubing 12r with an expandable tip 12q is attached to the expandable member 10. The expandable member is positioned in the desired location with expandable lip 12q in its enlarged configuration. The expandable tip 12q can be an inflatable member or an expandable framework. After expandable member 10em is positioned, it is enlarged to the desired size using the removable inflation tubing 12r. When the desired size is reached, the expandable lip 12q is collapsed, the removable inflation tubing 12r is retracted and the tip 12q is removed through the self-sealing valve 15. This embodiment makes the procedure shorter and less complicated by removing the implanted conduit and adjustment member 80 described above in other embodiments. However, an adjustment member 80 will typically be provided for convenient, repeatable accessibility to adjust the amount of pressure or degree of expansion of the expandable member.

Figure 47:
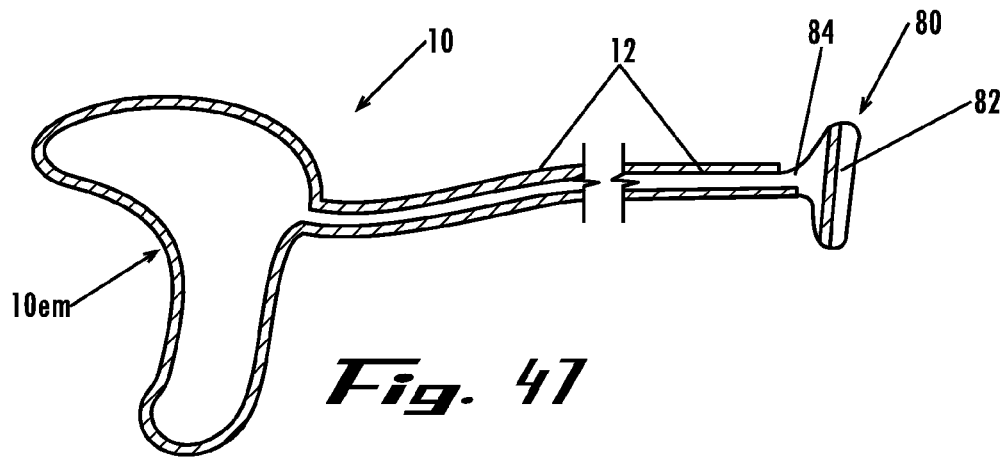
FIG. 47 illustrates a sectional view of a device having an inflatable expandable member in fluid communication with an adjustment member via a conduit.

FIG. 47 illustrates a sectional view of device 10 having an inflatable expandable member 10em in fluid communication with adjustment member 80 via conduit 12. Adjustment member 80 includes a port 84 through which fluid such as liquid and/or gas can be inputted into conduit 12 for delivery to the expandable member 10em. A valve mechanism 82 is provided to maintain the pressure within expandable member 82 and to only selectively allow fluid to be inputted to or extracted from expandable member 10em. For example, valve mechanism 82 can comprise an elastomeric seal (e.g., made from "self-sealing" silicone) to allow entry into port 82 via a needle or other appropriately configured delivery mechanism and/or an additional valve mechanism as described previously.

Figure 48A:
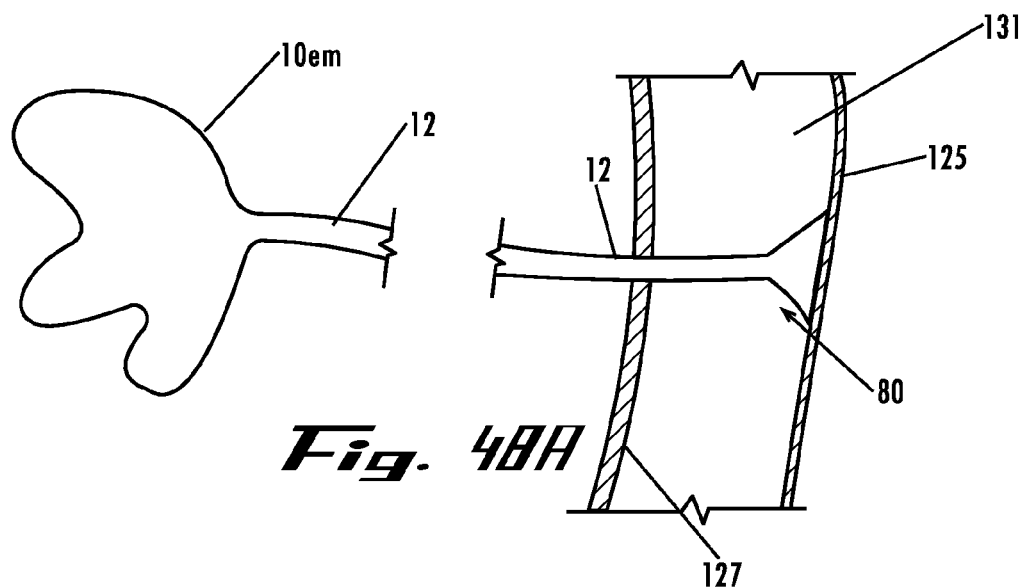
FIG. 48A illustrates anchoring of an adjustment member subcutaneously to an inner layer of the skin.

Adjustment member 80 should be anchored where it will be easy to be located from outside the patient to access it for maintenance or adjustment of the volume within the expandable member. In this regard, anchoring of adjustment member 80, such as by suturing, and/or other fixation means, subcutaneously to an inner layer of the skin, as illustrated in FIG. 48A, places it closest to the outside of the patient for easiest access. Accordingly, a surgeon may find this location of adjustment member 80 the easiest implantation location to later find the adjustment member and properly align and engage an inflation needle in port 84. Also, length requirements for an inflation needle used are minimized. However, this placement can present aesthetic issues, as adjustment member 80 can begin to show as a protrusion against the skin 125, due to the length of the conduit 12 between the skin 125 and the abdominal wall (e.g., abdominal muscle) 127, as conduit 12 will typically be anchored and/or adhered to the abdominal wall 127 and therefore the length of conduit 12 between the abdominal wall 127 and skin 125 remains fixed, while the thickness of the fat layer 131 reduces as weight is lost.

Figure 48B:
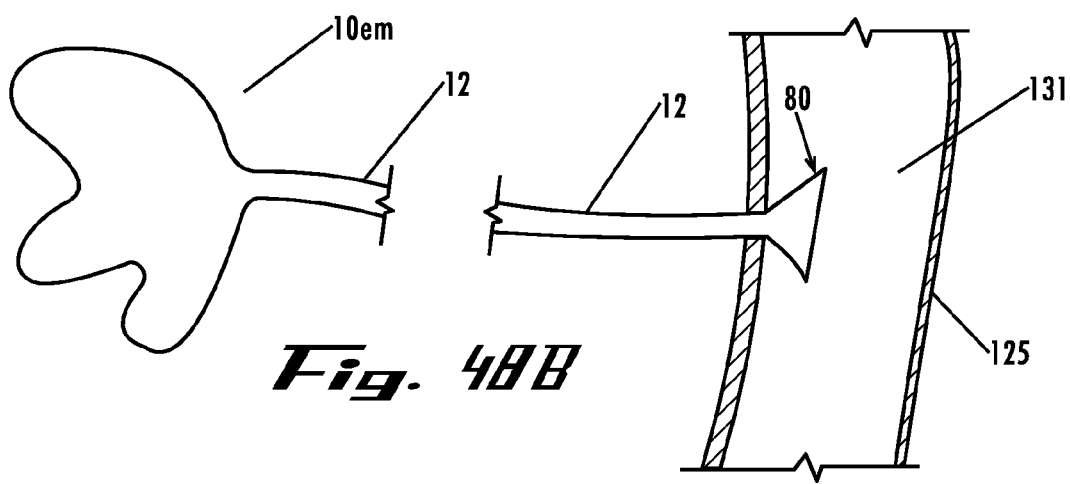
FIG. 48B illustrates attachment of an adjustment member adjacent the abdominal wall.

Alternatively, adjustment member 80 can be attached adjacent the abdominal wall 127, as illustrated in FIG. 48B. This makes location of adjustment member 80 by the surgeon for maintenance or adjustment procedures somewhat more difficult, and requires a longer needle or inflation tool to reach port 84, but doesn't cause aesthetic problems when weight is lost, due to the reduction in the thickness of the fat layer 131, as some fat layer thickness generally remains.

Figure 49:
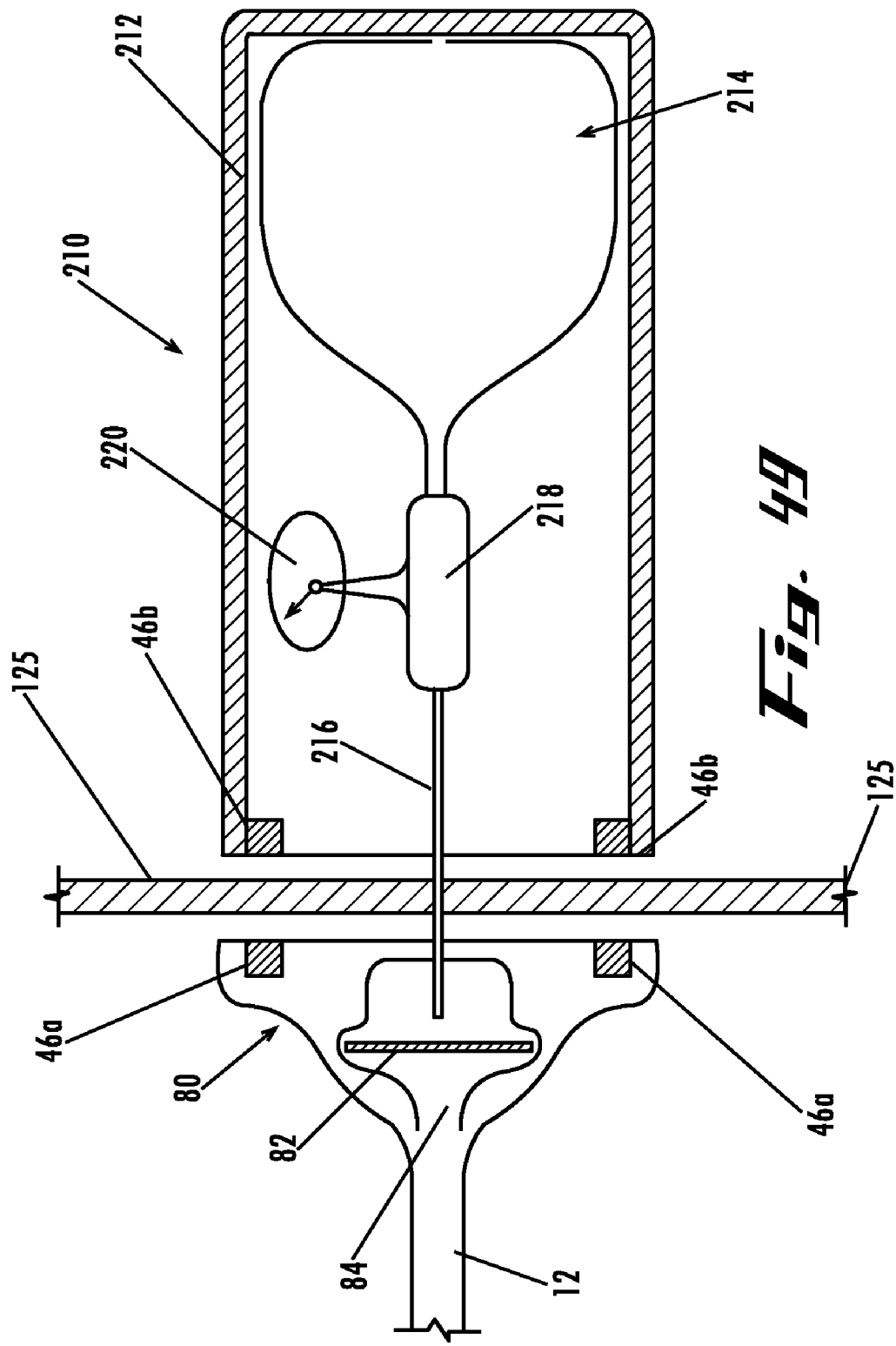
FIG. 49 illustrates a partial sectional view of an arrangement in which, in order to provide assistance in locating an adjustment member and properly aligning an inflation tool with the port of the adjustment mechanism, the adjustment member is provided with magnets and the inflation tool is provided with magnets arranged to be attracted to corresponding magnets on the adjustment mechanism.

In order to provide assistance in locating adjustment member 80 and properly align an inflation tool with port 84, FIG. 49 illustrates a partial sectional view of an arrangement in which adjustment member 80 is provided with magnets 46 peripherally on a proximal portion thereof that faces toward the skin 125 of the patient. At least one pair of oppositely disposed magnets 46a are typically included, and three or more magnets can be disposed radially about the perimeter of the face of adjustment member 80. Magnets 46a can be fixed to adjustment member by any of the techniques described above, and can be fixed to the surface of the face of adjustment member 80, inserted into recesses in the face so that the surfaces of magnets 46 are flush with the face of adjustment member 80, or embedded within the adjustment member 80, beneath the face.

Figure 50:
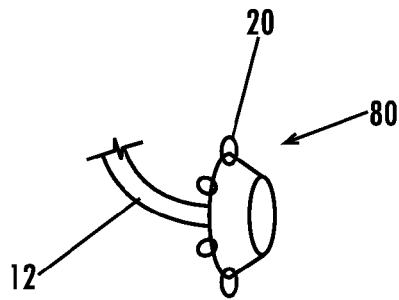
FIG. 50 illustrates an example of an adjustment member provided with suture loops.

Adjustment member 80 can be fixed by suturing and/or other fixation features, as described above. FIG. 50 illustrates an example of adjustment member 80 provided with suture loops 20. Alternatively, the adjustment member can be provided with a suture collar of material that is easily pierced by a needle, but resistant to radial tearing out of the sutures once they have been placed. Other fixation features can be alternatively or additionally provided, such as staples, hooks, barbs, adhesives or mesh located at the edge of adjustment member 80 or at the output conduit 86. In the example shown in FIG. 49, adjustment member 80 is fixed just beneath the skin 125. However, this arrangement can also be used when adjustment member is fixed to the abdominal wall as described with regard to FIG. 48B. Inflation tool 210 is provided with a housing or main body 212 that is configured and dimensioned to be comfortably held in the hand of an operator, and thus functions as a handle. Main body 212 contains a fluid reservoir 214, that typically holds a pressurized gas supply, but can hold liquid. Reservoir 214 is in fluid communication with inflation needle 216 via a pressure regulator 218 and a pressure meter 220 that can be mounted in the surface of housing 212, or housing 212 can be provided with a window to permit visualization of the pressure meter 220. Inflation needle 216 is configured and dimensioned to be docked into port 84 after piercing through valve 82 to deliver the pressurized pas (or withdraw gas) through conduit 12. Needle 216 is designed to have sufficient length to reach port 84, and this length can vary depending upon the location that the adjustment member is fixed to. The distal face of tool 210 is provided with magnets 46b positioned to align with magnets 46a on adjustment member 80. Magnets 46b are oriented on tool 210 so that the polarity of the magnets of the distal faces of magnets 46b is opposite to the polarity of the proximal facing surfaces of magnets 46a of adjustment member 80. Accordingly, a surgeon can locate the general location of adjustment member 80 by palpitation or using imaging tools, for example. Once the general location has been identified, needle 216 is inserted in the center of the location identified. Magnets 46b on tool 210 are attracted to mating magnets 46a on adjustment member 80 as needle 216 is inserted, thereby acting as a homing mechanism and accurately aligning tool 210 with adjustment member 80 to facilitate the docking of needle 216 into port 84.

Figure 51:
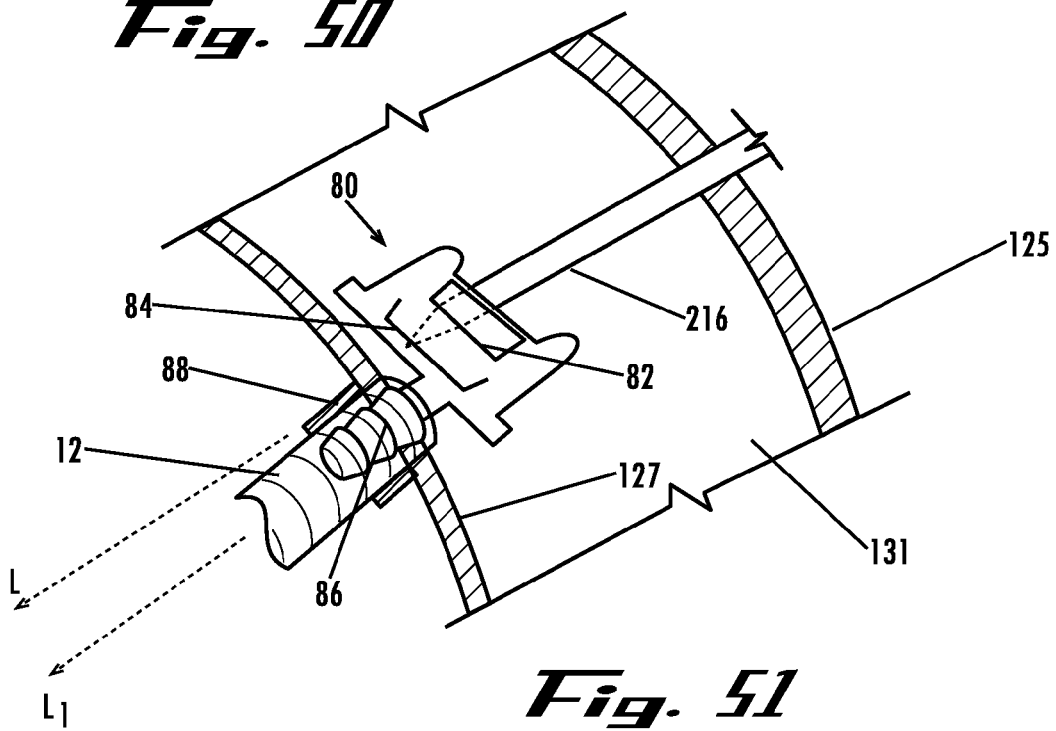
FIG. 51 illustrates an adjustment member having a feature designed to prevent flipping.

FIG. 51 illustrates an adjustment member having a feature designed to prevent flipping (i.e., a situation where an access port rotates about it's longitudinal axis so that it no longer lays flat against the abdominal wall or other position where it was attached). By offsetting the output conduit 86 from the input and port 84 of adjustment member 80 as shown by the comparing the longitudinal axis L1 of the output conduit 86 to the longitudinal axis L of the input and port 84, the output conduit 86 acts to stabilize adjustment member 80 more when needle 216 is docked in port 84 and potentially applying pressure thereto, as counter-torque is provided by the conduit 86 over the lever arm generated by the distance between L and L1. Additionally a collet 88, or other reinforcing structure can be fixed to the abdominal wall 127 and surrounding conduit 86, to further reinforce the conduit against torquing forces generated by the needle 216 against the adjustment member 80.

Figure 52:
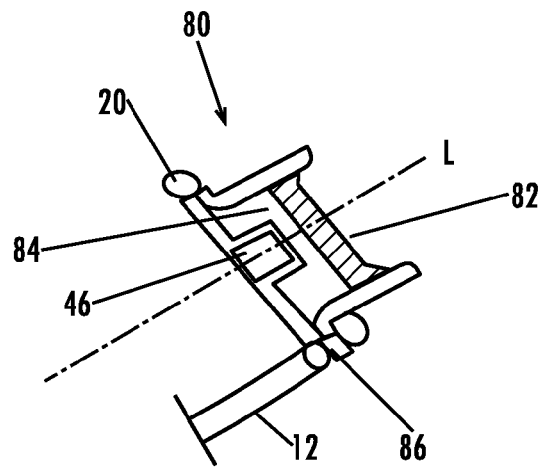
FIG. 52 illustrates an adjustment member provided with a variation of a magnetic homing arrangement.

FIG. 52 illustrates an adjustment member 80 provided with a variation of a magnetic homing arrangement. In this arrangement, magnet 46 is fixed within port 84, such as in a center position of the adjustment member 80 aligned with the longitudinal axis L. The output conduit is offset like that described above with regard to FIG. 51. Needle 216 can be provided with a magnet that seeks magnet 46 in adjustment member 80, or alternatively, a metal needle can be magnetically drawn to magnet 46 upon insertion of the needle 216 through layer 82, thereby homing the needle into a desired location to deliver pressurized fluid through port 84 and out of the outlet conduit 86.

Figure 53A:
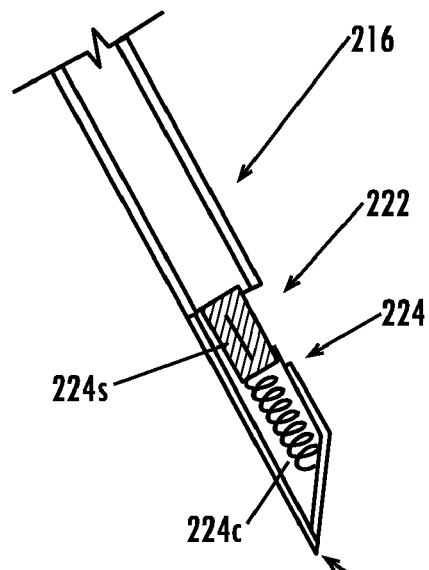
FIG. 53A is a cutaway illustration of an inflation needle provided with a safety valve mechanism for preventing inadvertent flow of gas or liquid into a patient.
Figure 53B:
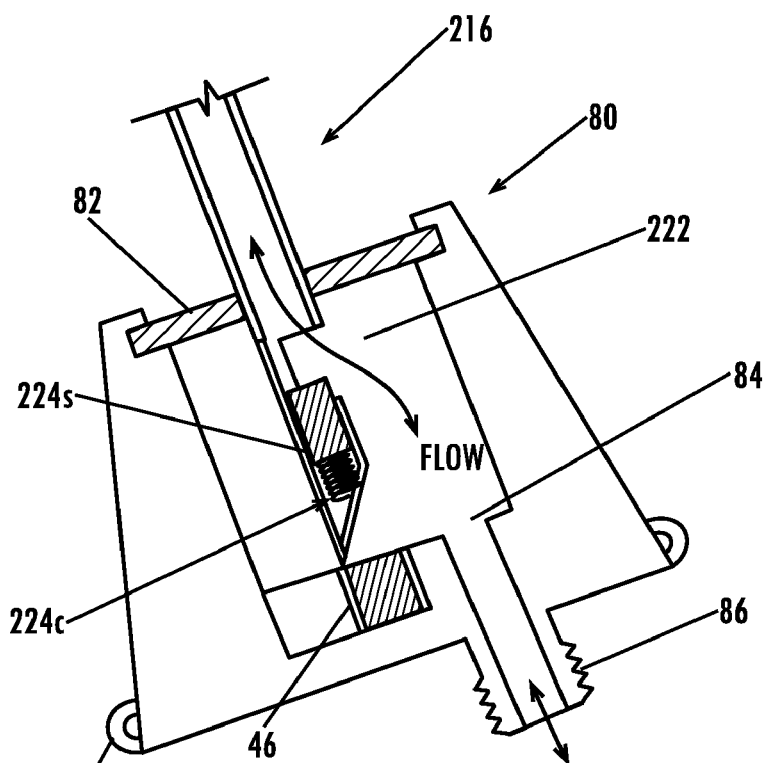
FIG. 53B illustrates use of the needle of FIG. 53A with an adjustment member of a type described with regard to FIG. 52.

FIG. 53A is a cutaway illustration of an inflation needle provided with a safety valve mechanism for preventing inadvertent flow of gas or liquid into a patient, such as in the subdermal fat layer, for example, if the needle has not yet been properly docked in port 84, and FIG. 53B illustrates use of needle 216 with an adjustment member of a type described above with regard to FIG. 52. Needle 216 is configured for side delivery of pressurized fluid through side opening 222. The distal end of needle 216d is pointed or otherwise sharpened to pierce through the skin and fat layers of the patient, as well as self-sealing layer 82 for docking with port 84. Needle 216 is preferably a non-coring needle, to minimize the breach of the layer 82 to facilitate resealing. A spring loaded valve mechanism 224 is provided in the distal end portion of needle 216 to maintain opening 222 sealed shut when needle is not properly docked with port 84 to prevent outflow of pressurized fluid through opening 222. The distal end 216 of needle 216 is closed off so that pressurized fluid does not flow therethrough. The valve seal 224s is magnetic, and configured and oriented to be attracted to magnet 46 in adjustment member 80 (FIG. 53B). A compression spring 224c is interposed between valve seal 224s and the distal end of needle 216, within the distal end portion of needle 216. Thus, valve seal 224s is slidable within needle 216 and is resiliently biased toward the sealed or closed configuration shown in FIG. 53A.

Upon piercing member 82 in a location estimated to be aligned with magnet 42 and advancement of needle 216 into adjustment member, valve seal 224s remains in the closed configuration until it gets close enough to magnet 46 to cause the attractive magnetism between magnet 46 and valve seal 224s to become great enough to overcome the biasing force of spring 224c. At this time, biasing spring 224 compresses as valve seal 224s is drawn toward magnet 46, thereby exposing opening 222 to the flow of pressurized fluid, as shown in FIG. 53B. Pressurized fluid then either flows out the side of needle 216 or is drawn in through opening 222, depending upon whether the operator is increasing or decreasing the pressure in the expandable device. When sufficient flow has been delivered, needle 216 is retracted, and valve seal 224s closes opening 222 before opening 222 passes back through member 82.

Figure 53C:
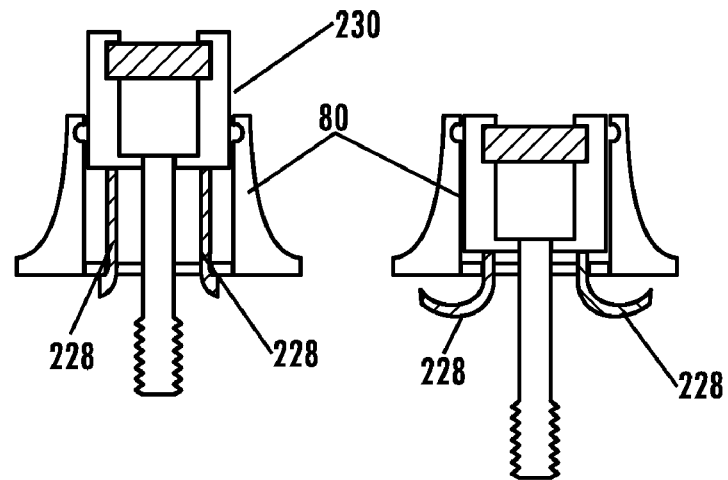
FIG. 53C is a sectional view of an adjustment member with curved hooks attached to a self-sealing valve.
Figure 53D:
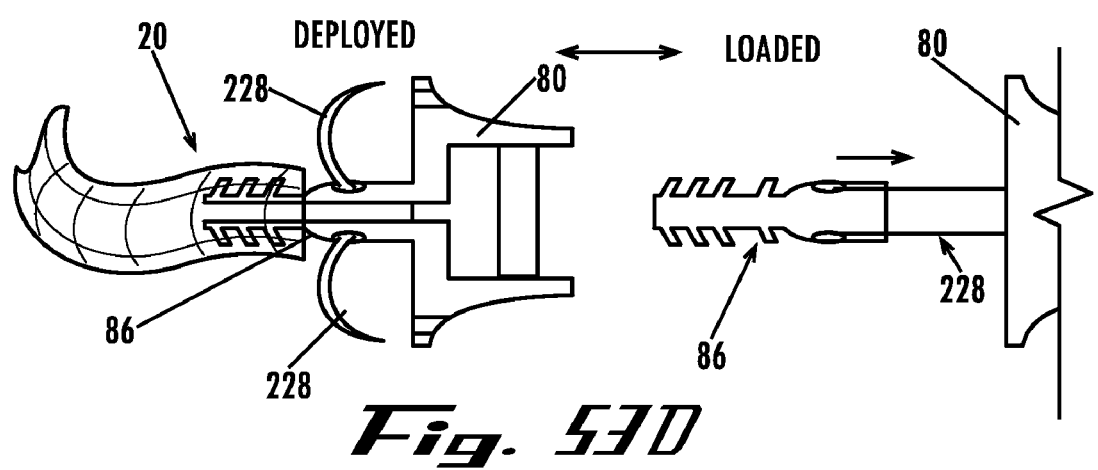
FIG. 53D is a sectional view of an adjustment member with curved hooks attached thereto.

FIG. 53C is a sectional view of an adjustment member 80 with curved hooks 228 attached to self-sealing valve 230. The bottom of adjustment member 80 is placed on the abdominal wall and the self-sealing valve housing is pressed down by the physician which deploys the curved hooks 228. FIG. 53D is a sectional view of an adjustment member 80 with curved hooks 228 attached thereto. Initially, curved hooks 228 are held constrained in outlet conduit 86. Outlet conduit 86 is connected to conduit 12 in the patient and then adjustment member 80 is retracted slightly allowing the curved hooks 228 to be released from the outlet conduit 86 and pulled into the abdominal muscle to anchor the adjustment member 80 thereto.

Figure 54:
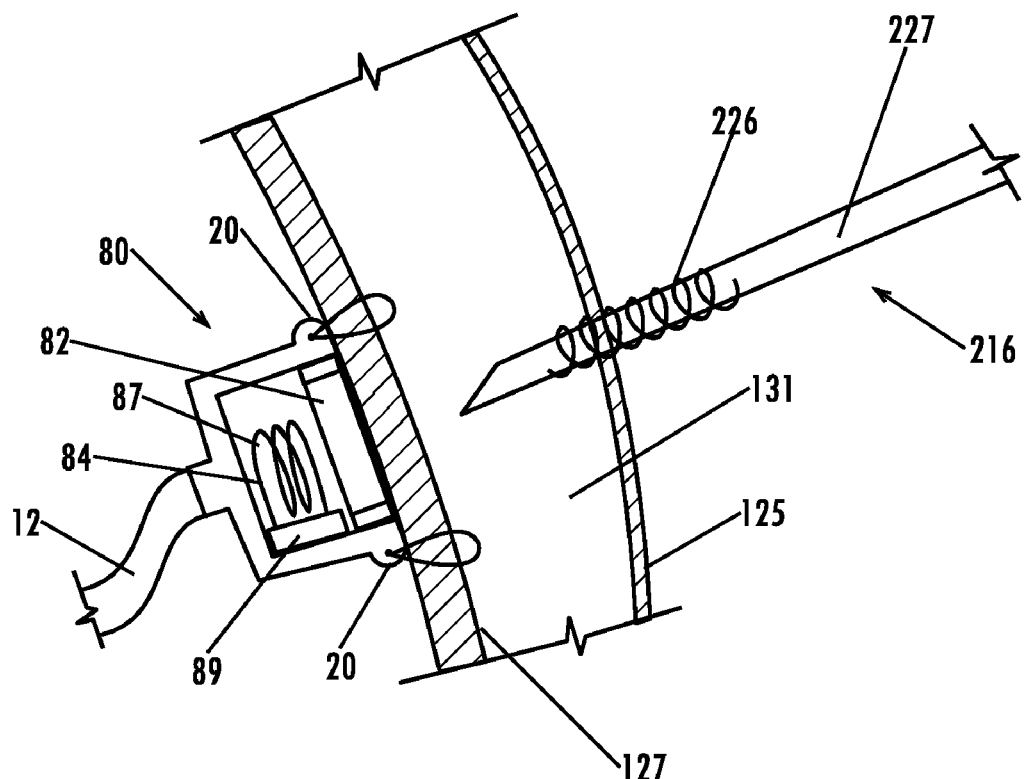
FIG. 54 illustrates another variation of a homing mechanism provided in an adjustment member and delivers needle.

FIG. 54 illustrates another variation of a homing mechanism provided in adjustment member 80 and delivered needle 216. In FIG. 54, the adjustment member is shown having been fixed to the internal wall of the abdominal muscle, such as by sutures, clips, staples or the like, passed through loops 20 or other fixation features provided on adjustment member 80. It is noted that all other embodiments of adjustment member 80 described herein can also be optionally fixed to the internal surface of the abdominal wall 127 similarly. Port 84 of adjustment member is surrounded by coils 87 that are electrically connected to an electronic circuit 89. Needle 216 has a coil 226 wrapped around a distal end portion thereof that is configured to pass through and be located within coil 87 when the distal tip of needle 216 docks with port 84. An electrical wire 227 extends along, preferably within, but it can pass externally of needle 216 for connection to an electrical power source proximally of needle 216, and is electrically connected to coil 226. Electrical power is applied to coil 226 when needle 216 is inserted into adjustment member 80. When the distal tip of needle 216 is properly docked with port 84, the electro-motive force (emf) induced by coil 226 within coil 87 is sensed by circuit 89 which sends a signal to the operator of the needle indicating the field strength of the emf. An RF wireless signal or ultrasound or magnetic pulse can be used to send a signal to the operator of the needle. The circuit on the receiving end in the RF/electromagnetic case is a magnetic field. A signal is sent by the coil on the needle which induces a current in the coil in the implant. That current loads a capacitor with or without a switch and powers a small transmitter circuit which sends a signal back to the same or a different coil which then sends a response signal to a coil on the needle. The response signal received by the coil on the needle is then sent to an amplifier in the handpiece where it can be detected by the physician or other operator. A threshold minimal field strength can be shows on a monitor gauge, which is a level beyond which the operator can conclude that the needle 216 is properly aligned and docked in port 84.

Figure 54A:
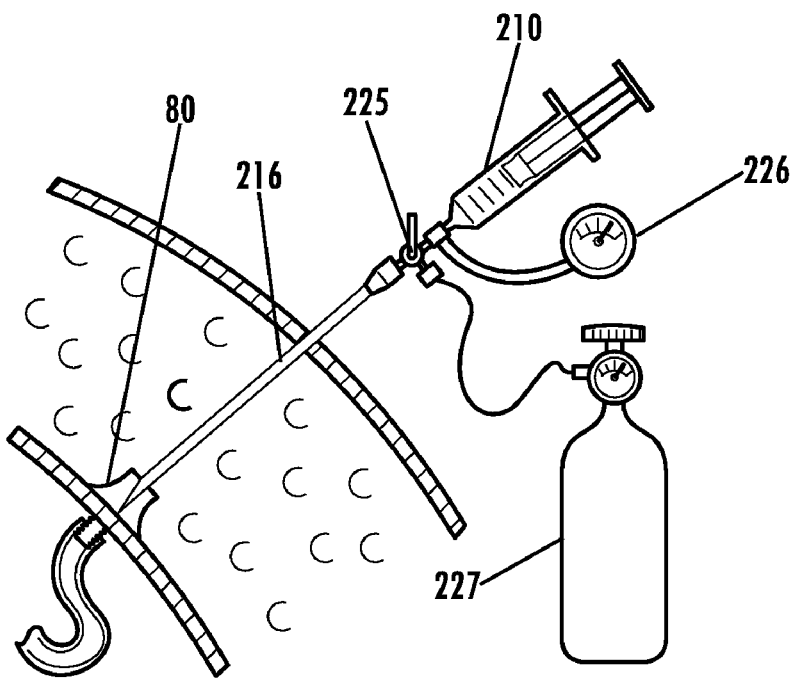
FIG. 54A illustrates a method of filling an expandable member with a pressurized gas.

FIG. 54A illustrates a method of filling the expandable member with a pressurized gas. Attached to needle 216 is a valve 225 with an inflation tool 210. A gauge 226 is attached to another opening on valve 225. Initially, the needle 216 is inserted in adjustment member 80 with valve 225 set to measure the pressure in the expandable member via gauge 226 with the gas source 227 closed off to the gauge and needle. The valve 225 is then moved to close off fluid access to adjustment member 80 and open the gas source 227 to inflation tool 210 to fill the inflation tool with the desired amount of gas. The valve to the gas source is then closed and opened to the needle. The inflation tool 210 is used to inject gas into the expandable member via the needle 216 and adjustment member 80. This process is repeated until the desired volume and/or pressure is reached in the inflatable member.

Intra-Gastric Sizing

Visualization of the deformation of the stomach caused by expanding one or more expandable members 10em thereagainst can be carried out endoscopically, fluoroscopically, ultrasonically or using some other visualization technology (or can be viewed directly if an open surgical procedure is performed through a large incision), as a measure of how much to expand the one or more expandable members, and consequently how much deformation of the stomach is to be accomplished, Intra-gastric sizing procedures can be carried out alternatively, or in addition to these visualization monitoring techniques to provide the surgeon with a more well-defined, objective feedback regarding when to halt the expansion of the one or more expandable members.

Figure 55A:
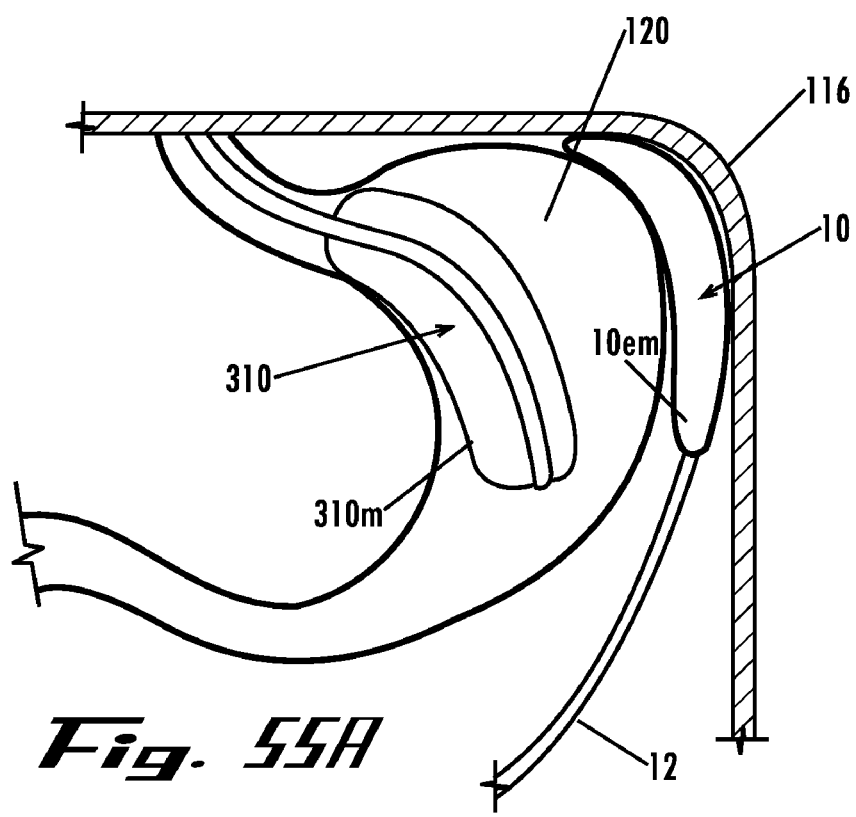
FIGS. 55A-55B illustrate two stages of a procedure for implanting an extra-gastric, expandable device with the aid of an expandable, intra-gastric sizing device.
Figure 55B:
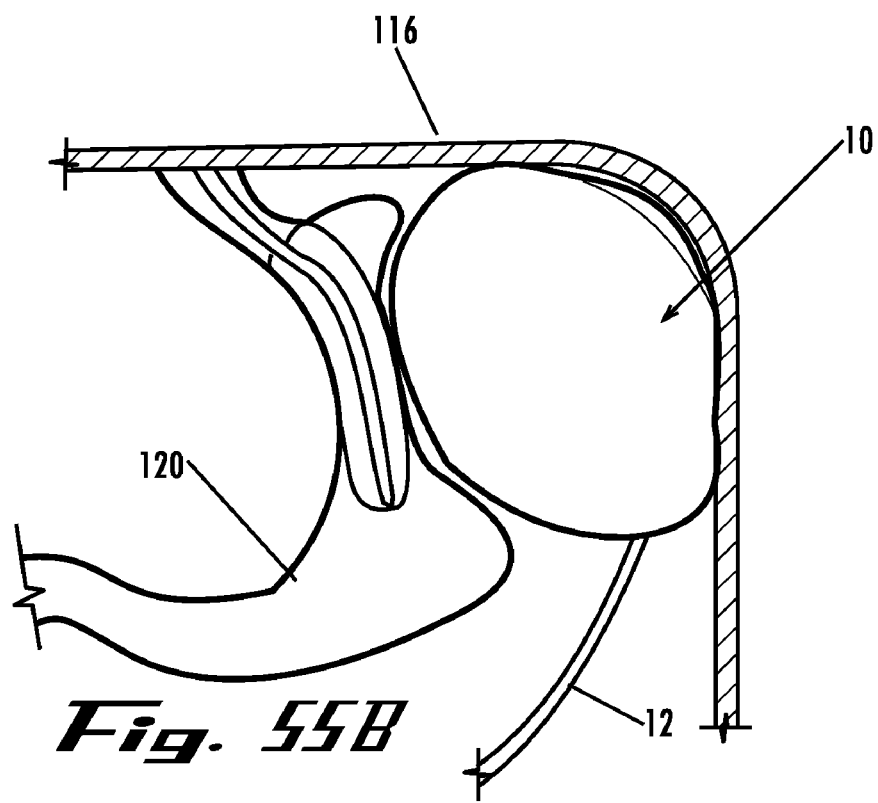

FIGS. 55A-55B illustrate two stages of a procedure for implanting an extra-gastric, expandable device 10 with the aid of an expandable, intra-gastric sizing device 310. Prior to expanding the expandable member 10em of device 10, which can be before or after positioning device 10 in the desired surgical target area, intra-gastric sizing device 310 is passed trans-orally into the patient and advanced until sizing member 31m is positioned within the cavity of the stomach 120, see FIG. 55A. Sizing member 310m is configured to assume a compressed or deflated configuration to facilitate passing it trans-orally and through the esophagus of the patient, and an expanded configuration, as shown in FIG. 55A, having an enlarged cross-sectional area configured to define a dimension of the reduced-volume intra-gastric cavity to be established by forces from extra-gastric device(s) 10. Sizing member can be inflatable (such as the example shown in FIG. 55A) or mechanically expandable, using any of the construction configurations discussed above with regard to expandable members 103m. Sizing member 310m can be expandable to a predetermined expanded size, or can be adjustable expandable, to vary the cross-section area of sizing member over a range of expanded sizes.

When sizing member 310m has been properly positioned within the stomach as desired, which can be confirmed using visualization techniques, expandable member 10em is next expanded to begin pressing on the wall of the stomach 120. Expandable member 10em can be expanded until it has been visually confirmed that the inner surface of the wall of the stomach 120 that expandable member 10em is pressing against contacts sizing member 310m. Alternatively, sizing member 310m can include a pressure sensor that measures the pressure within sizing member 310, particularly when sizing member 310m is inflatable, or one or more strain gauges can be mounted on the surface of expandable member 310m that is to be contacted by the inner surface of the stomach wall, and compression of the stomach and expansion of expandable member 20em can continue in this case until a predetermined amount of pressure or strain has been measured. Further alternatively sizing member 310m can be provided with a sensor (e.g., an ultrasonic sensor or the like) that can measure the distance between the inner wall surface of the stomach wall and sizing member 310, wherein expansion of expandable member 10em can be halted when a predetermined distance between the inner surface of the stomach wall and the sizing member 310m has been achieved.

Figure 56:
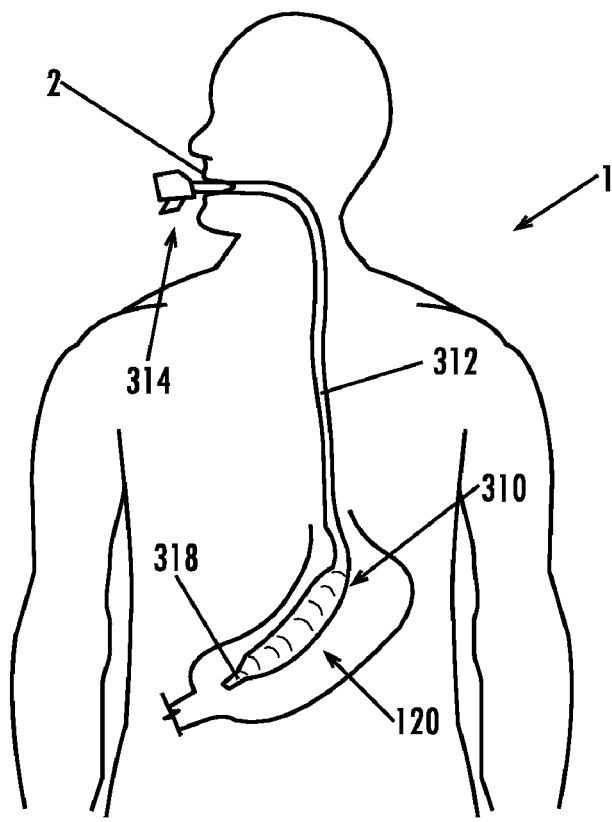
FIG. 56 illustrates an intra-gastric sizing device having been passed trans-orally through the mouth of a patient and positioned in the stomach.
Figure 57A:
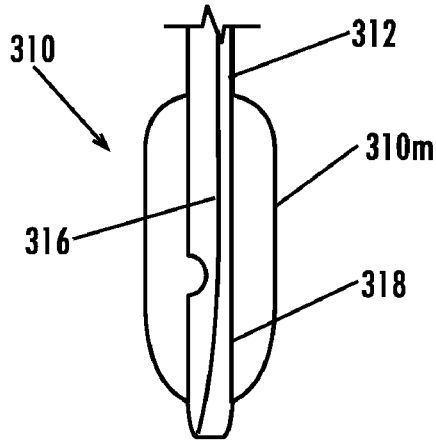
FIGS. 57A-57B illustrate that a conduit of an intra-gastric device described herein can contain multiple lumens.
Figure 57B:
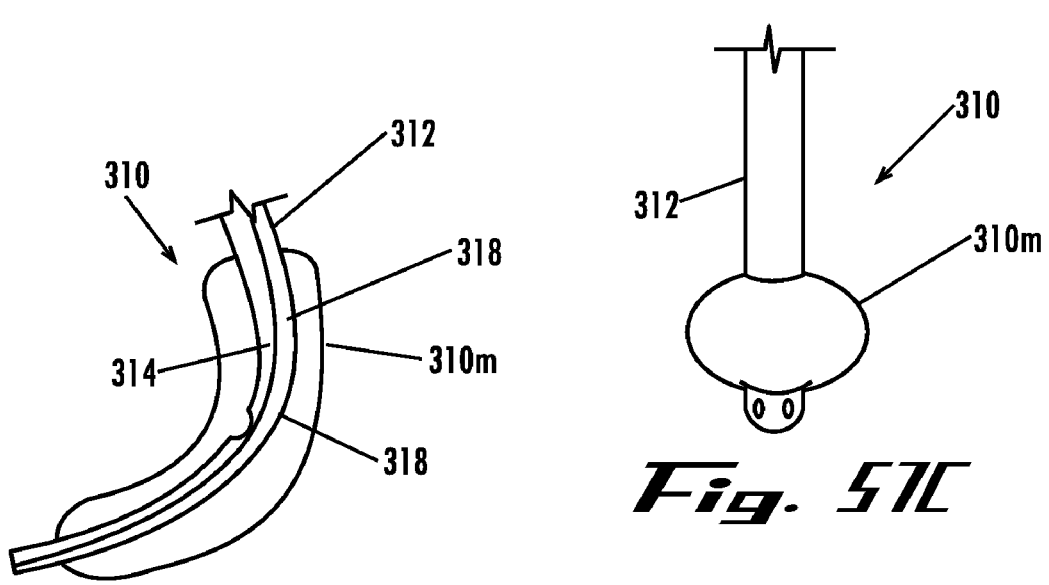
Figure 57C:
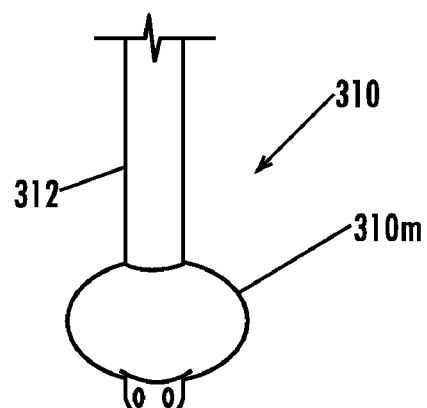
FIGS. 57C-57F show additional variations that may be provided in the configuration of an expandable member of an intra-gastric device.
Figure 57D:
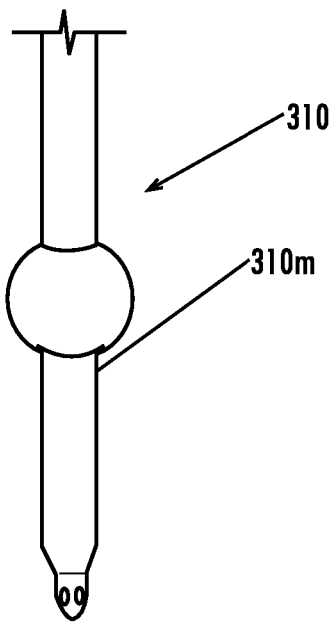
Figure 57E:
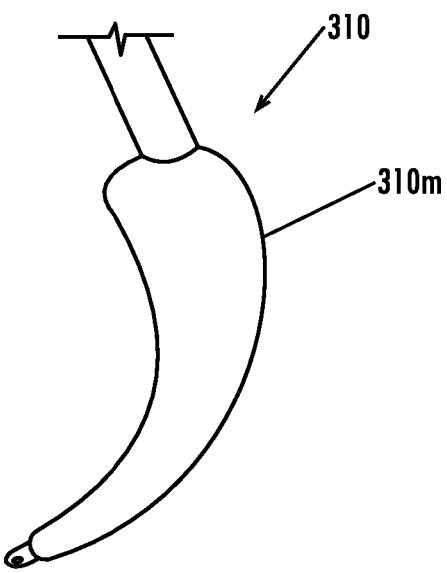
Figure 57F:
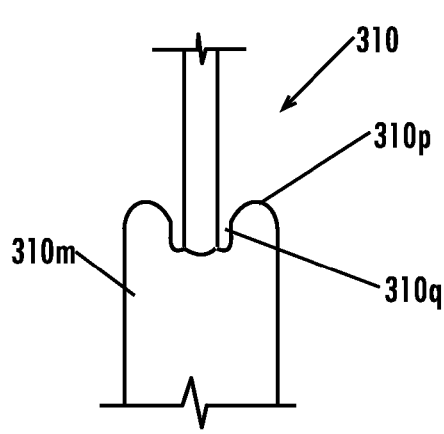

FIG. 56 illustrates intra-gastric sizing device having been passed trans-orally through the mouth 2 of patient 1 and positioned in the stomach 120 as described above. Conduit 312 is of sufficient length so that a proximal end portion thereof extends out of the mouth 2 of the patient 1 when expandable member 310m is positioned in the desired location within the stomach cavity. A valve or stopcock 314 can be provided at the proximal end of conduit 312 to control the delivery of fluids therethrough, as well as to maintain the fluids used to expand member 310m (when expandable member 310m is an inflatable member) under pressure. Conduit 312 can contain multiple lumens, such as shown in FIGS. 57A-57B, and can include a first lumen 316 for delivery or withdrawal of pressurized fluid to or from expandable member 310m. A second lumen 318 can be provided to open to the outside of expandable member 310m and can be used to irrigate the stomach cavity (such as with saline, for example) to apply suction to withdraw contents within the stomach cavity, and/or to deliver a contrast agent into the stomach cavity. In addition to the straight, elongated ("hot-dog shaped") and curved, elongated ("banana shaped") configurations of expandable member 310m shown in FIGS. 57A-57B, expandable member can alternately be formed to be substantially spherical or "donut shaped" (FIG. 57C), elongated with a spherical or bulbous proximal end (FIG. 57D) or curved, elongated and tapered ("pepper shaped") (FIG. 57E). Other configurations can also be employed. To create a better proximal shoulder, the proximal end 310p of inflatable member 310m can be rolled in upon itself to form a separation or gap 10g between conduit 312 and proximal end 310p, as shown in FIG. 57F. Essentially, the goals of all these shapes is to find an optimum configuration to limit the available volume for stomach expansion, produce more rapid satiety minimize discomfort, minimize any poor cosmetic effects, reduce any pressure points on the stomach, fit more seamlessly into the surrounding anatomy without damaging any peripheral structures such as the spleen or aorta, and/or improve stability of the implant.

Figure 58A:
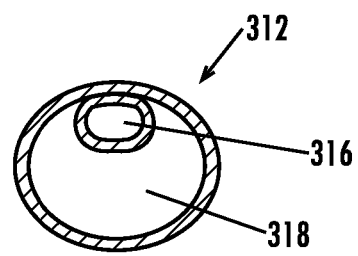
Figure 58B:
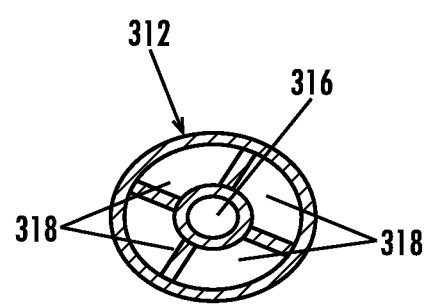

FIGS. 58A-58C show examples of cross-sectional illustrations of different configurations for providing lumens 316 and 318 to pass through expandable member 310m. The expandable member 310m, when inflatable, can be formed of a soft elastomeric material, such as silicone or latex rubber, or the like. A dual layer expandable member can include a soft elastomeric material as the outer layer or outer inflatable member and a less porous inner layer or inner inflatable member, such as described previously for construction of expandable member 10em. A mechanically expandable member 310m can also be coated with a soft elastomeric polymer. A composite expandable member that includes both mechanically expandable and inflatably expandable components can be constructed, similarly to what was described above with regard to construction of expandable member 10em.

Radiopacity

Portions of device 10, as well as device 310 and other devices that are either temporarily or permanently placed within the body of the patient can be provided with radiopaque markers and/or constructed partially or in whole from materials that are radiopaque. "Radiopaque" refers to the ability of the marker or material to be visualized under X-ray visualization. In FIG. 59, the adjustment member is formed partially of metal and can thus be detected radiographically. Conduit 12 can be provided with a radiopaque stripe 330 running the length thereof, bands circling the conduit in a transverse direction to the longitudinal axis of the conduit and/or dots so that the conduit can be visualized under X-ray when the conduit has been placed into the abdominal cavity, of a patient. Likewise, expandable member 10em can be provided with radiographic dots, stripes, bands or other marker to indicate the perimeter of the member, whether inflated or not, under X-ray, when placed inside the patient. Expandable member 310m and conduit 312 can be similarly provided with radiopaque markers.

The radiopaque markers can be adhered to the surfaces of the components, or, for polymeric components molded into the polymer of the components. Further, radiopaque contrast agent can be delivered into the cavity, of the stomach to visualize the stomach cavity volume wider X-ray. As the stomach cavity, volume is compressed by one or more expandable members 10em, the reduction in volume of the stomach cavity is readily observed the reduction in the area of the contrast agent visualized.

Tools and Instruments

In addition to the tools and instruments already described above, this section describes details of tools and instruments that can be used to facilitate the implantation of devices described herein. Additional tools and instruments can be described and referred to in the "Methods" section below.

FIG. 60 shows an instrument (e.g., deliver device) 350 for delivering an extra-gastric expandable device 10 to a target surgical location within the abdominal cavity of a patient. Instrument 350 is designed to deliver device 10 through a port or other small opening during a minimally invasive procedure. Instrument 350 includes a blunt, atraumatic distal tip or "nosecone" 352 that is configured to be driven through a small access opening to guide the instrument 350 and device 10 to the target surgical location. Some blunt dissection can also be performed using distal tip 352, if needed. Distal tip 352 is connected to drive handle 354 by a slender rigid rod 356 that permits distal tip 352 to be driven by pushing on handle 354, without buckling of rod 356. Expandable device 10 (shown in phantom lines) is received, in a contracted configuration, within rigid or flexible cannula 358 which is slidable over the length of rod 356. If rigid, cannula 358 can be articulated and steerable to direct device 10 to the intended location. At least the proximal end portion of nosecone 352 is receivable within the distal opening of cannula 358, as shown in FIG. 60. Device 10 can be folded in the compressed configuration around rod 356 or can extend adjacent rod 356. A stop member 360 is provided in the proximal end portion of cannula 358 and is fixed with respect to cannula 358 while being slidable over rod 356. Thus, stop member 360 functions to help keep cannula 358 centered over rod 356 and prevent device 10 from sliding out the proximal end of cannula 358 as cannula 358 is slid distally with respect to rod 356. In this way, stop member 360 can also function as a pusher to drive device 10 distally. A locking mechanism 362 can be provided to maintain the cannula in the distal most position shown in FIG. 60. As shown, locking mechanism 362 comprises a brace that connects handle 354 with the proximal end of cannula 358. However, other locking mechanisms can be substituted, as would be apparent to those of ordinary skill in the art. The functioning of delivers device 350 is described in further detail below in the "Methods" section.

Figure 61:
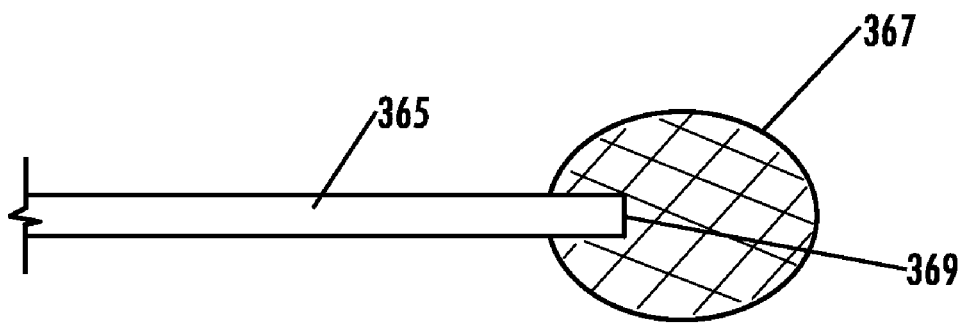
FIG. 61 illustrates a distal end portion of an endoscope fitted with a cage.

The delivers and placement of expandable device 10 can be performed under various imaging guidance, such as X-ray, ultrasound, direct visualization and/or visualization with a camera and/or endoscope. For visualization using an endoscope, the endoscope tip, which typically includes the viewing port or lens can become obscured by tissues or organs in the abdominal cavity when traversing the endoscope into the abdominal cavity, without insufflation, to attempt to locate and identify a desired view. In order to provide a clear view in a percutaneous procedure, the distal end portion of endoscope 365 is fitted with a cage 367 to keep tissues and organs from contacting the lens or viewing port 369 at the distal tip of the endoscope, as illustrated in FIG. 61. Cage 367 can be permanently fixed to endoscope 365 by adhesives, various forms of welding or other fixation means, or can be removable, such as by a threadably attaching cage 367 to endoscope 365. Cage 367 can be compressible and self-expanding so that cage 367 can be compressed for insertion through a minimally invasive port or opening, after which it expands when it enters the abdominal cavity.

Figure 62:
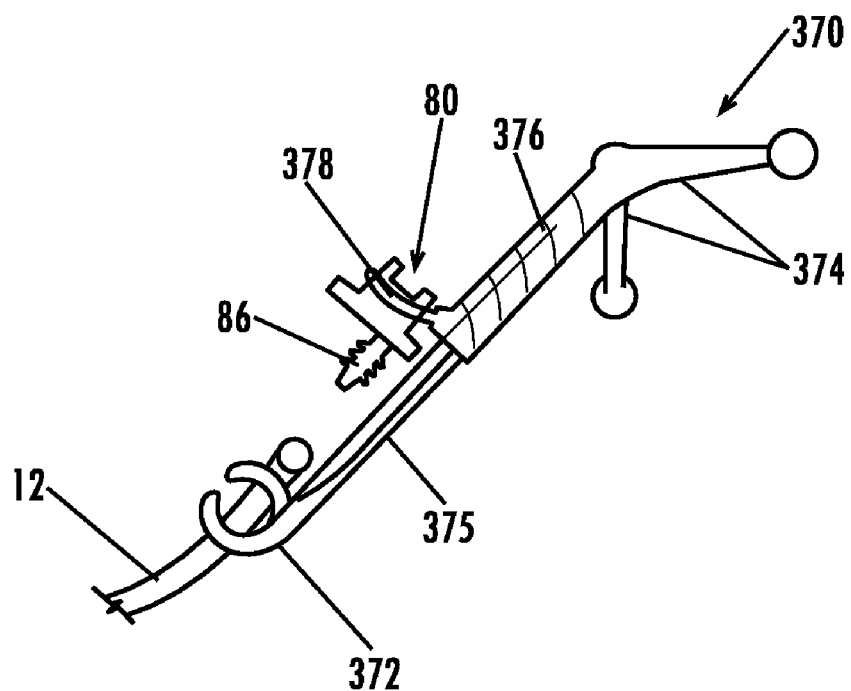
FIG. 62 illustrates a tool useful for placement and connection an adjustment member to a conduit.

FIG. 62 is an illustration of a tool 370 useful for placement and connection of adjustment member 80 to conduit 12. The distal end portion includes a grasper-like clamp mechanism 372 that is operable to clamp down on conduit 12 by squeezing handles 374 together. Portions of clamp jaws 372 can optionally include opposing cutting edges so that conduit 12 can be cut to a desired length using the same tool. Alternatively, separately operable cutting jaws (not shown) can be provided to be operated independently of the clamping jaws.

A tube 376 that is slidable over the main shaft 375 of tool 370 includes an adjustment member mount 378 that is configured to releasably hold adjustment member. For example, mount 378 can be formed of spring steel biased to a curvature to compress against adjustment member 80 when wrapped around adjustment member 80. When conduit 12 is of acceptable length or has been cut to an acceptable length and then clamped by the jaws of clamping mechanism 372, adjustment member 80 having been mounted in mount 378 is advanced toward conduit 12 by sliding tube 376 distally with respect to main shaft 375. Conduit 86 is then driven into conduit 12 to form a fluid tight connection by pressure fitting. The connection can optionally be further secured by adhesives, healing, or installation of an external clamp around the proximal end portion of conduit 12 to further compress it against conduit 86, for example. Jaws 372 are then released from conduit and withdrawal of tool 370 breaks adjustment member 80 free of mount 378.

Figure 63:
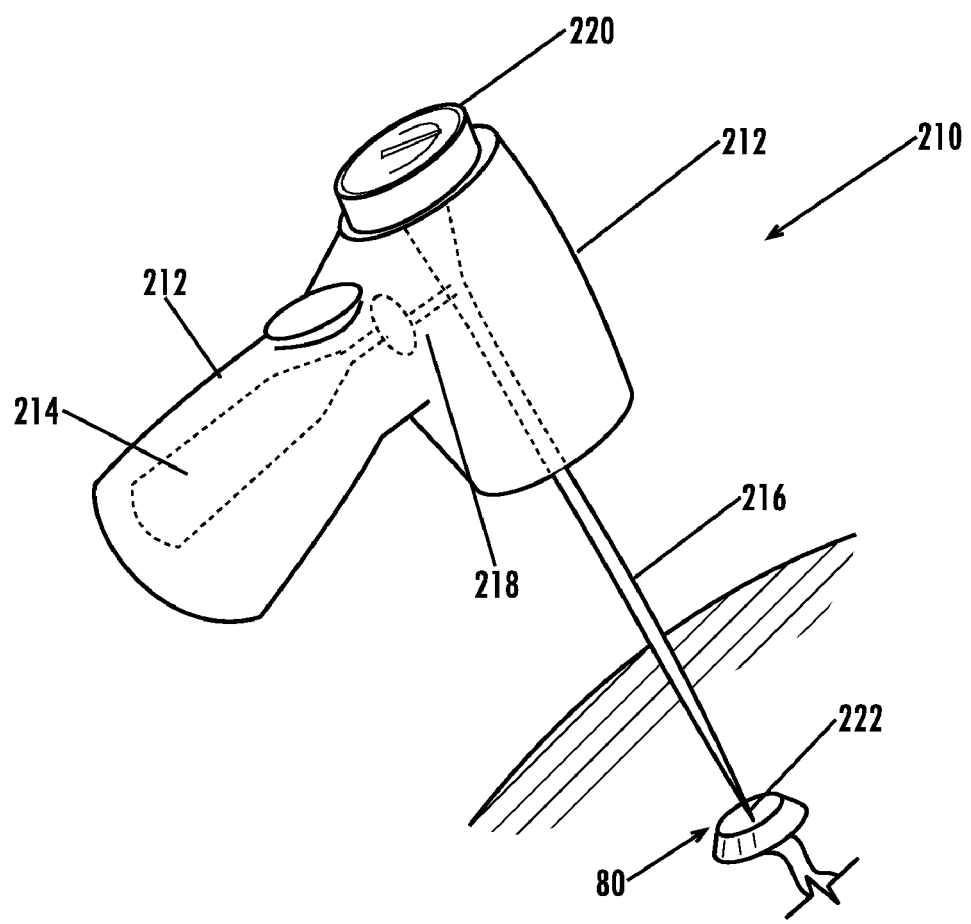
FIG. 63 shows another embodiment of an inflation tool that can be used to access an adjustment member for delivery or withdrawal of fluid to or from an expandable member of a device.

FIG. 63 shows another embodiment of an inflation tool 210 that can be used to access adjustment member 80 for delivery or withdrawal of fluid to or from device 10. Inflation tool 210 is provided with a housing or main body 212 that is configured and dimensioned to be comfortably held in the hand of an operator, and thus functions as a handle. Main body 212 can contain a fluid reservoir 214 that typically holds a pressurized gas supply, but can hold liquid. Alternatively, tool 210 can be connected to an external source of pressurized gas or liquid. Reservoir 214 is in fluid communication with inflation needle 216 via a pressure regulator 218. A pressure meter 220 is in fluid communication with needle 216 to measure the amount of pressure therein, and is mounted on the surface of housing 212 to permit visualization of the pressure meter 220. A control knob 221 is provided that can be switched (e.g., rotated) to open the fluid pathway between reservoir 214 and needle 216 for the input of pressurized fluid to device 10, or to close the reservoir 214 off and divert the fluid pathway leading to needle 216 for withdrawal of pressurized fluid from device 10. Additionally, or alternatively, control knob 220 can be set to a predetermined pressure reading, to deliver or withdraw pressure until the predetermined, set pressure level has been achieved, at which time flow between the instrument and the adjustment member 80 is automatically shut off. Inflation needle 216 can be configured according to any of the embodiments discussed previously. In the example shown, inflation needle includes side opening 222 and optionally can contain the safety valve mechanism 224 (not shown).

Methods

In addition to the methods already described above, this section describes details of methods that can be employed to implant the devices described herein. It is to be understood that the methods described herein are only examples of methods that can be employed, as alternative techniques, placement of devices, anchoring of devices, locations or structures to which devices are anchored, etc. can be employed.

Figure 64A:
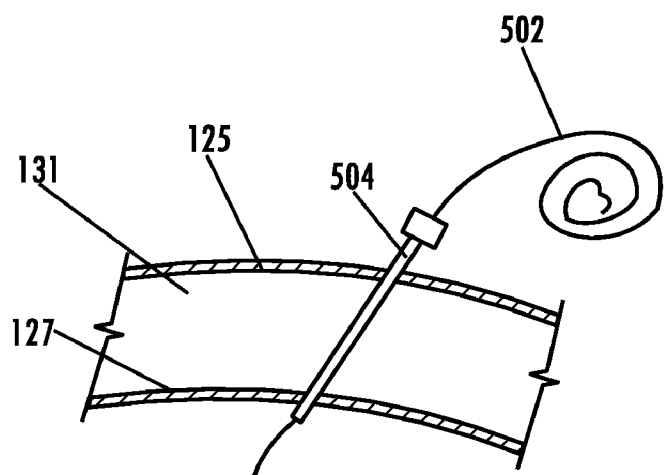
FIGS. 64A-64G illustrate steps of a method of percutaneously implanting an expandable extra-gastric device according to one embodiment of the present invention.
Figure 64B:
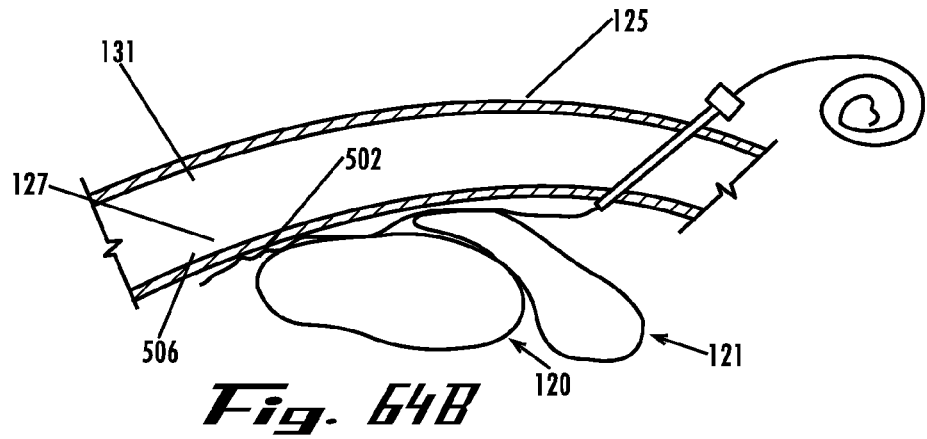
Figure 64C:
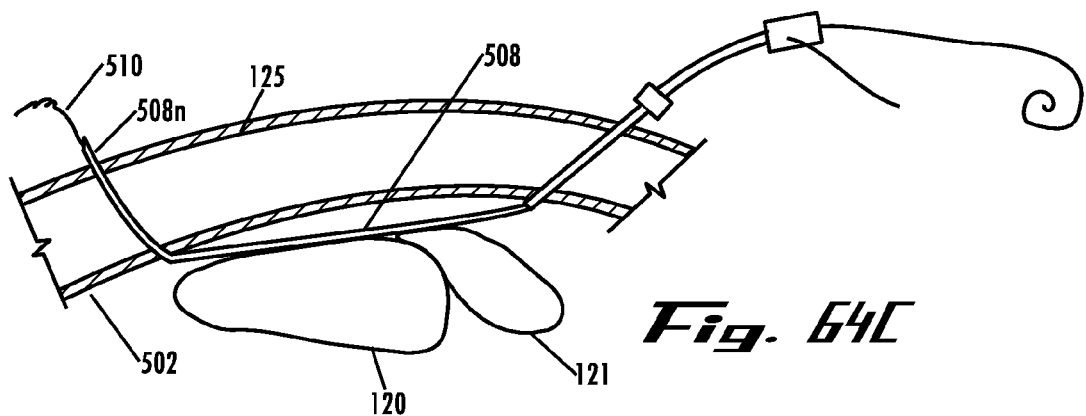
Figure 64D:
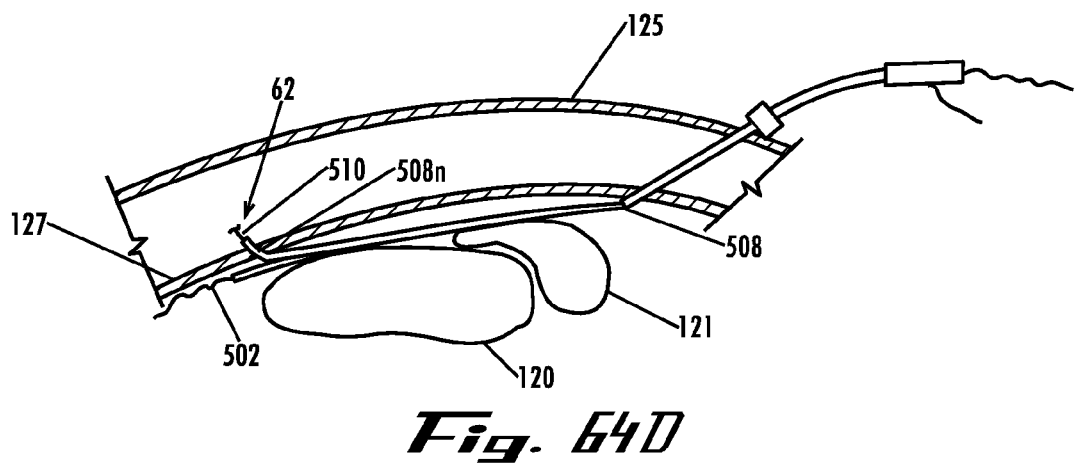

FIGS. 64A-64G illustrate steps of a method of percutaneously implanting an expandable extra-gastric device according to one embodiment of the present invention. At FIG. 64A, a veress needle 501 or other instrument is used to access the abdominal cavity. A conventional veress needle does not have a lumen for a guidewire. By adding a small sheath outside the shaft of the veress needle apparatus, a modified veress needle is created such that a guidewire can be easily introduced through the sheath. With visual guidance such as by fluoroscopy, ultrasound, or endoscope, for example, a guidewire 502 is advanced to a surgical target area 506, passing between the liver 121 and the peritoneum 127 and between the stomach 120 and peritoneum 127, as illustrated in FIG. 64B. Next, a side-deploying needle catheter 508 is advanced over guidewire 502 to form an opening from the target area 506 to outside of the body, and a body floss wire 510 is advanced through the catheter 508 so as to extend from the opening formed by the veress needle and the opening formed by the needle catheter and traverse the distance therebetween, inside the peritoneum, see FIG. 64C. Alternatively, the side deploying needle 508n of side deploying needle catheter 508 may only need to be deployed into the tissue external of and adjacent to the peritoneum (the tissue adjacent to the peritoneum is muscle first, then fat, then skin) and not have to extend back out through the skin 125 if the body floss wire is provided with a fixation structure 62 (e.g., such as one of the fixation structures described above with reference to FIGS. 39A-39C, or the like) at a distal end thereof, which facilitates fixation of the distal end of guidewire without having to pass back out of the skin as illustrated in FIG. 64D.

Figure 64E:
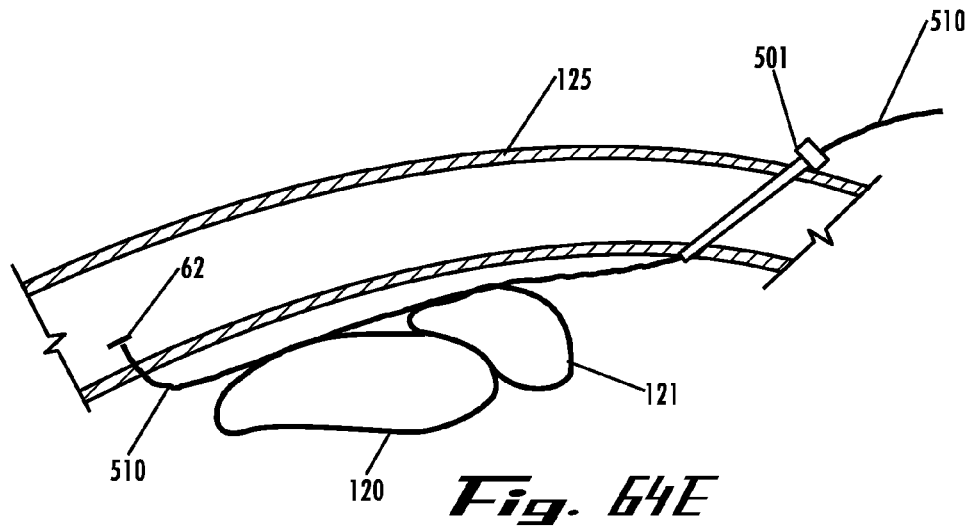
Figure 64F:
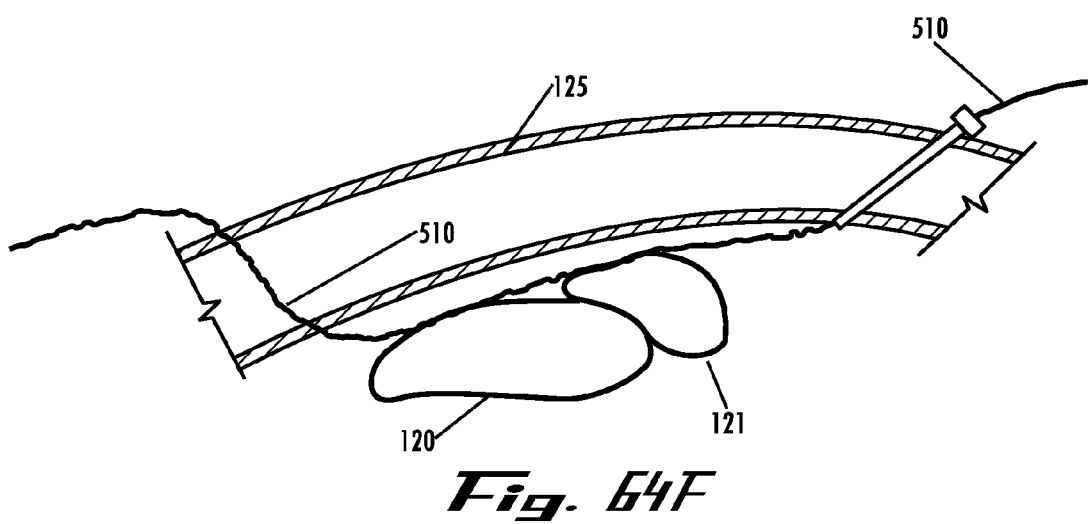

After placement of the body floss wire 510, side-deploying catheter 508 and guidewire 502 are withdrawn, leaving the body floss wire as show in FIGS. 64E-64F, depending upon whether or not a fixation structure 62 was attached to the distal end of body floss wire 510. Further optionally, a needle catheter that deploys from the distal end thereof ("front-deploying catheter) can be used in place of side-deploying catheter 508. In this case, once the front-deploying catheter is placed over the guidewire, guidewire 502 is withdrawn to allow routing of body floss wire 510 through the front-deploying catheter. Alternatively, guidewire 502 can be configured to function as the body floss wire, in which case guidewire 502 would not need to be withdrawn, but would rather be directed through the peritoneum 127 and anchored or passed out of the skin.

Figure 64G:
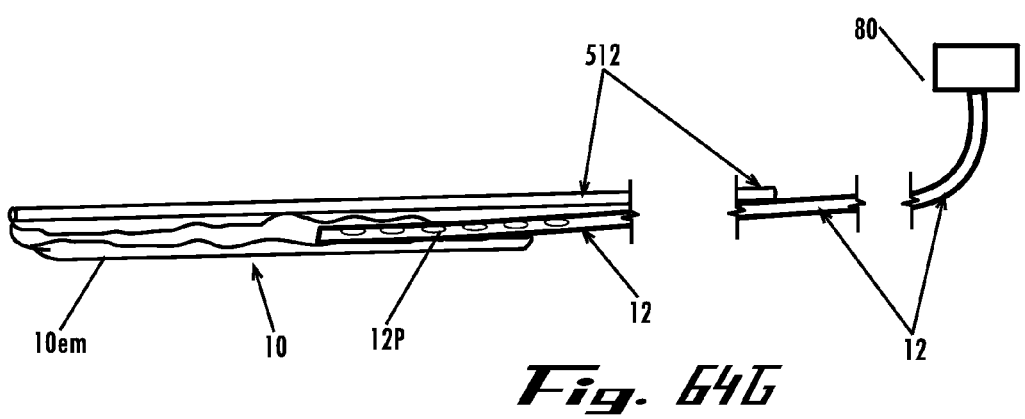

When the distal end of body floss wire 5100 or guidewire 502 is passed back out through the skin, as illustrated in FIG. 64F it is tied off or otherwise secured from outside of the body. Once body floss wire 510 has been distally secured by either method, device 10 is ready to be delivered to the target surgical site. As illustrated in FIG. 64G, expandable member 10em of device 10 is provided in a compressed configuration, which can be folded if expandable member 10em is noncompliant or semi-compliant, but is simply contracted if expandable member 10em is compliant. A rail 512 is fixed longitudinally along expandable member 10em and conduit 12 and is configured to ride over body floss wired 510 during the delivery of device 10 to the target surgical site. FIG. 64G also illustrates inflation ports 12p in conduit 12 used to inflate expandable member 10em. Rail 512 of device 10 is threaded over body floss wire 510 and device 10 is passed through the proximal opening where body floss wire 510 enters the body, by sliding device 10 over the body floss wire 510. Device 10 is advanced until its distal end is positioned at or near the target surgical location 506. Adjustment member 80 is fixed in one of the positions described above, and expandable member 10em is inflated by delivering pressurized fluid through adjustment member 80 and conduit 12. The proximal end portion of the body floss wire can be tied off against adjustment member 80, thereby anchoring expandable member by tethering it to this location and at location 506. The lumen that rides over the guidewire will typically be adjacent to adjustment member 80 and not pass through it. However, it ma be rigidly attached to adjustment member 80 which in turn is anchored to the body, as described above, and this secures the lumen. Prior to, or after inflation, expandable member 10em can optionally be additionally anchored at one or more locations using any of the anchoring techniques and features described above.

Figure 65D:
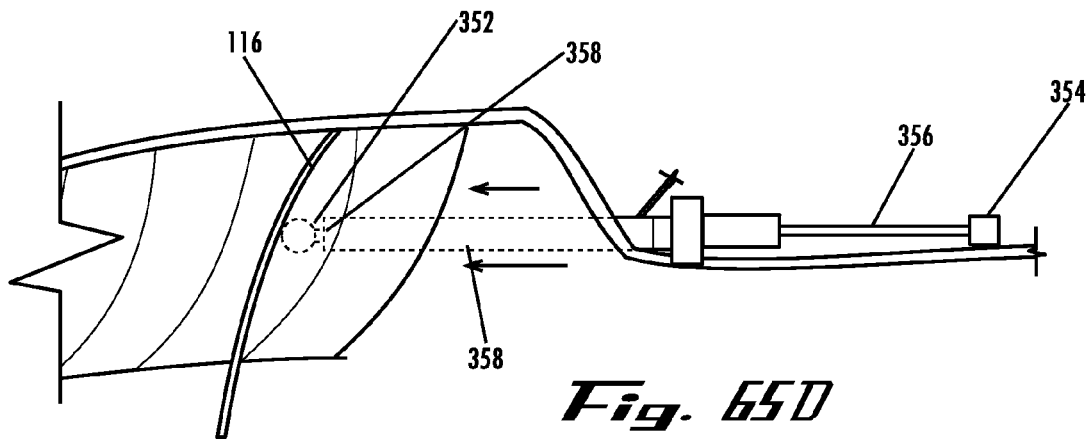

FIGS. 65A-65G illustrate steps of a method of percutaneously implanting an expandable extra-gastric device 110 according to another embodiment of the present invention. A veress needle 501 or other instrument is used to access the abdominal cavity, see FIG. 65A. The ribs 129, in this case, the left ribs, are illustrated as overlying diaphragm 116 which forms a superior boundary of the abdominal cavity. After removing the tool used to form the access opening into the abdominal cavity, instrument 350, containing device 10 in a compressed configuration within cannula 358 is inserted into the opening, with distal tip 352 functioning to further dilate the opening to traverse the abdominal cavity without damaging organs or other structures therein. In the illustration of FIG. 65B, cannula 358 is shown in a proximal most location with respect to distal tip 352, to be distally advanced in a later step, as described below. Accordingly, cannula 358 is provided with a tapered, atraumatic distal end portion 358d. Distal end portion 358d is flexible enough to expand to accommodate elements passing there through. Alternatively, cannula 358 (and device 10 within) can be advanced to a distal most position (e.g., see FIG. 59), and advanced through the opening along with distal tip 352. In this instance, distal end portion 358d is omitted, as the distal opening of cannula 358 interfaces with the proximal end portion of distal tip 352. After inserting distal tip 352 (and optionally, cannula 358 and device 10) into the abdominal cavity as illustrated, device 350 is then rotated into a position to point the distal tip 352 of tool 350 toward the target surgical location, as illustrated in phantom in FIG. 65B. In this example the target surgical location is the inner surface of the diaphragm 116 on the left ribs 129 side, although other target locations for implantation of device 10 can be chosen, as noted previously.

Figure 65E:
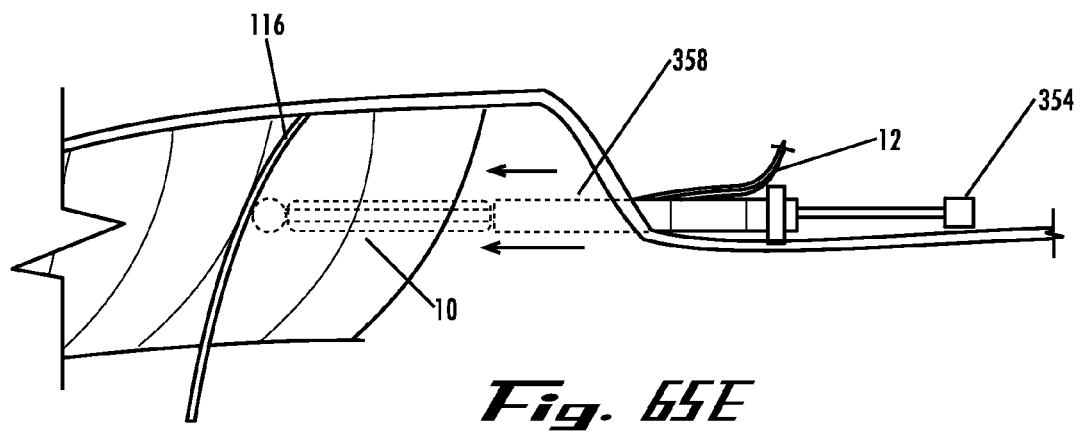
Figure 65F:
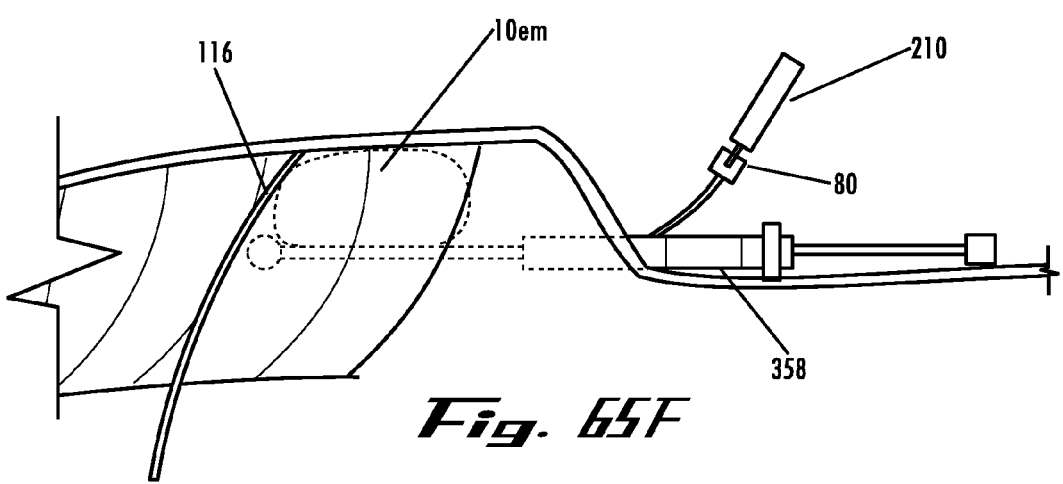

Tool 350 is next advanced toward the target surgical area until distal tip 352 reaches the target surgical area as illustrated in FIG. 65C. Cannula 358 and device are then slid distally with respect to shaft 356 until the distal end of cannula 358 contacts or is closely adjacent to the proximal end portion of distal tip 352, as illustrated in FIG. 65D. Note, that in the optional procedure where cannula 358 and device 10 are positioned in their distal-most positions relative to 356 when initially inserting distal tip into the opening, this step will be omitted. In either case, cannula 358 is next retracted (i.e., slid proximally with respect to rod 356) while maintaining tip 352 stationary, such as by steadying handle 354 and/or shat 356. As cannula 358 is retracted, device 310 is left in position in the target surgical area, as illustrated in FIG. 65E. Expandable member 10em is next expanded to an expanded configuration as illustrated in FIG. 65F. If expandable member 10em is an inflatable member or a portion of expandable member 10em is inflatable, then inflation can be performed by inputting pressurized fluid through adjustment member 80 using one of the inflation tools 210 described above, or other pressurized fluid source. If all or a portion of expandable member 10em is a mechanically expandable member, then the mechanically expanding member can self-expand upon retraction of cannula 358, or can be expanded using one of the techniques described above. Tool 350 can then be removed from the patient (FIG. 65G) leaving the expanded device 10 in place at the surgical site. Expandable member can be anchored to one or more internal structures, such as the diaphragm 116, internal surface of abdominal wall, or other structure, at one or more locations, using any of the techniques and anchors described above. Adjustment member 80 can be fixed in one of the locations described above using one or more of the fixation techniques described.

Figure 66B:
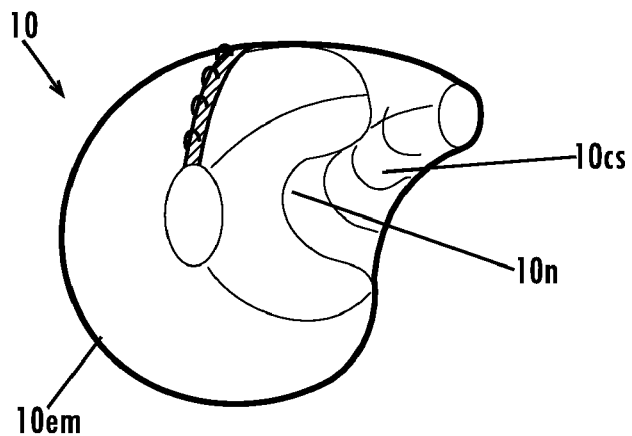
Figure 66C:
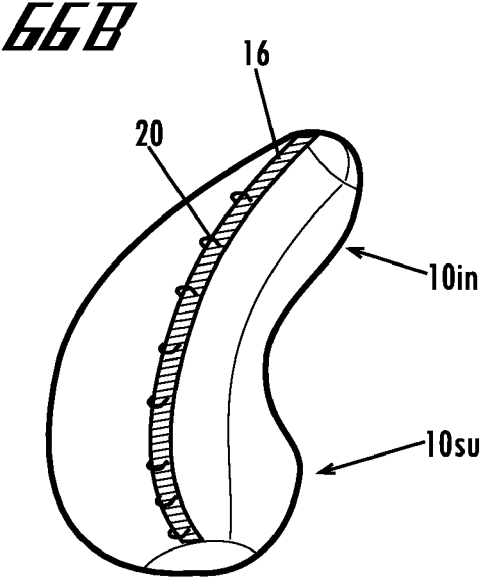

FIGS. 66A-66L illustrate device 10 and steps of a method of percutaneously implanting device 10 according to another embodiment of the present invention. FIGS. 66A-66C show side, top and inverted front views of device 10 to be implanted by the method described. Like the embodiment shown in FIG. 3L, expandable member 10em of device 10 has a bulbous superior portion 10su and an inferior portion 10in having a reduced cross-sectional area that join to form concavity 10cs on surface 10a.

Figure 66D:
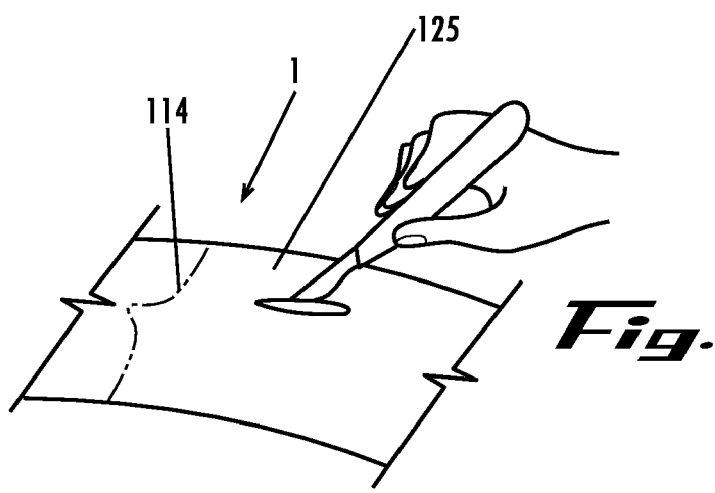
Figure 66E:
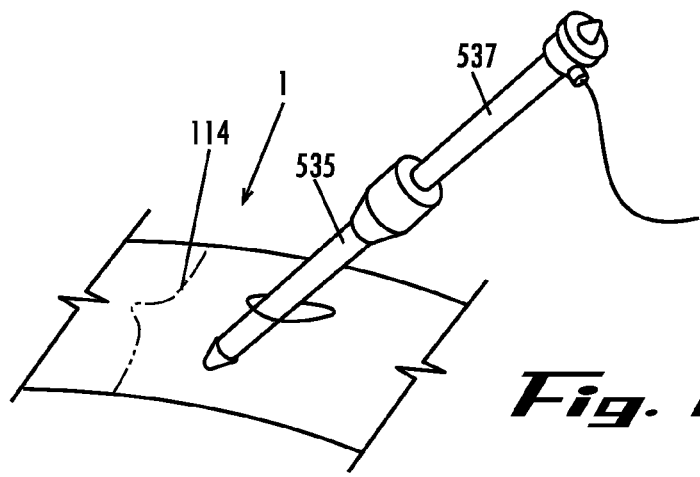

An incision is made through the skin 125 of the patient 1 as shown in FIG. 66D, in a location where device 10 is to be inserted through. For example, the location can be in the vicinity of 126 shown in FIG. 1. After dilation and initial blunt dissection of the fat layer, a cannula 535 is installed to provide an opening into the abdominal cavity. As shown in FIG. 66E, an endoscope 537 can be inserted through cannula 535 to view the abdominal cavity and locate the appropriate entry route for delivery and placement of device 10. Endoscope 537 can be configured to pass guidewire 502 therethrough, so that the distal end of guidewire 502 can be placed initially between the stomach 120 and diaphragm 116 under endoscopic visualization. After initial placement of the distal end of guidewire 502, endoscope 537 is removed, while maintaining guidewire 502 in its current position. Alternatively, the guidewire can be inserted after a cannula is intra-abdominally positioned and a blunt dissector tip and endoscope are removed.

Figure 66F:
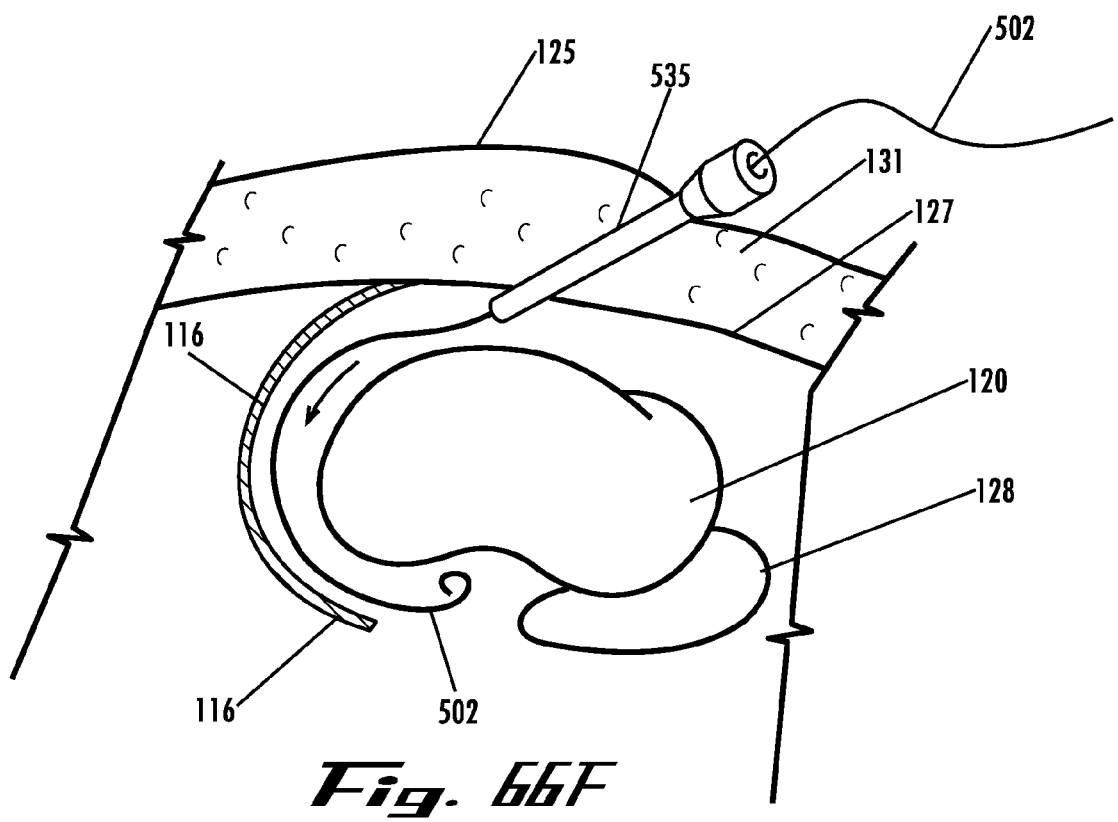

Next, guidewire 502 is advanced to traverse guidewire 502 to establish the delivery pathway along which device 10 is to be delivered for placement and anchoring. As guidewire 502 is advanced, it is guided by the natural curvature of diaphragm 116, as illustrated in FIG. 66F.

Figure 66G:
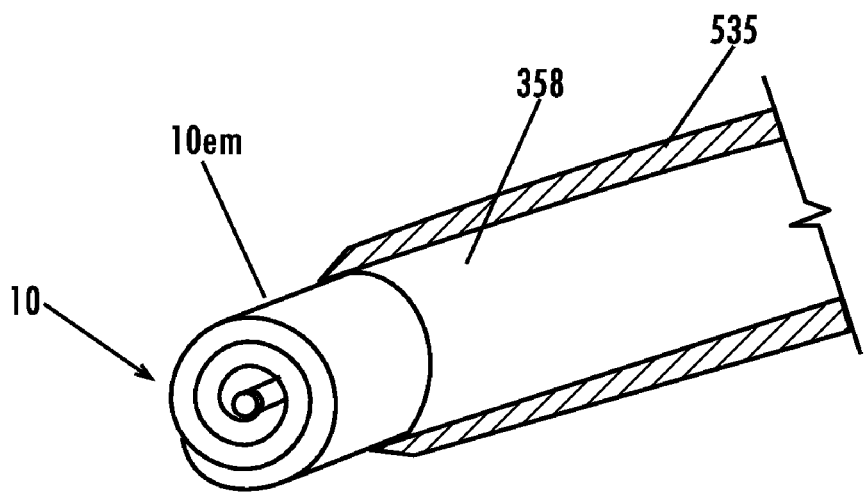
Figure 66H:
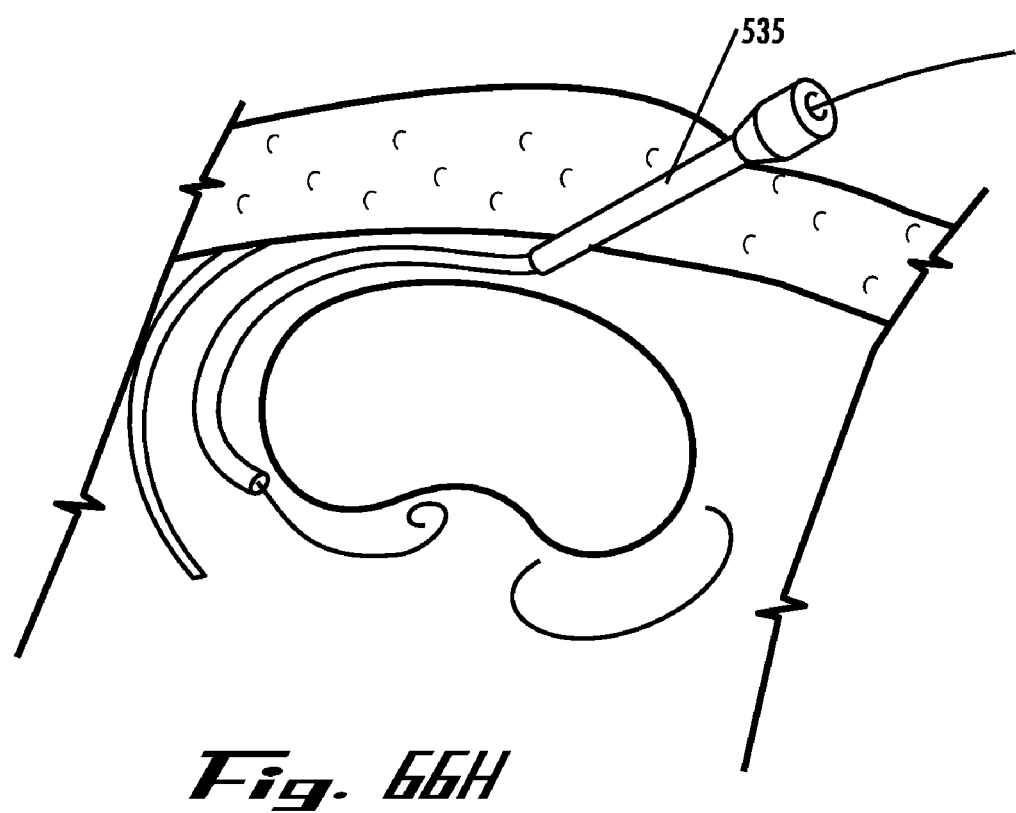
Figure 66I:
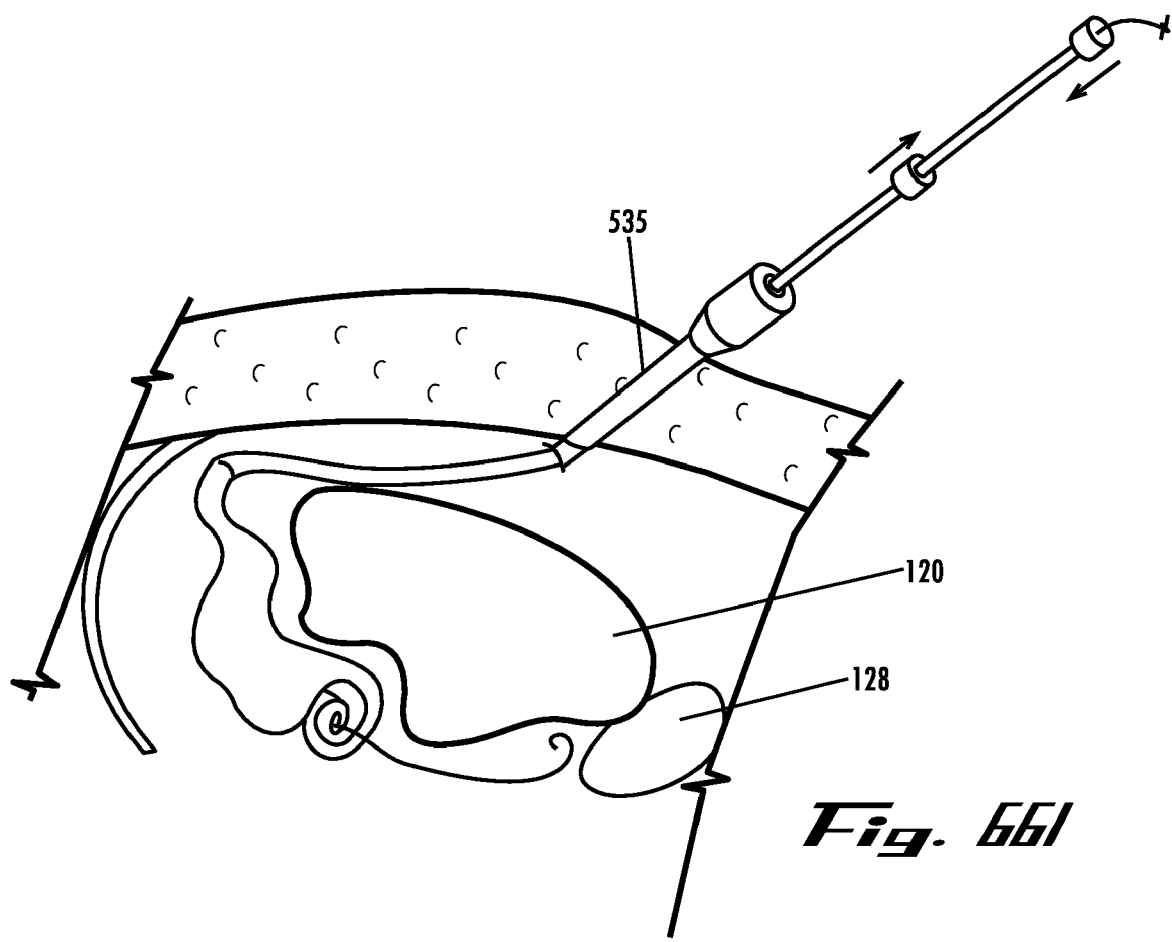

FIG. 66G shows the expandable member rolled up in a delivery sheath (not shown). A guidewire lumen can be optionally provided on the expandable member, so that, in the rolled up state, the lumen can be tracked over the guidewire to guide the deliver of the expandable member. The expandable member is inserted through the port and optionally over the guidewire and passed down around the stomach between the diaphragm and the stomach (see FIG. 66H). The sheath is then retracted (see arrows in FIG. 66I) releasing the coiled (rolled up) expandable member and allowing the expandable member to be expanded in situ. Once fully deployed the sheath apparatus is removed, leaving the expandable member and conduit in place.

Figure 66J:
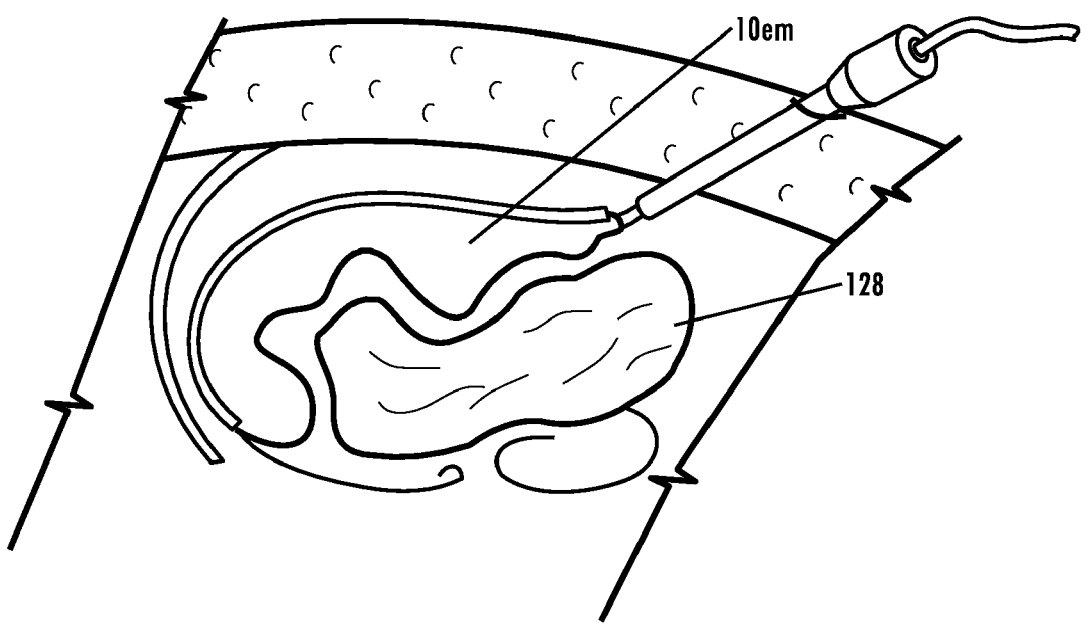
Figure 66K:
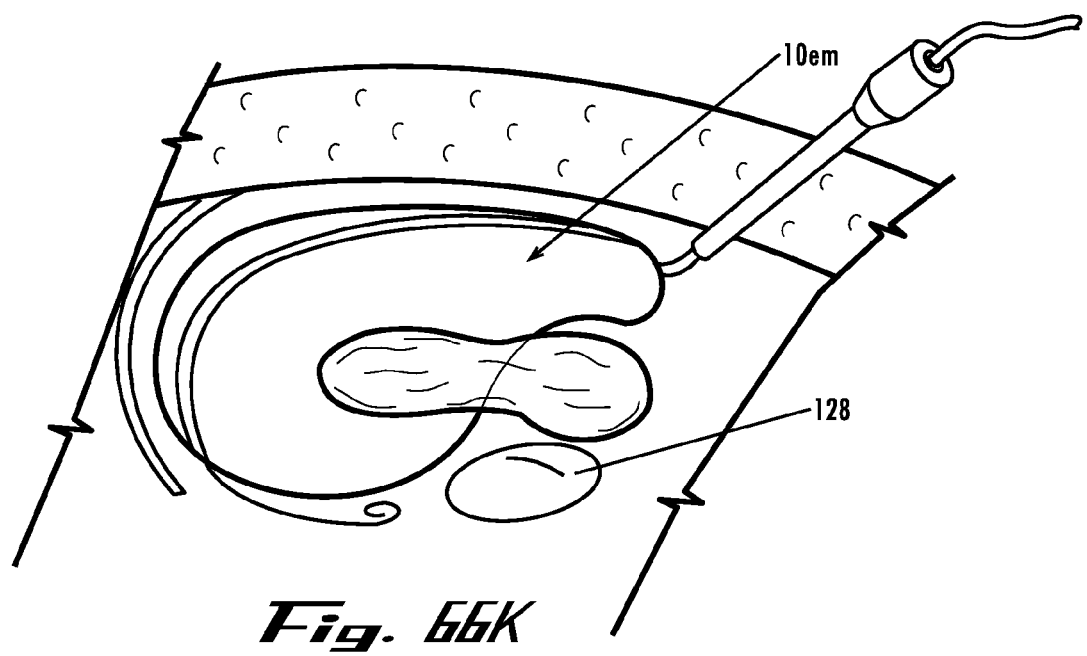

FIGS. 66J-66K show how the expandable member moves the stomach out of its position as the expandable member expands. The spleen is shown inferiorly of the expandable member.

Figure 66L:
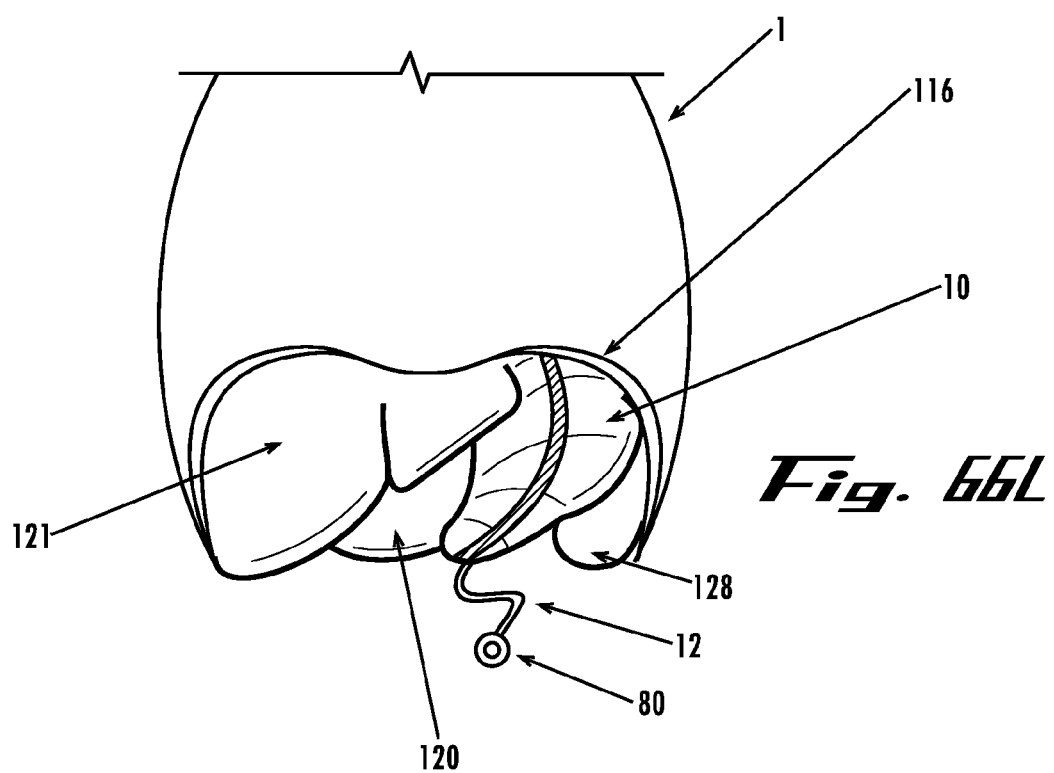

FIG. 66L is an illustration of device 10 in its position relative to organs in the abdominal cavity after implantation of the device as described above. Device 10, when inflated abuts and is anchored to the inner surface of the diaphragm 116, and compresses the stomach 120 medially and in a downward (inferior) direction. The left lobe of the liver 121 lies anterior to device 10 and the reduced cross sectional area of portion 10in lies medially of the spleen 128 for minimization of contact or compression thereof. Inferior portion 10in is also directed medially, relative to superior portion 10su, to provide compression of the body of the stomach 120.

Figure 66M:
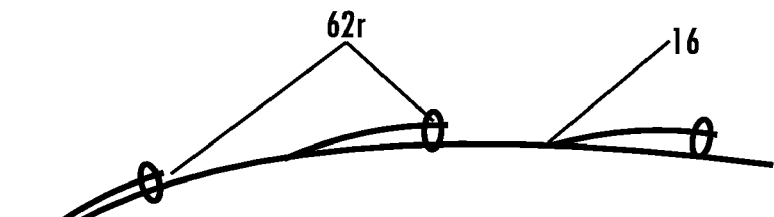
FIGS. 66M-66P show two examples of deployment mechanism and fixation structures that can be provided for anchoring a device in the procedure described with regard to FIGS. 66A-66L.
Figure 66N:
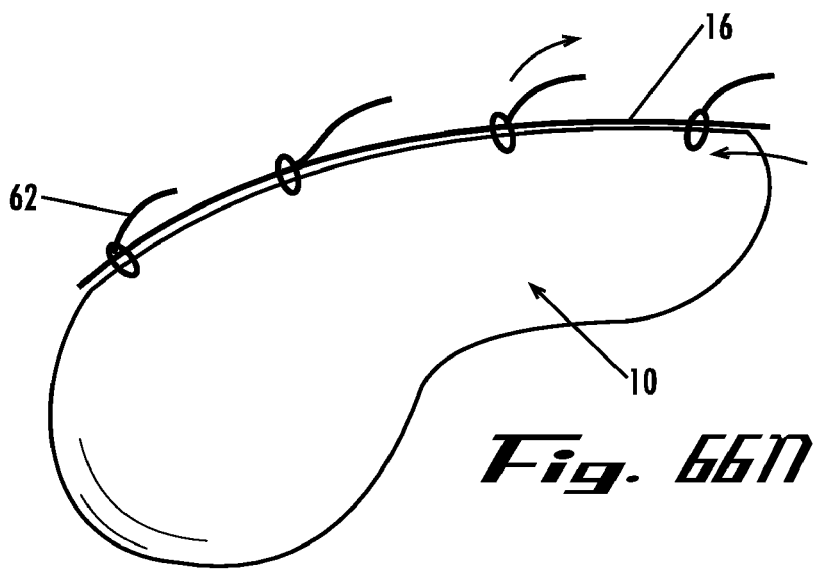

FIGS. 66M-66P show two examples of deployment mechanism and fixation structures that can be provided for anchoring device 10 in the procedure described above with regard to FIGS. 66A-66L. These fixation features or deployment mechanisms can also be employed with other embodiments of device 10, as well as in other procedures. Also, other fixation structures and techniques as discussed herein can be substituted or used in combination with the structures now discussed. In FIG. 66M, expandable member 10em is provided with a line of anchoring teeth 62 (which can optionally be barbed) and are configured to lie down against the surface or reinforcement 16 when device 10 is being delivered to the target surgical site. Reinforcement strip 16 is laterally slidable with regard to expandable member 10*em*. FIG. 66M illustrates reinforcement strip 16 as slid proximally to a closed orientation with respect to expandable member 10*em* and teeth 62. Teeth 62 can be sharpened at their free ends to facilitate piercing of tissue during an anchoring procedure, but need not be. Teeth 16 are configured to move to an open orientation, such as by being pivotally mounted and biased toward the configuration shown in FIG. 66N or by providing elastically deformable teeth which are biased to the open orientation. By sliding reinforcing strip distally with respect to expandable member 10*em* in the direction of the arrow shown in FIG. 66N, rings 62*r* slide to the bases (or pivot points) of teeth 62, thereby freeing them to move to their open orientations as shown in FIG. 66N. Teeth 62, which have single or no barbs, allow for easy reversal of the anchoring procedure, such as when device 10 is to be removed or repositioned, since simply moving the expandable member 10*em* distally will act to pull teeth 62 out of the structures to which they had been anchored.

Figure 66O:
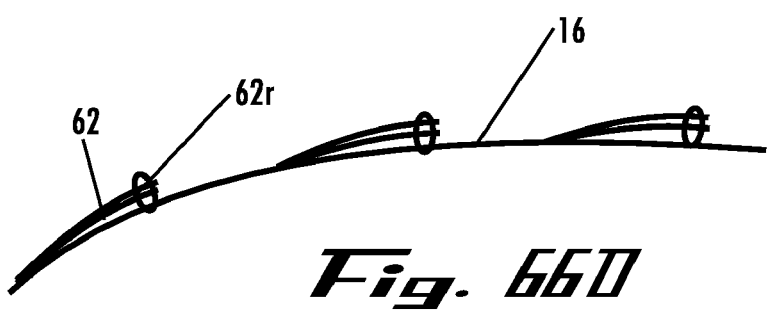
Figure 66P:
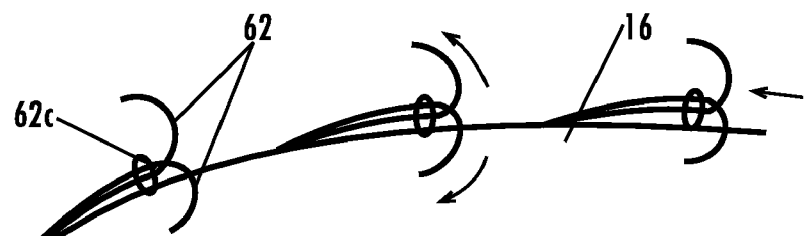

FIGS. 66O-66P illustrate closed and open configurations, respectively, of dual-barbed fixation structures 62 that can be substituted for those described above with regard to FIGS. 66M-66N. In this embodiment, anchoring is more secure as provided by a pair of barbs on each structure 62 that extend in different directions, when opened to engage a structure. Opening and closing are carried out in the same manner as described above with regard to FIGS. 66M-66N. In any of the embodiments of FIGS. 66M-66P, the fixation structures can be mounted on reinforcement strip and rings 62*r* can be mounted to the main body of expandable member and pass through longitudinal slots provided in the reinforcing member 16. In this case, reinforcing member is slid proximally with respect to expandable member 10*em* to permit fixation structures 62 to move to the open orientation.

Figure 67:
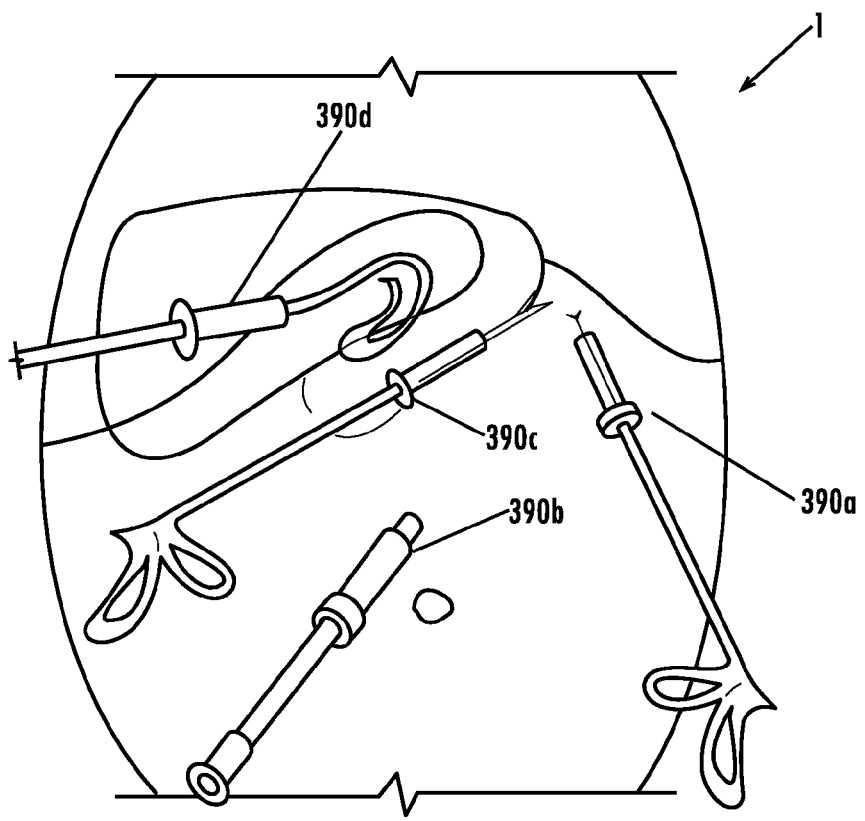
FIG. 67 illustrates port locations that can be used in laparoscopic implantation of a device in the same location as described with regard to the percutaneous procedure of FIGS. 66A-66L.
Figure 68A:
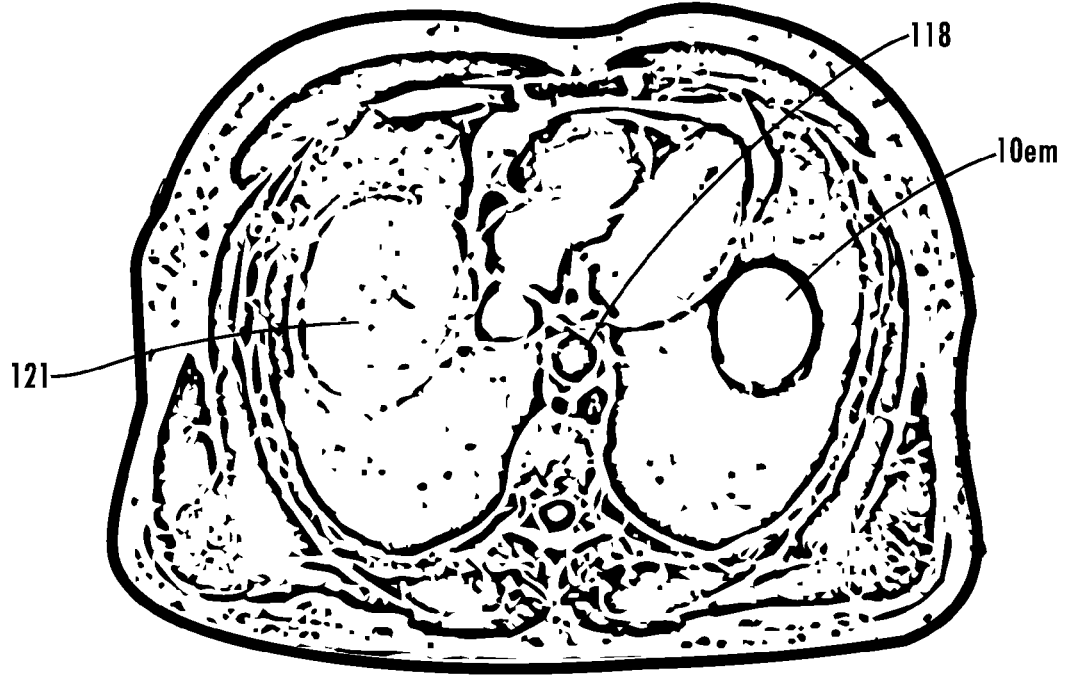
FIGS. 68A-68K are transverse cross-sectional illustrations of the abdominal cavity shown at sequential, incremental locations along the cavity, which correspond to the illustrations of FIGS. 2A-2K, respectively, but in which an expandable member, implanted in a position as described with regard to FIGS. 66A-67, is also shown.
Figure 68B:
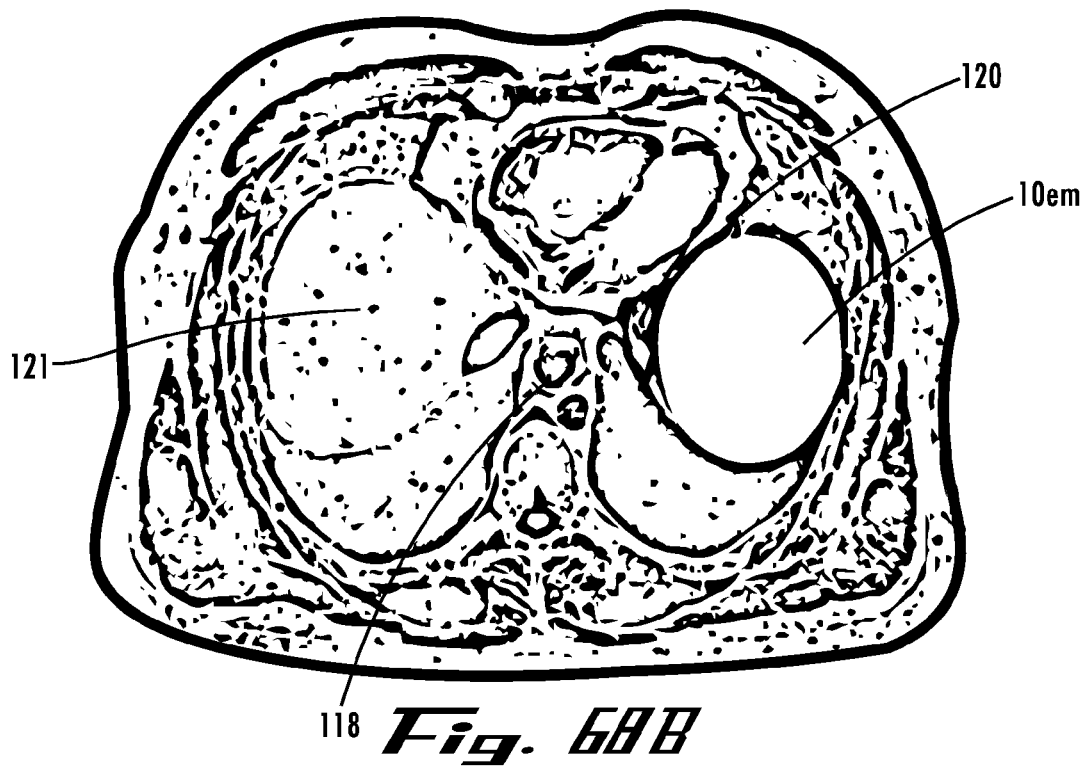
Figure 68C:
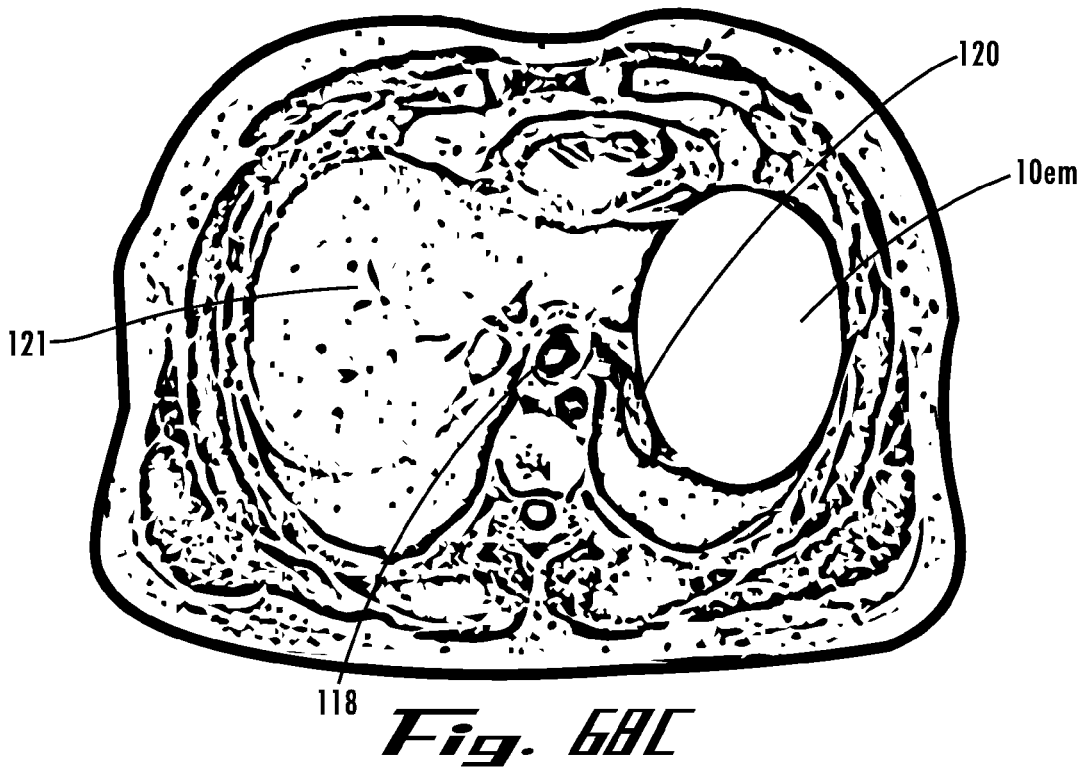
Figure 68D:
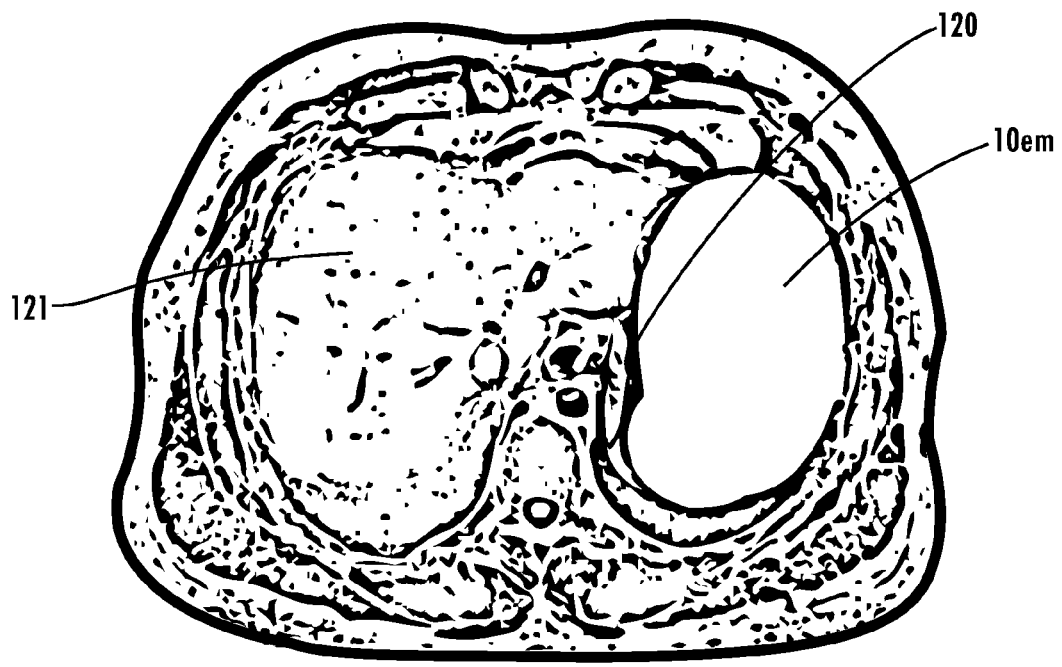
Figure 68E:
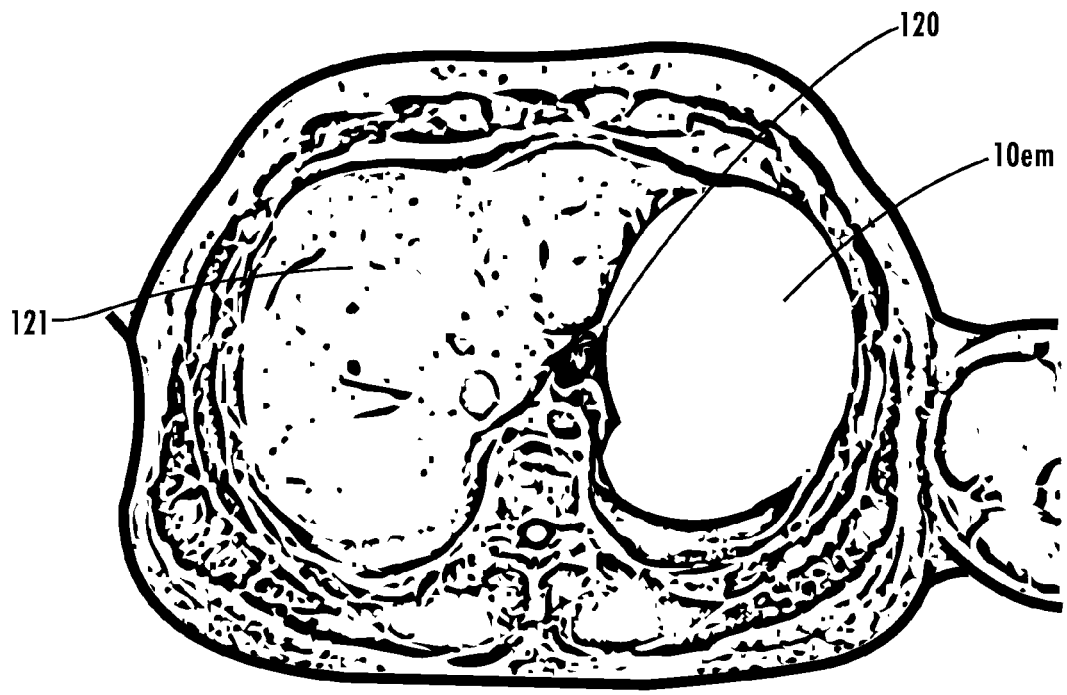
Figure 68F:
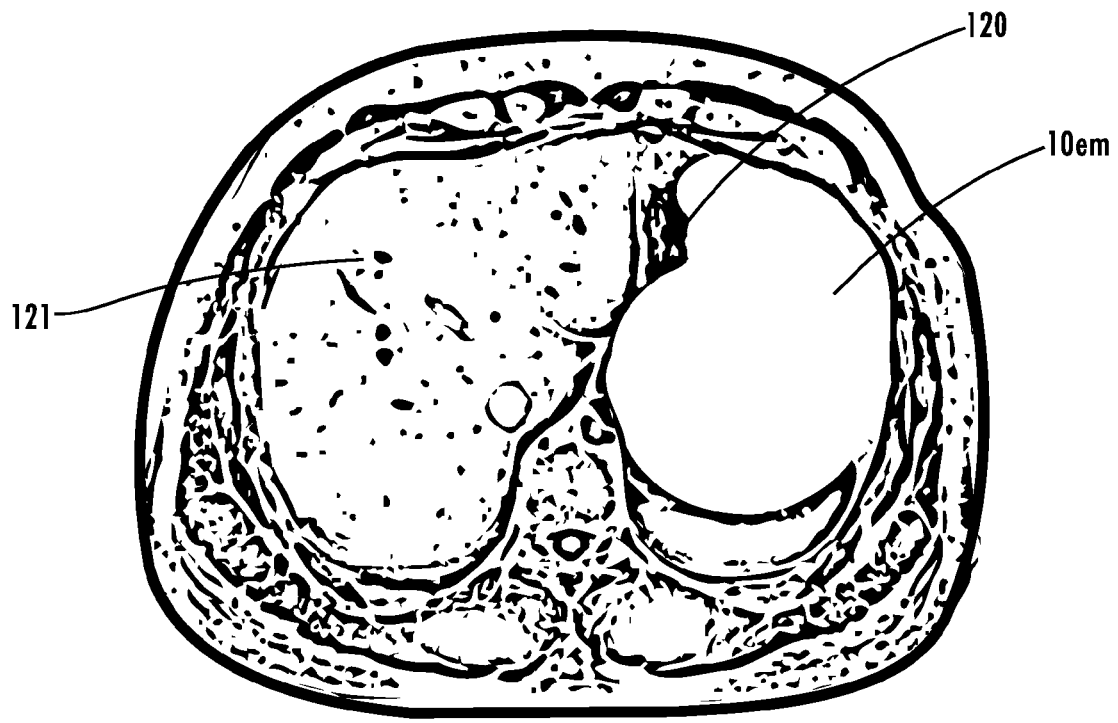
Figure 68G:
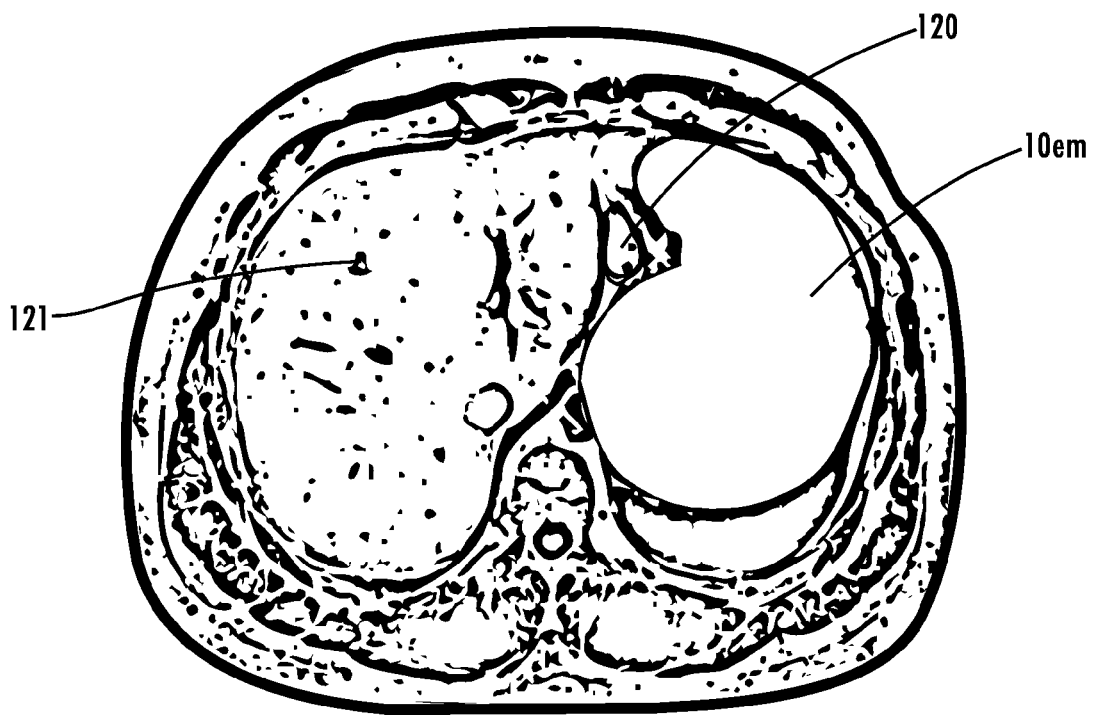
Figure 68H:
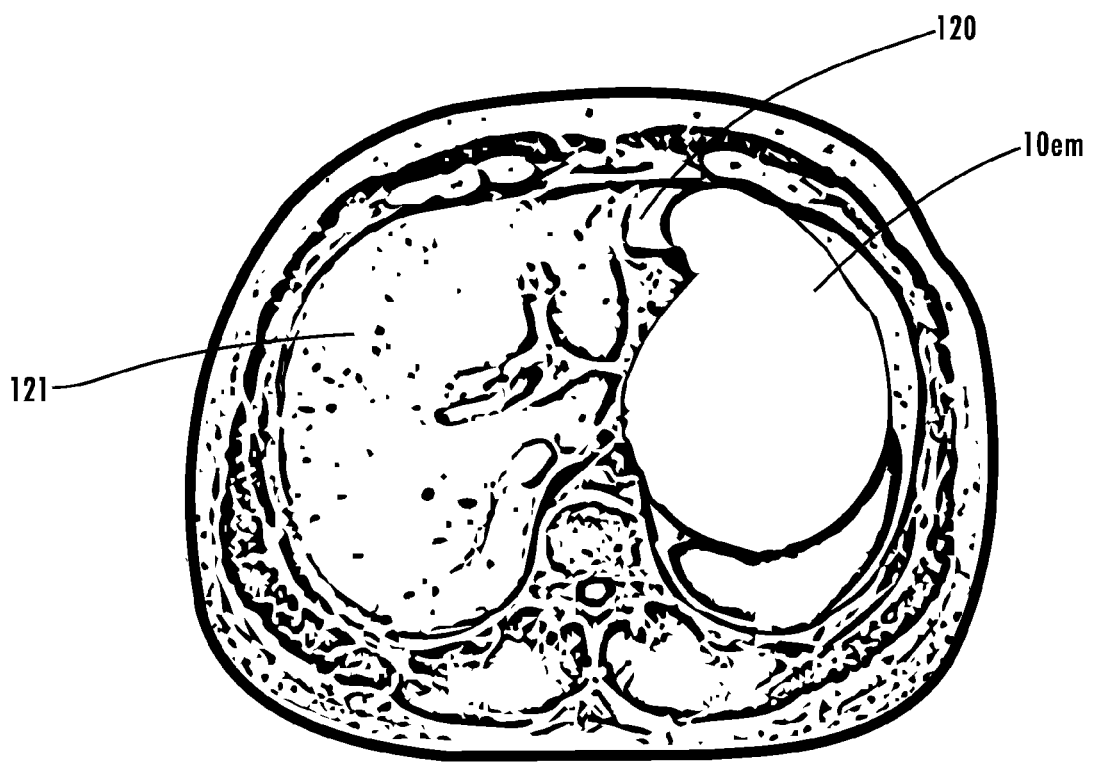
Figure 68I:
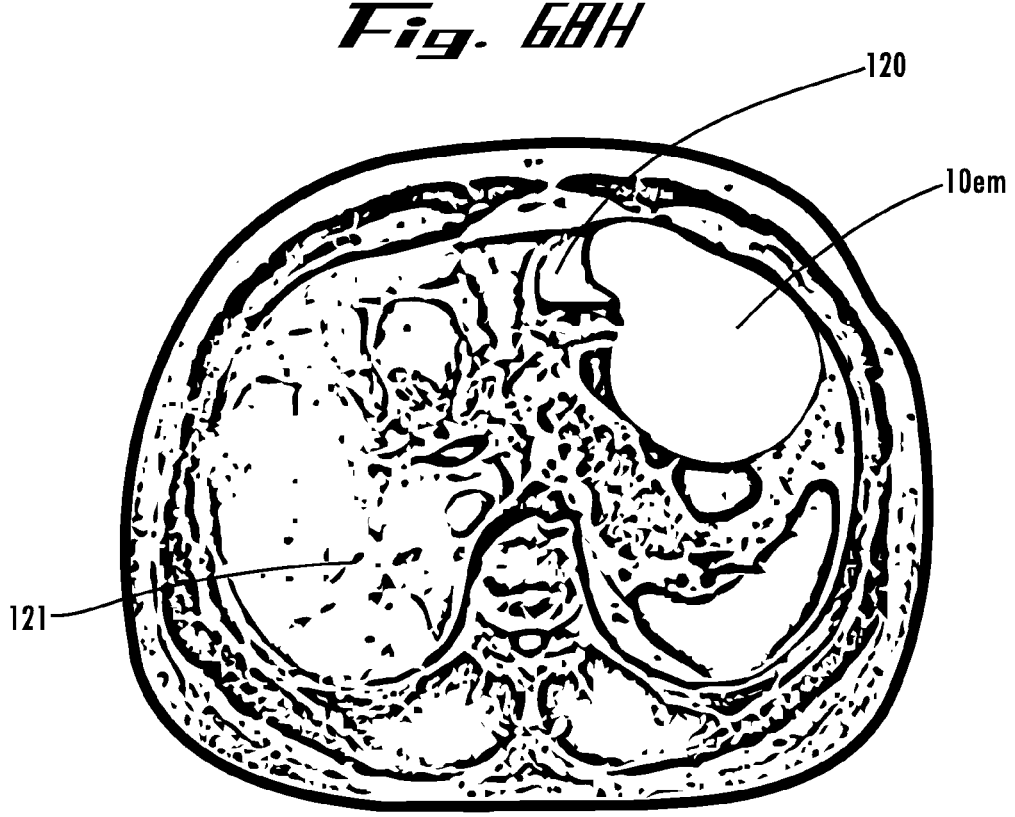
Figure 68J:
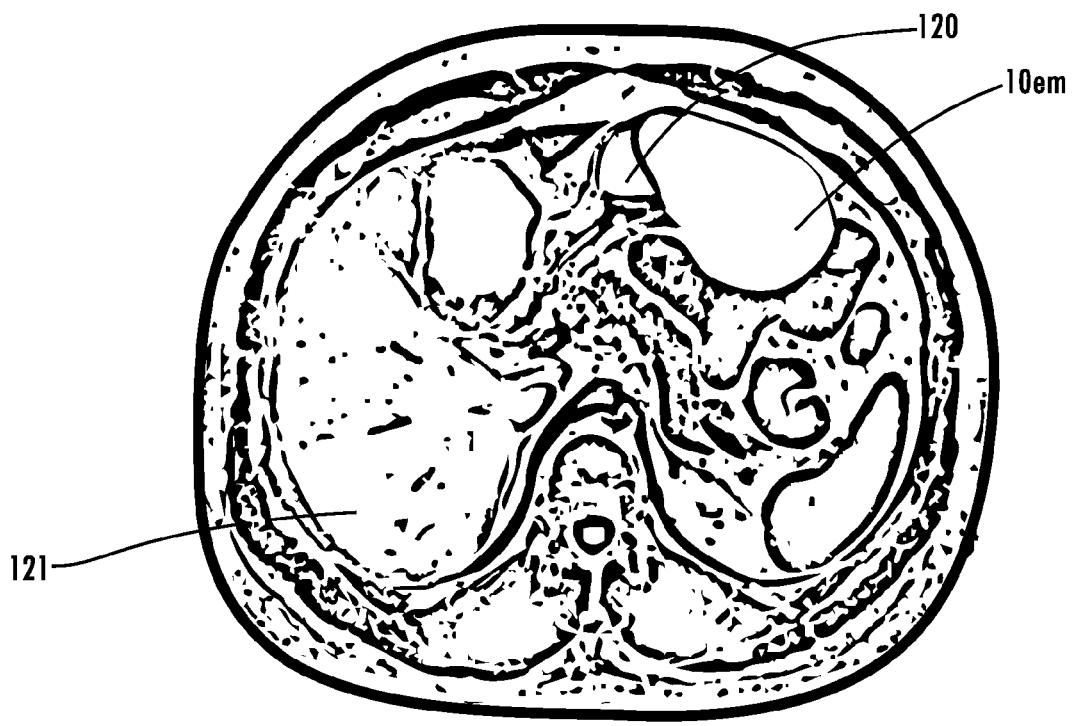
Figure 68K:
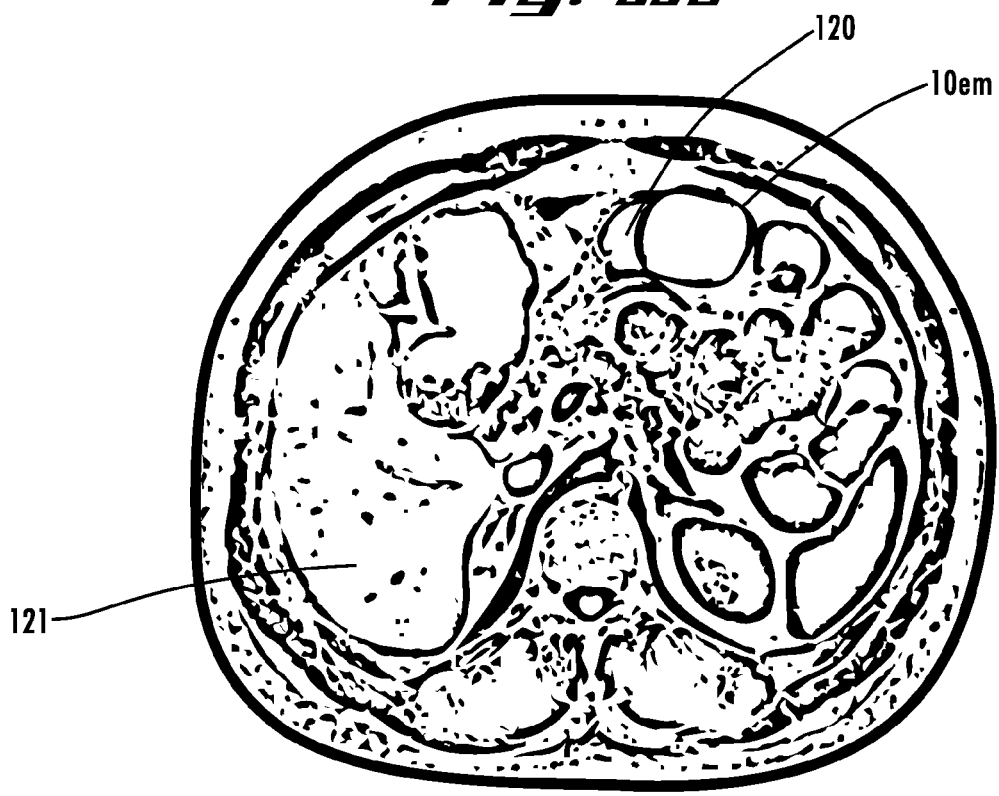

FIG. 67 illustrates port locations for use in laparoscopic implantation of a device in the same location as described above with regard to the percutaneous procedure of FIGS. 66A-66L. In this procedure, port 390*a* is provided in a similar location to where the insertion was made for the percutaneous procedure described in FIGS. 66A-66L. Additional ports 390*b*, 390*c* and 390*d* are provided for insertion of an endoscope to visualize the procedure, a retractor, grasper or other tool for pulling the omentum out of the target surgical site, and a retractor for retracting the left lobe of the liver, respectively.

FIGS. 68A-68K are transverse cross-sectional illustrations of the abdominal cavity shown at sequential, incremental locations of the cavity, which correspond to the illustrations of FIGS. 2A-2K, respectively, but in which expandable member 10*em*, implanted in a position as described with regard to FIGS. 66A-67 above, is also shown. By, comparing the various sectional illustrations, it can be seen that expandable member 10*em* varies greatly in the amount and direction of displacement of the stomach at various locations along the stomach. The residual stomach outline and volume is illustrated adjacent the medial edge of the balloon. These slices illustrate the three-dimensional nature of the interaction between expandable member 10*em* and the stomach 120 and are provided to further show that it is not merely a simple anterior or lateral "push" that is applied to the stomach wall, but rather, the expandable member 10*em* provides a complex geometry that fills a targeted cavity, thereby leaving only a small residual space for the stomach 120 to reside.

Figure 69A:
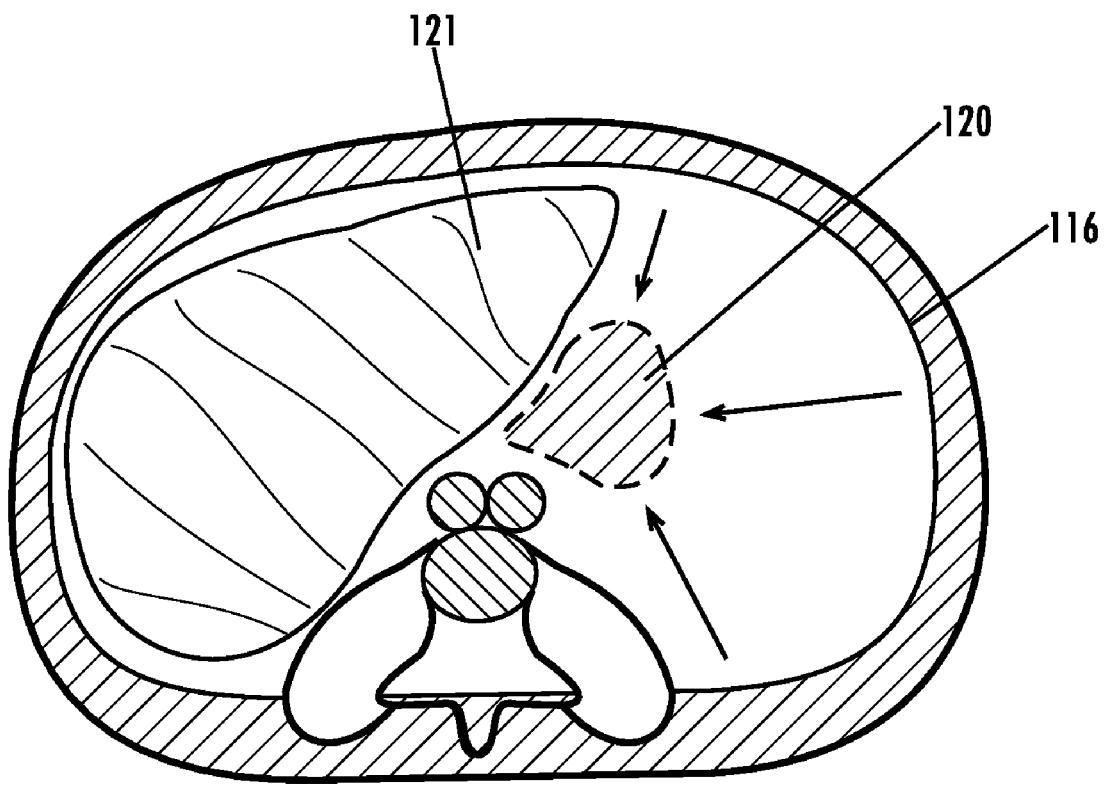
FIGS. 69A-69C illustrate advantages of placement of a single expandable member with a complex shape, for example, like the device implanted and positioned as described with regard to FIGS. 66A-67.
Figure 69B:
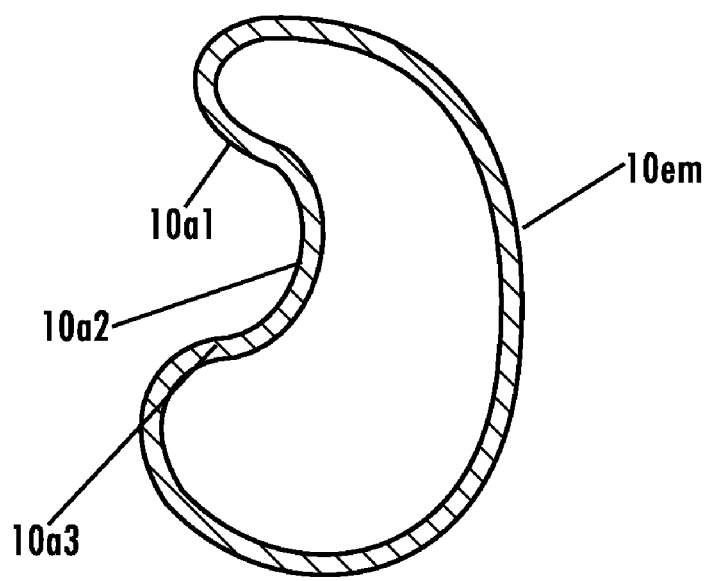
Figure 69C:
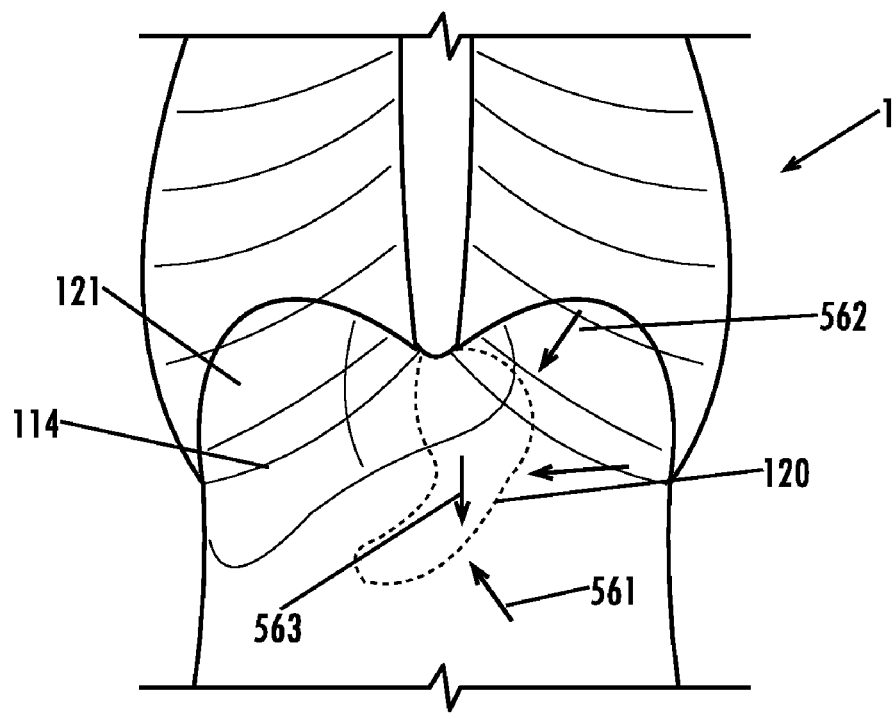

FIGS. 69A-69C illustrate advantages of placement of a single expandable member with a complex shape, for example, like device 10 implanted and positioned as described above with regard to FIGS. 66A-67. The arrows shown in the sectional illustration of FIG. 69A show the directions of force applied by surfaces 10*a*1, 10*a*2 and 10*a*3 (see FIG. 69B which shows a sectional view or expandable member 10*em* taken in the same section of the abdominal cavity shown in FIG. 69A, when expandable member 10*em* is implanted in a position as described above with regard to FIGS. 66A-67). Thus, since surface 10*a* "wraps around" the surface of the stomach somewhat, both anteriorly and posteriorly, a multi-directional compression is applied to the surface of the stomach by expandable member 10*em*.

FIG. 69C is an partial illustration from an anterior view of the patient 1, which shows that device 10 when implanted in a position as described above with regard to FIGS. 66A-67, in addition to the transverse forces shown in FIG. 69A, also applies forces in superior-medial and inferior-medial directions, and potentially in an inferior direction, as indicated by arrows 561, 562 and 563, respectively.

Figure 70A:
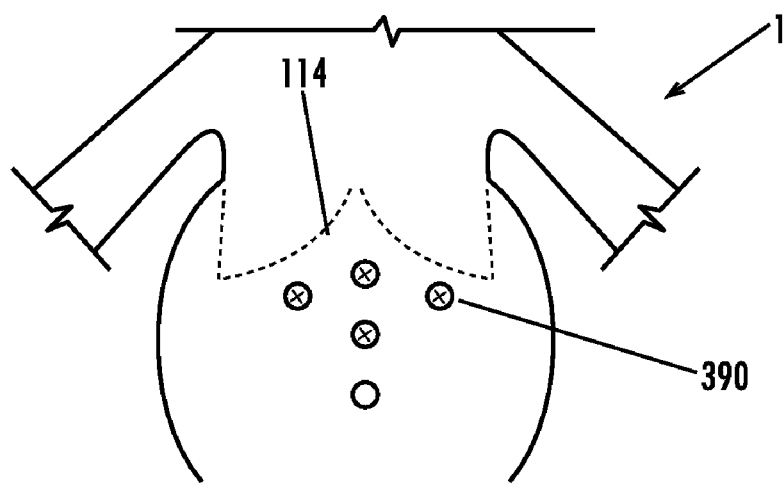
FIGS. 70A-70D illustrate steps of a laparoscopic method of implanting an expandable extra-gastric device according to one embodiment of the present invention.

FIGS. 70A-70D illustrate steps of a laparoscopic method of implanting an expandable extra-gastric device 10 according to one embodiment of the present invention. FIG. 70A illustrates that multiple access ports 390 (e.g., four or five) are installed through the abdomen of the patient 1, one for insertion of an endoscope for viewing the procedure, one for delivery of device 10 therethrough, and one or more for insertion of instruments into the target surgical area. An endoscope 356 is inserted through one of ports 390 and manipulated to locate anchoring locations on one or more internal structures to which device 10 is to be anchored. For example, one or more anchoring locations can be identified on the internal surface of the diaphragm and or chest wall. A suture, tether or other tensioning member 59 is next advanced through one of ports 390 for fixation to an anchoring location. At least one suture, tether or other tensioning member 59 is installed at each anchoring location selected, with all sutures, tethers or other tensioning members being passed through the same port 390.

Figure 70B:
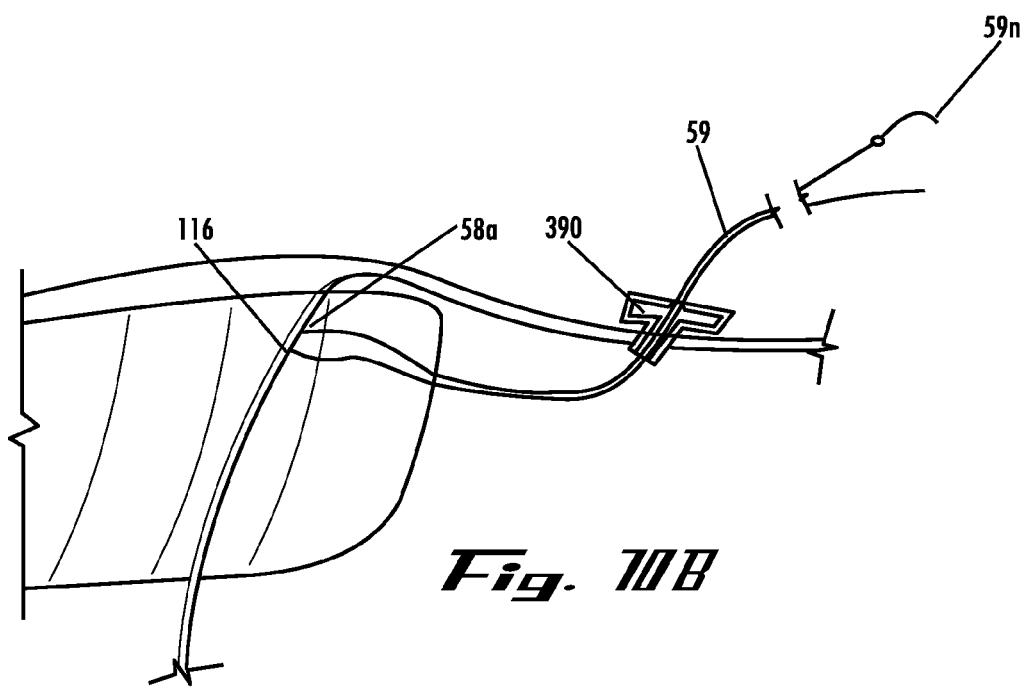

FIG. 70B illustrates a suture in the process of being installed at an anchoring location 58*a* on the diaphragm 116. A suture 59 having a needle 59*n* is advanced, needle first through port 390 and directed to the anchoring location 58*a*, using graspers or other laparoscopic surgical instrument. Needle 59*n* is passed into the target surgical area and drawn back out, wherein needle 59 then is withdrawn back out of port 390, while suture 59 is drawn through the pathway created by passing the needle into and out of the tissue at the anchoring location 58*a*. In the example shown, needle 59*n* can be driven all the way through the diaphragm wall 116 and then passed back through from outside to inside. Typically, however, needle 59*n* is passed through only a portion of the thickness of the wall of diaphragm 116 and does not pierce through the external surface. Suture 59 at this point has proximal and distal ends that extend proximally of port 390, as shown in FIG. 70B. This process can be repeated for as man sutures, tethers or other tensioning members 59 that are desired to be fixed to anchoring locations.

Figure 70C:
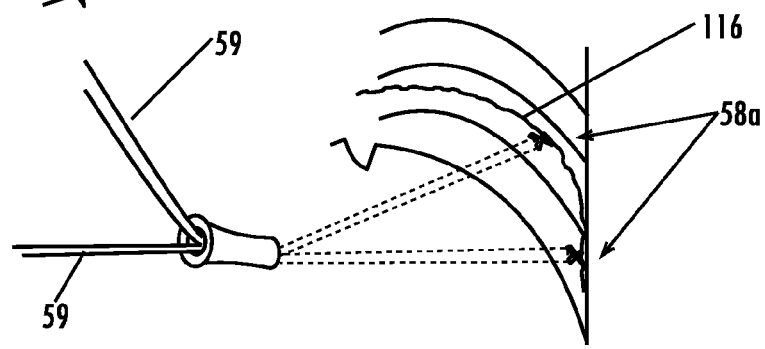
Figure 70D:
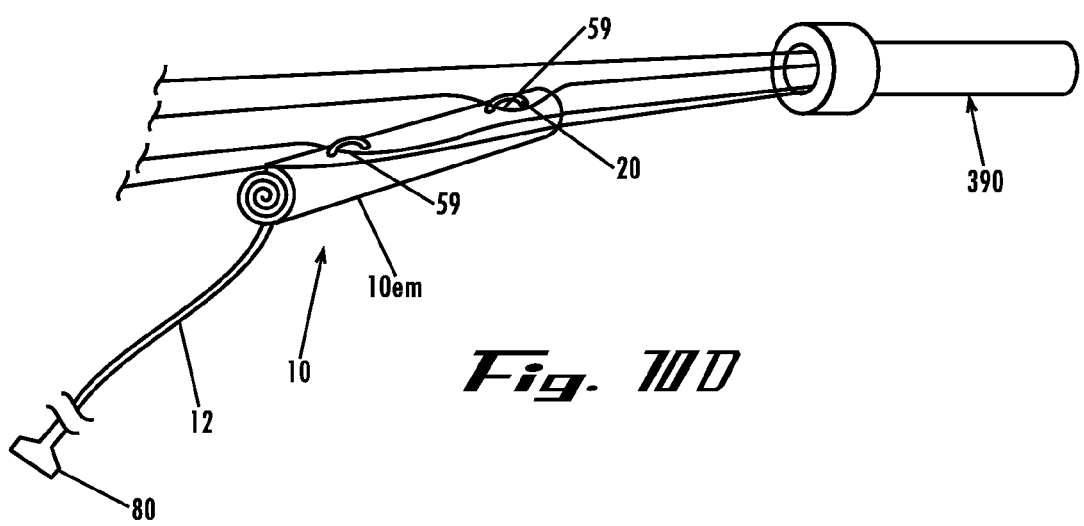

FIG. 70C illustrates a procedure where sutures 59 have been installed at two anchoring locations 58*a* on diaphragm 116. Next, as illustrated in FIG. 70D, a device 10 in a compacted configuration is threaded over sutures 59, via loops 20 or other guide features that can be included on the expandable member 10*em*. While holding sutures 59 relatively stationary, device 10 is then advanced distally with respect thereto, inserted through access port 390 and advanced further distally to the target surgical area, guided by the attachment of sutures 59 to anchoring locations 58a. Alternatively, one end of suture 59 that passes through loop 20 can be tied to loop 20 for each loop 20. After insertion of device 10 through port 390, the opposite ends of sutures 59 can then be retracted out of port 390, thereby drawing device 10 into position at the target surgical site.

Expandable member 10em is next expanded to an expanded configuration. If expandable member 10em is an inflatable member or a portion of expandable member 10em is inflatable, then inflation can be performed by inputting pressurized fluid through adjustment member 80 using one of the inflation tools 210 described above, or other pressurized fluid source. If all or a portion of expandable member 10em is a mechanically expandable member, then the mechanically expanding member can be expanded using one of the techniques described above. Expandable member 10em can be anchored to anchoring locations 58a by tying off sutures 59 against loops 20 and cutting the remainder of the sutures that extend proximally of the tie off locations. Adjustment member 80 can be fixed in one of the locations described above using one or more of the fixation techniques described.

Figure 71:
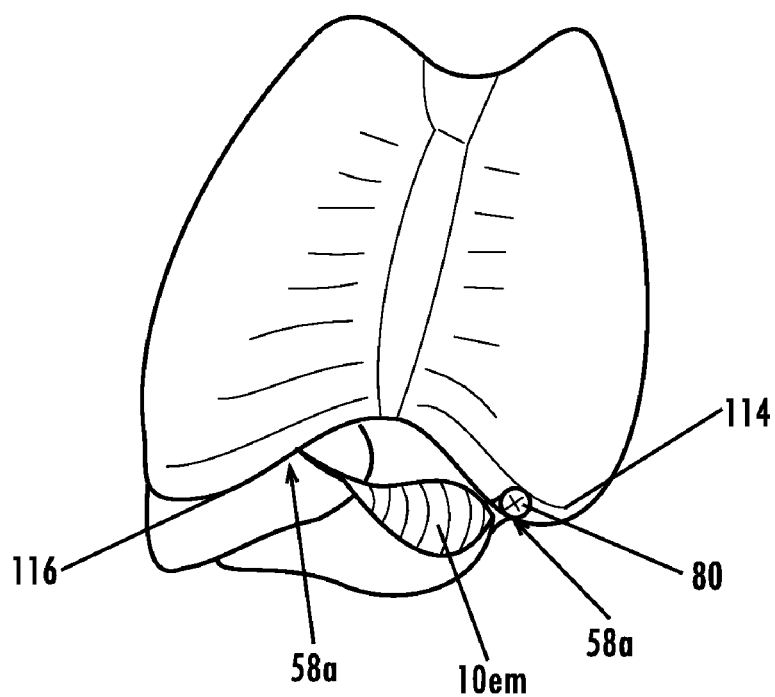
FIG. 71 illustrates the device shown in FIG. 37 having been tethered to two anchoring locations with a single suture, tether or other tensioning mechanism using percutaneous or laparoscopic procedures as described herein.

FIG. 71 illustrates device 10 of FIG. 37 having been tethered to two anchoring locations 58a with a single suture, tether or other tensioning mechanism 59 using percutaneous or laparoscopic procedures as described herein. Additionally, adjustment member 80 has been installed so that conduit 12 passes through diaphragm 116 (like described with regard to FIG. 32) and is fixed to draw expandable member 10em against diaphragm 116 thereby functioning as an additional anchor.

Figure 72A:
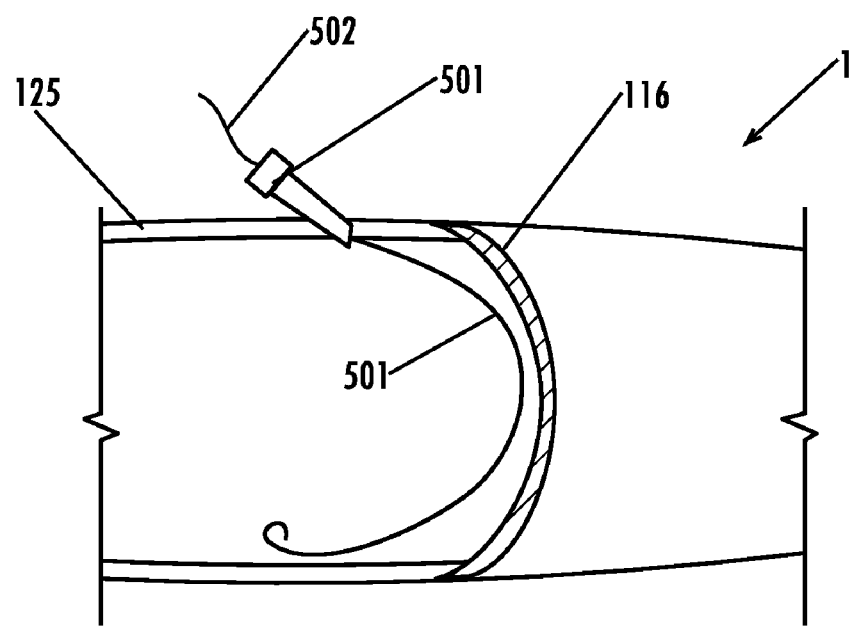
Figure 12B:
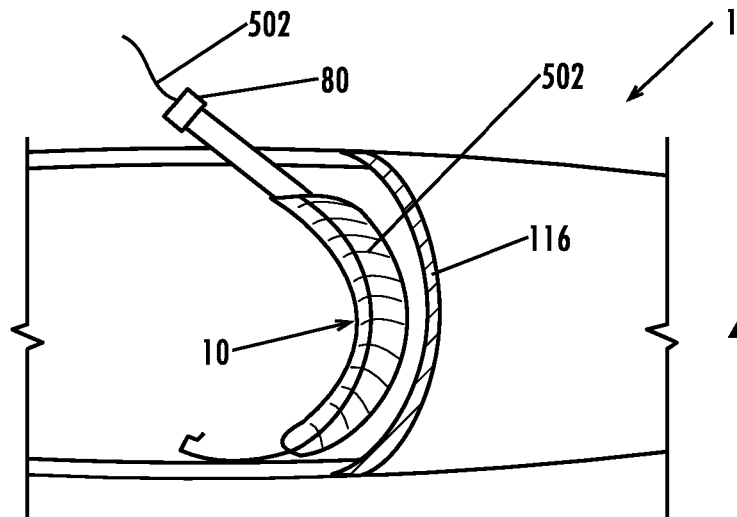
Figure 12C:
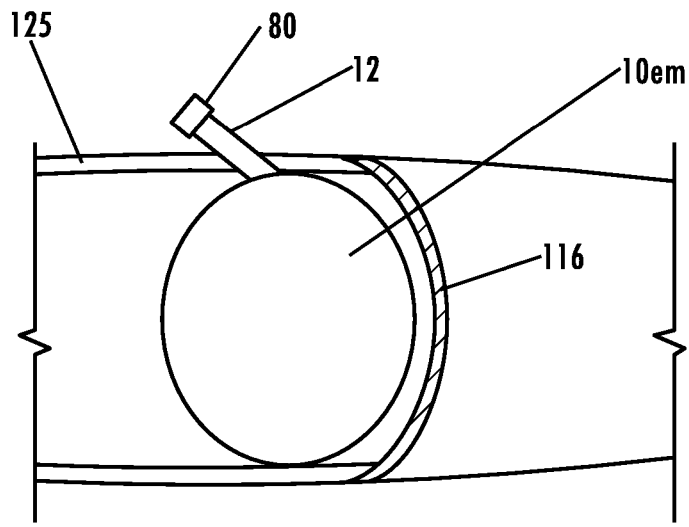

FIGS. 72A-72C illustrate steps of a method of percutaneously implanting an expandable extra-gastric device 10 according to another embodiment of the present invention. A veress or other access needle 501 is inserted to create an opening 3 into the abdominal cavity and a guidewire 502 is inserted through the opening and advanced (e.g., under fluoroscopic visualization or other visualization technique) into the patient 1. As guidewire 502 is advanced, it is guided by the natural curvature of diaphragm 116, as illustrated in FIG. 72A. Expandable device 10, in a contracted configuration, is next inserted through opening 3, and guided over guidewire 502 for example by passing a rail 512, loops 20 or other guiding features that are attached to device 10, over guidewire 502 so that guidewire 502 guides the positioning of device 10 into the desired target surgical location as illustrated in FIG. 72B. Veress needle 510 can be withdrawn and opening 3 can be dilated prior to insertion of device 11.

Once expandable member 10em has been positioned as desired, guidewire 502 can be removed, and expandable member 10em is expanded to an expanded configuration, as illustrated in FIG. 72C. If expandable member 10em is an inflatable member or a portion of expandable member 10em is inflatable, then inflation can be performed by inputting pressurized fluid through adjustment member 80 using one of the inflation tools 210 described above, or other pressurized fluid source. If all or a portion of expandable member 10em is a mechanically expandable member, then the mechanically expanding member can be expanded using one of the techniques described above. Expandable member 10em can be anchored to anchoring locations 58a by tying off sutures 59 against loops 20 and cutting the remainder of the sutures that extend proximally of the tie off locations. Adjustment member 80 can be fixed in one of the locations described above using one or more of the fixation techniques described. Expandable member 10em can be anchored to one or more internal structures, such as the diaphragm 116, internal surface of abdominal wall, or other structure, at one or more locations, using an, of the techniques and anchors described above.

Figure 73B:
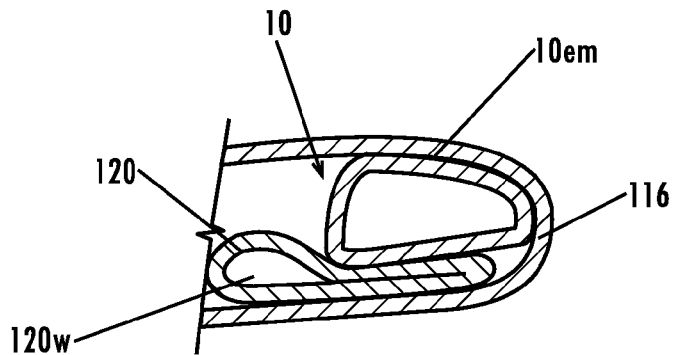

FIGS. 73A-73B illustrate placement of a device 10 having a single expandable member 10em. Expandable member 10em of device 10 is positioned anteriorly of the stomach 120 as shown in FIG. 73A. Expandable member 10em is shaped and dimensioned to match the shape and size of the void in the abdominal cavity bounded by the stomach 120, the diaphragm 116, chest wall, and the bottom edge of the ribs 114. Thus expandable member 10em is positioned beneath the ribs within the abdominal cavity, and anterior to the stomach 120, as illustrated. Expandable member 10em can have a relatively flat surface 102a on one side, posterior facing surface, as shown, that presses down on the anterior surface of the stomach 120 after placement of device 10 as shown and expansion of expandable member 10em. The other surfaces of expandable member 10em can be shaped to match the typical contour of the diaphragm 116 and the chest wall. Anchoring of device 10 can be performed at one or more of the indicated locations 58 along the diaphragm 116, lateral rib cage wall and chest wall. As positioned and expanded or inflated, device 10 drives against and flattens out the fundus and a portion of the body of the stomach 120, such that the walls of these portions of the stomach 120 appose each other, as illustrated in the sectional illustration of FIG. 73B. The displacement of the stomach walls as described reduces the internal cavity of the stomach to the shape of a small lumen 120w that passes down along the medial side of the stomach 120 toward the lesser curvature, for receiving food, similar to the results of a sleeve gastrectomy.

Figure 74A:
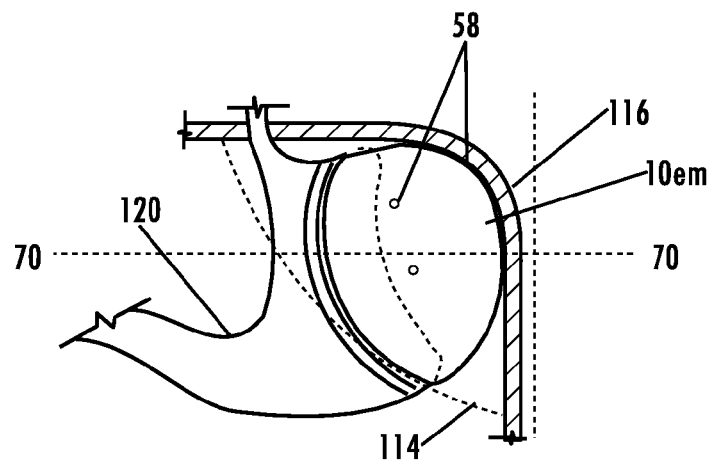
FIGS. 74A-74B illustrate another embodiment of placement of a device having a single expandable member.
Figure 74B:
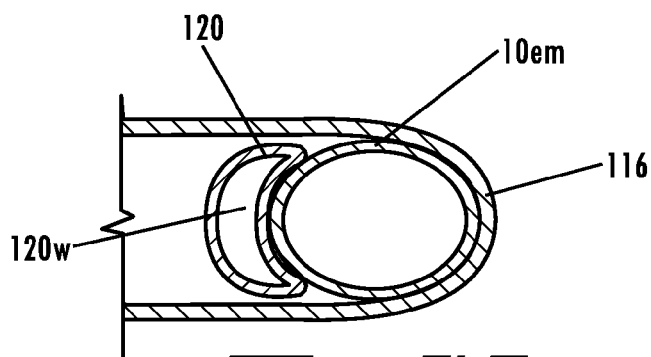

FIGS. 74A-74B illustrate placement of another device 10 having a single expandable member 10em. Expandable member 10em of device 10 in this example is positioned in a similar location as that described with regard to FIGS. 73A-73B, but in this case is placed laterally of the stomach, between the stomach 120 and the diaphragm 116, as shown in FIG. 74A. The posterior surface of expandable member 10em in this case is not flat, but convex, when expanded so that the expanded configuration of expandable member 10em is closer to spherical than that described with regard to FIGS. 73A-B. Also, surface 10a is a lateral surface that occupies the space of the fundus of the stomach 120 laterally and is almost spherical in the area of contact with the fundus, while tapering down where it contacts the body of the stomach, so that it does not expand by as great a distance as it does against the fundus. Device 10, as expanded follows the outline of the edge 114 of the lowest rib. Upon expansion, expandable member 10em holds the stomach 120 medially from its natural position, and leaves a channel 120w that will take in food, as shown in the sectional illustration of FIG. 74B.

As noted above, devices 10 can be implanted using a variety of different surgical techniques, including open surgical procedures, laparoscopic procedures and percutaneous procedures. Open surgical procedures are the easiest methods of implanting device 10, but also are the most invasive and thus associated with higher morbidity and require longer healing time, more scarring etc. In one example of an open surgical procedure, a midline incision can be made to expose the abdominal cavity. Device 10 can be placed in the desired location in the abdominal cavity and anchored into place with the use of sutures, staples or any other fixation structures or techniques described herein. Device 10 can have reinforced tabs or loops 20 that facilitate anchoring by sutures, hooks, staples, etc. as already noted above. Once anchored in position, device 10 can be expanded, such as by inflation, mechanical expansion or a combination of these. After anchoring and expansion of device 10, the midline incision can be sewn back up. For inflatable members 10em, conduit 12 can be extended out of the midline incision and the adjustment member can then be fixed in place (e.g., to the abdominal fascia) in a manner as described above.

To perform a laparoscopic procedure, multiple access ports are used to perform the procedure in a less invasive want. The peritoneal cavity is filled with pressurized CO2 to create a pneumoperitoneum (i.e., a "tent" inside the abdominal cavity). There are many different procedural steps that one can take to position and anchor device 10 in the desired location. One embodiment of such as procedure is described here. Implant 10 is inserted into the abdominal cavity through an access port. Device 10 can be rolled up like a cigar and sent down the port or it can be loaded up on a sheathed introducer device to be sent down the access port. Once in the abdominal cavity, device 10 can be unrolled and positioned in the target area.

Once it has been confirmed that the positioning of device 10 is appropriate, sutures, staples or other anchoring techniques or structures, as described herein, can be used to anchor expandable member 10em onto one or more internal body structures (e.g., diaphragm, chest wall and/or other internal structures) to secure it in place. If expandable member includes an inflatable member, then conduit 12 (e.g. inflation tubing) can be connected to adjustment member 80 next. An inflation adapter can be in fluid communication with an external carbon dioxide ($CO_2$) supply, or a self-contained $CO_2$ inflation device can be used to inflate expandable member 10em and check its positioning. During this step, an intra-gastric sizing balloon 310 (e.g., a hot dog shaped balloon which preserves the residual stomach lumen desired) can be used to determine when to stop the expansion or inflation of expandable member 10em. Once the positioning and amount of expansion have been determined and set, adjustment member 80 can be attached to an area (e.g., the abdominal fascia) to secure it in place.

When performing a percutaneous procedure, it is desired to use local anesthesia to perform the procedure in the most minimally invasive manner. Ideally, a single insertion point will enable the physician to perform the entire procedure. Imaging guidance is used to safely position and anchor device 10. Potential imaging modalities include fluoroscopy (i.e., real-time x-ray), ultrasound, endoscopy, MRI, and CT. One embodiment of a percutaneous procedure includes placing a catheter trans-orally into the inner chamber (cavity) of the stomach. The stomach is occluded by inflating a balloon attached to the catheter and pulling the inflated balloon back to the gastro-esophageal (GE) junction. A contrast agent can then be injected into the stomach cavity to enhance visualization of the stomach cavity under fluoroscopy.

Using a veress needle, the intra-peritoneal (abdominal) cavity is next accessed by inserting the needle through the skin of the patient and into the abdominal cavity. A guidewire is next inserted through the needle, and the anterior surface of the stomach is accessed, up to the superior region of the fundus. The guidewire can be sent around to the posterior side of the fundus, against the surface of the fundal-diaphragmatic interface. Once the guidewire has been properly positioned thusly, an instrument that can sequentially deploy an anchor with a tether wire or suture is passed over the guidewire.

The anchor deployment instrument deploys an anchor on the diaphragm near the superior aspect of the fundus first. Then, it can be pulled back to the mid-rib-cage region to deploy a second anchor. Then, if desired, a third anchor can be deployed near the bottom edge of the rib-cage. Once the anchors are deployed, the instrument is pulled out of the patient, leaving multiple tether wires which are accessible on the outside of the body, through the access port. The tether wires can be "loaded" onto a device deliver, instrument. Each of the tether wires can be inserted into specific loops or tabs on device 10 to match the position of the device 10 where it is to be placed in the corresponding position where that tether is anchored.

The device delivery instrument is then ridden over the guidewire and tether wires to the target implantation site. Once the device delivery instrument is in the correct position, the tether wires can be fixed into place with a locking mechanism built into the delivery instrument or the delivery instrument can just release the implant and the tether wires can be locked into place by using a separate instrument, which can ride over the tether wires individually to cinch dozen or lock the tethers in place.

With device 10 now anchored in the desired position, the device delivery instrument is removed, and adjustment member 80 can be attached to conduit 12. If expandable member contains an inflatable member, like described previously expandable member 10em can be inflated next. In this step, an intra-gastric sizing balloon can also be used, in a manner as noted above. In fact, the initial access balloon which was used to put contrast into the stomach can be shaped like a hot-dog or other shaped described herein, to serve this purpose. Next, the adjustment member can be secured, such as to the abdominal fascia, for example.

Figure 75:
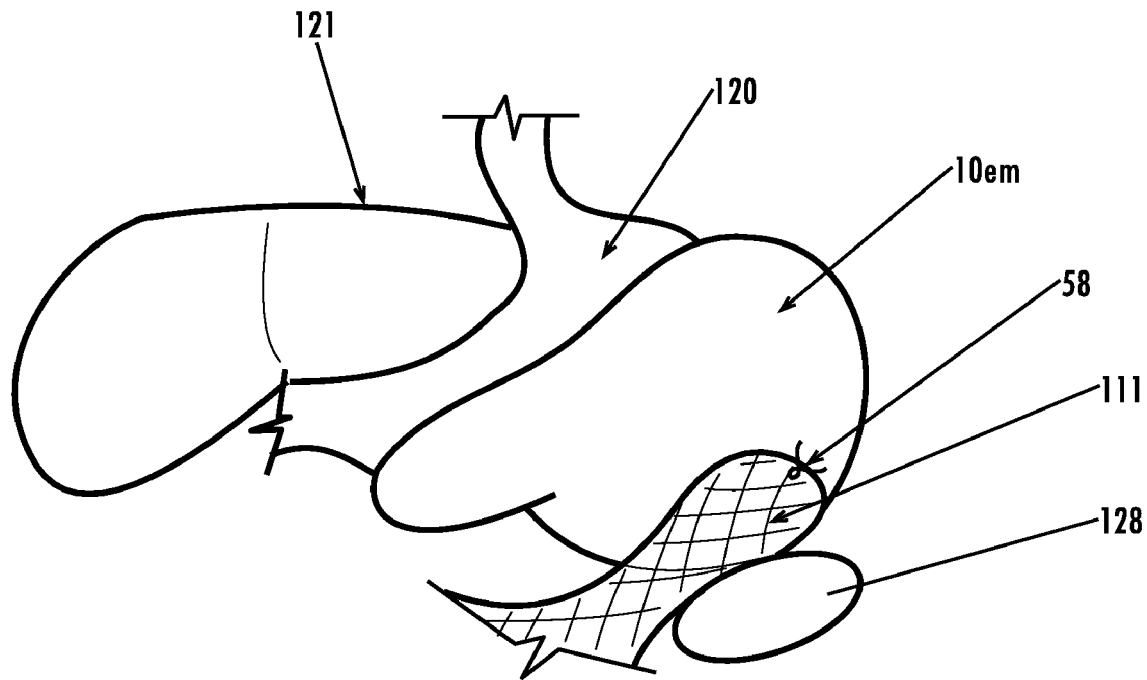
FIG. 75 illustrates a technique for protecting the spleen and/or diverting compressive forces away from the spleen.

FIG. 75 illustrates a technique for protecting the spleen 128 and/or diverting compressive forces away from the spleen 128. Using this technique, the omentum 111 is anchored 58 to expandable member 10em to provide a cushion between the spleen 128 and surface 10p of expandable member. The attachment may be provided under tension, but a simple clipped, glued or sewn attachment is typically sufficient.

Devices 10 described herein can be relatively easily removed or deactivated. Various different simple procedures available for such removal or deactivation include, but are not limited to: cutting of sutures or other anchoring members and compressing expandable member 10em and then withdrawing it; compressing expandable member 400 and withdrawing it; rupturing or deflating inflatable expandable member 10em to deactivate it, without removal; providing a self deactivating feature, whereby if an inflatable member 10em migrates beyond a predetermined distance, it becomes disconnected from conduit 12 and deflates.

Devices 10 described herein can be electrically connected to a sensor on the stomach wall to function as a "barosensor", so that when the stomach 120 is empty, there is no pressure or stress, or a predetermined pressure level or stress level on the barosensor. Upon eating, as the stomach 120 expands, pressure or stress on the barosensor increases. When a predetermined pressure or stress or strain level has been sensed, device 10 responds by delivering one or more drugs and/or electrical stimulus to facilitate the feeling of satiety. In this way, a direct method of sensing is provided for real time, immediate sensing of when a person is eating, to provide a therapy at that time, whether directly into the blood stream or locally, with a hormonal drug, obesity treatment drug, electrical signal, which can including pacing signals from a pacing device, and/or some other form of treatment. A drug pump can be included either integrally with the device 10 or separately, but connected to the barosensor to act as a trigger mechanism/actuator.

Figure 76:
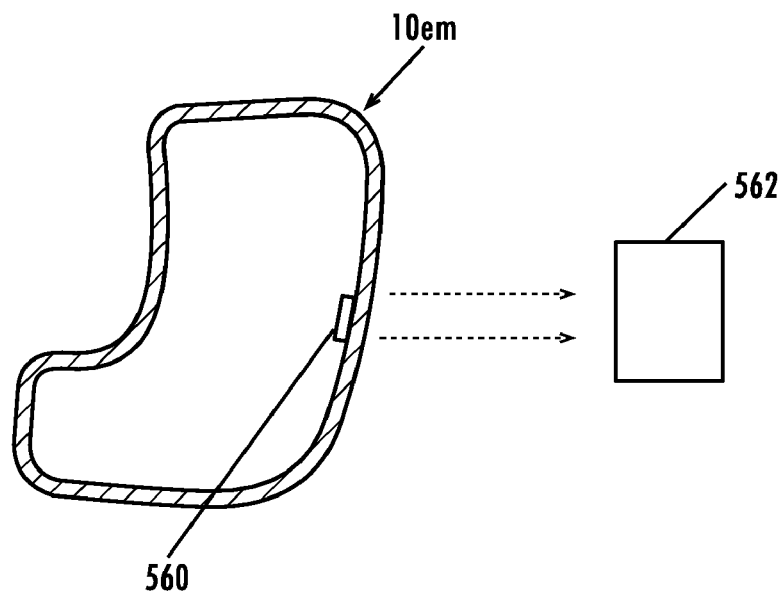
FIG. 76 illustrates an expandable member of a device having a pressure sensor and transmitter fixed to an inner wall of the expandable member.

Expandable member 10em (e.g., an inflatable expandable member) can be provided with a pressure sensor inside the chamber of the inflatable member 10e, such as on the inner wall for example. Sensor 570 can be electrically connected therewith, or incorporated therein, a transmitter, such as a radio-frequency identification (RFID) chip or other circuit for transmitting by radio frequency or other frequency commonly used for telemetry to communicate externally of the patient. FIG. 76 illustrates an expandable member 10em of device 10 having a pressure sensor and transmitter 560 fixed to an inner wall of expandable member 10em. Sensor and transmitter 560 can also function as a receiver for receiving signals telemetrically. In this example, the patient is provided with a pager or cellular phone, PDA or other device 562 that is tuned to receive the frequency of transmission of sensor/transmitter 560 and which can call out or send other electronic transmissions (such as email, page, text messaging, etc.). Sensor and transmitter 560 can be programmed with upper and lower pressure thresholds. When the pressure inside expandable member 10em is less than the lower threshold or greater than the upper threshold, sensor and transmitter transmits a signal which, if device 562 is in range, is received by device 562. Device 562 can be programmed to then automatically contact the patient's physician, such as by telephone, email, text messaging, paging etc.

Additionally or alternatively, device 562 can be configured with an output port so that information from device 562 can be downloaded to a computer or other microprocessor. Further device can be configured to communicate with or query sensor and transmitter 560 to request a pressure reading anytime that device 562 queries sensor and transmitter 560. In response, the transmitter of sensor and transmitter 560 transmits a pressure reading to device 562 telemetrically. In this way, device 562 can record a run chart of the pressure in expandable member 10em, for later downloading and/or transmittal to the physician.

A device 10 having multiple inflatable expandable members 10em can be provided with a controllable valving mechanism between two members that is controllable by the patient into which it is implanted, through the manual operation of an actuator that can be subcutaneously implanted. When the patient is in a state of satiety, a first expandable member can be in an expanded or inflated state and a second expandable member can be in a contracted or deflated state. When the patient is ready to eat or becomes hungry, the patient can actuate the activating mechanism which controls the valving mechanism to transfer the inflation fluid from the first expandable member 10em to the second expandable member 10em. In this state, first expandable member can be in a contracted or deflated state and the second expandable member can be in an expanded or inflated state. When the second member is in an expanded state, it presses against the stomach wall to assist the patient in reaching satiety at an earlier stage than he or she normally would. When the second member is in a contracted state, it does not deform the stomach wall. The expansion of the second expandable member can also function as an active mechanical stimulant, as gastric massage can paralyze the peristaltic action of the stomach temporarily.

EXAMPLE

The following example is put forth so as to provide those of ordinary skill in the art with a complete disclosure and description of how to make and use the present invention, and are not intended to limit the scope of what the inventors regard as their invention nor are the intended to represent that the experiment below was the only experiment performed.

Figure 77A:
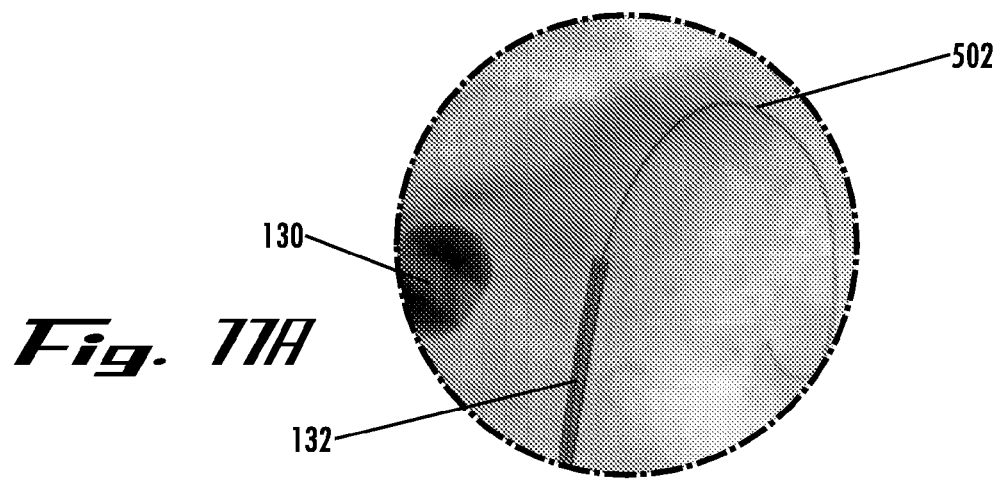
FIGS. 77A-77F are radiographs taken during the placement of an expandable device in a human cadaver.
Figure 77B:
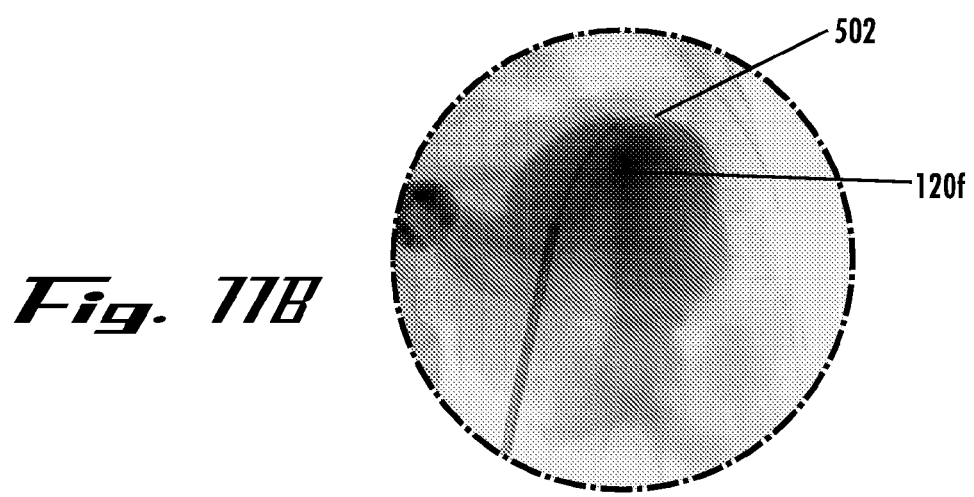
Figure 77C:
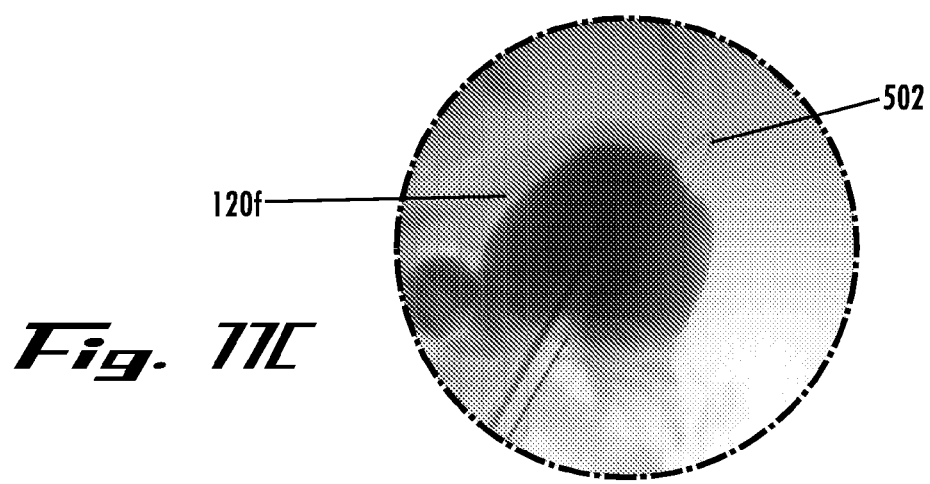
Figure 77D:
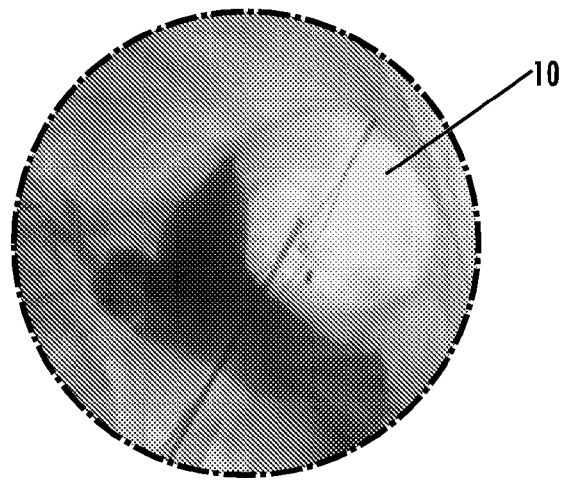
Figure 77E:
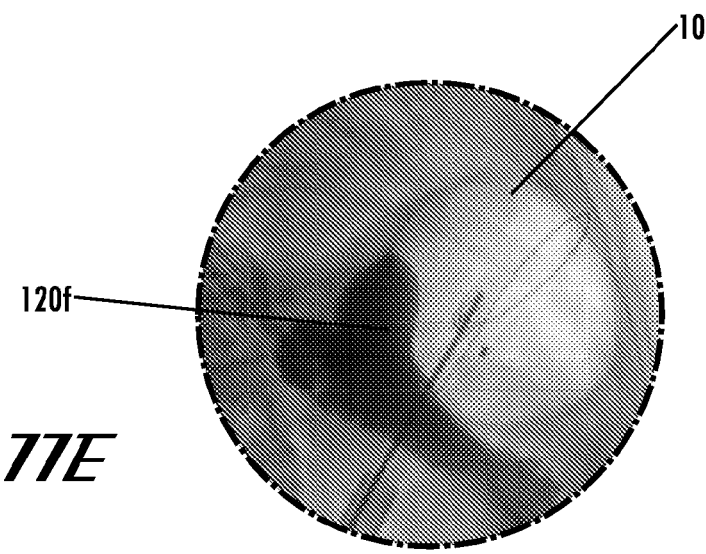
Figure 77F:
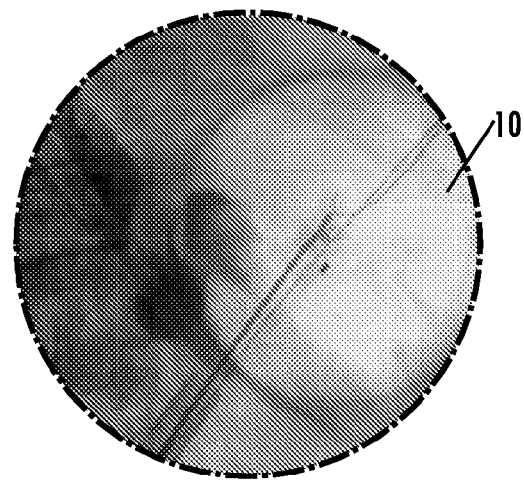

FIGS. 77A-77F are radiographs taken during the placement of an expandable device in a human cadaver in the location described above. Initially a balloon catheter 130 was inserted trans-orally and advanced to place the distal up at the gastro-esophageal junction, as shown in FIG. 77A. The abdominal cavity was next accessed using a veress needle and a guidewire (0.035" Cordis guidewire, CORDIS®, http://www.cordis.com/) 134 that were inserted through the abdomen in the location indicated by 126 in FIG. 1.

As the guidewire 502 was advanced, it was naturally guided along the curvature of the surface of the diaphragm 116, as can be seen in the curvature of the guidewire 502 shown in FIG. 77A. Thus, the diaphragm 116 acted as a natural guide to guide the guidewire 502 around the fundus of the stomach 120f to a location superior of the fundus 120f and inferior of the diaphragm 116. The diaphragm 116 is shaped like an umbrella (see FIGS. 1A and 78A-78B). The guidewire 502 rode along the entire curvature of the diaphragm 116. The fundus curvature matched the curvature of the diaphragm and the guidewire 502 inserted between the diaphragm 116 and the fundus.

A contrast agent mixture of meglumine and saline was injected into the stomach via balloon catheter to enhance the visualization of the stomach. The fundus 120f can be seen in FIG. 77B. Additionally, it can be observed that guidewire 502 has been guided (by the diaphragm wall 116, as noted) closely around the exterior surface of the fundus 120f. An expandable device 10 was next delivered over the guidewire 134 in the form of a balloon catheter at FIG. 77C and was then inflated with air (FIG. 77D) to expand the device 10. As the inflation progressed (FIGS. 77D, 77E and 77F), the contrast agent showed a clear visualization of the fundus 120f being compressed, as the contrast agent was driven from within the fundus 120f.

Figure 78H:
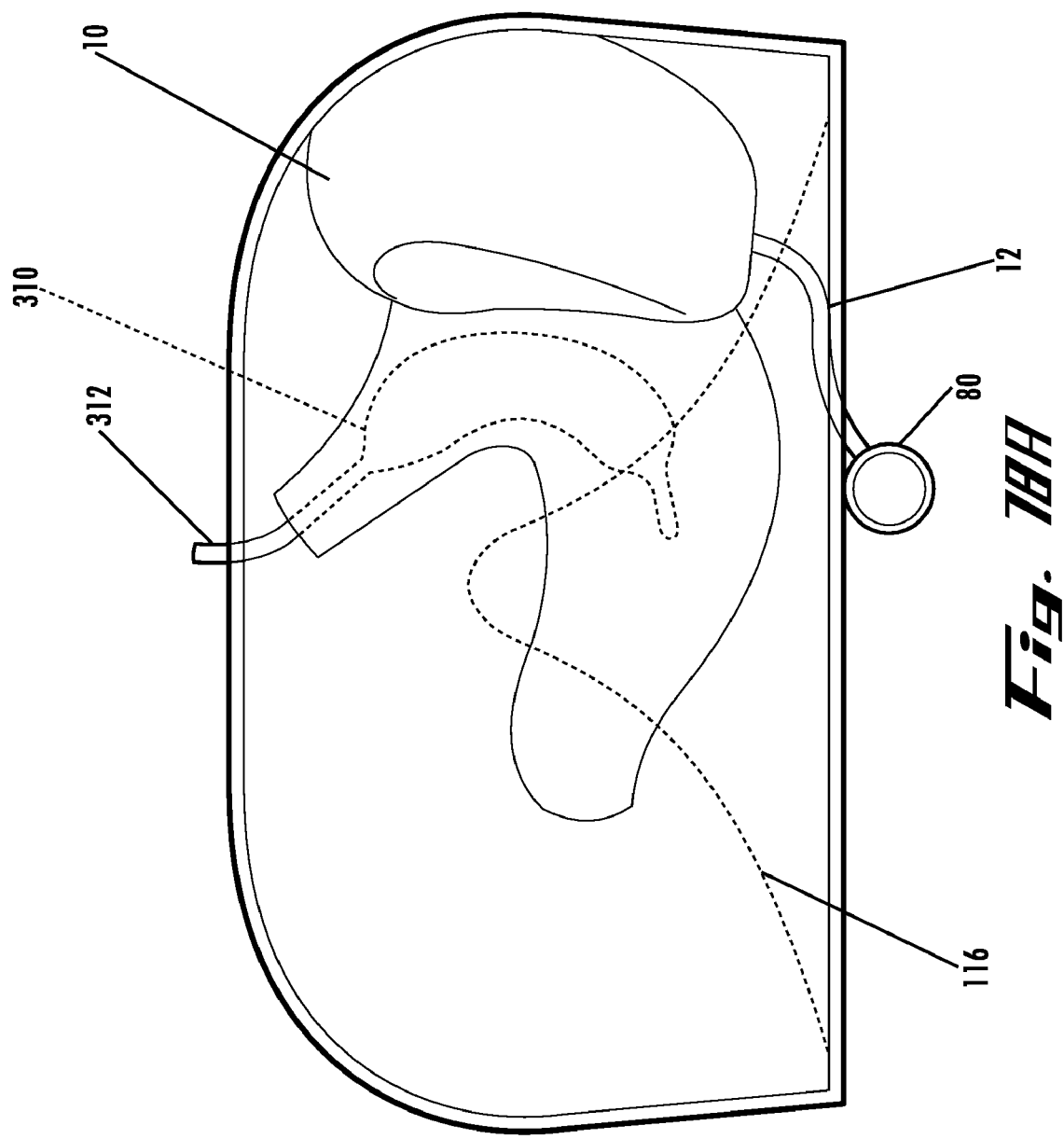
FIGS. 78A-78B illustrate a device positioned in the sulcular aspect of the diaphragmatic corella, bounded by the diaphragm and ribs on anterior, posterior, superior and lateral sides, so that when device is expanded, the expansion is somewhat concealed from observation externally of the patient.
Figure 78B:
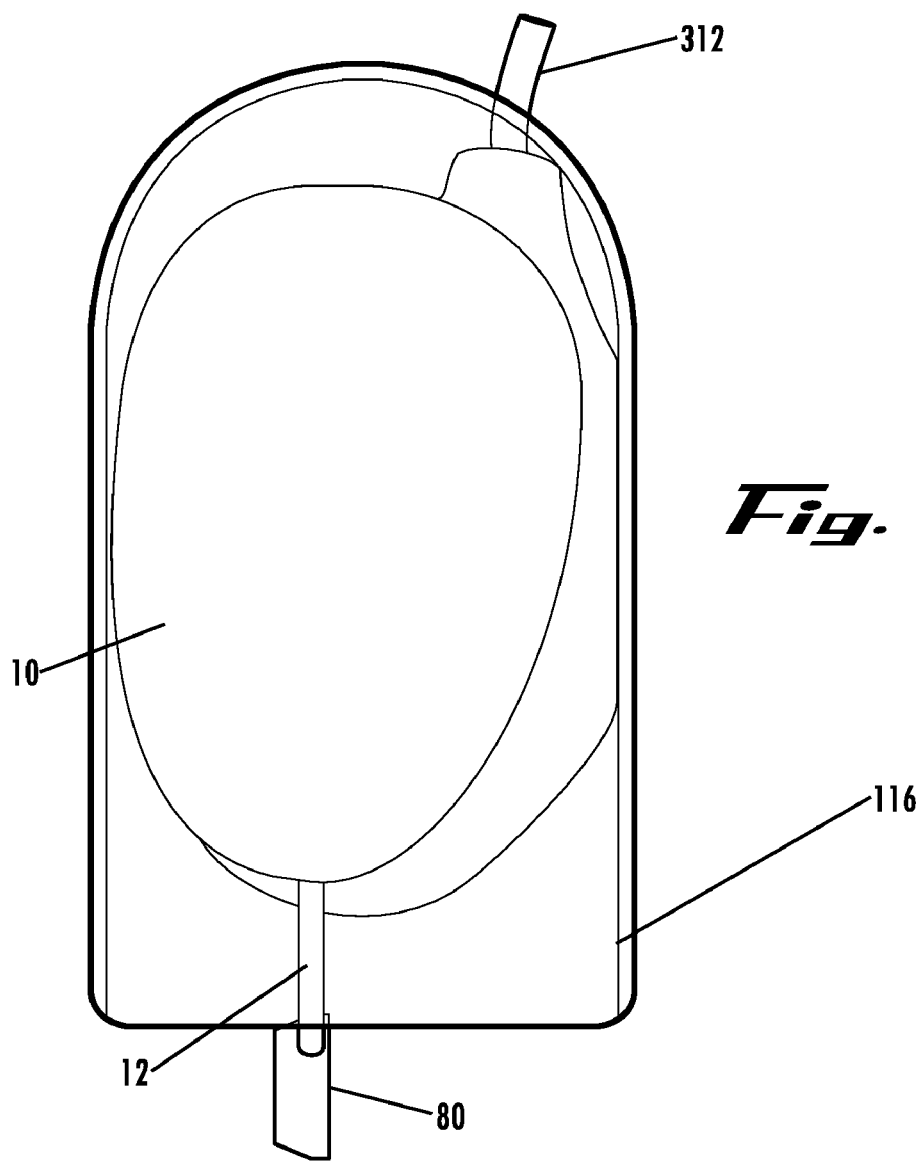

By positioning the device 10 in the sulcular aspect of the diaphragmatic corella 116 superior and/or posterior to the fundus 120f, device 10 is bounded by the diaphragm 116 and ribs on anterior, posterior, superior and lateral sides, so that when device 10 is expanded, the expansion is somewhat concealed from observation externally of the patient (see FIGS. 78A-78B). Thus, unlike some other placements, this placement of device 10 allows device 10 to be expanded without creating a substantial external "bulge" that is noticeable on the exterior (e.g., skin) of the patient. This location of placement is also a natural nook that is where the fundus normally expands to when a large amount of food and/or liquid are ingested and enter the stomach. Variations of the placement of expandable device 10 are also possible, such as a more lateral position of device 10 relative to the fundus 120f, between the fundus 120f and the diaphragm 116 wall, or a position anterior of the fundus 120f. Further variations of placement of the device, as well as various embodiments of the device placed, are described below.

While the present invention has been described with reference to the specific embodiments thereof, it should be understood by those skilled in the art that various changes can be made and equivalents can be substituted without departing from the true spirit and scope of the invention. In addition, many modifications can be made to adapt a particular situation, material, composition of matter, process, process step or steps, to the objective, spirit and scope of the present invention. All such modifications are intended to be within the scope of the claims appended hereto.

That which is claimed is:

1. A method of creating a feeling of satiety comprising:
providing an expandable member comprising a bulbous superior portion that tapers to an inferior tubular portion mounted on a distal end portion of a rigid elongate member of a delivery instrument;
inserting the expandable member with the delivery instrument into the abdominal cavity of a patient;

positioning the expandable member in a sub-diaphragmatic space in proximity to a stomach without penetrating a wall of the stomach; and expanding the expandable member to reduce an achievable maximum volume of the stomach, wherein the stomach is free to move; and removing the delivery instrument from the patient, while leaving the expandable member in position in the abdominal cavity.

2. A method of treating obesity in a patient, said method comprising:

making a percutaneous opening to the abdominal cavity of the patient;

passing at least one tether through the percutaneous opening and into the abdominal cavity;

passing an expandable device, while in a contracted configuration, through said opening and guiding said expandable device along said at least one tether to deliver said expandable device into the abdominal cavity;

positioning the expandable device in the abdominal cavity, external of the stomach;

expanding the expandable device; and anchoring the expandable device, relative to at least one structure in the abdominal cavity, without piercing through a wall of the stomach, wherein said anchoring comprises tethering at least two locations of the expandable device to at least one structure in the abdominal cavity using said at least one tether, said at least one tether extending between said at least two locations and fixing at least one said tether to the at least one structure at each of said at least two locations.

3. The method of claim 2, wherein said anchoring comprises anchoring the expandable device to the diaphragm of the patient to maintain contact between the diaphragm and the expandable device.

4. The method of claim 2, further comprising passing a guidewire through the percutaneous opening to deliver a distal end of the guidewire to a target area where the expandable device is to be positioned; and fixing the guidewire to a structure in the abdominal cavity, wherein said passing an expandable device comprises sliding the expandable device over the guidewire.

5. The method of claim 4, wherein the guidewire is guided along the curved surface of the diaphragm of the patient during said passing a guidewire.

6. The method of claim 2, further comprising anchoring an adjustment member to an internal wall of the abdominal muscles.

7. The method of claim 2, further comprising anchoring an adjustment member to an external wall of the abdominal muscles.

8. The method of claim 2, further comprising anchoring an adjustment member subdermally and external of a fat layer external of the abdominal muscles.

9. The method of claim 2, wherein said positioning the expandable device in the abdominal cavity, external of the stomach comprises positioning the expandable device between the stomach and the diaphragm of the patient.

10. A method of treating obesity in a patient, said method comprising:

making a percutaneous opening to the abdominal cavity of the patient;

passing an expandable device, while in a contracted configuration, through said opening;

positioning the expandable device in the abdominal cavity, external of the stomach;

expanding the expandable device; and anchoring the expandable device, relative to at least one structure in the abdominal cavity, without piercing through a wall of the stomach;

wherein the device further comprises an adjustment member that is connected to the expandable member via a conduit, and wherein said anchoring the expandable device, relative to at least one structure in the abdominal cavity comprises forming an opening through the diaphragm of the patient, passing the conduit out through the diaphragm, and anchoring the expandable device to the diaphragm by anchoring the adjustment member at a location on the opposite side of the diaphragm.

11. The method of claim 10 performed minimally invasively under fluoroscopic visualization.

12. The method of claim 10 performed minimally invasively under ultrasonic visualization.

13. A method of treating obesity in a patient, said method comprising:

making a percutaneous opening to the abdominal cavity of the patient;

passing at least two guide sutures through the percutaneous opening and anchoring distal portions of the guide sutures to at least two different locations on or more internal structures in the abdominal cavity of the patient, wherein proximal ends of the sutures remain outside of the percutaneous opening;

threading an expandable device over the proximal ends of the at least two guide sutures and sliding the expandable device over the guide sutures and into position against the one or more internal structures;

expanding the expandable device; and anchoring the expandable device, relative to the one or more internal structures, without piercing through a wall of the stomach.

14. The method of claim 13, wherein the at least two guide sutures are anchored to the diaphragm of the patient.

15. The method of claim 13, wherein said anchoring the expandable device, relative to the one or more internal structures in the abdominal cavity, comprises suturing the expandable device to the one or more internal structures, using the at least two guide sutures.

* * * * *